US012509510B2

(12) United States Patent
Choi et al.

(10) Patent No.: US 12,509,510 B2
(45) Date of Patent: Dec. 30, 2025

(54) IL31-BINDING POLYPEPTIDES AND USES THEREOF

(71) Applicant: Attovia Therapeutics, Inc., San Carlos, CA (US)

(72) Inventors: Jin Wook Choi, Pleasanton, CA (US); Lam Nguyen, Union City, CA (US); Shyr Jiann Li, Millbrae, CA (US); Jing Zhang, San Jose, CA (US); David Bellovin, San Jose, CA (US); Ole Petter Veiby, Redwood City, CA (US); Hangjun Zhan, Foster City, CA (US)

(73) Assignee: Attovia Therapeutics, Inc., San Carlos, CA (US)

( * ) Notice: Subject to any disclaimer, the term of this patent is extended or adjusted under 35 U.S.C. 154(b) by 0 days.

(21) Appl. No.: 19/187,342

(22) Filed: Apr. 23, 2025

(65) Prior Publication Data

US 2025/0326833 A1 Oct. 23, 2025

Related U.S. Application Data

(60) Provisional application No. 63/770,198, filed on Mar. 11, 2025, provisional application No. 63/690,297, filed on Sep. 3, 2024, provisional application No. 63/637,775, filed on Apr. 23, 2024.

(51) Int. Cl.
*C07K 16/24* (2006.01)
*A61K 39/00* (2006.01)

(52) U.S. Cl.
CPC ...... *C07K 16/244* (2013.01); *A61K 2039/505* (2013.01); *C07K 2317/24* (2013.01); *C07K 2317/52* (2013.01); *C07K 2317/569* (2013.01); *C07K 2317/92* (2013.01); *C07K 2317/94* (2013.01)

(58) Field of Classification Search
CPC .............. C07K 16/244; C07K 2317/24; C07K 2317/52; C07K 2317/569; C07K 2317/92; C07K 2317/94; A61K 2039/505
See application file for complete search history.

(56) References Cited

U.S. PATENT DOCUMENTS

| | | | |
|---|---|---|---|
| 5,648,237 | A | 7/1997 | Carter |
| 5,789,199 | A | 8/1998 | Joly et al. |
| 5,821,337 | A | 10/1998 | Carter et al. |
| 5,840,523 | A | 11/1998 | Simmons et al. |
| 5,959,177 | A | 9/1999 | Hein et al. |
| 6,040,498 | A | 3/2000 | Stomp et al. |
| 6,417,429 | B1 | 7/2002 | Hein et al. |
| 6,420,548 | B1 | 7/2002 | Vezina et al. |
| 6,982,321 | B2 | 1/2006 | Winter |
| 7,087,409 | B2 | 8/2006 | Barbas, III et al. |
| 7,125,978 | B1 | 10/2006 | Vezina et al. |
| 7,527,791 | B2 | 5/2009 | Adams et al. |
| 2006/0270045 | A1 | 11/2006 | Cregg et al. |

FOREIGN PATENT DOCUMENTS

| | | | |
|---|---|---|---|
| WO | WO-0075314 | A1 | 12/2000 |
| WO | WO-03060090 | A2 | 7/2003 |
| WO | WO-2004003140 | A2 | 1/2004 |
| WO | WO-2006122079 | A1 | 11/2006 |
| WO | WO-2007143231 | A2 | 12/2007 |
| WO | WO-2008028192 | A2 | 3/2008 |
| WO | WO-2009071696 | A2 | 6/2009 |
| WO | WO-2022136669 | A1 | 6/2022 |
| WO | WO-2022136672 | A1 | 6/2022 |
| WO | WO-2022147463 | A2 | 7/2022 |

OTHER PUBLICATIONS

Almagro, J.C., and Fransson, J., "Humanization of Antibodies," Frontiers in Bioscience 13:1619-1633, Frontiers In Bioscience Publications, United States (Jan. 2008).

Baca, M., et al., "Antibody Humanization Using Monovalent Phage Display," The Journal of Biological Chemistry 272(16):10678-10684, American Society for Biochemistry and Molecular Biology, United States (Apr. 1997).

Benatuil, L., et al., "An Improved Yeast Transformation Method for the Generation of Very Large Human Antibody Libraries," Protein Engineering Design Selection 23(4):155-159, Oxford University Press, United Kingdom (Apr. 2010).

Carter, P., et al., "Humanization of an Anti-p185HER2 Antibody for Human Cancer Therapy," Proceedings of the National Academy of Sciences USA 89(10):4285-4289, National Academy of Sciences, United States (May 1992).

Charlton, K.A., "Expression and Isolation of Recombinant Antibody Fragments in *E. coli*," in Methods in Molecular Biology, vol. 248, Lo, B.K.C., ed., pp. 245-254, Humana Press, United States (2004).

Dall'acqua, W.F., et al., "Antibody Humanization by Framework Shuffling," Methods 36(1):43-60, Elsevier, United States (May 2005).

Endo, Y., and Sawasaki, T., "High-throughput, Genome-scale Protein Production Method Based on the Wheat Germ Cell-free Expression System," Biotechnology Advances 21(8):695-713, Elsevier Science, United Kingdom (Nov. 2003).

Ghilardi, N., et al., "A Novel Type I Cytokine Receptor Is Expressed on Monocytes, Signals Proliferation, and Activates STAT-3 and STAT-5," The Journal of Biological Chemistry 277(19):16831-16836, American Society for Biochemistry and Molecular Biology, United States (May 2002).

(Continued)

*Primary Examiner* — Chun W Dahle
*Assistant Examiner* — James Lyle Mclellan
(74) *Attorney, Agent, or Firm* — STERNE, KESSLER, GOLDSTEIN & FOX P.L.L.C.

(57) ABSTRACT

Provided herein are polypeptides that bind IL31 and methods of using IL31-binding polypeptides to modulate the biological activity of IL31. Also provided herein are nucleic acids, host cells, and methods of preparing polypeptides that bind IL31. Uses and methods provided herein include, but are not limited to, methods of treating an IL31-associated condition, such as a pruritic condition, atopic dermatitis, prurigo nodularis, and chronic spontaneous urticaria. Also provided herein are methods of detecting using the polypeptides that bind IL31.

19 Claims, 14 Drawing Sheets

Specification includes a Sequence Listing.

(56) References Cited

OTHER PUBLICATIONS

Graham, F.L., et al., "Characteristics of a Human Cell Line Transformed by DNA from Human Adenovirus Type 5," The Journal of General Virology 36(1):59-72, Society For General Microbiology, United Kingdom (Jul. 1977).
Jain, T., et al., "Biophysical Properties of the Clinical-stage Antibody Landscape," Proceedings of the National Academy of Sciences of the United States of America 114(5):944-949, National Academy of Sciences, United States (Jan. 2017).
Jonsson, U., et al., "Introducing a Biosensor Based Technology for Real-time Biospecific Interaction Analysis," Annales De Biologie Clinique 51(1):19-26, Elsevier, France (1993).
Kashmiri, S.V., et al., "SDR Grafting—a New Approach to Antibody Humanization," Methods 36(1):25-34, Elsevier, United States (2005).
Klimka, A., et al., "Human Anti-CD30 Recombinant Antibodies by Guided Phage Antibody Selection Using Cell Panning," British Journal of Cancer 83(2):252-260, Nature Publishing Group, United Kingdom (Jul. 2000).
Kraft, T.E., et al., "Heparin Chromatography as an in Vitro Predictor for Antibody Clearance Rate Through Pinocytosis," mAbs 12(1):1683432, Taylor & Francis, United States (Jan.-Dec. 2020).
Mather, J.P., "Establishment and Characterization of Two Distinct Mouse Testicular Epithelial Cell Lines," Biology of Reproduction 23(1):243-252, Society for the Study of Reproduction, United States (Aug. 1980).
Mather, J.P., et al., "Culture of Testicular Cells in Hormone-Supplemented Serum-Free Medium," Annals of the New York Academy of Sciences 383:44-68, New York Academy of Sciences, United States (1982).
Osbourn, J., et al., "From Rodent Reagents to Human Therapeutics using Antibody Guided Selection," Methods 36(1):61-68, Elsevier, United States (2005).
Padlan, E.A., "A Possible Procedure for Reducing the Immunogenicity of Antibody Variable Domains While Preserving their Ligand-binding Properties," Molecular Immunology 28(4-5):489-498, Pergamon Press, United Kingdom (Apr. 1991).
Presta, L.G., et al., "Humanization of an Antibody Directed Against IgE," The Journal of Immunology 151(5):2623-2632, The American Association of Immunologists, United States (Sep. 1993).
Queen, C., et al., "A Humanized Antibody that Binds to the Interleukin 2 Receptor," Proceedings of the National Academy of Sciences USA 86(24):10029-10033, National Academy of Sciences, United States (Dec. 1989).
Riechmann, L., et al., "Reshaping Human Antibodies for Therapy," Nature 332(6162):323-327, Nature Publishing Group, United Kingdom (Mar. 1988).
Rosok, M.J., et al., "A Combinatorial Library Strategy for the Rapid Humanization of Anticarcinoma BR96 Fab," The Journal of Biological Chemistry 271(37):22611-22618, Society for Biochemistry and Molecular Biology, United States (Sep. 1996).
Running Deer, J., and Allison, D.S., "High-level Expression of Proteins in Mammalian Cells Using Transcription Regulatory Sequences From the Chinese Hamster EF-1α Gene," Biotechnology Progress 20(3):880-889, American Institute of Chemical Engineers, United States (May-Jun. 2004).
Sims, M.J., et al., "A Humanized CD18 Antibody can Block Function without Cell Destruction," The Journal of Immunology 151(4):2296-2308, The American Association of Immunologists, United States (Aug. 1993).
Sitaraman, K., and Chatterjee, D.K., "High-throughput Protein Expression Using Cell-free System," Methods in Molecular Biology 498:229-244, Humana Press, United States (2009).
Spirin, A.S., "High-throughput Cell-free Systems for Synthesis of Functionally Active Proteins," Trends in Biotechnology 22(10):538-545, Elsevier Science Publishers, United Kingdom (Oct. 2004).
UniprotKB, "IL31_Human," Accession No. Q6EBC2, accessed at https://www.uniprot.org/uniprotkb/Q6EBC2, accessed on Apr. 17, 2025, 6 pages.
Urlaub, G., and Chasin, L.A., "Isolation of Chinese Hamster Cell Mutants Deficient in Dihydrofolate Reductase Activity," Proceedings of the National Academy of Sciences USA 77(7):4216-4220, National Academy of Sciences, United States (Jul. 1980).
Wang, Z., et al., "A New Yeast Display Vector Permitting Free Scfv Amino Termini Can Augment Ligand Binding Affinities," Protein Engineering Design Selection 18(7):337-343, Oxford University Press, United Kingdom (Jul. 2005).
Xu, Y., et al., "Addressing Polyspecificity of Antibodies Selected From an in Vitro Yeast Presentation System: a Facs-based, High-throughput Selection and Analytical Tool," Protein Engineering, Design and Selection 26(10):663-670, Oxford University Press, United Kingdom (Oct. 2013).
Yazaki, P. J., and Wu, A.M., "Expression of Recombinant Antibodies in Mammalian Cell Lines," in Methods in Molecular Biology, vol. 248, Lo, B.K.C., ed., pp. 255-268, Humana Press, United States (2003).
Alamar Biosciences, "ATTOBODY™ Platform | Improving on Nature's Selection," Alamar Biosciences, Inc., dated Apr. 13, 2023, accessed at https://alamarbio.com/technology/attobody_platform/, 4 pages.
Attovia Therapeutics, Inc., "Attovia Announces Second Tranche Closing of $60 Million Series A Financing and Highlights Progress Building a Best-in-Class Pipeline Leveraging the Attobody™ Platform," GlobeNewswire, dated Feb. 8, 2024, accessed at https://www.globenewswire.com/news-release/2024/02/08/2825910/0/en/Attovia-Announces-Second-Tranche-Closing-of-60-Million-Series-A-Financing-and-Highlights-Progress-Building-a-Best-in-Class-Pipeline-Leveraging-the-Attobody-Platform.html, 4 pages.
International Search Report and Written Opinion for International Application No. PCT/US2025/026000, European Patent Office, Netherlands, mailed on Sep. 9, 2025, 19 pages.
Rudikoff, S., et al., "Single amino acid substitution altering antigen-binding specificity," Proceedings of the National Academy of Sciences of the United States of America 79(6):1979-1983, National Academy of Sciences, United States (Mar. 1982).
Co-pending Application, U.S. Appl. No. 19/316,633, inventors Choi, J.W., et al., filed Sep. 2, 2025 (Not yet Published).

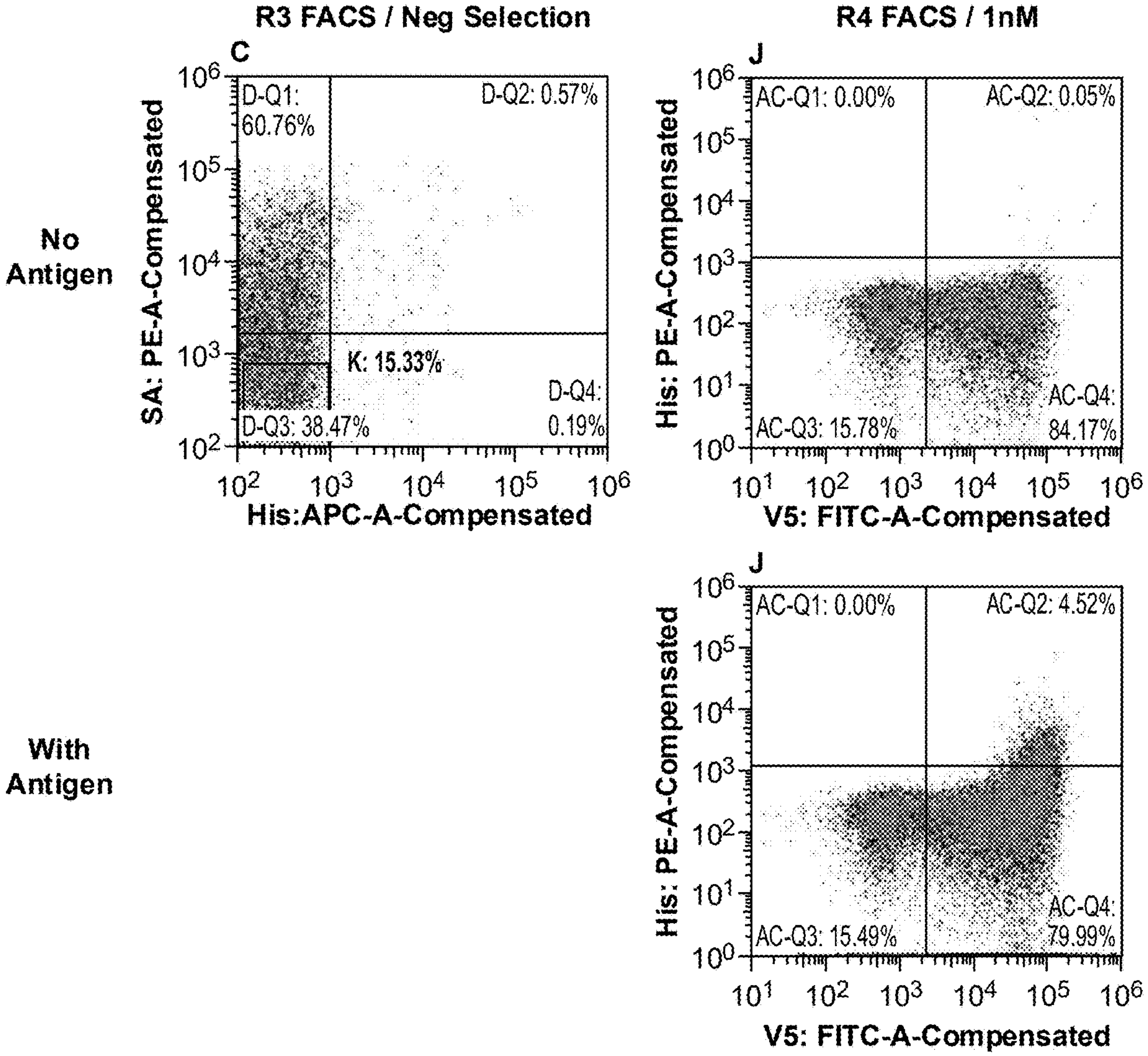
FIG. 4 (Cont. 1)

R5 FACS / 0.1nM
No Antigen
With Antigen
With Antigen
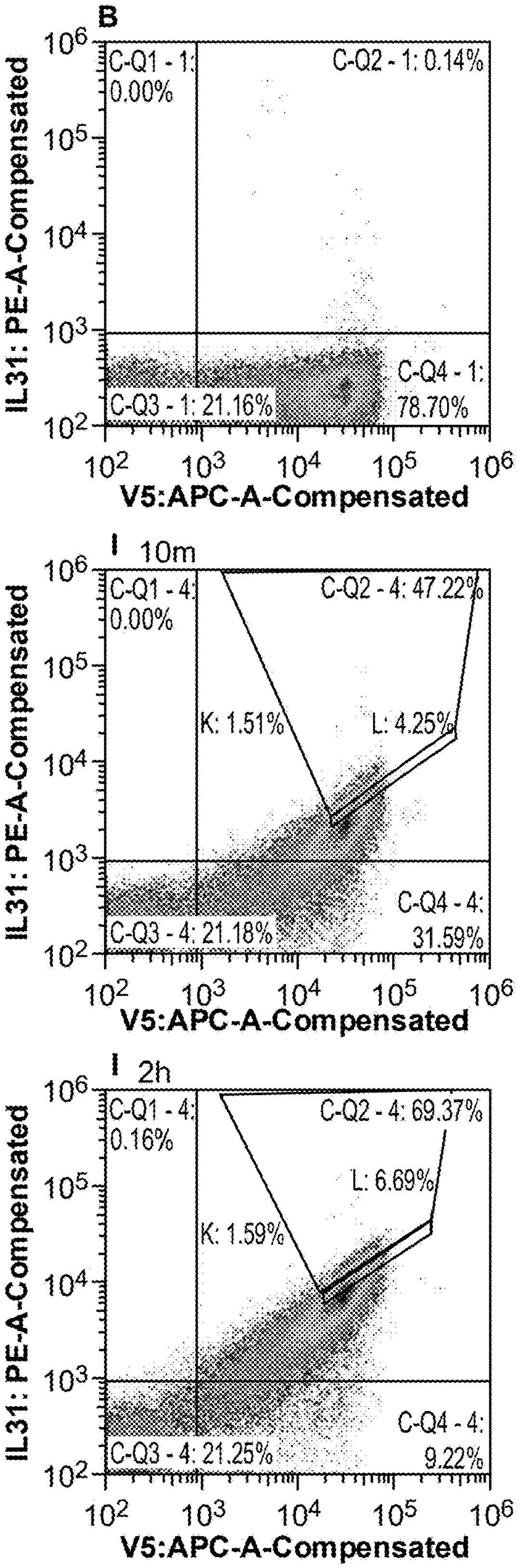
FIG. 4 (Cont. 2)

```
                                                                    CDR1                CDR2
(SEQ ID NO: 31) IL31_1H5_VHH1     EVQLVESGGGSVQAGGSLRLSCAASGGTFSSYAMAWFRQAPGKEREYVAGISSSGYTLYK   60
(SEQ ID NO: 17) IL31_1D1_VHH1     EVQLVESGGGLVQAGGSLRLSCAASGGTFSSYAMAWFRQAPGKEREYVAGISSSGYTLYK   60
(SEQ ID NO: 3)  IL31_1C10_VHH1    EVQLVESGGGLVQAGGSLRLSCAASGGTFSSYTMGWFRQAPGKEREYVGGISSSGYVMYN   60
(SEQ ID NO: 45) IL31_21H7_VHH1    EVQLVESGGGLVQAGGSLRLSCAASGGTFSSYTMGWFRQAPGKEREYVGGISSSGYVMYN   60
(SEQ ID NO: 65) IL31_20C7_VHH1    EVQLVESGGGSVQAGDSLRLSCAASGGTFSSYTMGWFRQAPGKEREYVGGISSSGYVMYN   60
(SEQ ID NO: 66) IL31_1H4_VHH2     EVQLVESGGDLVQAGGSLRLSCAASGGTFSSYAMAWFRQAPGKEREYVAGISSSGYTLYK   60
(SEQ ID NO: 67) IL31_1C2_VHH2     EVQLVESGGGSVQAGGSLRLSCAASGGTFSSYTMGWFRQAPGKEREYVGGISSSGYVMYN   60
(SEQ ID NO: 68) IL31_1E3_VHH1     EVQLVESGGGSVQAGGSLRLSCAASGGTFSSYAMAWFRQAPGKEREYVAGISSSGYTLYK   60
(SEQ ID NO: 69) IL31_1D12_VHH1    EVQLVESGGGSVQPGGSLRLSCAASGGTFSSYTMGWFRQAPGKEREYVGGISSSGYVMYN   60
(SEQ ID NO: 70) IL31_2H2_VHH1     EVQLVESGGGSVQPGGSLRLSCAASGGTFSSYTMGWFRQAPGKEREYVGGISSSGYVMYN   60
(SEQ ID NO: 71) IL31_1H2_VHH1     EVQLVESGGGSVQAGGSLRLSCAASGGTFSSYTMGWFRQAPGKEREYVGGISSSGYVMYN   60
(SEQ ID NO: 72) IL31_1C7_VHH1     EVQLVESGGGSVQPGGSLRLSCAASGGTFSSYTMGWFRQAPGKEREYVGGISSSGYVMYN   60
(SEQ ID NO: 73) IL31_1B10_VHH1    EVQLVESGGGSVQPGGSLRLSCAASGGTFSSYTMGWFRQAPGKEREYVGGISSSGYVMYN   60
(SEQ ID NO: 74) IL31_1G6_VHH1     EVQLVESGGGSVQAGGSLRLSCAASGGTFSSYAMAWFRQAPGKEREYVAGISSSGYTLYK   60
(SEQ ID NO: 75) IL31_1E2_VHH1     EVQLVESGGGSVQAGGSLRLSCAASGGTFSSYTMGWFRQAPGKEREYVGGISSSGYVMYN   60
(SEQ ID NO: 76) IL31_1B12_VHH2    QVKLEESGGGSVQAGGSLRLSCAASGGTFSSYTMGWFRQAPGKEREYVGGISSSGYVMYN   60
(SEQ ID NO: 77) Il31_1C3_VHH1     EVQLVESGGGSVQAGGSLRLSCAASGGTFSSYAMAWFRQAPGKEREYVAGISSSGYTLYK   60
```

FIG. 5

| | | | |
|---|---|---|---|
| (SEQ ID NO: 31) | IL31_1H5_VHH1 | SDSMKGRFTISRENAKNMVYLQMNSLKPEDTAVYSCAAGIFGRPYEYWGQGTQVTVSS | 118 |
| (SEQ ID NO: 17) | IL31_1D1_VHH1 | SDSMKGRFTISRENAKNMVYLQMNSLKPEDTAVYSCAAGIFGRPYEYWGQGTLVTVSS | 118 |
| (SEQ ID NO: 3) | IL31_1C10_VHH1 | SESMKGRFTISRENAKNMVYLQMNSLKPEDTAVYYCAAGTIGRPYDYWGQGTQVTVSS | 118 |
| (SEQ ID NO: 45) | IL31_21H7_VHH1 | SESMKGRFTISRENAKNMVYLQMNSLKPEDTAVYYCAAGTIGRPYDYWGQGTQVTVSS | 118 |
| (SEQ ID NO: 65) | IL31_20C7_VHH1 | SESMKGRFTISRENAKNMVYLQMNSLKPEDTAVYYCAAGTIGRPYDYWGQGTLVTVSS | 118 |
| (SEQ ID NO: 66) | IL31_1H4_VHH2 | ADSMKGRFTISRENAKNMVYLQMNSLKPEDTAVYSCAAGVFGRPYEYWGRGTQVTVSS | 118 |
| (SEQ ID NO: 67) | IL31_1C2_VHH2 | SESMKGRFTISRENAKNMVYLQMNSLKPEDTAVYYCAAGTIGRPYDYWGQGTQVTVSS | 118 |
| (SEQ ID NO: 68) | IL31_1E3_VHH1 | SDSMKGRFTISRENAKNMVYLQMNSLKPEDTAVYSCAAGIFGRPYEYWGQGTLVTVSS | 118 |
| (SEQ ID NO: 69) | IL31_1D12_VHH1 | SDSMKGRFTISRENAKNMVYLQMNSLKPEDTAVYYCAAGTIGRPYDFWGQGTLVTVSS | 118 |
| (SEQ ID NO: 70) | IL31_2H2_VHH1 | SESMKGRFTISRENAKNMVYLQMNSLKPEDTAVYYCAAGTIGRPYDYWGQGTLVTVSS | 118 |
| (SEQ ID NO: 71) | IL31_1H2_VHH1 | SESMKGRFTISRENAKNMVYLQMNSLKPEDTAVYYCAAGTIGRPYDYWGQGTQVTVSS | 118 |
| (SEQ ID NO: 72) | IL31_1C7_VHH1 | SESMKGRFTISRENAKNMVYLQMNSLKPEDTAVYYCAAGTIGRPYDYWGQGTQVTVSS | 118 |
| (SEQ ID NO: 73) | IL31_1B10_VHH1 | SDSMKGRFTISRENAKNMVYLQMNSLKPEDTAVYYCAAGTIGRPYDFWGQGTLVTVSS | 118 |
| (SEQ ID NO: 74) | IL31_1G6_VHH1 | SDSMKGRFTISRENAKNMVYLQMNSLKPEDTAVYSCAAGIFGRPYEYWGQGTQVTVSS | 118 |
| (SEQ ID NO: 75) | IL31_1E2_VHH1 | SESMKGRFTISRENAKNMVYLQMNSLKPEDTAVYYCAAGTIGRPYDYWGQGTQVTVSS | 118 |
| (SEQ ID NO: 76) | IL31_1B12_VHH2 | SESMKGRFTISRENAKNMVYLQMNSLKPEDTAVYYCAAGTIGRPYDYWGQGTLVTVSS | 118 |
| (SEQ ID NO: 77) | Il31_1C3_VHH1 | SDSMKGRFTISRENAKNMVYLQMNSLKPEDTAVYSCAAGIFGRPYEYWGQGTQVTVSS | 118 |

CDR2 CDR3

FIG. 5 (Cont.)

SEQUENCE LISTING

```
Sequence total quantity: 346
SEQ ID NO: 1            moltype = AA  length = 164
FEATURE                 Location/Qualifiers
source                  1..164
                        mol_type = protein
                        note = Human IL31 with signal sequence
                        organism = synthetic construct
SEQUENCE: 1
MASHSGPSTS VLFLFCCLGG WLASHTLPVR LLRPSDDVQK IVEELQSLSK MLLKDVEEEK  60
GVLVSQNYTL PCLSPDAQPP NNIHSPAIRA YLKTIRQLDN KSVIDEIIEH LDKLIFQDAP  120
ETNISVPTDT HECKRFILTI SQQFSECMDL ALKSLTSGAQ QATT                  164

SEQ ID NO: 2            moltype = AA  length = 141
FEATURE                 Location/Qualifiers
source                  1..141
                        mol_type = protein
                        note = Human IL31 without signal sequence
                        organism = synthetic construct
SEQUENCE: 2
SHTLPVRLLR PSDDVQKIVE ELQSLSKMLL KDVEEEKGVL VSQNYTLPCL SPDAQPPNNI  60
HSPAIRAYLK TIRQLDNKSV IDEIIEHLDK LIFQDAPETN ISVPTDTHEC KRFILTISQQ  120
FSECMDLALK SLTSGAQQAT T                                           141

SEQ ID NO: 3            moltype = AA  length = 118
FEATURE                 Location/Qualifiers
source                  1..118
                        mol_type = protein
                        note = 1C10 VHH1 single binder
                        organism = synthetic construct
SEQUENCE: 3
EVQLVESGGG LVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSS    118

SEQ ID NO: 4            moltype = AA  length = 118
FEATURE                 Location/Qualifiers
source                  1..118
                        mol_type = protein
                        note = Humanized 1C10 VHH1 single binder
                        organism = synthetic construct
SEQUENCE: 4
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSS    118

SEQ ID NO: 5            moltype = AA  length = 5
FEATURE                 Location/Qualifiers
```

```
source                  1..5
                        mol_type = protein
                        note = 1C10 VHH1 CDR1
                        organism = synthetic construct
SEQUENCE: 5
SYTMG                                                         5

SEQ ID NO: 6            moltype = AA  length = 17
FEATURE                 Location/Qualifiers
source                  1..17
                        mol_type = protein
                        note = 1C10 VHH1 CDR2
                        organism = synthetic construct
SEQUENCE: 6
GISSSGYVMY NSESMKG                                            17

SEQ ID NO: 7            moltype = AA  length = 9
FEATURE                 Location/Qualifiers
source                  1..9
                        mol_type = protein
                        note = 1C10 VHH1 CDR3
                        organism = synthetic construct
SEQUENCE: 7
GTIGRPYDY                                                     9

SEQ ID NO: 8            moltype = AA  length = 119
FEATURE                 Location/Qualifiers
source                  1..119
                        mol_type = protein
                        note = 1C10 VHH2 single binder
                        organism = synthetic construct
SEQUENCE: 8
VKLEESGGGL VQPGGSLILS CAASGDISSI VAMGWYRQAP GKQRELVAAI TSGGRTHYRD  60
SVKGRFTISG NNDNSALYLH MNSLKPEDTA VYYCAADRGW TSVGEYDYWG KGTLVTVSS   119

SEQ ID NO: 9            moltype = AA  length = 119
FEATURE                 Location/Qualifiers
source                  1..119
                        mol_type = protein
                        note = Humanized 1C10 VHH2 single binder
                        organism = synthetic construct
SEQUENCE: 9
VQLVESGGGL VQPGGSLRLS CAASGDISSI VAMGWYRQAP GKQRELVSAI TSGGRTHYRD  60
SVKGRFTISR DNAKNTLYLQ MNSLRAEDTA VYYCAADRGW TSVGEYDYWG QGTQVTVSS   119

SEQ ID NO: 10           moltype = AA  length = 5
FEATURE                 Location/Qualifiers
source                  1..5
                        mol_type = protein
                        note = 1C10 VHH2 CDR1
                        organism = synthetic construct
SEQUENCE: 10
IVAMG                                                         5

SEQ ID NO: 11           moltype = AA  length = 16
FEATURE                 Location/Qualifiers
source                  1..16
                        mol_type = protein
                        note = 1C10 VHH2 CDR2
                        organism = synthetic construct
SEQUENCE: 11
AITSGGRTHY RDSVKG                                             16

SEQ ID NO: 12           moltype = AA  length = 12
FEATURE                 Location/Qualifiers
source                  1..12
                        mol_type = protein
                        note = 1C10 VHH2 CDR3
                        organism = synthetic construct
SEQUENCE: 12
DRGWTSVGEY DY                                                 12

SEQ ID NO: 13           moltype = AA  length = 275
FEATURE                 Location/Qualifiers
source                  1..275
                        mol_type = protein
                        note = 1C10 co-binder
                        organism = synthetic construct
SEQUENCE: 13
```

```
EVQLVESGGG LVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSSGG  120
GSGGGGSGGG GSGGGGSGGG GSGGGGSGGG GSGMTGVKLE ESGGGLVQPG GSLILSCAAS  180
GDISSIVAMG WYRQAPGKQR ELVAAITSGG RTHYRDSVKG RFTISGNNDN SALYLHMNSL  240
KPEDTAVYYC AADRGWTSVG EYDYWGKGTL VTVSS                             275

SEQ ID NO: 14          moltype = AA  length = 275
FEATURE                Location/Qualifiers
source                 1..275
                       mol_type = protein
                       note = Humanized 1C10 co binder
                       organism = synthetic construct
SEQUENCE: 14
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 15          moltype = AA  length = 507
FEATURE                Location/Qualifiers
source                 1..507
                       mol_type = protein
                       note = 1C10 co-binder + huIgG1Fc_YTE_C S
                       organism = synthetic construct
SEQUENCE: 15
EVQLVESGGG LVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSSGG  120
GSGGGGSGGG GSGGGGSGGG GSGGGGSGGG GSGMTGVKLE ESGGGLVQPG GSLILSCAAS  180
GDISSIVAMG WYRQAPGKQR ELVAAITSGG RTHYRDSVKG RFTISGNNDN SALYLHMNSL  240
KPEDTAVYYC AADRGWTSVG EYDYWGKGTL VTVSSEPKSS DKTHTCPPCP APELLGGPSV  300
FLFPPKPKDT LYITREPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSRDELTK  420
NQVSLTCLVK GFYPSDIAVE WESNGQPENN YKTTPPVLDS DGSFFLYSKL TVDKSRWQQG  480
NVFSCSVMHE ALHNHYTQKS LSLSPGK                                      507

SEQ ID NO: 16          moltype = AA  length = 507
FEATURE                Location/Qualifiers
source                 1..507
                       mol_type = protein
                       note = Humanized 1C10 co binder + huIgG1Fc_YTE_C S
                       organism = synthetic construct
SEQUENCE: 16
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSSEPKSS DKTHTCPPCP APELLGGPSV  300
FLFPPKPKDT LYITREPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSRDELTK  420
NQVSLTCLVK GFYPSDIAVE WESNGQPENN YKTTPPVLDS DGSFFLYSKL TVDKSRWQQG  480
NVFSCSVMHE ALHNHYTQKS LSLSPGK                                      507

SEQ ID NO: 17          moltype = AA  length = 118
FEATURE                Location/Qualifiers
source                 1..118
                       mol_type = protein
                       note = 1D1 VHH1 single binder
                       organism = synthetic construct
SEQUENCE: 17
EVQLVESGGG LVQAGGSLRL SCAASGGTFS SYAMAWFRQA PGKEREYVAG ISSSGYTLYK  60
SDSMKGRFTI SRENAKNMVY LQMNSLKPED TAVYSCAAGI FGRPYEYWGQ GTLVTVSS    118

SEQ ID NO: 18          moltype = AA  length = 118
FEATURE                Location/Qualifiers
source                 1..118
                       mol_type = protein
                       note = Humanized 1D1 VHH1 single binder
                       organism = synthetic construct
SEQUENCE: 18
EVQLVESGGG LVQPGGSLRL SCAASGGTFS SYAMAWFRQA PGKEREYVAG ISSSGYTLYK  60
SDSMKGRFTI SRDNAKNTLY LQMNSLRAED TAVYYCAAGI FGRPYEYWGQ GTLVTVSS    118

SEQ ID NO: 19          moltype = AA  length = 5
FEATURE                Location/Qualifiers
source                 1..5
                       mol_type = protein
                       note = 1D1 VHH1 CDR1
                       organism = synthetic construct
```

```
SEQUENCE: 19
SYAMA                                                     5

SEQ ID NO: 20           moltype = AA  length = 17
FEATURE                 Location/Qualifiers
source                  1..17
                        mol_type = protein
                        note = 1D1 VHH1 CDR2
                        organism = synthetic construct
SEQUENCE: 20
GISSSGYTLY KSDSMKG                                        17

SEQ ID NO: 21           moltype = AA  length = 9
FEATURE                 Location/Qualifiers
source                  1..9
                        mol_type = protein
                        note = 1D1 VHH1 CDR3
                        organism = synthetic construct
SEQUENCE: 21
GIFGRPYEY                                                 9

SEQ ID NO: 22           moltype = AA  length = 119
FEATURE                 Location/Qualifiers
source                  1..119
                        mol_type = protein
                        note = 1D1 VHH2 single binder
                        organism = synthetic construct
SEQUENCE: 22
VKLEESGGGL VQAGGSLILS CAASGDIPSI VAMGWYRQAP GKQRELVAAI TSGGRTHYRD  60
SVKGRFTISG NNDNSALYLH MNSLKPEDTA VYYCAADMGL TAVGEYDYWG QGTQVTVSS   119

SEQ ID NO: 23           moltype = AA  length = 119
FEATURE                 Location/Qualifiers
source                  1..119
                        mol_type = protein
                        note = Humanized 1D1 VHH2 single binder
                        organism = synthetic construct
SEQUENCE: 23
VQLVESGGGL VQPGGSLRLS CAASGDIPSI VAMGWYRQAP GKQRELVSAI TSGGRTHYRD  60
SVKGRFTISR DNSKNTLYLQ MNSLRAEDTA VYYCAADMGL TAVGEYDYWG QGTQVTVSS   119

SEQ ID NO: 24           moltype = AA  length = 5
FEATURE                 Location/Qualifiers
source                  1..5
                        mol_type = protein
                        note = 1D1 VHH2 CDR1
                        organism = synthetic construct
SEQUENCE: 24
IVAMG                                                     5

SEQ ID NO: 25           moltype = AA  length = 16
FEATURE                 Location/Qualifiers
source                  1..16
                        mol_type = protein
                        note = 1D1 VHH2 CDR2
                        organism = synthetic construct
SEQUENCE: 25
AITSGGRTHY RDSVKG                                         16

SEQ ID NO: 26           moltype = AA  length = 12
FEATURE                 Location/Qualifiers
source                  1..12
                        mol_type = protein
                        note = 1D1 VHH2 CDR3
                        organism = synthetic construct
SEQUENCE: 26
DMGLTAVGEY DY                                             12

SEQ ID NO: 27           moltype = AA  length = 265
FEATURE                 Location/Qualifiers
source                  1..265
                        mol_type = protein
                        note = 1D1 co-binder
                        organism = synthetic construct
SEQUENCE: 27
EVQLVESGGG LVQAGGSLRL SCAASGGTFS SYAMAWFRQA PGKEREYVAG ISSSGYTLYK  60
SDSMKGRFTI SRENAKNMVY LQMNSLKPED TAVYSCAAGI FGRPYEYWGQ GTLVTVSSGG  120
GSGGGGSGGG GSGGGGSGGG GSPSMGVKLE ESGGGLVQAG GSLILSCAAS GDIPSIVAMG  180
WYRQAPGKQR ELVAAITSGG RTHYRDSVKG RFTISGNNDN SALYLHMNSL KPEDTAVYYC  240
```

```
AADMGLTAVG EYDYWGQGTQ VTVSS                                        265

SEQ ID NO: 28          moltype = AA  length = 265
FEATURE                Location/Qualifiers
source                 1..265
                       mol_type = protein
                       note = Humanized 1D1 co binder
                       organism = synthetic construct
SEQUENCE: 28
EVQLVESGGG LVQPGGSLRL SCAASGGTFS SYAMAWFRQA PGKEREYVAG ISSSGYTLYK  60
SDSMKGRFTI SRDNAKNTLY LQMNSLRAED TAVYYCAAGI FGRPYEYWGQ GTLVTVSSGG  120
GSGGGGSGGG GSGGGGSGGG GSPSMGVQLV ESGGGLVQPG GSLRLSCAAS GDIPSIVAMG  180
WYRQAPGKQR ELVSAITSGG RTHYRDSVKG RFTISRDNSK NTLYLQMNSL RAEDTAVYYC  240
AADMGLTAVG EYDYWGQGTQ VTVSS                                        265

SEQ ID NO: 29          moltype = AA  length = 497
FEATURE                Location/Qualifiers
source                 1..497
                       mol_type = protein
                       note = 1D1 co-binder + huIgG1Fc_YTE_C S
                       organism = synthetic construct
SEQUENCE: 29
EVQLVESGGG LVQAGGSLRL SCAASGGTFS SYAMAWFRQA PGKEREYVAG ISSSGYTLYK  60
SDSMKGRFTI SRENAKNMVY LQMNSLKPED TAVYSCAAGI FGRPYEYWGQ GTLVTVSSGG  120
GSGGGGSGGG GSGGGGSGGG GSPSMGVKLE ESGGGLVQAG GSLILSCAAS GDIPSIVAMG  180
WYRQAPGKQR ELVAAITSGG RTHYRDSVKG RFTISGNNDN SALYLHMNSL KPEDTAVYYC  240
AADMGLTAVG EYDYWGQGTQ VTVSSEPKSS DKTHTCPPCP APELLGGPSV FLFPPKPKDT  300
LYITREPEVT CVVVDVSHED PEVKFNWYVD GVEVHNAKTK PREEQYNSTY RVVSVLTVLH  360
QDWLNGKEYK CKVSNKALPA PIEKTISKAK GQPREPQVYT LPPSRDELTK NQVSLTCLVK  420
GFYPSDIAVE WESNGQPENN YKTTPPVLDS DGSFFLYSKL TVDKSRWQQG NVFSCSVMHE  480
ALHNHYTQKS LSLSPGK                                                 497

SEQ ID NO: 30          moltype = AA  length = 497
FEATURE                Location/Qualifiers
source                 1..497
                       mol_type = protein
                       note = Humanized 1D1 co binder + huIgG1Fc_YTE_CS
                       organism = synthetic construct
SEQUENCE: 30
EVQLVESGGG LVQPGGSLRL SCAASGGTFS SYAMAWFRQA PGKEREYVAG ISSSGYTLYK  60
SDSMKGRFTI SRDNAKNTLY LQMNSLRAED TAVYYCAAGI FGRPYEYWGQ GTLVTVSSGG  120
GSGGGGSGGG GSGGGGSGGG GSPSMGVQLV ESGGGLVQPG GSLRLSCAAS GDIPSIVAMG  180
WYRQAPGKQR ELVSAITSGG RTHYRDSVKG RFTISRDNSK NTLYLQMNSL RAEDTAVYYC  240
AADMGLTAVG EYDYWGQGTQ VTVSSEPKSS DKTHTCPPCP APELLGGPSV FLFPPKPKDT  300
LYITREPEVT CVVVDVSHED PEVKFNWYVD GVEVHNAKTK PREEQYNSTY RVVSVLTVLH  360
QDWLNGKEYK CKVSNKALPA PIEKTISKAK GQPREPQVYT LPPSRDELTK NQVSLTCLVK  420
GFYPSDIAVE WESNGQPENN YKTTPPVLDS DGSFFLYSKL TVDKSRWQQG NVFSCSVMHE  480
ALHNHYTQKS LSLSPGK                                                 497

SEQ ID NO: 31          moltype = AA  length = 118
FEATURE                Location/Qualifiers
source                 1..118
                       mol_type = protein
                       note = 1H5 VHH1 single binder
                       organism = synthetic construct
SEQUENCE: 31
EVQLVESGGG SVQAGGSLRL SCAASGGTFS SYAMAWFRQA PGKEREYVAG ISSSGYTLYK  60
SDSMKGRFTI SRENAKNMVY LQMNSLKPED TAVYSCAAGI FGRPYEYWGQ GTQVTVSS    118

SEQ ID NO: 32          moltype = AA  length = 118
FEATURE                Location/Qualifiers
source                 1..118
                       mol_type = protein
                       note = Humanized 1H5 VHH1
                       organism = synthetic construct
SEQUENCE: 32
EVQLVESGGG LVQPGGSLRL SCAASGGTFS SYAMAWFRQA PGKEREYVAG ISSSGYTLYK  60
SDSMKGRFTI SRDNAKNTLY LQMNSLRAED TAVYYCAAGI FGRPYEYWGQ GTQVTVSS    118

SEQ ID NO: 33          moltype = AA  length = 5
FEATURE                Location/Qualifiers
source                 1..5
                       mol_type = protein
                       note = 1H5 VHH1 CDR1
                       organism = synthetic construct
SEQUENCE: 33
SYAMA                                                              5

SEQ ID NO: 34          moltype = AA  length = 17
```

```
FEATURE                Location/Qualifiers
source                 1..17
                       mol_type = protein
                       note = 1H5 VHH1 CDR2
                       organism = synthetic construct
SEQUENCE: 34
GISSSGYTLY KSDSMKG                                          17

SEQ ID NO: 35          moltype = AA  length = 9
FEATURE                Location/Qualifiers
source                 1..9
                       mol_type = protein
                       note = 1H5 VHH1 CDR3
                       organism = synthetic construct
SEQUENCE: 35
GIFGRPYEY                                                   9

SEQ ID NO: 36          moltype = AA  length = 119
FEATURE                Location/Qualifiers
source                 1..119
                       mol_type = protein
                       note = 1H5 VHH2 single binder
                       organism = synthetic construct
SEQUENCE: 36
VQLVESGGGL VQAGGSLRLS CAASGSISSI HAMGWYRQAP GKQRELIAAI TSGGRRHYRD  60
SVKGRFTISG DNAKTNLYLQ MNSLKPEDTA VYYCAADTGR VAVGEYDYWG QGTLVTVSS   119

SEQ ID NO: 37          moltype = AA  length = 119
FEATURE                Location/Qualifiers
source                 1..119
                       mol_type = protein
                       note = Humanized 1H5 VHH2
                       organism = synthetic construct
SEQUENCE: 37
VQLVESGGGL VQPGGSLRLS CAASGSISSI HAMGWYRQAP GKQRELIAAI TSGGRRHYRD  60
SVKGRFTISR DNSKNTLYLQ MNSLRAEDTA VYYCAADTGR VAVGEYDYWG QGTLVTVSS   119

SEQ ID NO: 38          moltype = AA  length = 5
FEATURE                Location/Qualifiers
source                 1..5
                       mol_type = protein
                       note = 1H5 VHH2 CDR1
                       organism = synthetic construct
SEQUENCE: 38
IHAMG                                                       5

SEQ ID NO: 39          moltype = AA  length = 16
FEATURE                Location/Qualifiers
source                 1..16
                       mol_type = protein
                       note = 1H5 VHH2 CDR2
                       organism = synthetic construct
SEQUENCE: 39
AITSGGRRHY RDSVKG                                           16

SEQ ID NO: 40          moltype = AA  length = 12
FEATURE                Location/Qualifiers
source                 1..12
                       mol_type = protein
                       note = 1H5 VHH2 CDR3
                       organism = synthetic construct
SEQUENCE: 40
DTGRVAVGEY DY                                               12

SEQ ID NO: 41          moltype = AA  length = 256
FEATURE                Location/Qualifiers
source                 1..256
                       mol_type = protein
                       note = 1H5 co-binder
                       organism = synthetic construct
SEQUENCE: 41
EVQLVESGGG SVQAGGSLRL SCAASGGTFS SYAMAWFRQA PGKEREYVAG ISSSGYTLYK  60
SDSMKGRFTI SRENAKNMVY LQMNSLKPED TAVYSCAAGI FGRPYEYWGQ GTQVTVSSGG  120
GGSGGGGSGG GGSRSVGVQL VESGGGLVQA GGSLRLSCAA SGSISSIHAM GWYRQAPGKQ  180
RELIAAITSG GRRHYRDSVK GRFTISGDNA KTNLYLQMNS LKPEDTAVYY CAADTGRVAV  240
GEYDYWGQGT LVTVSS                                           256

SEQ ID NO: 42          moltype = AA  length = 256
FEATURE                Location/Qualifiers
```

```
source                 1..256
                       mol_type = protein
                       note = Humanized 1H5 co-binder
                       organism = synthetic construct
SEQUENCE: 42
EVQLVESGGG LVQPGGSLRL SCAASGGTFS SYAMAWFRQA PGKEREYVAG ISSSGYTLYK  60
SDSMKGRFTI SRDNAKNTLY LQMNSLRAED TAVYYCAAGI FGRPYEYWGQ GTQVTVSSGG  120
GGSGGGGSGG GGSRSVGVQL VESGGGLVQP GGSLRLSCAA SGSISSIHAM GWYRQAPGKQ  180
RELIAAITSG GRRHYRDSVK GRFTISRDNS KNTLYLQMNS LRAEDTAVYY CAADTGRVAV  240
GEYDYWGQGT LVTVSS                                                 256

SEQ ID NO: 43          moltype = AA  length = 488
FEATURE                Location/Qualifiers
source                 1..488
                       mol_type = protein
                       note = 1H5 co-binder + huIgG1Fc_YTE_CS
                       organism = synthetic construct
SEQUENCE: 43
EVQLVESGGG SVQAGGSLRL SCAASGGTFS SYAMAWFRQA PGKEREYVAG ISSSGYTLYK  60
SDSMKGRFTI SRENAKNMVY LQMNSLKPED TAVYSCAAGI FGRPYEYWGQ GTQVTVSSGG  120
GGSGGGGSGG GGSRSVGVQL VESGGGLVQA GGSLRLSCAA SGSISSIHAM GWYRQAPGKQ  180
RELIAAITSG GRRHYRDSVK GRFTISGDNA KTNLYLQMNS LKPEDTAVYY CAADTGRVAV  240
GEYDYWGQGT LVTVSSEPKS SDKTHTCPPC PAPELLGGPS VFLFPPKPKD TLYITREPEV  300
TCVVVDVSHE DPEVKFNWYV DGVEVHNAKT KPREEQYNST YRVVSVLTVL HQDWLNGKEY  360
KCKVSNKALP APIEKTISKA KGQPREPQVY TLPPSRDELT KNQVSLTCLV KGFYPSDIAV  420
EWESNGQPEN NYKTTPPVLD SDGSFFLYSK LTVDKSRWQQ GNVFSCSVMH EALHNHYTQK  480
SLSLSPGK                                                          488

SEQ ID NO: 44          moltype = AA  length = 488
FEATURE                Location/Qualifiers
source                 1..488
                       mol_type = protein
                       note = Humanized 1H5 co binder + huIgG1Fc_YTE_CS
                       organism = synthetic construct
SEQUENCE: 44
EVQLVESGGG LVQPGGSLRL SCAASGGTFS SYAMAWFRQA PGKEREYVAG ISSSGYTLYK  60
SDSMKGRFTI SRDNAKNTLY LQMNSLRAED TAVYYCAAGI FGRPYEYWGQ GTQVTVSSGG  120
GGSGGGGSGG GGSRSVGVQL VESGGGLVQP GGSLRLSCAA SGSISSIHAM GWYRQAPGKQ  180
RELIAAITSG GRRHYRDSVK GRFTISRDNS KNTLYLQMNS LRAEDTAVYY CAADTGRVAV  240
GEYDYWGQGT LVTVSSEPKS SDKTHTCPPC PAPELLGGPS VFLFPPKPKD TLYITREPEV  300
TCVVVDVSHE DPEVKFNWYV DGVEVHNAKT KPREEQYNST YRVVSVLTVL HQDWLNGKEY  360
KCKVSNKALP APIEKTISKA KGQPREPQVY TLPPSRDELT KNQVSLTCLV KGFYPSDIAV  420
EWESNGQPEN NYKTTPPVLD SDGSFFLYSK LTVDKSRWQQ GNVFSCSVMH EALHNHYTQK  480
SLSLSPGK                                                          488

SEQ ID NO: 45          moltype = AA  length = 118
FEATURE                Location/Qualifiers
source                 1..118
                       mol_type = protein
                       note = 21H7 VHH1 single binder
                       organism = synthetic construct
SEQUENCE: 45
EVQLVESGGG LVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSS    118

SEQ ID NO: 46          moltype = AA  length = 118
FEATURE                Location/Qualifiers
source                 1..118
                       mol_type = protein
                       note = Humanized 21H7 VHH1
                       organism = synthetic construct
SEQUENCE: 46
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSS    118

SEQ ID NO: 47          moltype = AA  length = 5
FEATURE                Location/Qualifiers
source                 1..5
                       mol_type = protein
                       note = 21H7 VHH1 CDR1
                       organism = synthetic construct
SEQUENCE: 47
SYTMG                                                             5

SEQ ID NO: 48          moltype = AA  length = 17
FEATURE                Location/Qualifiers
source                 1..17
                       mol_type = protein
                       note = 21H7 VHH1 CDR2
```

```
                        organism = synthetic construct
SEQUENCE: 48
GISSSGYVMY NSESMKG                                                 17

SEQ ID NO: 49           moltype = AA  length = 9
FEATURE                 Location/Qualifiers
source                  1..9
                        mol_type = protein
                        note = 21H7 VHH1 CDR3
                        organism = synthetic construct
SEQUENCE: 49
GTIGRPYDY                                                          9

SEQ ID NO: 50           moltype = AA  length = 120
FEATURE                 Location/Qualifiers
source                  1..120
                        mol_type = protein
                        note = 21H7 VHH2 single binder
                        organism = synthetic construct
SEQUENCE: 50
LVESGGGSVQ AGDSLRLSCA ASGRTFSTYI IGWFRQAPGK EREFVASISW GGRGTYYADS  60
VKDRFTISRD NPKNMVYLQM NSLKPEDTAV YYCAAGDLPG GRRALDYDYW GQGTLVTVSS  120

SEQ ID NO: 51           moltype = AA  length = 120
FEATURE                 Location/Qualifiers
source                  1..120
                        mol_type = protein
                        note = Humanized 21H7 VHH2
                        organism = synthetic construct
SEQUENCE: 51
LVESGGGLVQ PGGSLRLSCA ASGRTFSTYI IGWFRQAPGK EREFVASISW GGRGTYYADS  60
VKDRFTISRD NPKNMVYLQM NSLRAEDTAV YYCAAGDLPG GRRALDYDYW GQGTLVTVSS  120

SEQ ID NO: 52           moltype = AA  length = 5
FEATURE                 Location/Qualifiers
source                  1..5
                        mol_type = protein
                        note = 21H7 VHH2 CDR1
                        organism = synthetic construct
SEQUENCE: 52
TYIIG                                                              5

SEQ ID NO: 53           moltype = AA  length = 17
FEATURE                 Location/Qualifiers
source                  1..17
                        mol_type = protein
                        note = 21H7 VHH2 CDR2
                        organism = synthetic construct
SEQUENCE: 53
SISWGGRGTY YADSVKD                                                 17

SEQ ID NO: 54           moltype = AA  length = 14
FEATURE                 Location/Qualifiers
source                  1..14
                        mol_type = protein
                        note = 21H7 VHH2 CDR3
                        organism = synthetic construct
SEQUENCE: 54
GDLPGGRRAL DYDY                                                    14

SEQ ID NO: 55           moltype = AA  length = 276
FEATURE                 Location/Qualifiers
source                  1..276
                        mol_type = protein
                        note = 21H7 co-binder
                        organism = synthetic construct
SEQUENCE: 55
EVQLVESGGG LVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSSGG  120
GSGGGGSGGG GSGGGGSGGG GSGGGGSGGG GSEGVGLVES GGGSVQAGDS LRLSCAASGR  180
TFSTYIIGWF RQAPGKEREF VASISWGGRG TYYADSVKDR FTISRDNPKN MVYLQMNSLK  240
PEDTAVYYCA AGDLPGGRRA LDYDYWGQGT LVTVSS                            276

SEQ ID NO: 56           moltype = AA  length = 276
FEATURE                 Location/Qualifiers
source                  1..276
                        mol_type = protein
                        note = Humanized 21H7 co binder
                        organism = synthetic construct
```

```
SEQUENCE: 56
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSS                            276

SEQ ID NO: 57          moltype = AA  length = 508
FEATURE                Location/Qualifiers
source                 1..508
                       mol_type = protein
                       note = 21H7 co binder + huIgG1Fc_YTE_C S
                       organism = synthetic construct
SEQUENCE: 57
EVQLVESGGG LVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSSGG  120
GSGGGGSGGG GSGGGGSGGG GSGGGGSGGG GSEGVGLVES GGGSVQAGDS LRLSCAASGR  180
TFSTYIIGWF RQAPGKEREF VASISWGGRG TYYADSVKDR FTISRDNPKN MVYLQMNSLK  240
PEDTAVYYCA AGDLPGGRRA LDYDYWGQGT LVTVSSEPKS SDKTHTCPPC PAPELLGGPS  300
VFLFPPKPKD TLYITREPEV TCVVVDVSHE DPEVKFNWYV DGVEVHNAKT KPREEQYNST  360
YRVVSVLTVL HQDWLNGKEY KCKVSNKALP APIEKTISKA KGQPREPQVY TLPPSRDELT  420
KNQVSLTCLV KGFYPSDIAV EWESNGQPEN NYKTTPPVLD SDGSFFLYSK LTVDKSRWQQ  480
GNVFSCSVMH EALHNHYTQK SLSLSPGK                                     508

SEQ ID NO: 58          moltype = AA  length = 508
FEATURE                Location/Qualifiers
source                 1..508
                       mol_type = protein
                       note = Humanized 21H7 co binder + huIgG1Fc_YTE_C S
                       organism = synthetic construct
SEQUENCE: 58
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSSEPKS SDKTHTCPPC PAPELLGGPS  300
VFLFPPKPKD TLYITREPEV TCVVVDVSHE DPEVKFNWYV DGVEVHNAKT KPREEQYNST  360
YRVVSVLTVL HQDWLNGKEY KCKVSNKALP APIEKTISKA KGQPREPQVY TLPPSRDELT  420
KNQVSLTCLV KGFYPSDIAV EWESNGQPEN NYKTTPPVLD SDGSFFLYSK LTVDKSRWQQ  480
GNVFSCSVMH EALHNHYTQK SLSLSPGK                                     508

SEQ ID NO: 59          moltype =   length =
SEQUENCE: 59
000

SEQ ID NO: 60          moltype = AA  length = 17
FEATURE                Location/Qualifiers
source                 1..17
                       mol_type = protein
                       note = Exemplary VHH1 CDR2 consensus sequence (Kabat
                        numbering)
                       organism = synthetic construct
VARIANT                8
                       note = X is T or V
VARIANT                9
                       note = X is L or M
VARIANT                11
                       note = X is K or N
VARIANT                13
                       note = X is D or E
SEQUENCE: 60
GISSSGYXXY XSXSMKG                                                 17

SEQ ID NO: 61          moltype = AA  length = 9
FEATURE                Location/Qualifiers
source                 1..9
                       mol_type = protein
                       note = Exemplary VHH1 CDR3 consensus sequence (Kabat
                        numbering)
                       organism = synthetic construct
VARIANT                2
                       note = X is I or T
VARIANT                3
                       note = X is F or I
VARIANT                8
                       note = X is E or D
SEQUENCE: 61
GXXGRPYXY                                                          9
```

-continued

```
SEQ ID NO: 62           moltype = AA  length = 232
FEATURE                 Location/Qualifiers
source                  1..232
                        mol_type = protein
                        note = huIgG1Fc_YTE_C S
                        organism = synthetic construct
SEQUENCE: 62
EPKSSDKTHT CPPCPAPELL GGPSVFLFPP KPKDTLYITR EPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 63           moltype = AA  length = 17
FEATURE                 Location/Qualifiers
source                  1..17
                        mol_type = protein
                        note = Exemplary VHH CDR2 consensus sequence (Kabat
                         numbering)
                        organism = synthetic construct
VARIANT                 8
                        note = X is T or V
VARIANT                 9
                        note = X is L or M
VARIANT                 11
                        note = X is K or N
VARIANT                 12
                        note = X is S or A
VARIANT                 13
                        note = X is D or E
SEQUENCE: 63
GISSSGYXXY XXXSMKG                                                 17

SEQ ID NO: 64           moltype = AA  length = 9
FEATURE                 Location/Qualifiers
source                  1..9
                        mol_type = protein
                        note = Exemplary VHH CDR3 consensus sequence (Kabat
                         numbering)
                        organism = synthetic construct
VARIANT                 2
                        note = X is I, T, or V
VARIANT                 3
                        note = X is F or I
VARIANT                 8
                        note = X is E or D
VARIANT                 9
                        note = X is Y or F
SEQUENCE: 64
GXXGRPYXX                                                          9

SEQ ID NO: 65           moltype = AA  length = 118
FEATURE                 Location/Qualifiers
source                  1..118
                        mol_type = protein
                        note = 20C7 VHH1 single binder
                        organism = synthetic construct
SEQUENCE: 65
EVQLVESGGG SVQAGDSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTLVTVSS    118

SEQ ID NO: 66           moltype = AA  length = 118
FEATURE                 Location/Qualifiers
source                  1..118
                        mol_type = protein
                        note = 1H4 VHH2 single binder
                        organism = synthetic construct
SEQUENCE: 66
EVQLVESGGD LVQAGGSLRL SCAASGGTFS SYAMAWFRQA PGKEREYVAG ISSSGYTLYK  60
ADSMKGRFTI SRENAKNMVY LQMNSLKPED TAVYSCAAGV FGRPYEYWGR GTQVTVSS    118

SEQ ID NO: 67           moltype = AA  length = 118
FEATURE                 Location/Qualifiers
source                  1..118
                        mol_type = protein
                        note = 1C2 VHH2 single binder
                        organism = synthetic construct
SEQUENCE: 67
EVQLVESGGG SVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSS    118
```

```
SEQ ID NO: 68          moltype = AA  length = 118
FEATURE                Location/Qualifiers
source                 1..118
                       mol_type = protein
                       note = 1E3 VHH1 single binder
                       organism = synthetic construct
SEQUENCE: 68
EVQLVESGGG SVQAGGSLRL SCAASGGTFS SYAMAWFRQA PGKEREYVAG ISSSGYTLYK  60
SDSMKGRFTI SRENAKNMVY LQMNSLKPED TAVYSCAAGI FGRPYEYWGQ GTLVTVSS    118

SEQ ID NO: 69          moltype = AA  length = 118
FEATURE                Location/Qualifiers
source                 1..118
                       mol_type = protein
                       note = 1D12 VHH1 single binder
                       organism = synthetic construct
SEQUENCE: 69
EVQLVESGGG SVQPGGSLRL SCAASGGTFS SYTMGWFRQA PGKEREYVGG ISSSGYVMYN  60
SDSMKGRFTI SRENAKNMVY LQMNSLKPED TAVYYCAAGT IGRPYDFWGQ GTLVTVSS    118

SEQ ID NO: 70          moltype = AA  length = 118
FEATURE                Location/Qualifiers
source                 1..118
                       mol_type = protein
                       note = 2H2 VHH1 single binder
                       organism = synthetic construct
SEQUENCE: 70
EVQLVESGGG SVQPGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTLVTVSS    118

SEQ ID NO: 71          moltype = AA  length = 118
FEATURE                Location/Qualifiers
source                 1..118
                       mol_type = protein
                       note = 1H2 VHH1 single binder
                       organism = synthetic construct
SEQUENCE: 71
EVQLVESGGG SVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSS    118

SEQ ID NO: 72          moltype = AA  length = 118
FEATURE                Location/Qualifiers
source                 1..118
                       mol_type = protein
                       note = 1C7 VHH1 single binder
                       organism = synthetic construct
SEQUENCE: 72
EVQLVESGGG SVQPGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSS    118

SEQ ID NO: 73          moltype = AA  length = 118
FEATURE                Location/Qualifiers
source                 1..118
                       mol_type = protein
                       note = 1B10 VHH1 single binder
                       organism = synthetic construct
SEQUENCE: 73
EVQLVESGGG SVQPGGSLRL SCAASGGTFS SYTMGWFRQA PGKEREYVGG ISSSGYVMYN  60
SDSMKGRFTI SRENAKNMVY LQMNSLKPED TAVYYCAAGT IGRPYDFWGQ GTLVTVSS    118

SEQ ID NO: 74          moltype = AA  length = 118
FEATURE                Location/Qualifiers
source                 1..118
                       mol_type = protein
                       note = 1G6 VHH1 single binder
                       organism = synthetic construct
SEQUENCE: 74
EVQLVESGGG SVQAGGSLRL SCAASGGTFS SYAMAWFRQA PGKEREYVAG ISSSGYTLYK  60
SDSMKGRFTI SRENAKNMVY LQMNSLKPED TAVYSCAAGI FGRPYEYWGQ GTQVTVSS    118

SEQ ID NO: 75          moltype = AA  length = 118
FEATURE                Location/Qualifiers
source                 1..118
                       mol_type = protein
                       note = 1E2 VHH1 single binder
                       organism = synthetic construct
SEQUENCE: 75
EVQLVESGGG SVQAGGSLRL SCAASGGTFS SYTMGWFRQA PGKEREYVGG ISSSGYVMYN  60
```

```
SESMKGRFTI SRENAKNMVY LQMNSLKPED TAVYYCAAGT IGRPYDYWGQ GTQVTVSS    118

SEQ ID NO: 76          moltype = AA  length = 118
FEATURE                Location/Qualifiers
source                 1..118
                       mol_type = protein
                       note = 1B12 VHH2 single binder
                       organism = synthetic construct
SEQUENCE: 76
QVKLEESGGG SVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTLVTVSS    118

SEQ ID NO: 77          moltype = AA  length = 118
FEATURE                Location/Qualifiers
source                 1..118
                       mol_type = protein
                       note = 1C3 VHH1 single binder
                       organism = synthetic construct
SEQUENCE: 77
EVQLVESGGG SVQAGGSLRL SCAASGGTFS SYAMAWFRQA PGKEREYVAG ISSSGYTLYK  60
SDSMKGRFTI SRENAKNMVY LQMNSLKPED TAVYSCAAGI FGRPYEYWGQ GTQVTVSS    118

SEQ ID NO: 78          moltype = AA  length = 8
FEATURE                Location/Qualifiers
source                 1..8
                       mol_type = protein
                       note = 1C10 VHH1 CDR1 (IMGT numbering)
                       organism = synthetic construct
SEQUENCE: 78
GGTFSSYT                                                          8

SEQ ID NO: 79          moltype = AA  length = 8
FEATURE                Location/Qualifiers
source                 1..8
                       mol_type = protein
                       note = 1C10 VHH1 CDR2 (IMGT numbering)
                       organism = synthetic construct
SEQUENCE: 79
ISSSGYVM                                                          8

SEQ ID NO: 80          moltype = AA  length = 11
FEATURE                Location/Qualifiers
source                 1..11
                       mol_type = protein
                       note = 1C10 VHH1 CDR3 (IMGT numbering)
                       organism = synthetic construct
SEQUENCE: 80
AAGTIGRPYD Y                                                      11

SEQ ID NO: 81          moltype = AA  length = 7
FEATURE                Location/Qualifiers
source                 1..7
                       mol_type = protein
                       note = 1C10 VHH1 CDR1 (Chothia numbering)
                       organism = synthetic construct
SEQUENCE: 81
GGTFSSY                                                           7

SEQ ID NO: 82          moltype = AA  length = 6
FEATURE                Location/Qualifiers
source                 1..6
                       mol_type = protein
                       note = 1C10 VHH1 CDR2 (Chothia numbering)
                       organism = synthetic construct
SEQUENCE: 82
SSSGYV                                                            6

SEQ ID NO: 83          moltype = AA  length = 9
FEATURE                Location/Qualifiers
source                 1..9
                       mol_type = protein
                       note = 1C10 VHH1 CDR3 (Chothia numbering)
                       organism = synthetic construct
SEQUENCE: 83
GTIGRPYDY                                                         9

SEQ ID NO: 84          moltype = AA  length = 8
FEATURE                Location/Qualifiers
source                 1..8
```

```
                        mol_type = protein
                        note = 1C10 VHH2 CDR1 (IMGT numbering)
                        organism = synthetic construct
SEQUENCE: 84
GDISSIVA                                                            8

SEQ ID NO: 85           moltype = AA  length = 7
FEATURE                 Location/Qualifiers
source                  1..7
                        mol_type = protein
                        note = 1C10 VHH2 CDR2 (IMGT numbering)
                        organism = synthetic construct
SEQUENCE: 85
ITSGGRT                                                             7

SEQ ID NO: 86           moltype = AA  length = 14
FEATURE                 Location/Qualifiers
source                  1..14
                        mol_type = protein
                        note = 1C10 VHH2 CDR3 (IMGT numbering)
                        organism = synthetic construct
SEQUENCE: 86
AADRGWTSVG EYDY                                                     14

SEQ ID NO: 87           moltype = AA  length = 7
FEATURE                 Location/Qualifiers
source                  1..7
                        mol_type = protein
                        note = 1C10 VHH2 CDR1 (Chothia numbering)
                        organism = synthetic construct
SEQUENCE: 87
GDISSIV                                                             7

SEQ ID NO: 88           moltype = AA  length = 5
FEATURE                 Location/Qualifiers
source                  1..5
                        mol_type = protein
                        note = 1C10 VHH2 CDR2 (Chothia numbering)
                        organism = synthetic construct
SEQUENCE: 88
TSGGR                                                               5

SEQ ID NO: 89           moltype = AA  length = 12
FEATURE                 Location/Qualifiers
source                  1..12
                        mol_type = protein
                        note = 1C10 VHH2 CDR3 (Chothia numbering)
                        organism = synthetic construct
SEQUENCE: 89
DRGWTSVGEY DY                                                       12

SEQ ID NO: 90           moltype = AA  length = 232
FEATURE                 Location/Qualifiers
source                  1..232
                        mol_type = protein
                        note = huIgG1Fc_YTE_LALA_C S
                        organism = synthetic construct
SEQUENCE: 90
EPKSSDKTHT CPPCPAPEAA GGPSVFLFPP KPKDTLYITR EPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 91           moltype = AA  length = 507
FEATURE                 Location/Qualifiers
source                  1..507
                        mol_type = protein
                        note = 1C10 co-binder + huIgG1Fc_ YTE_LALA_C S
                        organism = synthetic construct
SEQUENCE: 91
EVQLVESGGG LVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSSGG  120
GSGGGGSGGG GSGGGGSGGG GSGGGGSGGG GSGMTGVKLE ESGGGLVQPG GSLILSCAAS  180
GDISSIVAMG WYRQAPGKQR ELVAAITSGG RTHYRDSVKG RFTISGNNDN SALYLHMNSL  240
KPEDTAVYYC AADRGWTSVG EYDYWGKGTL VTVSSEPKSS DKTHTCPPCP APEAAGGPSV  300
FLFPPKPKDT LYITREPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSRDELTK  420
NQVSLTCLVK GFYPSDIAVE WESNGQPENN YKTTPPVLDS DGSFFLYSKL TVDKSRWQQG  480
NVFSCSVMHE ALHNHYTQKS LSLSPGK                                       507
```

```
SEQ ID NO: 92           moltype = AA  length = 507
FEATURE                 Location/Qualifiers
source                  1..507
                        mol_type = protein
                        note = Humanized 1C10 co binder + huIgG1Fc_ YTE_LALA_C S
                        organism = synthetic construct
SEQUENCE: 92
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSSEPKSS DKTHTCPPCP APEAAGGPSV  300
FLFPPKPKDT LYITREPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSRDELTK  420
NQVSLTCLVK GFYPSDIAVE WESNGQPENN YKTTPPVLDS DGSFFLYSKL TVDKSRWQQG  480
NVFSCSVMHE ALHNHYTQKS LSLSPGK                                    507

SEQ ID NO: 93           moltype = AA  length = 118
FEATURE                 Location/Qualifiers
source                  1..118
                        mol_type = protein
                        note = Humanized 1C10 VHH1 with N-terminal consensus residue
                        organism = synthetic construct
VARIANT                 1
                        note = X is E or Q
SEQUENCE: 93
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSS    118

SEQ ID NO: 94           moltype = AA  length = 118
FEATURE                 Location/Qualifiers
source                  1..118
                        mol_type = protein
                        organism = synthetic construct
VARIANT                 1
                        note = X is E or Q
VARIANT                 33
                        note = X is A or T
VARIANT                 35
                        note = X is A or G
SEQUENCE: 94
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGT IGRPYDYWGQ GTQVTVSS    118

SEQ ID NO: 95           moltype = AA  length = 118
FEATURE                 Location/Qualifiers
source                  1..118
                        mol_type = protein
                        note = Humanized 1C10 VHH1 with N-terminal consensus
                         residue, and consensus CDR2A
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
                        note = X is D or E
SEQUENCE: 95
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGT IGRPYDYWGQ GTQVTVSS    118

SEQ ID NO: 96           moltype = AA  length = 118
FEATURE                 Location/Qualifiers
source                  1..118
                        mol_type = protein
                        note = Humanized 1C10 VHH1 with N-terminal consensus
                         residue, and consensus CDR3A
                        organism = synthetic construct
VARIANT                 1
                        note = X is E or Q
VARIANT                 100
                        note = X is I or T
VARIANT                 101
                        note = X is F or I
```

```
VARIANT                 106
                        note = X is E or D
SEQUENCE: 96
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXYWGQ GTQVTVSS    118

SEQ ID NO: 97           moltype = AA  length = 118
FEATURE                 Location/Qualifiers
source                  1..118
                        mol_type = protein
                        note = Humanized 1C10 VHH1 with N-terminal consensus
                         residue, and consensus CDRs1 and 2A
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 62
                        note = X is D or E
SEQUENCE: 97
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGT IGRPYDYWGQ GTQVTVSS    118

SEQ ID NO: 98           moltype = AA  length = 118
FEATURE                 Location/Qualifiers
source                  1..118
                        mol_type = protein
                        note = Humanized 1C10 VHH1 with N-terminal consensus
                         residue, and consensus CDRs1 and 3A
                        organism = synthetic construct
VARIANT                 1
                        note = X is E or Q
VARIANT                 33
                        note = X is A or T
VARIANT                 35
                        note = X is A or G
VARIANT                 100
                        note = X is I or T
VARIANT                 101
                        note = X is F or I
VARIANT                 106
                        note = X is E or D
SEQUENCE: 98
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXYWGQ GTQVTVSS    118

SEQ ID NO: 99           moltype = AA  length = 118
FEATURE                 Location/Qualifiers
source                  1..118
                        mol_type = protein
                        note = Humanized 1C10 VHH1 with N-terminal consensus
                         residue, and consensus CDRs2A and 3A
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
                        note = X is D or E
VARIANT                 100
                        note = X is I or T
VARIANT                 101
                        note = X is F or I
VARIANT                 106
                        note = X is E or D
SEQUENCE: 99
XVQLVESGGG LVQPGGSLRL SCAASGGTFS SYTMGWFRQA PGKEREYVGG ISSSGYXXYX  60
```

```
SXSMKGRFTI SRDNAKNTLY LQMNSLRAED TAVYYCAAGX XGRPYXYWGQ GTQVTVSS    118

SEQ ID NO: 100         moltype = AA  length = 118
FEATURE                Location/Qualifiers
source                 1..118
                       mol_type = protein
                       note = Humanized 1C10 VHH1 with N-terminal consensus
                        residue, and consensus CDRs1, 2A and 3A
                       organism = synthetic construct
VARIANT                1
                       note = X is E or Q
VARIANT                33
                       note = X is A or T
VARIANT                35
                       note = X is A or G
VARIANT                57
                       note = X is T or V
VARIANT                58
                       note = X is L or M
VARIANT                60
                       note = X is K or N
VARIANT                62
                       note = X is D or E
VARIANT                100
                       note = X is I or T
VARIANT                101
                       note = X is F or I
VARIANT                106
                       note = X is E or D
SEQUENCE: 100
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGX XGRPYXYWGQ GTQVTVSS    118

SEQ ID NO: 101         moltype = AA  length = 120
FEATURE                Location/Qualifiers
source                 1..120
                       mol_type = protein
                       note = Humanized 1C10 VHH2 with one amino acid consensus
                        addition at N-terminus
                       organism = synthetic construct
VARIANT                1
                       note = X is E or Q
SEQUENCE: 101
XVQLVESGGG LVQPGGSLRL SCAASGDISS IVAMGWYRQA PGKQRELVSA ITSGGRTHYR  60
DSVKGRFTIS RDNAKNTLYL QMNSLRAEDT AVYYCAADRG WTSVGEYDYW GQGTQVTVSS  120

SEQ ID NO: 102         moltype = AA  length = 118
FEATURE                Location/Qualifiers
source                 1..118
                       mol_type = protein
                       note = Humanized 1C10 VHH2 with one amino acid deletion at
                        N-terminus
                       organism = synthetic construct
SEQUENCE: 102
QLVESGGGLV QPGGSLRLSC AASGDISSIV AMGWYRQAPG KQRELVSAIT SGGRTHYRDS  60
VKGRFTISRD NAKNTLYLQM NSLRAEDTAV YYCAADRGWT SVGEYDYWGQ GTQVTVSS    118

SEQ ID NO: 103         moltype = AA  length = 117
FEATURE                Location/Qualifiers
source                 1..117
                       mol_type = protein
                       note = Humanized 1C10 VHH2 with two amino acid deletion at
                        N-terminus
                       organism = synthetic construct
SEQUENCE: 103
LVESGGGLVQ PGGSLRLSCA ASGDISSIVA MGWYRQAPGK QRELVSAITS GGRTHYRDSV  60
KGRFTISRDN AKNTLYLQMN SLRAEDTAVY YCAADRGWTS VGEYDYWGQG TQVTVSS     117

SEQ ID NO: 104         moltype = AA  length = 38
FEATURE                Location/Qualifiers
source                 1..38
                       mol_type = protein
                       note = Humanized 1C10 linker connecting VHH1 and VHH2
                       organism = synthetic construct
SEQUENCE: 104
GGGSGGGGSG GGGSGGGGSG GGGSGGGGSG GGGSGMTG                          38

SEQ ID NO: 105         moltype = AA  length = 276
FEATURE                Location/Qualifiers
```

```
source                  1..276
                        mol_type = protein
                        note = Humanized 1C10 co-binder with VHH2 having one amino
                         acid consensus addition at N-terminus
                        organism = synthetic construct
VARIANT                 157
                        note = X is E or Q
SEQUENCE: 105
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 106          moltype = AA  length = 274
FEATURE                 Location/Qualifiers
source                  1..274
                        mol_type = protein
                        note = Humanized 1C10 co-binder with VHH2 having one amino
                         acid deletion at N-terminus
                        organism = synthetic construct
SEQUENCE: 106
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274

SEQ ID NO: 107          moltype = AA  length = 273
FEATURE                 Location/Qualifiers
source                  1..273
                        mol_type = protein
                        note = Humanized 1C10 co-binder with VHH2 having two amino
                         acid deletion at N-terminus
                        organism = synthetic construct
SEQUENCE: 107
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                               273

SEQ ID NO: 108          moltype = AA  length = 275
FEATURE                 Location/Qualifiers
source                  1..275
                        mol_type = protein
                        note = Humanized 1C10 co-binder with VHH1 N-terminal
                         consensus residue
                        organism = synthetic construct
VARIANT                 1
                        note = X is E or Q
SEQUENCE: 108
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 109          moltype = AA  length = 276
FEATURE                 Location/Qualifiers
source                  1..276
                        mol_type = protein
                        note = Humanized 1C10 co-binder with VHH1 N-terminal
                         consensus residue, and VHH2 with one amino acid consensus
                         addition at N-terminus
                        organism = synthetic construct
VARIANT                 1
                        note = X is E or Q
VARIANT                 157
                        note = X is E or Q
SEQUENCE: 109
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 110          moltype = AA  length = 274
FEATURE                 Location/Qualifiers
```

```
source                  1..274
                        mol_type = protein
                        note = Humanized 1C10 co-binder with VHH1 N-terminal
                         consensus residue, and VHH2 with one amino acid deletion
                         at N-terminus
                        organism = synthetic construct
VARIANT                 1
                        note = X is E or Q
SEQUENCE: 110
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274

SEQ ID NO: 111          moltype = AA  length = 273
FEATURE                 Location/Qualifiers
source                  1..273
                        mol_type = protein
                        note = Humanized 1C10 co-binder with VHH1 N-terminal
                         consensus residue, and VHH2 with two amino acid deletion
                         at N-terminus
                        organism = synthetic construct
VARIANT                 1
                        note = X is E or Q
SEQUENCE: 111
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                               273

SEQ ID NO: 112          moltype = AA  length = 275
FEATURE                 Location/Qualifiers
source                  1..275
                        mol_type = protein
                        note = Humanized 1C10 co-binder with VHH1 N-terminal
                         consensus residue and consensus CDR1
                        organism = synthetic construct
VARIANT                 1
                        note = X is E or Q
VARIANT                 33
                        note = X is A or T
VARIANT                 35
                        note = X is A or G
SEQUENCE: 112
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 113          moltype = AA  length = 276
FEATURE                 Location/Qualifiers
source                  1..276
                        mol_type = protein
                        note = Humanized 1C10 co-binder with VHH1 N-terminal
                         consensus residue and consensus CDR1, and VHH2 with one
                         amino acid consensus addition at N-terminus
                        organism = synthetic construct
VARIANT                 1
                        note = X is E or Q
VARIANT                 33
                        note = X is A or G
VARIANT                 35
                        note = X is E or Q
VARIANT                 157
                        note = X is E or Q
SEQUENCE: 113
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 114          moltype = AA  length = 274
FEATURE                 Location/Qualifiers
source                  1..274
                        mol_type = protein
```

```
                        note = Humanized 1C10 co-binder with VHH1 N-terminal
                         consensus residue and consensus CDR1, and VHH2 with one
                         amino acid deletion at N-terminus
                        organism = synthetic construct
VARIANT                 1
                        note = X is E or Q
VARIANT                 33
                        note = X is A or T
VARIANT                 35
                        note = X is A or G
SEQUENCE: 114
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274

SEQ ID NO: 115          moltype = AA  length = 273
FEATURE                 Location/Qualifiers
source                  1..273
                        mol_type = protein
                        note = Humanized 1C10 co-binder with VHH1 N-terminal
                         consensus residue and consensus CDR1, and VHH2 with two
                         amino acid deletion at N-terminus
                        organism = synthetic construct
VARIANT                 1
                        note = X is E or Q
VARIANT                 33
                        note = X is A or T
VARIANT                 35
                        note = X is A or G
SEQUENCE: 115
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                               273

SEQ ID NO: 116          moltype = AA  length = 275
FEATURE                 Location/Qualifiers
source                  1..275
                        mol_type = protein
                        note = Humanized 1C10 co-binder with VHH1 N-terminal
                         consensus residue and consensus CDR2A
                        organism = synthetic construct
VARIANT                 1
                        note = X is E or Q
VARIANT                 57
                        note = X is T or V
VARIANT                 58
                        note = X is L or M
VARIANT                 60
                        note = X is L or M
VARIANT                 62
                        note = X is D or E
SEQUENCE: 116
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 117          moltype = AA  length = 276
FEATURE                 Location/Qualifiers
source                  1..276
                        mol_type = protein
                        note = Humanized 1C10 co-binder with VHH1 N-terminal
                         consensus residue and consensus CDR2A, and VHH2 with one
                         amino acid consensus addition at N-terminus
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
```

```
                        note = X is D or E
VARIANT                 157
                        note = X is E or Q
SEQUENCE: 117
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 118          moltype = AA  length = 274
FEATURE                 Location/Qualifiers
source                  1..274
                        mol_type = protein
                        note = Humanized 1C10 co-binder with VHH1 N-terminal
                         consensus residue and consensus CDR2A, and VHH2 with one
                         amino acid deletion at N-terminus
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
                        note = X is D or E
SEQUENCE: 118
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274

SEQ ID NO: 119          moltype = AA  length = 273
FEATURE                 Location/Qualifiers
source                  1..273
                        mol_type = protein
                        note = Humanized 1C10 co-binder with VHH1 N-terminal
                         consensus residue and consensus CDR2A, and VHH2 with two
                         amino acid deletion at N-terminus
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
                        note = X is D or E
SEQUENCE: 119
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                               273

SEQ ID NO: 120          moltype = AA  length = 275
FEATURE                 Location/Qualifiers
source                  1..275
                        mol_type = protein
                        note = Humanized 1C10 co-binder with VHH1 N-terminal
                         consensus residue and consensus CDR3A
                        organism = synthetic construct
VARIANT                 1
                        note = X is E or Q
VARIANT                 100
                        note = X is I or T
VARIANT                 101
                        note = X is F or I
VARIANT                 106
                        note = X is E or D
SEQUENCE: 120
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGVQLV ESGGGLVQPG GSLRLSCAAS  180
```

```
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 121         moltype = AA  length = 276
FEATURE                Location/Qualifiers
source                 1..276
                       mol_type = protein
                       note = Humanized 1C10 co-binder with VHH1 N-terminal
                        consensus residue and consensus CDR3A, and VHH2 with one
                        amino acid consensus addition at N-terminus
                       organism = synthetic construct
VARIANT                1
                       note = X is E or Q
VARIANT                100
                       note = X is I or T
VARIANT                101
                       note = X is F or I
VARIANT                106
                       note = X is E or D
VARIANT                157
                       note = X is E or Q
SEQUENCE: 121
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 122         moltype = AA  length = 274
FEATURE                Location/Qualifiers
source                 1..274
                       mol_type = protein
                       note = Humanized 1C10 co-binder with VHH1 N-terminal
                        consensus residue and consensus CDR3A, and VHH2 with one
                        amino acid deletion at N-terminus
                       organism = synthetic construct
VARIANT                1
                       note = X is E or Q
VARIANT                100
                       note = X is I or T
VARIANT                101
                       note = X is F or I
VARIANT                106
                       note = X is E or D
SEQUENCE: 122
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274

SEQ ID NO: 123         moltype = AA  length = 273
FEATURE                Location/Qualifiers
source                 1..273
                       mol_type = protein
                       note = Humanized 1C10 co-binder with VHH1 N-terminal
                        consensus residue and consensus CDR3A, and VHH2 with two
                        amino acid deletion at N-terminus
                       organism = synthetic construct
VARIANT                1
                       note = X is E or Q
VARIANT                100
                       note = X is I or T
VARIANT                101
                       note = X is F or I
VARIANT                106
                       note = X is E or D
SEQUENCE: 123
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                               273

SEQ ID NO: 124         moltype = AA  length = 275
FEATURE                Location/Qualifiers
source                 1..275
                       mol_type = protein
                       note = Humanized 1C10 co-binder with VHH1 N-terminal
```

```
                        consensus residue and consensus CDRs1 and 2A
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 62
                        note = X is D or E
SEQUENCE: 124
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 125          moltype = AA  length = 276
FEATURE                 Location/Qualifiers
source                  1..276
                        mol_type = protein
                        note = Humanized 1C10 co-binder with VHH1 N-terminal
                         consensus residue and consensus CDRs1 and 2A, and VHH2
                         with one amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 62
                        note = X is D or E
VARIANT                 157
                        note = X is E or Q
SEQUENCE: 125
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 126          moltype = AA  length = 274
FEATURE                 Location/Qualifiers
source                  1..274
                        mol_type = protein
                        note = Humanized 1C10 co-binder with VHH1 N-terminal
                         consensus residue and consensus CDRs1 and 2A, and VHH2
                         with one amino acid deletion at N-terminus
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 62
                        note = X is D or E
SEQUENCE: 126
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
```

```
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274

SEQ ID NO: 127         moltype = AA  length = 273
FEATURE                Location/Qualifiers
source                 1..273
                       mol_type = protein
                       note = Humanized 1C10 co-binder with VHH1 N-terminal
                        consensus residue and consensus CDRs1 and 2A, and VHH2
                        with two amino acid deletion at N-terminus
                       organism = synthetic construct
VARIANT                1
                       note = X is E or Q
VARIANT                33
                       note = X is A or T
VARIANT                35
                       note = X is A or G
VARIANT                57
                       note = X is T or V
VARIANT                58
                       note = X is L or M
VARIANT                60
                       note = X is K or N
VARIANT                62
                       note = X is D or E
SEQUENCE: 127
XVQLVESGGG LVQPGGSLRL SCAASGGTFS SYXMXWFRQA PGKEREYVGG ISSSGYXXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                               273

SEQ ID NO: 128         moltype = AA  length = 275
FEATURE                Location/Qualifiers
source                 1..275
                       mol_type = protein
                       note = Humanized 1C10 co-binder with VHH1 N-terminal
                        consensus residue and consensus CDRs1 and 3A
                       organism = synthetic construct
VARIANT                1
                       note = X is E or Q
VARIANT                33
                       note = X is A or T
VARIANT                35
                       note = X is A or G
VARIANT                100
                       note = X is I or T
VARIANT                101
                       note = X is F or I
VARIANT                106
                       note = X is E or D
SEQUENCE: 128
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 129         moltype = AA  length = 276
FEATURE                Location/Qualifiers
source                 1..276
                       mol_type = protein
                       note = Humanized 1C10 co-binder with VHH1 N-terminal
                        consensus residue and consensus CDRs1 and 3A, and VHH2
                        with one amino acid consensus addition at N-terminus
                       organism = synthetic construct
VARIANT                1
                       note = X is E or Q
VARIANT                33
                       note = X is A or T
VARIANT                35
                       note = X is A or G
VARIANT                100
                       note = X is I or T
VARIANT                101
                       note = X is F or I
VARIANT                106
                       note = X is E or D
```

```
VARIANT                157
                       note = X is E or Q
SEQUENCE: 129
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 130         moltype = AA  length = 274
FEATURE                Location/Qualifiers
source                 1..274
                       mol_type = protein
                       note = Humanized 1C10 co-binder with VHH1 N-terminal
                        consensus residue and consensus CDRs1 and 3A, and VHH2
                        with one amino acid deletion at N-terminus
                       organism = synthetic construct
VARIANT                1
                       note = X is E or Q
VARIANT                33
                       note = X is A or T
VARIANT                35
                       note = X is A or G
VARIANT                100
                       note = X is I or T
VARIANT                101
                       note = X is F or I
VARIANT                106
                       note = X is E or D
SEQUENCE: 130
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274

SEQ ID NO: 131         moltype = AA  length = 273
FEATURE                Location/Qualifiers
source                 1..273
                       mol_type = protein
                       note = Humanized 1C10 co-binder with VHH1 N-terminal
                        consensus residue and consensus CDRs1 and 3A, and VHH2
                        with two amino acid deletion at N-terminus
                       organism = synthetic construct
VARIANT                1
                       note = X is E or Q
VARIANT                33
                       note = X is A or T
VARIANT                35
                       note = X is A or G
VARIANT                100
                       note = X is I or T
VARIANT                101
                       note = X is F or I
VARIANT                106
                       note = X is E or D
SEQUENCE: 131
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                               273

SEQ ID NO: 132         moltype = AA  length = 275
FEATURE                Location/Qualifiers
source                 1..275
                       mol_type = protein
                       note = Humanized 1C10 co-binder with VHH1 N-terminal
                        consensus residue and consensus CDRs2A and 3A
                       organism = synthetic construct
VARIANT                1
                       note = X is E or Q
VARIANT                57
                       note = X is T or V
VARIANT                58
                       note = X is L or M
VARIANT                60
                       note = X is K or N
VARIANT                62
```

```
                         note = X is D or E
VARIANT                  100
                         note = X is I or T
VARIANT                  101
                         note = X is F or I
VARIANT                  106
                         note = X is E or D
SEQUENCE: 132
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 133           moltype = AA  length = 276
FEATURE                  Location/Qualifiers
source                   1..276
                         mol_type = protein
                         note = Humanized 1C10 co-binder with VHH1 N-terminal
                          consensus residue and consensus CDRs2A and 3A, and VHH2
                          with one amino acid consensus addition at N-terminus
                         organism = synthetic construct
VARIANT                  1
                         note = X is E or Q
VARIANT                  57
                         note = X is T or V
VARIANT                  58
                         note = X is L or M
VARIANT                  60
                         note = X is K or N
VARIANT                  62
                         note = X is D or E
VARIANT                  100
                         note = X is I or T
VARIANT                  101
                         note = X is F or I
VARIANT                  106
                         note = X is E or D
VARIANT                  157
                         note = X is E or Q
SEQUENCE: 133
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 134           moltype = AA  length = 274
FEATURE                  Location/Qualifiers
source                   1..274
                         mol_type = protein
                         note = Humanized 1C10 co-binder with VHH1 N-terminal
                          consensus residue and consensus CDRs2A and 3A, and VHH2
                          with one amino acid deletion at N-terminus
                         organism = synthetic construct
VARIANT                  1
                         note = X is E or Q
VARIANT                  57
                         note = X is T or V
VARIANT                  58
                         note = X is L or M
VARIANT                  60
                         note = X is K or N
VARIANT                  62
                         note = X is D or E
VARIANT                  100
                         note = X is I or T
VARIANT                  101
                         note = X is F or I
VARIANT                  106
                         note = X is E or D
SEQUENCE: 134
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274

SEQ ID NO: 135           moltype = AA  length = 273
```

```
FEATURE                Location/Qualifiers
source                 1..273
                       mol_type = protein
                       note = Humanized 1C10 co-binder with VHH1 N-terminal
                        consensus residue and consensus CDRs2A and 3A, and VHH2
                        with two amino acid deletion at N-terminus
                       organism = synthetic construct
VARIANT                1
                       note = X is E or Q
VARIANT                57
                       note = X is T or V
VARIANT                58
                       note = X is L or M
VARIANT                60
                       note = X is K or N
VARIANT                62
                       note = X is D or E
VARIANT                100
                       note = X is I or T
VARIANT                101
                       note = X is F or I
VARIANT                106
                       note = X is E or D
SEQUENCE: 135
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                               273

SEQ ID NO: 136         moltype = AA  length = 275
FEATURE                Location/Qualifiers
source                 1..275
                       mol_type = protein
                       note = Humanized 1C10 co-binder with VHH1 N-terminal
                        consensus residue and consensus CDRs1, 2A and 3A
                       organism = synthetic construct
VARIANT                1
                       note = X is E or Q
VARIANT                33
                       note = X is A or T
VARIANT                35
                       note = X is A or G
VARIANT                57
                       note = X is T or V
VARIANT                58
                       note = X is L or M
VARIANT                60
                       note = X is K or N
VARIANT                62
                       note = X is D or E
VARIANT                100
                       note = X is I or T
VARIANT                101
                       note = X is F or I
VARIANT                106
                       note = X is E or D
SEQUENCE: 136
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 137         moltype = AA  length = 276
FEATURE                Location/Qualifiers
source                 1..276
                       mol_type = protein
                       note = Humanized 1C10 co-binder with VHH1 N-terminal
                        consensus residue and consensus CDRs1, 2A and 3A, and VHH2
                        with one amino acid consensus addition at N-terminus
                       organism = synthetic construct
VARIANT                1
                       note = X is E or Q
VARIANT                33
                       note = X is A or T
VARIANT                35
                       note = X is A or G
VARIANT                57
```

```
                          note = X is T or V
VARIANT                   58
                          note = X is L or M
VARIANT                   60
                          note = X is K or N
VARIANT                   62
                          note = X is D or E
VARIANT                   100
                          note = X is I or T
VARIANT                   101
                          note = X is F or I
VARIANT                   106
                          note = X is E or D
VARIANT                   157
                          note = X is E or Q
SEQUENCE: 137
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 138            moltype = AA  length = 274
FEATURE                   Location/Qualifiers
source                    1..274
                          mol_type = protein
                          note = Humanized 1C10 co-binder with VHH1 N-terminal
                           consensus residue and consensus CDRs1, 2A and 3A, and VHH2
                           with one amino acid deletion at N-terminus
                          organism = synthetic construct
VARIANT                   1
                          note = X is E or Q
VARIANT                   33
                          note = X is A or T
VARIANT                   35
                          note = X is A or G
VARIANT                   57
                          note = X is T or V
VARIANT                   58
                          note = X is L or M
VARIANT                   60
                          note = X is K or N
VARIANT                   62
                          note = X is D or E
VARIANT                   100
                          note = X is I or T
VARIANT                   101
                          note = X is F or I
VARIANT                   106
                          note = X is E or D
SEQUENCE: 138
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274

SEQ ID NO: 139            moltype = AA  length = 273
FEATURE                   Location/Qualifiers
source                    1..273
                          mol_type = protein
                          note = Humanized 1C10 co-binder with VHH1 N-terminal
                           consensus residue and consensus CDRs1, 2A and 3A, and VHH2
                           with two amino acid deletion at N-terminus
                          organism = synthetic construct
VARIANT                   1
                          note = X is E or Q
VARIANT                   33
                          note = X is A or T
VARIANT                   35
                          note = X is A or G
VARIANT                   57
                          note = X is T or V
VARIANT                   58
                          note = X is L or M
VARIANT                   60
                          note = X is K or N
VARIANT                   62
                          note = X is D or E
```

```
VARIANT                 100
                        note = X is I or T
VARIANT                 101
                        note = X is F or I
VARIANT                 106
                        note = X is E or D
SEQUENCE: 139
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                               273

SEQ ID NO: 140          moltype = AA  length = 118
FEATURE                 Location/Qualifiers
source                  1..118
                        mol_type = protein
                        note = Humanized 1C10 VHH1 with N-terminal consensus
                         residue, and consensus CDR2B
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
SEQUENCE: 140
XVQLVESGGG LVQPGGSLRL SCAASGGTFS SYTMGWFRQA PGKEREYVGG ISSSGYXXXYX  60
XXSMKGRFTI SRDNAKNTLY LQMNSLRAED TAVYYCAAGT IGRPYDYWGQ GTQVTVSS    118

SEQ ID NO: 141          moltype = AA  length = 118
FEATURE                 Location/Qualifiers
source                  1..118
                        mol_type = protein
                        note = Humanized 1C10 VHH1 with N-terminal consensus
                         residue, and consensus CDR3B
                        organism = synthetic construct
VARIANT                 1
                        note = X is E or Q
VARIANT                 100
                        note = X is I, T, or V
VARIANT                 101
                        note = X is F or I
VARIANT                 106
                        note = X is E or D
VARIANT                 107
                        note = X is Y or F
SEQUENCE: 141
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXXWGQ GTQVTVSS    118

SEQ ID NO: 142          moltype = AA  length = 118
FEATURE                 Location/Qualifiers
source                  1..118
                        mol_type = protein
                        note = Humanized 1C10 VHH1 with N-terminal consensus
                         residue, and consensus CDRs1 and 2B
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
```

```
                         note = X is D or E
SEQUENCE: 142
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGT IGRPYDYWGQ GTQVTVSS    118

SEQ ID NO: 143           moltype = AA  length = 118
FEATURE                  Location/Qualifiers
source                   1..118
                         mol_type = protein
                         note = Humanized 1C10 VHH1 with N-terminal consensus
                          residue, and consensus CDRs1 and 3B
                         organism = synthetic construct
VARIANT                  1
                         note = X is E or Q
VARIANT                  33
                         note = X is A or T
VARIANT                  35
                         note = X is A or G
VARIANT                  100
                         note = X is I, T, or V
VARIANT                  101
                         note = X is F or I
VARIANT                  107
                         note = X is Y or F
VARIANT                  106
                         note = X is E or D
SEQUENCE: 143
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXXWGQ GTQVTVSS    118

SEQ ID NO: 144           moltype = AA  length = 118
FEATURE                  Location/Qualifiers
source                   1..118
                         mol_type = protein
                         note = Humanized 1C10 VHH1 with N-terminal consensus
                          residue, and consensus CDRs2B and 3B
                         organism = synthetic construct
VARIANT                  1
                         note = X is E or Q
VARIANT                  57
                         note = X is T or V
VARIANT                  58
                         note = X is L or M
VARIANT                  60
                         note = X is K or N
VARIANT                  61
                         note = X is S or A
VARIANT                  62
                         note = X is D or E
VARIANT                  100
                         note = X is I, T, or V
VARIANT                  101
                         note = X is F or I
VARIANT                  106
                         note = X is E or D
VARIANT                  107
                         note = X is Y or F
SEQUENCE: 144
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGX XGRPYXXWGQ GTQVTVSS    118

SEQ ID NO: 145           moltype = AA  length = 118
FEATURE                  Location/Qualifiers
source                   1..118
                         mol_type = protein
                         note = Humanized 1C10 VHH1 with N-terminal consensus
                          residue, and consensus CDRs1, 2B and 3B
                         organism = synthetic construct
VARIANT                  1
                         note = X is E or Q
VARIANT                  33
                         note = X is A or T
VARIANT                  35
                         note = X is A or G
VARIANT                  57
                         note = X is T or V
VARIANT                  58
                         note = X is L or M
VARIANT                  60
```

```
                          note = X is K or N
VARIANT                   61
                          note = X is S or A
VARIANT                   62
                          note = X is D or E
VARIANT                   100
                          note = X is I, T, or V
VARIANT                   101
                          note = X is F or I
VARIANT                   106
                          note = X is E or D
VARIANT                   107
                          note = X is Y or F
SEQUENCE: 145
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGX XGRPYXXWGQ GTQVTVSS    118

SEQ ID NO: 146            moltype = AA  length = 120
FEATURE                   Location/Qualifiers
source                    1..120
                          mol_type = protein
                          note = Humanized 1C10 VHH2 with N-terminal consensus
                           residues at position 1 and 3
                          organism = synthetic construct
VARIANT                   1
                          note = X is E or Q
VARIANT                   3
                          note = X is Q or K
SEQUENCE: 146
XVXLVESGGG LVQPGGSLRL SCAASGDISS IVAMGWYRQA PGKQRELVSA ITSGGRTHYR  60
DSVKGRFTIS RDNAKNTLYL QMNSLRAEDT AVYYCAADRG WTSVGEYDYW GQGTQVTVSS  120

SEQ ID NO: 147            moltype = AA  length = 275
FEATURE                   Location/Qualifiers
source                    1..275
                          mol_type = protein
                          note = Humanized 1C10 co-binder with VHH1 N-terminal
                           consensus residue, and consensus CDR2B
                          organism = synthetic construct
VARIANT                   1
                          note = X is E or Q
VARIANT                   57
                          note = X is T or V
VARIANT                   58
                          note = X is L or M
VARIANT                   60
                          note = X is K or N
VARIANT                   61
                          note = X is S or A
VARIANT                   62
                          note = X is D or E
SEQUENCE: 147
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 148            moltype = AA  length = 276
FEATURE                   Location/Qualifiers
source                    1..276
                          mol_type = protein
                          note = Humanized 1C10 co-binder with VHH1 N-terminal
                           consensus residue and consensus CDR2B, and VHH2 with one
                           amino acid consensus addition at N-terminus
                          organism = synthetic construct
VARIANT                   1
                          note = X is E or Q
VARIANT                   57
                          note = X is T or V
VARIANT                   58
                          note = X is L or M
VARIANT                   60
                          note = X is K or N
VARIANT                   61
                          note = X is S or A
VARIANT                   62
                          note = X is D or E
VARIANT                   157
```

```
                        note = X is E or Q
SEQUENCE: 148
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                           276

SEQ ID NO: 149          moltype = AA  length = 274
FEATURE                 Location/Qualifiers
source                  1..274
                        mol_type = protein
                        note = Humanized 1C10 co-binder with VHH1 N-terminal
                         consensus residue and consensus CDR2B, and VHH2 with one
                         amino acid deletion at N-terminus
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
SEQUENCE: 149
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                             274

SEQ ID NO: 150          moltype = AA  length = 273
FEATURE                 Location/Qualifiers
source                  1..273
                        mol_type = protein
                        note = Humanized 1C10 co-binder with VHH1 N-terminal
                         consensus residue and consensus CDR2B, and VHH2 with two
                         amino acid deletion at N-terminus
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
SEQUENCE: 150
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                              273

SEQ ID NO: 151          moltype = AA  length = 276
FEATURE                 Location/Qualifiers
source                  1..276
                        mol_type = protein
                        note = Humanized 1C10 co-binder with VHH1 N-terminal
                         consensus residue and consensus CDR2B, and VHH2 with
                         N-terminal consensus residues at position 1 and 3
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 61
```

```
                        note = X is S or A
VARIANT                 62
                        note = X is D or E
VARIANT                 157
                        note = X is E or Q
VARIANT                 159
                        note = X is Q or K
SEQUENCE: 151
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGXVXL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 152          moltype = AA  length = 275
FEATURE                 Location/Qualifiers
source                  1..275
                        mol_type = protein
                        note = Humanized 1C10 co-binder with VHH1 N-terminal
                         consensus residue, and consensus CDR3B
                        organism = synthetic construct
VARIANT                 1
                        note = X is E or Q
VARIANT                 100
                        note = X is I, T, or V
VARIANT                 101
                        note = X is F or I
VARIANT                 106
                        note = X is E or D
VARIANT                 107
                        note = X is Y or F
SEQUENCE: 152
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 153          moltype = AA  length = 276
FEATURE                 Location/Qualifiers
source                  1..276
                        mol_type = protein
                        note = Humanized 1C10 co-binder with VHH1 N-terminal
                         consensus residue and consensus CDR3B, and VHH2 with one
                         amino acid consensus addition at N-terminus
                        organism = synthetic construct
VARIANT                 1
                        note = X is E or Q
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is E or Q
SEQUENCE: 153
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 154          moltype = AA  length = 274
FEATURE                 Location/Qualifiers
source                  1..274
                        mol_type = protein
                        note = Humanized 1C10 co-binder with VHH1 N-terminal
                         consensus residue and consensus CDR3B, and VHH2 with one
                         amino acid deletion at N-terminus
                        organism = synthetic construct
VARIANT                 1
                        note = X is E or Q
VARIANT                 100
                        note = X is I, T, or V
VARIANT                 101
                        note = X is F or I
```

```
VARIANT                 106
                        note = X is E or D
VARIANT                 107
                        note = X is Y or F
SEQUENCE: 154
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274

SEQ ID NO: 155          moltype = AA  length = 273
FEATURE                 Location/Qualifiers
source                  1..273
                        mol_type = protein
                        note = Humanized 1C10 co-binder with VHH1 N-terminal
                         consensus residue and consensus CDR3B, and VHH2 with two
                         amino acid deletion at N-terminus
                        organism = synthetic construct
VARIANT                 1
                        note = X is E or Q
VARIANT                 100
                        note = X is I, T, or V
VARIANT                 101
                        note = X is F or I
VARIANT                 106
                        note = X is E or D
VARIANT                 107
                        note = X is Y or F
SEQUENCE: 155
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                               273

SEQ ID NO: 156          moltype = AA  length = 276
FEATURE                 Location/Qualifiers
source                  1..276
                        mol_type = protein
                        note = Humanized 1C10 co-binder with VHH1 N-terminal
                         consensus residue and consensus CDR3B, and VHH2 with
                         N-terminal consensus residues at position 1 and 3
                        organism = synthetic construct
VARIANT                 1
                        note = X is E or Q
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is E or Q
VARIANT                 159
                        note = X is Q or K
SEQUENCE: 156
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGXVXL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 157          moltype = AA  length = 275
FEATURE                 Location/Qualifiers
source                  1..275
                        mol_type = protein
                        note = Humanized 1C10 co-binder with VHH1 N-terminal
                         consensus residue, and consensus CDRs1 and 2B
                        organism = synthetic construct
VARIANT                 1
                        note = X is E or Q
VARIANT                 33
                        note = X is A or T
VARIANT                 35
                        note = X is A or G
VARIANT                 58
```

```
                        note = X is T or V
VARIANT                 58
                        note = X is L or M
VARIANT                 60
                        note = X is K or N
VARIANT                 61
                        note = X is S or A
VARIANT                 62
                        note = X is D or E
SEQUENCE: 157
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 158          moltype = AA  length = 276
FEATURE                 Location/Qualifiers
source                  1..276
                        mol_type = protein
                        note = Humanized 1C10 co-binder with VHH1 N-terminal
                         consensus residue and consensus CDRs1 and 2B, and VHH2
                         with one amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 157
                        note = X is E or Q
SEQUENCE: 158
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 159          moltype = AA  length = 274
FEATURE                 Location/Qualifiers
source                  1..274
                        mol_type = protein
                        note = Humanized 1C10 co-binder with VHH1 N-terminal
                         consensus residue and consensus CDRs1 and 2B, and VHH2
                         with one amino acid deletion at N-terminus
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
SEQUENCE: 159
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274
```

```
SEQ ID NO: 160          moltype = AA  length = 273
FEATURE                 Location/Qualifiers
source                  1..273
                        mol_type = protein
                        note = Humanized 1C10 co-binder with VHH1 N-terminal
                         consensus residue and consensus CDRs1 and 2B, and VHH2
                         with two amino acid deletion at N-terminus
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
SEQUENCE: 160
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                               273

SEQ ID NO: 161          moltype = AA  length = 276
FEATURE                 Location/Qualifiers
source                  1..276
                        mol_type = protein
                        note = Humanized 1C10 co-binder with VHH1 N-terminal
                         consensus residue and consensus CDRs1 and 2B, and VHH2
                         with N-terminal consensus residues at position 1 and 3
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 157
                        note = X is E or Q
VARIANT                 159
                        note = X is Q or K
SEQUENCE: 161
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGXVXL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 162          moltype = AA  length = 275
FEATURE                 Location/Qualifiers
source                  1..275
                        mol_type = protein
                        note = Humanized 1C10 co-binder with VHH1 N-terminal
                         consensus residue, and consensus CDRs1 and 3B
                        organism = synthetic construct
VARIANT                 1
                        note = X is E or Q
VARIANT                 33
                        note = X is A or T
VARIANT                 35
```

```
                         note = X is A or G
VARIANT                  100
                         note = X is I, T, or V
VARIANT                  101
                         note = X is F or I
VARIANT                  106
                         note = X is E or D
VARIANT                  107
                         note = X is Y or F
SEQUENCE: 162
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 163           moltype = AA  length = 276
FEATURE                  Location/Qualifiers
source                   1..276
                         mol_type = protein
                         note = Humanized 1C10 co-binder with VHH1 N-terminal
                          consensus residue, and consensus CDRs1 and 3B, and VHH2
                          with one amino acid consensus addition at N-terminus
                         organism = synthetic construct
VARIANT                  1
                         note = X is E or Q
VARIANT                  33
                         note = X is A or T
VARIANT                  35
                         note = X is A or G
VARIANT                  100
                         note = X is I, T, or V
VARIANT                  101
                         note = X is F or I
VARIANT                  106
                         note = X is E or D
VARIANT                  107
                         note = X is Y or F
VARIANT                  157
                         note = X is E or Q
SEQUENCE: 163
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 164           moltype = AA  length = 274
FEATURE                  Location/Qualifiers
source                   1..274
                         mol_type = protein
                         note = Humanized 1C10 co-binder with VHH1 N-terminal
                          consensus residue, and consensus CDRs1 and 3B, and VHH2
                          with one amino acid deletion at N-terminus
                         organism = synthetic construct
VARIANT                  1
                         note = X is E or Q
VARIANT                  33
                         note = X is A or T
VARIANT                  35
                         note = X is A or G
VARIANT                  100
                         note = X is I, T, or V
VARIANT                  101
                         note = X is F or I
VARIANT                  106
                         note = X is E or D
VARIANT                  107
                         note = X is Y or F
SEQUENCE: 164
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274

SEQ ID NO: 165           moltype = AA  length = 273
FEATURE                  Location/Qualifiers
source                   1..273
```

```
                         mol_type = protein
                         note = Humanized 1C10 co-binder with VHH1 N-terminal
                          consensus residue, and consensus CDRs1 and 3B, and VHH2
                          with two amino acid deletion at N-terminus
                         organism = synthetic construct
VARIANT                  1
                         note = X is E or Q
VARIANT                  33
                         note = X is A or T
VARIANT                  35
                         note = X is A or G
VARIANT                  100
                         note = X is I, T, or V
VARIANT                  101
                         note = X is F or I
VARIANT                  106
                         note = X is E or D
VARIANT                  107
                         note = X is Y or F
SEQUENCE: 165
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                               273

SEQ ID NO: 166           moltype = AA  length = 276
FEATURE                  Location/Qualifiers
source                   1..276
                         mol_type = protein
                         note = Humanized 1C10 co-binder with VHH1 N-terminal
                          consensus residue, and consensus CDRs1 and 3B, and VHH2
                          with N-terminal consensus residues at position 1 and 3
                         organism = synthetic construct
VARIANT                  1
                         note = X is E or Q
VARIANT                  33
                         note = X is A or T
VARIANT                  35
                         note = X is A or G
VARIANT                  100
                         note = X is I, T, or V
VARIANT                  101
                         note = X is F or I
VARIANT                  106
                         note = X is E or D
VARIANT                  107
                         note = X is Y or F
VARIANT                  157
                         note = X is E or Q
VARIANT                  159
                         note = X is Q or K
SEQUENCE: 166
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGXVXL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 167           moltype = AA  length = 275
FEATURE                  Location/Qualifiers
source                   1..275
                         mol_type = protein
                         note = Humanized 1C10 co-binder with VHH1 N-terminal
                          consensus residue, and consensus CDRs2B and 3B
                         organism = synthetic construct
VARIANT                  1
                         note = X is E or Q
VARIANT                  57
                         note = X is T or V
VARIANT                  58
                         note = X is L or M
VARIANT                  60
                         note = X is K or N
VARIANT                  61
                         note = X is S or A
VARIANT                  62
                         note = X is D or E
VARIANT                  100
```

```
                         note = X is I, T, or V
VARIANT                  62
                         note = X is D or E
VARIANT                  101
                         note = X is F or I
VARIANT                  106
                         note = X is E or D
VARIANT                  107
                         note = X is Y or F
SEQUENCE: 167
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 168           moltype = AA  length = 276
FEATURE                  Location/Qualifiers
source                   1..276
                         mol_type = protein
                         note = Humanized 1C10 co-binder with VHH1 N-terminal
                          consensus residue, and consensus CDRs2B and 3B, and VHH2
                          with one amino acid consensus addition at N-terminus
                         organism = synthetic construct
VARIANT                  1
                         note = X is E or Q
VARIANT                  57
                         note = X is T or V
VARIANT                  58
                         note = X is L or M
VARIANT                  60
                         note = X is K or N
VARIANT                  61
                         note = X is S or A
VARIANT                  62
                         note = X is D or E
VARIANT                  100
                         note = X is I, T, or V
VARIANT                  101
                         note = X is F or I
VARIANT                  106
                         note = X is E or D
VARIANT                  107
                         note = X is Y or F
VARIANT                  157
                         note = X is E or Q
SEQUENCE: 168
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 169           moltype = AA  length = 274
FEATURE                  Location/Qualifiers
source                   1..274
                         mol_type = protein
                         note = Humanized 1C10 co-binder with VHH1 N-terminal
                          consensus residue, and consensus CDRs2B and 3B, and VHH2
                          with one amino acid deletion at N-terminus
                         organism = synthetic construct
VARIANT                  1
                         note = X is E or Q
VARIANT                  57
                         note = X is T or V
VARIANT                  58
                         note = X is L or M
VARIANT                  60
                         note = X is K or N
VARIANT                  61
                         note = X is S or A
VARIANT                  62
                         note = X is D or E
VARIANT                  100
                         note = X is I, T, or V
VARIANT                  101
                         note = X is F or I
VARIANT                  106
                         note = X is E or D
```

```
VARIANT                 107
                        note = X is Y or F
SEQUENCE: 169
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274

SEQ ID NO: 170          moltype = AA  length = 273
FEATURE                 Location/Qualifiers
source                  1..273
                        mol_type = protein
                        note = Humanized 1C10 co-binder with VHH1 N-terminal
                         consensus residue, and consensus CDRs2B and 3B, and VHH2
                         with two amino acid deletion at N-terminus
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 100
                        note = X is I, T, or V
VARIANT                 101
                        note = X is F or I
VARIANT                 106
                        note = X is E or D
VARIANT                 107
                        note = X is Y or F
SEQUENCE: 170
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGLVES GGGLVQPGGS LRLSCAASGD  180
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                               273

SEQ ID NO: 171          moltype = AA  length = 276
FEATURE                 Location/Qualifiers
source                  1..276
                        mol_type = protein
                        note = Humanized 1C10 co-binder with VHH1 N-terminal
                         consensus residue, and consensus CDRs2B and 3B, and VHH2
                         with N-terminal consensus residues at position 1 and 3
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is E or Q
VARIANT                 159
                        note = X is Q or K
SEQUENCE: 171
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
```

-continued

```
GSGGGGSGGG GSGGGGSGGG GSGGGGSGGG GSGMTGXVXL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 172          moltype = AA  length = 275
FEATURE                 Location/Qualifiers
source                  1..275
                        mol_type = protein
                        note = Humanized 1C10 co-binder with VHH1 N-terminal
                         consensus residue, and consensus CDRs1, 2B and 3B
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 100
                        note = X is I, T, or V
VARIANT                 101
                        note = X is F or I
VARIANT                 106
                        note = X is E or D
VARIANT                 107
                        note = X is Y or F
SEQUENCE: 172
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                             275

SEQ ID NO: 173          moltype = AA  length = 276
FEATURE                 Location/Qualifiers
source                  1..276
                        mol_type = protein
                        note = Humanized 1C10 co-binder with VHH1 N-terminal
                         consensus residue, and consensus CDRs1, 2B and 3B, and
                         VHH2 with one amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is E or Q
SEQUENCE: 173
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
```

```
GSGGGGSGGG GSGGGGSGGG GSGGGGSGGG GSGMTGXVQL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                            276

SEQ ID NO: 174          moltype = AA  length = 274
FEATURE                 Location/Qualifiers
source                  1..274
                        mol_type = protein
                        note = Humanized 1C10 co-binder with VHH1 N-terminal
                         consensus residue, and consensus CDRs1, 2B and 3B, and
                         VHH2 with one amino acid deletion at N-terminus
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 100
                        note = X is I, T, or V
VARIANT                 101
                        note = X is F or I
VARIANT                 106
                        note = X is E or D
VARIANT                 107
                        note = X is Y or F
SEQUENCE: 174
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGQLVE SGGGLVQPGG SLRLSCAASG  180
DISSIVAMGW YRQAPGKQRE LVSAITSGGR THYRDSVKGR FTISRDNAKN TLYLQMNSLR  240
AEDTAVYYCA ADRGWTSVGE YDYWGQGTQV TVSS                              274

SEQ ID NO: 175          moltype = AA  length = 273
FEATURE                 Location/Qualifiers
source                  1..273
                        mol_type = protein
                        note = Humanized 1C10 co-binder with VHH1 N-terminal
                         consensus residue, and consensus CDRs1, 2B and 3B, and
                         VHH2 with two amino acid deletion at N-terminus
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 100
                        note = X is I, T, or V
VARIANT                 101
                        note = X is F or I
VARIANT                 106
                        note = X is E or D
VARIANT                 107
                        note = X is Y or F
SEQUENCE: 175
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGLVES GGGLVQPGGS LRLSCAASGD  180
```

```
ISSIVAMGWY RQAPGKQREL VSAITSGGRT HYRDSVKGRF TISRDNAKNT LYLQMNSLRA  240
EDTAVYYCAA DRGWTSVGEY DYWGQGTQVT VSS                              273

SEQ ID NO: 176          moltype = AA  length = 276
FEATURE                 Location/Qualifiers
source                  1..276
                        mol_type = protein
                        note = Humanized 1C10 co-binder with VHH1 N-terminal
                         consensus residue, and consensus CDRs1, 2B and 3B, and
                         VHH2 with N-terminal consensus residues at position 1 and 3
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is E or Q
VARIANT                 159
                        note = X is Q or K
SEQUENCE: 176
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSGMTGXVXL VESGGGLVQP GGSLRLSCAA  180
SGDISSIVAM GWYRQAPGKQ RELVSAITSG GRTHYRDSVK GRFTISRDNA KNTLYLQMNS  240
LRAEDTAVYY CAADRGWTSV GEYDYWGQGT QVTVSS                           276

SEQ ID NO: 177          moltype = AA  length = 118
FEATURE                 Location/Qualifiers
source                  1..118
                        mol_type = protein
                        note = Humanized 21H7 VHH1 with N-terminal consensus residue
                        organism = synthetic construct
VARIANT                 1
                        note = X is E or Q
SEQUENCE: 177
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSS    118

SEQ ID NO: 178          moltype = AA  length = 118
FEATURE                 Location/Qualifiers
source                  1..118
                        mol_type = protein
                        note = Humanized 21H7 VHH1 with N-terminal consensus
                         residue, and consensus CDR1
                        organism = synthetic construct
VARIANT                 1
                        note = X is E or Q
VARIANT                 33
                        note = X is A or T
VARIANT                 35
                        note = X is A or G
SEQUENCE: 178
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGT IGRPYDYWGQ GTQVTVSS    118

SEQ ID NO: 179          moltype = AA  length = 118
FEATURE                 Location/Qualifiers
source                  1..118
                        mol_type = protein
```

```
                        note = Humanized 21H7 VHH1 with N-terminal consensus
                         residue, and consensus CDR2A
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
                        note = X is D or E
SEQUENCE: 179
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGT IGRPYDYWGQ GTQVTVSS    118

SEQ ID NO: 180          moltype = AA  length = 118
FEATURE                 Location/Qualifiers
source                  1..118
                        mol_type = protein
                        note = Humanized 21H7 VHH1 with N-terminal consensus
                         residue, and consensus CDR3A
                        organism = synthetic construct
VARIANT                 1
                        note = X is E or Q
VARIANT                 100
                        note = X is I or T
VARIANT                 101
                        note = X is F or I
VARIANT                 106
                        note = X is E or D
SEQUENCE: 180
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXYWGQ GTQVTVSS    118

SEQ ID NO: 181          moltype = AA  length = 118
FEATURE                 Location/Qualifiers
source                  1..118
                        mol_type = protein
                        note = Humanized 21H7 VHH1 with N-terminal consensus
                         residue, and consensus CDRs1 and 2A
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 62
                        note = X is D or E
SEQUENCE: 181
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGT IGRPYDYWGQ GTQVTVSS    118

SEQ ID NO: 182          moltype = AA  length = 118
FEATURE                 Location/Qualifiers
source                  1..118
                        mol_type = protein
                        note = Humanized 21H7 VHH1 with N-terminal consensus
                         residue, and consensus CDRs1 and 3A
                        organism = synthetic construct
VARIANT                 1
                        note = X is E or Q
VARIANT                 33
                        note = X is A or T
VARIANT                 35
                        note = X is A or G
VARIANT                 100
                        note = X is I or T
VARIANT                 101
                        note = X is F or I
VARIANT                 106
```

```
                         note = X is E or D
SEQUENCE: 182
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXYWGQ GTQVTVSS    118

SEQ ID NO: 183           moltype = AA  length = 118
FEATURE                  Location/Qualifiers
source                   1..118
                         mol_type = protein
                         note = Humanized 21H7 VHH1 with N-terminal consensus
                          residue, and consensus CDRs2A and 3A
                         organism = synthetic construct
VARIANT                  1
                         note = X is E or Q
VARIANT                  57
                         note = X is T or V
VARIANT                  58
                         note = X is L or M
VARIANT                  60
                         note = X is K or N
VARIANT                  62
                         note = X is D or E
VARIANT                  100
                         note = X is I or T
VARIANT                  101
                         note = X is F or I
VARIANT                  106
                         note = X is E or D
SEQUENCE: 183
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGX XGRPYXYWGQ GTQVTVSS    118

SEQ ID NO: 184           moltype = AA  length = 118
FEATURE                  Location/Qualifiers
source                   1..118
                         mol_type = protein
                         note = Humanized 21H7 VHH1 with N-terminal consensus
                          residue, and consensus CDRs1, 2A and 3A
                         organism = synthetic construct
VARIANT                  1
                         note = X is E or Q
VARIANT                  33
                         note = X is A or T
VARIANT                  35
                         note = X is A or G
VARIANT                  57
                         note = X is T or V
VARIANT                  58
                         note = X is L or M
VARIANT                  60
                         note = X is K or N
VARIANT                  62
                         note = X is D or E
VARIANT                  100
                         note = X is I or T
VARIANT                  101
                         note = X is F or I
VARIANT                  106
                         note = X is E or D
SEQUENCE: 184
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGX XGRPYXYWGQ GTQVTVSS    118

SEQ ID NO: 185           moltype = AA  length = 121
FEATURE                  Location/Qualifiers
source                   1..121
                         mol_type = protein
                         note = Humanized 21H7 VHH2 with one amino acid consensus
                          addition at N-terminus
                         organism = synthetic construct
VARIANT                  1
                         note = X is Q or K
SEQUENCE: 185
XLVESGGGLV QPGGSLRLSC AASGRTFSTY IIGWFRQAPG KEREFVASIS WGGRGTYYAD  60
SVKDRFTISR DNPKNMVYLQ MNSLRAEDTA VYYCAAGDLP GGRRALDYDY WGQGTLVTVS  120
S                                                                 121

SEQ ID NO: 186           moltype = AA  length = 122
FEATURE                  Location/Qualifiers
```

```
source                  1..122
                        mol_type = protein
                        note = Humanized 21H7 VHH2 with two amino acid consensus
                         addition at N-terminus
                        organism = synthetic construct
VARIANT                 1
                        note = X is V
VARIANT                 2
                        note = X is Q or K
SEQUENCE: 186
XXLVESGGGL VQPGGSLRLS CAASGRTFST YIIGWFRQAP GKEREFVASI SWGGRGTYYA  60
DSVKDRFTIS RDNPKNMVYL QMNSLRAEDT AVYYCAAGDL PGGRRALDYD YWGQGTLVTV  120
SS                                                                 122

SEQ ID NO: 187          moltype = AA  length = 123
FEATURE                 Location/Qualifiers
source                  1..123
                        mol_type = protein
                        note = Humanized 21H7 VHH2 with three amino acid consensus
                         addition at N-terminus
                        organism = synthetic construct
VARIANT                 1
                        note = X is E or Q
VARIANT                 2
                        note = X is V
VARIANT                 3
                        note = X is Q or K
SEQUENCE: 187
XXXLVESGGG LVQPGGSLRL SCAASGRTFS TYIIGWFRQA PGKEREFVAS ISWGGRGTYY  60
ADSVKDRFTI SRDNPKNMVY LQMNSLRAED TAVYYCAAGD LPGGRRALDY DYWGQGTLVT  120
VSS                                                                123

SEQ ID NO: 188          moltype = AA  length = 38
FEATURE                 Location/Qualifiers
source                  1..38
                        mol_type = protein
                        note = Humanized 21H7 linker connecting VHH1 and VHH2
                        organism = synthetic construct
SEQUENCE: 188
GGGSGGGGSG GGGSGGGGSG GGGSGGGGSG GGGSEGVG                          38

SEQ ID NO: 189          moltype = AA  length = 276
FEATURE                 Location/Qualifiers
source                  1..276
                        mol_type = protein
                        note = Humanized 21H7 co-binder with VHH1 N-terminal
                         consensus residue
                        organism = synthetic construct
VARIANT                 1
                        note = X is E or Q
SEQUENCE: 189
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSS                            276

SEQ ID NO: 190          moltype = AA  length = 277
FEATURE                 Location/Qualifiers
source                  1..277
                        mol_type = protein
                        note = Humanized 21H7 co-binder with VHH1 N-terminal
                         consensus residue, and VHH2 with one amino acid consensus
                         addition at N-terminus
                        organism = synthetic construct
VARIANT                 1
                        note = X is E or Q
VARIANT                 157
                        note = X is Q or K
SEQUENCE: 190
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                           277

SEQ ID NO: 191          moltype = AA  length = 278
FEATURE                 Location/Qualifiers
source                  1..278
```

```
                        mol_type = protein
                        note = Humanized 21H7 co-binder with VHH1 N-terminal
                         consensus residue, and VHH2 with two amino acid consensus
                         addition at N-terminus
                        organism = synthetic construct
VARIANT                 1
                        note = X is E or Q
VARIANT                 157
                        note = X is V
VARIANT                 158
                        note = X is Q or K
SEQUENCE: 191
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                          278

SEQ ID NO: 192          moltype = AA  length = 279
FEATURE                 Location/Qualifiers
source                  1..279
                        mol_type = protein
                        note = Humanized 21H7 co-binder with VHH1 N-terminal
                         consensus residue, and VHH2 with three amino acid
                         consensus addition at N-terminus
                        organism = synthetic construct
VARIANT                 1
                        note = X is E or Q
VARIANT                 157
                        note = X is E or Q
VARIANT                 159
                        note = X is Q or K
VARIANT                 158
                        note = X is V
SEQUENCE: 192
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXXXL VESGGGLVQP GGSLRLSCAA  180
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                         279

SEQ ID NO: 193          moltype = AA  length = 276
FEATURE                 Location/Qualifiers
source                  1..276
                        mol_type = protein
                        note = Humanized 21H7 co-binder with VHH1 N-terminal
                         consensus residue and consensus CDR1
                        organism = synthetic construct
VARIANT                 1
                        note = X is E or Q
VARIANT                 33
                        note = X is A or T
VARIANT                 35
                        note = X is A or G
SEQUENCE: 193
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSS                            276

SEQ ID NO: 194          moltype = AA  length = 277
FEATURE                 Location/Qualifiers
source                  1..277
                        mol_type = protein
                        note = Humanized 21H7 co-binder with VHH1 N-terminal
                         consensus residue and consensus CDR1, and VHH2 with one
                         amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 157
                        note = X is Q or K
SEQUENCE: 194
XVQLVESGGG LVQPGGSLRL SCAASGGTFS SYXMXWFRQA PGKEREYVGG ISSSGYVMYN  60
```

```
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                           277

SEQ ID NO: 195          moltype = AA  length = 278
FEATURE                 Location/Qualifiers
source                  1..278
                        mol_type = protein
                        note = Humanized 21H7 co-binder with VHH1 N-terminal
                         consensus residue and consensus CDR1, and VHH2 with two
                         amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 157
                        note = X is V
VARIANT                 158
                        note = X is Q or K
SEQUENCE: 195
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                          278

SEQ ID NO: 196          moltype = AA  length = 279
FEATURE                 Location/Qualifiers
source                  1..279
                        mol_type = protein
                        note = Humanized 21H7 co-binder with VHH1 N-terminal
                         consensus residue and consensus CDR1, and VHH2 with three
                         amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 157
                        note = X is E or Q
VARIANT                 158
                        note = X is V
VARIANT                 159
                        note = X is Q or K
SEQUENCE: 196
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXXXL VESGGGLVQP GGSLRLSCAA  180
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                         279

SEQ ID NO: 197          moltype = AA  length = 276
FEATURE                 Location/Qualifiers
source                  1..276
                        mol_type = protein
                        note = Humanized 21H7 co-binder with VHH1 N-terminal
                         consensus residue and consensus CDR2A
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
                        note = X is D or E
SEQUENCE: 197
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
```

```
AEDTAVYYCA AGDLPGGRRA LDYDYWGQGT LVTVSS                          276

SEQ ID NO: 198          moltype = AA  length = 277
FEATURE                 Location/Qualifiers
source                  1..277
                        mol_type = protein
                        note = Humanized 21H7 co-binder with VHH1 N-terminal
                         consensus residue and consensus CDR2A, and VHH2 with one
                         amino acid consensus addition at N-terminus
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
                        note = X is D or E
VARIANT                 157
                        note = X is Q or K
SEQUENCE: 198
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                         277

SEQ ID NO: 199          moltype = AA  length = 278
FEATURE                 Location/Qualifiers
source                  1..278
                        mol_type = protein
                        note = Humanized 21H7 co-binder with VHH1 N-terminal
                         consensus residue and consensus CDR2A, and VHH2 with two
                         amino acid consensus addition at N-terminus
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
                        note = X is D or E
VARIANT                 158
                        note = X is Q or K
VARIANT                 157
                        note = X is V
SEQUENCE: 199
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                        278

SEQ ID NO: 200          moltype = AA  length = 279
FEATURE                 Location/Qualifiers
source                  1..279
                        mol_type = protein
                        note = Humanized 21H7 co-binder with VHH1 N-terminal
                         consensus residue and consensus CDR2A, and VHH2 with three
                         amino acid consensus addition at N-terminus
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
                        note = X is D or E
VARIANT                 157
                        note = X is E or Q
VARIANT                 158
```

```
                        note = X is V
VARIANT                 159
                        note = X is Q or K
SEQUENCE: 200
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXXXL VESGGGLVQP GGSLRLSCAA  180
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                        279

SEQ ID NO: 201          moltype = AA  length = 276
FEATURE                 Location/Qualifiers
source                  1..276
                        mol_type = protein
                        note = Humanized 21H7 co binder with VHH1 N-terminal
                         consensus residue and consensus CDR3A
                        organism = synthetic construct
VARIANT                 1
                        note = X is E or Q
VARIANT                 100
                        note = X is I or T
VARIANT                 101
                        note = X is F or I
VARIANT                 106
                        note = X is E or D
SEQUENCE: 201
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSS                           276

SEQ ID NO: 202          moltype = AA  length = 277
FEATURE                 Location/Qualifiers
source                  1..277
                        mol_type = protein
                        note = Humanized 21H7 co-binder with VHH1 N-terminal
                         consensus residue and consensus CDR3A, and VHH2 with one
                         amino acid consensus addition at N-terminus
                        organism = synthetic construct
VARIANT                 1
                        note = X is E or Q
VARIANT                 100
                        note = X is I or T
VARIANT                 101
                        note = X is F or I
VARIANT                 106
                        note = X is E or D
VARIANT                 157
                        note = X is Q or K
SEQUENCE: 202
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                          277

SEQ ID NO: 203          moltype = AA  length = 278
FEATURE                 Location/Qualifiers
source                  1..278
                        mol_type = protein
                        note = Humanized 21H7 co-binder with VHH1 N-terminal
                         consensus residue and consensus CDR3A, and VHH2 with two
                         amino acid consensus addition at N-terminus
                        organism = synthetic construct
VARIANT                 1
                        note = X is E or Q
VARIANT                 100
                        note = X is I or T
VARIANT                 101
                        note = X is F or I
VARIANT                 106
                        note = X is E or D
VARIANT                 157
                        note = X is V
VARIANT                 158
                        note = X is Q or K
SEQUENCE: 203
XVQLVESGGG LVQPGGSLRL SCAASGGTFS SYTMGWFRQA PGKEREYVGG ISSSGYVMYN  60
```

```
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                          278

SEQ ID NO: 204          moltype = AA  length = 279
FEATURE                 Location/Qualifiers
source                  1..279
                        mol_type = protein
                        note = Humanized 21H7 co-binder with VHH1 N-terminal
                         consensus residue and consensus CDR3A, and VHH2 with three
                         amino acid consensus addition at N-terminus
                        organism = synthetic construct
VARIANT                 1
                        note = X is E or Q
VARIANT                 100
                        note = X is I or T
VARIANT                 101
                        note = X is F or I
VARIANT                 106
                        note = X is E or D
VARIANT                 157
                        note = X is E or Q
VARIANT                 158
                        note = X is V
VARIANT                 159
                        note = X is Q or K
SEQUENCE: 204
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGXXXL VESGGGLVQP GGSLRLSCAA  180
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                         279

SEQ ID NO: 205          moltype = AA  length = 276
FEATURE                 Location/Qualifiers
source                  1..276
                        mol_type = protein
                        note = Humanized 21H7 co-binder with VHH1 N-terminal
                         consensus residue and consensus CDRs1 and 2A
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 62
                        note = X is D or E
SEQUENCE: 205
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSS                            276

SEQ ID NO: 206          moltype = AA  length = 277
FEATURE                 Location/Qualifiers
source                  1..277
                        mol_type = protein
                        note = Humanized 21H7 co-binder with VHH1 N-terminal
                         consensus residue and consensus CDRs1 and 2A, and VHH2
                         with one amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
```

```
                        note = X is L or M
VARIANT                 60
                        note = 5 is K or N
VARIANT                 62
                        note = X is D or E
VARIANT                 157
                        note = X is Q or K
SEQUENCE: 206
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                          277

SEQ ID NO: 207          moltype = AA  length = 278
FEATURE                 Location/Qualifiers
source                  1..278
                        mol_type = protein
                        note = Humanized 21H7 co-binder with VHH1 N-terminal
                         consensus residue and consensus CDRs1 and 2A, and VHH2
                         with two amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 62
                        note = X is D or E
VARIANT                 158
                        note = X is Q or K
VARIANT                 157
                        note = X is V
SEQUENCE: 207
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                         278

SEQ ID NO: 208          moltype = AA  length = 279
FEATURE                 Location/Qualifiers
source                  1..279
                        mol_type = protein
                        note = Humanized 21H7 co-binder with VHH1 N-terminal
                         consensus residue and consensus CDRs1 and 2A, and VHH2
                         with three amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 62
                        note = X is D or E
VARIANT                 157
                        note = X is E or Q
VARIANT                 158
                        note = X is V
VARIANT                 159
                        note = X is Q or K
SEQUENCE: 208
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXXXL VESGGGLVQP GGSLRLSCAA  180
```

```
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                         279

SEQ ID NO: 209          moltype = AA  length = 276
FEATURE                 Location/Qualifiers
source                  1..276
                        mol_type = protein
                        note = Humanized 21H7 co-binder with VHH1 N-terminal
                         consensus residue and consensus CDRs1 and 3A
                        organism = synthetic construct
VARIANT                 1
                        note = X is E or Q
VARIANT                 33
                        note = X is A or T
VARIANT                 35
                        note = X is A or G
VARIANT                 100
                        note = X is I or T
VARIANT                 101
                        note = X is F or I
VARIANT                 106
                        note = X is E or D
SEQUENCE: 209
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSS                            276

SEQ ID NO: 210          moltype = AA  length = 277
FEATURE                 Location/Qualifiers
source                  1..277
                        mol_type = protein
                        note = Humanized 21H7 co-binder with VHH1 N-terminal
                         consensus residue and consensus CDRs1 and 3A, and VHH2
                         with one amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 100
                        note = X is I or T
VARIANT                 101
                        note = X is F or I
VARIANT                 106
                        note = X is E or D
VARIANT                 157
                        note = X is Q or K
SEQUENCE: 210
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                           277

SEQ ID NO: 211          moltype = AA  length = 278
FEATURE                 Location/Qualifiers
source                  1..278
                        mol_type = protein
                        note = Humanized 21H7 co-binder with VHH1 N-terminal
                         consensus residue and consensus CDRs1 and 3A, and VHH2
                         with two amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 100
                        note = X is I or T
VARIANT                 101
                        note = X is F or I
VARIANT                 106
                        note = X is E or D
VARIANT                 157
```

```
                        note = X is V
VARIANT                 158
                        note = X is Q or K
SEQUENCE: 211
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                          278

SEQ ID NO: 212          moltype = AA  length = 279
FEATURE                 Location/Qualifiers
source                  1..279
                        mol_type = protein
                        note = Humanized 21H7 co-binder with VHH1 N-terminal
                         consensus residue and consensus CDRs1 and 3A, and VHH2
                         with three amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 100
                        note = X is I or T
VARIANT                 101
                        note = X is F or I
VARIANT                 106
                        note = X is E or D
VARIANT                 157
                        note = X is E or Q
VARIANT                 158
                        note = X is V
VARIANT                 159
                        note = X is Q or K
SEQUENCE: 212
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGXXXL VESGGGLVQP GGSLRLSCAA  180
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                         279

SEQ ID NO: 213          moltype = AA  length = 276
FEATURE                 Location/Qualifiers
source                  1..276
                        mol_type = protein
                        note = Humanized 21H7 co-binder with VHH1 N-terminal
                         consensus residue and consensus CDRs2A and 3A
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
                        note = X is D or E
VARIANT                 100
                        note = X is I or T
VARIANT                 101
                        note = X is F or I
VARIANT                 106
                        note = X is E or D
SEQUENCE: 213
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSS                            276

SEQ ID NO: 214          moltype = AA  length = 277
FEATURE                 Location/Qualifiers
source                  1..277
                        mol_type = protein
                        note = Humanized 21H7 co-binder with VHH1 N-terminal
                         consensus residue and consensus CDRs2A and 3A, and VHH2
```

```
                         with one amino acid consensus addition at N-terminus
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
                        note = X is D or E
VARIANT                 100
                        note = X is I or T
VARIANT                 101
                        note = X is F or I
VARIANT                 106
                        note = X is E or D
VARIANT                 157
                        note = X is Q or K
SEQUENCE: 214
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                          277

SEQ ID NO: 215          moltype = AA  length = 278
FEATURE                 Location/Qualifiers
source                  1..278
                        mol_type = protein
                        note = Humanized 21H7 co-binder with VHH1 N-terminal
                         consensus residue and consensus CDRs2A and 3A, and VHH2
                         with two amino acid consensus addition at N-terminus
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
                        note = X is D or E
VARIANT                 100
                        note = X is I or T
VARIANT                 101
                        note = X is F or I
VARIANT                 106
                        note = X is E or D
VARIANT                 157
                        note = X is V
VARIANT                 158
                        note = X is Q or K
SEQUENCE: 215
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                         278

SEQ ID NO: 216          moltype = AA  length = 279
FEATURE                 Location/Qualifiers
source                  1..279
                        mol_type = protein
                        note = Humanized 21H7 co-binder with VHH1 N-terminal
                         consensus residue and consensus CDRs2A and 3A, and VHH2
                         with three amino acid consensus addition at N-terminus
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 62
```

```
                         note = X is D or E
VARIANT                  100
                         note = X is I or T
VARIANT                  101
                         note = X is F or I
VARIANT                  106
                         note = X is E or D
VARIANT                  157
                         note = X is E or Q
VARIANT                  158
                         note = X is V
VARIANT                  159
                         note = X is Q or K
SEQUENCE: 216
XVQLVESGGG LVQPGGSLRL SCAASGGTFS SYTMGWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGXXXL VESGGGLVQP GGSLRLSCAA  180
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                         279

SEQ ID NO: 217           moltype = AA  length = 276
FEATURE                  Location/Qualifiers
source                   1..276
                         mol_type = protein
                         note = Humanized 21H7 co-binder with VHH1 N-terminal
                          consensus residue and consensus CDRs1, 2A and 3A
                         organism = synthetic construct
VARIANT                  1
                         note = X is E or Q
VARIANT                  33
                         note = X is A or T
VARIANT                  35
                         note = X is A or G
VARIANT                  57
                         note = X is T or V
VARIANT                  58
                         note = X is L or M
VARIANT                  60
                         note = X is K or N
VARIANT                  62
                         note = X is D or E
VARIANT                  100
                         note = X is I or T
VARIANT                  101
                         note = X is F or I
VARIANT                  106
                         note = X is E or D
SEQUENCE: 217
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSS                            276

SEQ ID NO: 218           moltype = AA  length = 277
FEATURE                  Location/Qualifiers
source                   1..277
                         mol_type = protein
                         note = Humanized 21H7 co-binder with VHH1 N-terminal
                          consensus residue and consensus CDRs1, 2A and 3A, and VHH2
                          with one amino acid consensus addition at N-terminus
                         organism = synthetic construct
VARIANT                  1
                         note = X is E or Q
VARIANT                  33
                         note = X is A or T
VARIANT                  35
                         note = X is A or G
VARIANT                  57
                         note = X is T or V
VARIANT                  58
                         note = X is L or M
VARIANT                  60
                         note = X is K or N
VARIANT                  62
                         note = X is D or E
VARIANT                  100
                         note = X is I or T
VARIANT                  101
```

```
                         note = X is F or I
VARIANT                  106
                         note = X is E or D
VARIANT                  157
                         note = X is Q or K
SEQUENCE: 218
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                           277

SEQ ID NO: 219           moltype = AA  length = 278
FEATURE                  Location/Qualifiers
source                   1..278
                         mol_type = protein
                         note = Humanized 21H7 co-binder with VHH1 N-terminal
                          consensus residue and consensus CDRs1, 2A and 3A, and VHH2
                          with two amino acid consensus addition at N-terminus
                         organism = synthetic construct
VARIANT                  1
                         note = X is E or Q
VARIANT                  33
                         note = X is A or T
VARIANT                  35
                         note = X is A or G
VARIANT                  57
                         note = X is T or V
VARIANT                  58
                         note = X is L or M
VARIANT                  60
                         note = X is K or N
VARIANT                  62
                         note = X is D or E
VARIANT                  100
                         note = X is I or T
VARIANT                  101
                         note = X is F or I
VARIANT                  106
                         note = 9 is E or D
VARIANT                  157
                         note = X is V
VARIANT                  158
                         note = X is Q or K
SEQUENCE: 219
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                          278

SEQ ID NO: 220           moltype = AA  length = 279
FEATURE                  Location/Qualifiers
source                   1..279
                         mol_type = protein
                         note = Humanized 21H7 co-binder with VHH1 N-terminal
                          consensus residue and consensus CDRs1, 2A and 3A, and VHH2
                          with three amino acid consensus addition at N-terminus
                         organism = synthetic construct
VARIANT                  1
                         note = X is E or Q
VARIANT                  33
                         note = X is A or T
VARIANT                  35
                         note = X is A or G
VARIANT                  57
                         note = X is T or V
VARIANT                  58
                         note = X is L or M
VARIANT                  60
                         note = X is K or N
VARIANT                  62
                         note = X is D or E
VARIANT                  100
                         note = X is I or T
VARIANT                  101
                         note = X is F or I
VARIANT                  106
                         note = X is E or D
```

```
VARIANT                157
                       note = X is E or Q
VARIANT                158
                       note = X is V
VARIANT                159
                       note = X is Q or K
SEQUENCE: 220
XVQLVESGGG LVQPGGSLRL SCAASGGTFS SYXMXWFRQA PGKEREYVGG ISSSGYXXYX  60
SXSMKGRFTI SRDNAKNTLY LQMNSLRAED TAVYYCAAGX XGRPYXYWGQ GTQVTVSSGG  120
GSGGGGSGGG GSGGGGSGGG GSGGGGSGGG GSEGVGXXXL VESGGGLVQP GGSLRLSCAA  180
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                         279

SEQ ID NO: 221         moltype = AA  length = 118
FEATURE                Location/Qualifiers
source                 1..118
                       mol_type = protein
                       note = Humanized 21H7 VHH1 with N-terminal consensus
                        residue, and consensus CDR2B
                       organism = synthetic construct
VARIANT                1
                       note = X is E or Q
VARIANT                57
                       note = X is T or V
VARIANT                58
                       note = X is L or M
VARIANT                60
                       note = X is K or N
VARIANT                61
                       note = X is S or A
VARIANT                62
                       note = X is D or E
SEQUENCE: 221
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGT IGRPYDYWGQ GTQVTVSS    118

SEQ ID NO: 222         moltype = AA  length = 118
FEATURE                Location/Qualifiers
source                 1..118
                       mol_type = protein
                       note = Humanized 21H7 VHH1 with N-terminal consensus
                        residue, and consensus CDR3B
                       organism = synthetic construct
VARIANT                1
                       note = X is E or Q
VARIANT                100
                       note = X is I, T, or V
VARIANT                101
                       note = X is F or I
VARIANT                106
                       note = X is E or D
VARIANT                107
                       note = X is Y or F
SEQUENCE: 222
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXXWGQ GTQVTVSS    118

SEQ ID NO: 223         moltype = AA  length = 118
FEATURE                Location/Qualifiers
source                 1..118
                       mol_type = protein
                       note = Humanized 21H7 VHH1 with N-terminal consensus
                        residue, and consensus CDRs1 and 2B
                       organism = synthetic construct
VARIANT                1
                       note = X is E or Q
VARIANT                33
                       note = X is A or T
VARIANT                35
                       note = X is A or G
VARIANT                57
                       note = X is T or V
VARIANT                58
                       note = X is L or M
VARIANT                60
                       note = X is K or N
VARIANT                61
                       note = X is S or A
VARIANT                62
```

```
                         note = X is D or E
SEQUENCE: 223
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGT IGRPYDYWGQ GTQVTVSS    118

SEQ ID NO: 224           moltype = AA  length = 118
FEATURE                  Location/Qualifiers
source                   1..118
                         mol_type = protein
                         note = Humanized 21H7 VHH1 with N-terminal consensus
                          residue, and consensus CDRs1 and 3B
                         organism = synthetic construct
VARIANT                  1
                         note = X is E or Q
VARIANT                  33
                         note = X is A or T
VARIANT                  35
                         note = X is A or G
VARIANT                  100
                         note = X is I, T, or V
VARIANT                  101
                         note = X is F or I
VARIANT                  106
                         note = X is E or D
VARIANT                  107
                         note = X is Y or F
SEQUENCE: 224
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXXWGQ GTQVTVSS    118

SEQ ID NO: 225           moltype = AA  length = 118
FEATURE                  Location/Qualifiers
source                   1..118
                         mol_type = protein
                         note = Humanized 21H7 VHH1 with N-terminal consensus
                          residue, and consensus CDRs2B and 3B
                         organism = synthetic construct
VARIANT                  1
                         note = X is E or Q
VARIANT                  57
                         note = X is T or V
VARIANT                  58
                         note = X is L or M
VARIANT                  60
                         note = X is K or N
VARIANT                  61
                         note = X is S or A
VARIANT                  62
                         note = X is D or E
VARIANT                  100
                         note = X is I, T, or V
VARIANT                  101
                         note = X is F or I
VARIANT                  106
                         note = X is E or D
VARIANT                  107
                         note = X is Y or F
SEQUENCE: 225
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGX XGRPYXXWGQ GTQVTVSS    118

SEQ ID NO: 226           moltype = AA  length = 118
FEATURE                  Location/Qualifiers
source                   1..118
                         mol_type = protein
                         note = Humanized 21H7 VHH1 with N-terminal consensus
                          residue, and consensus CDRs1, 2B and 3B
                         organism = synthetic construct
VARIANT                  1
                         note = X is E or Q
VARIANT                  33
                         note = X is A or T
VARIANT                  35
                         note = X is A or G
VARIANT                  57
                         note = X is T or V
VARIANT                  58
                         note = X is L or M
VARIANT                  60
```

```
                          note = X is K or N
VARIANT                   61
                          note = X is S or A
VARIANT                   62
                          note = X is D or E
VARIANT                   100
                          note = X is I, T, or V
VARIANT                   101
                          note = X is F or I
VARIANT                   106
                          note = X is E or D
VARIANT                   107
                          note = X is Y or F
SEQUENCE: 226
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGX XGRPYXXWGQ GTQVTVSS    118

SEQ ID NO: 227            moltype = AA  length = 276
FEATURE                   Location/Qualifiers
source                    1..276
                          mol_type = protein
                          note = Humanized 21H7 co-binder with VHH1 N-terminal
                           consensus residue, and consensus CDR2B
                          organism = synthetic construct
VARIANT                   1
                          note = X is E or Q
VARIANT                   57
                          note = X is T or V
VARIANT                   58
                          note = X is L or M
VARIANT                   60
                          note = X is K or N
VARIANT                   61
                          note = X is S or A
VARIANT                   62
                          note = X is D or E
SEQUENCE: 227
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSS                            276

SEQ ID NO: 228            moltype = AA  length = 277
FEATURE                   Location/Qualifiers
source                    1..277
                          mol_type = protein
                          note = Humanized 21H7 co-binder with VHH1 N-terminal
                           consensus residue, and consensus CDR2B, and VHH2 with one
                           amino acid consensus addition at N-terminus
                          organism = synthetic construct
VARIANT                   1
                          note = X is E or Q
VARIANT                   57
                          note = X is T or V
VARIANT                   58
                          note = X is L or M
VARIANT                   60
                          note = X is K or N
VARIANT                   61
                          note = X is S or A
VARIANT                   62
                          note = X is D or E
VARIANT                   157
                          note = X is Q or K
SEQUENCE: 228
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                           277

SEQ ID NO: 229            moltype = AA  length = 278
FEATURE                   Location/Qualifiers
source                    1..278
                          mol_type = protein
                          note = Humanized 21H7 co-binder with VHH1 N-terminal
                           consensus residue, and consensus CDR2B, and VHH2 with two
                           amino acid consensus addition at N-terminus
```

```
                         organism = synthetic construct
VARIANT                  1
                         note = X is E or Q
VARIANT                  57
                         note = X is T or V
VARIANT                  58
                         note = X is L or M
VARIANT                  60
                         note = X is K or N
VARIANT                  61
                         note = X is S or A
VARIANT                  62
                         note = X is D or E
VARIANT                  158
                         note = X is Q or K
VARIANT                  157
                         note = X is V
SEQUENCE: 229
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                          278

SEQ ID NO: 230           moltype = AA  length = 279
FEATURE                  Location/Qualifiers
source                   1..279
                         mol_type = protein
                         note = Humanized 21H7 co-binder with VHH1 N-terminal
                          consensus residue, and consensus CDR2B, and VHH2 with
                          three amino acid consensus addition at N-terminus
                         organism = synthetic construct
VARIANT                  1
                         note = X is E or Q
VARIANT                  57
                         note = X is T or V
VARIANT                  58
                         note = X is L or M
VARIANT                  60
                         note = X is K or N
VARIANT                  61
                         note = X is S or A
VARIANT                  62
                         note = X is D or E
VARIANT                  157
                         note = X is E or Q
VARIANT                  158
                         note = X is V
VARIANT                  159
                         note = X is Q or K
SEQUENCE: 230
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXXXL VESGGGLVQP GGSLRLSCAA  180
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                         279

SEQ ID NO: 231           moltype = AA  length = 276
FEATURE                  Location/Qualifiers
source                   1..276
                         mol_type = protein
                         note = Humanized 21H7 co-binder with VHH1 N-terminal
                          consensus residue, and consensus CDR3B
                         organism = synthetic construct
VARIANT                  1
                         note = X is E or Q
VARIANT                  100
                         note = X is I, T, or V
VARIANT                  101
                         note = X is F or I
VARIANT                  106
                         note = X is E or D
VARIANT                  107
                         note = X is Y or F
SEQUENCE: 231
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
```

```
AEDTAVYYCA AGDLPGGRRA LDYDYWGQGT LVTVSS                          276

SEQ ID NO: 232          moltype = AA  length = 277
FEATURE                 Location/Qualifiers
source                  1..277
                        mol_type = protein
                        note = Humanized 21H7 co-binder with VHH1 N-terminal
                         consensus residue, and consensus CDR3B, and VHH2 with one
                         amino acid consensus addition at N-terminus
                        organism = synthetic construct
VARIANT                 1
                        note = X is E or Q
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is Q or K
SEQUENCE: 232
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                         277

SEQ ID NO: 233          moltype = AA  length = 278
FEATURE                 Location/Qualifiers
source                  1..278
                        mol_type = protein
                        note = Humanized 21H7 co-binder with VHH1 N-terminal
                         consensus residue, and consensus CDR3B, and VHH2 with two
                         amino acid consensus addition at N-terminus
                        organism = synthetic construct
VARIANT                 1
                        note = X is E or Q
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is V
VARIANT                 158
                        note = X is Q or K
SEQUENCE: 233
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                        278

SEQ ID NO: 234          moltype = AA  length = 279
FEATURE                 Location/Qualifiers
source                  1..279
                        mol_type = protein
                        note = Humanized 21H7 co-binder with VHH1 N-terminal
                         consensus residue, and consensus CDR3B, and VHH2 with
                         three amino acid consensus addition at N-terminus
                        organism = synthetic construct
VARIANT                 1
                        note = X is E or Q
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is E or Q
VARIANT                 158
```

```
                        note = X is V
VARIANT                 159
                        note = X is Q or K
SEQUENCE: 234
XVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGXXXL VESGGGLVQP GGSLRLSCAA  180
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                         279

SEQ ID NO: 235          moltype = AA  length = 276
FEATURE                 Location/Qualifiers
source                  1..276
                        mol_type = protein
                        note = Humanized 21H7 co-binder with VHH1 N-terminal
                         consensus residue, and consensus CDRs1 and 2B
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
SEQUENCE: 235
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSS                            276

SEQ ID NO: 236          moltype = AA  length = 277
FEATURE                 Location/Qualifiers
source                  1..277
                        mol_type = protein
                        note = Humanized 21H7 co-binder with VHH1 N-terminal
                         consensus residue, and consensus CDRs1 and 2B, and VHH2
                         with one amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 157
                        note = X is Q or K
SEQUENCE: 236
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                           277

SEQ ID NO: 237          moltype = AA  length = 278
FEATURE                 Location/Qualifiers
source                  1..278
                        mol_type = protein
                        note = Humanized 21H7 co-binder with VHH1 N-terminal
                         consensus residue, and consensus CDRs1 and 2B, and VHH2
```

```
                       with two amino acid consensus addition at N-terminus
                      organism = synthetic construct
VARIANT               1
                      note = X is E or Q
VARIANT               33
                      note = X is A or T
VARIANT               35
                      note = X is A or G
VARIANT               57
                      note = X is T or V
VARIANT               58
                      note = X is L or M
VARIANT               60
                      note = X is K or N
VARIANT               61
                      note = X is S or A
VARIANT               62
                      note = X is D or E
VARIANT               157
                      note = X is V
VARIANT               158
                      note = X is Q or K
SEQUENCE: 237
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                          278

SEQ ID NO: 238        moltype = AA  length = 279
FEATURE               Location/Qualifiers
source                1..279
                      mol_type = protein
                      note = Humanized 21H7 co-binder with VHH1 N-terminal
                       consensus residue, and consensus CDRs1 and 2B, and VHH2
                       with three amino acid consensus addition at N-terminus
                      organism = synthetic construct
VARIANT               1
                      note = X is E or Q
VARIANT               33
                      note = X is A or T
VARIANT               35
                      note = X is A or G
VARIANT               57
                      note = X is T or V
VARIANT               58
                      note = X is L or M
VARIANT               60
                      note = X is K or N
VARIANT               61
                      note = X is S or A
VARIANT               62
                      note = X is D or E
VARIANT               157
                      note = X is E or Q
VARIANT               158
                      note = X is V
VARIANT               159
                      note = X is Q or K
SEQUENCE: 238
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSEGVGXXXL VESGGGLVQP GGSLRLSCAA  180
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                         279

SEQ ID NO: 239        moltype = AA  length = 276
FEATURE               Location/Qualifiers
source                1..276
                      mol_type = protein
                      note = Humanized 21H7 co-binder with VHH1 N-terminal
                       consensus residue, and consensus CDRs1 and 3B
                      organism = synthetic construct
VARIANT               1
                      note = X is E or Q
VARIANT               33
                      note = X is A or T
VARIANT               35
                      note = X is A or G
```

```
VARIANT                 100
                        note = X is I, T, or V
VARIANT                 101
                        note = X is F or I
VARIANT                 106
                        note = X is E or D
VARIANT                 107
                        note = X is Y or F
SEQUENCE: 239
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSS                          276

SEQ ID NO: 240          moltype = AA  length = 277
FEATURE                 Location/Qualifiers
source                  1..277
                        mol_type = protein
                        note = Humanized 21H7 co-binder with VHH1 N-terminal
                         consensus residue, and consensus CDRs1 and 3B, and VHH2
                         with one amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is Q or K
SEQUENCE: 240
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                         277

SEQ ID NO: 241          moltype = AA  length = 278
FEATURE                 Location/Qualifiers
source                  1..278
                        mol_type = protein
                        note = Humanized 21H7 co-binder with VHH1 N-terminal
                         consensus residue, and consensus CDRs1 and 3B, and VHH2
                         with two amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is V
VARIANT                 158
                        note = X is Q or K
SEQUENCE: 241
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                        278
```

```
SEQ ID NO: 242          moltype = AA  length = 279
FEATURE                 Location/Qualifiers
source                  1..279
                        mol_type = protein
                        note = Humanized 21H7 co-binder with VHH1 N-terminal
                         consensus residue, and consensus CDRs1 and 3B, and VHH2
                         with three amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is E or Q
VARIANT                 158
                        note = X is V
VARIANT                 159
                        note = X is Q or K
SEQUENCE: 242
XVQLVESGGG LVQPGGSLRL SCAASGGTFS SYXMXWFRQA PGKEREYVGG ISSSGYVMYN  60
SESMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGXXXL VESGGGLVQP GGSLRLSCAA  180
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                         279

SEQ ID NO: 243          moltype = AA  length = 276
FEATURE                 Location/Qualifiers
source                  1..276
                        mol_type = protein
                        note = Humanized 21H7 co-binder with VHH1 N-terminal
                         consensus residue, and consensus CDRs2B and 3B
                        organism = synthetic construct
VARIANT                 1
                        note = X is E or Q
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 100
                        note = X is I, T, or V
VARIANT                 101
                        note = X is F or I
VARIANT                 106
                        note = X is E or D
VARIANT                 107
                        note = X is Y or F
SEQUENCE: 243
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSS                            276

SEQ ID NO: 244          moltype = AA  length = 277
FEATURE                 Location/Qualifiers
source                  1..277
                        mol_type = protein
                        note = Humanized 21H7 co-binder with VHH1 N-terminal
                         consensus residue, and consensus CDRs2B and 3B, and VHH2
                         with one amino acid consensus addition at N-terminus
                        organism = synthetic construct
VARIANT                 1
                        note = X is E
```

```
VARIANT               57
                      note = X is T or V
VARIANT               58
                      note = X is L or M
VARIANT               60
                      note = X is K or N
VARIANT               61
                      note = X is S or A
VARIANT               62
                      note = X is D or E
VARIANT               100
                      note = X is I, T, or V
VARIANT               101
                      note = X is F or I
VARIANT               106
                      note = X is E or D
VARIANT               107
                      note = X is Y or F
VARIANT               157
                      note = X is Q or K
SEQUENCE: 244
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                           277

SEQ ID NO: 245        moltype = AA  length = 278
FEATURE               Location/Qualifiers
source                1..278
                      mol_type = protein
                      note = Humanized 21H7 co-binder with VHH1 N-terminal
                       consensus residue, and consensus CDRs2B and 3B, and VHH2
                       with two amino acid consensus addition at N-terminus
                      organism = synthetic construct
VARIANT               1
                      note = X is E or Q
VARIANT               57
                      note = X is T or V
VARIANT               58
                      note = X is L or M
VARIANT               60
                      note = X is K or N
VARIANT               61
                      note = X is S or A
VARIANT               62
                      note = X is D or E
VARIANT               100
                      note = X is I, T, or V
VARIANT               101
                      note = X is F or I
VARIANT               106
                      note = X is E or D
VARIANT               107
                      note = X is Y or F
VARIANT               157
                      note = X is V
VARIANT               158
                      note = X is Q or K
SEQUENCE: 245
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                          278

SEQ ID NO: 246        moltype = AA  length = 279
FEATURE               Location/Qualifiers
source                1..279
                      mol_type = protein
                      note = Humanized 21H7 co-binder with VHH1 N-terminal
                       consensus residue, and consensus CDRs2B and 3B, and VHH2
                       with three amino acid consensus addition at N-terminus
                      organism = synthetic construct
VARIANT               1
                      note = X is E or Q
VARIANT               57
                      note = X is T or V
VARIANT               58
```

```
                        note = X is L or M
VARIANT                 60
                        note = X is K or N
VARIANT                 61
                        note = X is S or A
VARIANT                 62
                        note = X is D or E
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is E or Q
VARIANT                 158
                        note = X is V
VARIANT                 159
                        note = X is Q or K
SEQUENCE: 246
XVQLVESGGG LVQPGGSLRL SCAASGGTFS SYTMGWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGXXXL VESGGGLVQP GGSLRLSCAA  180
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                         279

SEQ ID NO: 247          moltype = AA  length = 276
FEATURE                 Location/Qualifiers
source                  1..276
                        mol_type = protein
                        note = Humanized 21H7 co-binder with VHH1 N-terminal
                         consensus residue, and consensus CDRs1, 2B and 3B
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 100
                        note = X is I, T, or V
VARIANT                 101
                        note = X is F or I
VARIANT                 106
                        note = X is E or D
VARIANT                 107
                        note = X is Y or F
SEQUENCE: 247
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGLVES GGGLVQPGGS LRLSCAASGR  180
TFSTYIIGWF RQAPGKEREF VASISWGGRG TYYADSVKDR FTISRDNPKN MVYLQMNSLR  240
AEDTAVYYCA AGDLPGGRRA LDYDYWGQGT LVTVSS                            276

SEQ ID NO: 248          moltype = AA  length = 277
FEATURE                 Location/Qualifiers
source                  1..277
                        mol_type = protein
                        note = Humanized 21H7 co-binder with VHH1 N-terminal
                         consensus residue, and consensus CDRs1, 2B and 3B, VHH2
                         with one amino acid consensus addition at N-terminus
                        organism = synthetic construct
VARIANT                 1
                        note = X is E or Q
VARIANT                 33
                        note = X is A or T
VARIANT                 35
```

```
                        note = X is A or G
VARIANT                 57
                        note = X is T or V
VARIANT                 58
                        note = X is L or M
NON_STD                 60
                        note = X is K or N
NON_STD                 61
                        note = X is S or A
VARIANT                 62
                        note = X is D or E
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is Q or K
SEQUENCE: 248
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGXLVE SGGGLVQPGG SLRLSCAASG  180
RTFSTYIIGW FRQAPGKERE FVASISWGGR GTYYADSVKD RFTISRDNPK NMVYLQMNSL  240
RAEDTAVYYC AAGDLPGGRR ALDYDYWGQG TLVTVSS                           277

SEQ ID NO: 249          moltype = AA  length = 278
FEATURE                 Location/Qualifiers
source                  1..278
                        mol_type = protein
                        note = Humanized 21H7 co-binder with VHH1 N-terminal
                         consensus residue, and consensus CDRs1, 2B and 3B, and
                         VHH2 with two amino acid consensus addition at N-terminus
                        organism = synthetic construct
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is V
VARIANT                 158
                        note = X is Q or K
SEQUENCE: 249
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGXXLV ESGGGLVQPG GSLRLSCAAS  180
GRTFSTYIIG WFRQAPGKER EFVASISWGG RGTYYADSVK DRFTISRDNP KNMVYLQMNS  240
LRAEDTAVYY CAAGDLPGGR RALDYDYWGQ GTLVTVSS                          278

SEQ ID NO: 250          moltype = AA  length = 279
FEATURE                 Location/Qualifiers
source                  1..279
                        mol_type = protein
                        note = Humanized 21H7 co-binder with VHH1 N-terminal
                         consensus residue, and consensus CDRs1, 2B and 3B, and
                         VHH2 with three amino acid consensus addition at N-terminus
                        organism = synthetic construct
```

```
VARIANT                 1
                        note = X is E or Q
VARIANT                 33
                        note = X is A or T
VARIANT                 35
                        note = X is A or G
VARIANT                 57
                        note = X is T or V
VARIANT                 58
                        note = X is L or M
VARIANT                 60
                        note = X is K or N
VARIANT                 61
                        note = X is S or A
VARIANT                 62
                        note = X is D or E
VARIANT                 100
                        note = X is I, T, or V
VARIANT                 101
                        note = X is F or I
VARIANT                 106
                        note = X is E or D
VARIANT                 107
                        note = X is Y or F
VARIANT                 157
                        note = X is E or Q
VARIANT                 158
                        note = X is V
VARIANT                 159
                        note = X is Q or K
SEQUENCE: 250
XVQLVESGGG LVQPGGSLRL SCAASGGTFS SYXMXWFRQA PGKEREYVGG ISSSGYXXYX  60
XXSMKGRFTI SRDNAKNTLY LQMNSLRAED TAVYYCAAGX XGRPYXXWGQ GTQVTVSSGG  120
GSGGGGSGGG GSGGGGSGGG GSGGGGSGGG GSEGVGXXXL VESGGGLVQP GGSLRLSCAA  180
SGRTFSTYII GWFRQAPGKE REFVASISWG GRGTYYADSV KDRFTISRDN PKNMVYLQMN  240
SLRAEDTAVY YCAAGDLPGG RRALDYDYWG QGTLVTVSS                         279

SEQ ID NO: 251          moltype = AA  length = 5
FEATURE                 Location/Qualifiers
source                  1..5
                        mol_type = protein
                        note = Exemplary VHH2 consensus CDR1 (Kabat numbering)
                        organism = synthetic construct
VARIANT                 2
                        note = X is V, H, or Q
SEQUENCE: 251
IXAMG                                                              5

SEQ ID NO: 252          moltype = AA  length = 16
FEATURE                 Location/Qualifiers
source                  1..16
                        mol_type = protein
                        note = Exemplary VHH2 consensus CDR2 (Kabat numbering)
                        organism = synthetic construct
VARIANT                 8
                        note = X is T or R
SEQUENCE: 252
AITSGGRXHY RDSVKG                                                  16

SEQ ID NO: 253          moltype = AA  length = 12
FEATURE                 Location/Qualifiers
source                  1..12
                        mol_type = protein
                        note = Exemplary VHH2 consensus CDR3 (Kabat numbering)
                        organism = synthetic construct
VARIANT                 2
                        note = X is R, M, or T
VARIANT                 4
                        note = X is W, L, or R
VARIANT                 5
                        note = X is T or V
VARIANT                 6
                        note = X is S or A
SEQUENCE: 253
DXGXXXVGEY DY                                                      12

SEQ ID NO: 254          moltype = AA  length = 119
FEATURE                 Location/Qualifiers
source                  1..119
```

```
                        mol_type = protein
                        note = 20C7 VHH2 single binder
                        organism = synthetic construct
SEQUENCE: 254
VQLVESGGGL VQAGGSLRLS CAASGSISSI YAMGWYRQAP GKQRELVAAI TYGGRSHYRD  60
SVKGRFTISG NSDNSALYLH MNSLKPEDTA VYYCAADRGL TAVGEYDYWG QGTQVTVSS   119

SEQ ID NO: 255          moltype = AA  length = 114
FEATURE                 Location/Qualifiers
source                  1..114
                        mol_type = protein
                        note = 1H4 VHH1 single binder
                        organism = synthetic construct
SEQUENCE: 255
EVQLVESGGG SVQPGGSLRL SCAASGSIFI LNVMGWYRQA PGNQRELVAL MSSGGSTKYA  60
DSVKGRFTIS RDNVRDTVYL QMNSLKPEDT AVYYCTLRTE NDYWGQGTQV TVSS        114

SEQ ID NO: 256          moltype = AA  length = 123
FEATURE                 Location/Qualifiers
source                  1..123
                        mol_type = protein
                        note = 1C2 VHH1 single binder
                        organism = synthetic construct
SEQUENCE: 256
QVQLVESGGG LVQAGGSLRL SCAASGRTFS SYAMGWFRQG PGKEREFVAA ISWSGGGTYY  60
ADSVKGRFTI SRDNAKNTVY LQMNSLKPED TAVYYCAAGD LPWSRSDLEY DYWGQGTLVT  120
VSS                                                                123

SEQ ID NO: 257          moltype = AA  length = 121
FEATURE                 Location/Qualifiers
source                  1..121
                        mol_type = protein
                        note = 1E3 VHH2 single binder
                        organism = synthetic construct
SEQUENCE: 257
LEESGGGSVQ AGGSLRLSCA ASGRTFSTYA MGWLRQAPGK EREFVAGISW GGGRTDYADS  60
VKDRFTISRD NPKNTVYLQM NSLKPEDTAV YYCAAKDLPS GWGRTSEYDY WGQGTQVTVS  120
S                                                                  121

SEQ ID NO: 258          moltype = AA  length = 114
FEATURE                 Location/Qualifiers
source                  1..114
                        mol_type = protein
                        note = 1D12 VHH2 single binder
                        organism = synthetic construct
SEQUENCE: 258
EVQLVESGGG SVQPGGSLRL SCAGSGSIFP LNVMGWYRQA PGKEREFIAL ITSGGSTKHA  60
DSVKGRFTIS RDNFKNTVYL QMNSLKPEDT AVYYCYLDQS RQYWGQGTLV TVSS        114

SEQ ID NO: 259          moltype = AA  length = 111
FEATURE                 Location/Qualifiers
source                  1..111
                        mol_type = protein
                        note = 2H2 VHH2 single binder
                        organism = synthetic construct
SEQUENCE: 259
LVESGGGSVQ PGGSLRLSCA ASGSIFVLNS MGWYREAPGK ERELVAVSTS GGSTGYADSV  60
KGRFTISREN FKNTVYLQMN SLKPEDTAVY YCYLETDRRF WGQGTLVTVS S           111

SEQ ID NO: 260          moltype = AA  length = 119
FEATURE                 Location/Qualifiers
source                  1..119
                        mol_type = protein
                        note = 1H2 VHH2 single binder
                        organism = synthetic construct
SEQUENCE: 260
LVESGGGSVQ AGGSLRLSCA ASGRTFSSYA MGWFRLAPGK EREFVAAISW GGRGTYYADS  60
VKGRFTISRD NAKNTVYLQM NSLKPEDTAV YYCAAGDLPV VAGTEYEYWG QGTQVTVSS   119

SEQ ID NO: 261          moltype = AA  length = 122
FEATURE                 Location/Qualifiers
source                  1..122
                        mol_type = protein
                        note = 1C7 VHH2 single binder
                        organism = synthetic construct
SEQUENCE: 261
VQLVESGGGL VQPGGSLRLS CAASGFTFST YAMGWFRQAP GKEREFVAAI SWGGRGTYYA  60
DFAKGRFTIS RDNAKNTVYL QMNSLKPEDT AAYYCGAGDL PGATVQEEYN YWGQGTQVTV  120
SS                                                                 122
```

```
SEQ ID NO: 262          moltype = AA  length = 114
FEATURE                 Location/Qualifiers
source                  1..114
                        mol_type = protein
                        note = 1B10 VHH2 single binder
                        organism = synthetic construct
SEQUENCE: 262
EVQLVESGGG SVQPGGSLRL SCAGSGSIFP LNVMGWYRQA PGKEREFIAL ITSGGSTKHA  60
DSVKGRFTIS RDNFKNTVYL QMNSLKPEDT AVYYCYLDQS RQYWGQGTLV TVSS        114

SEQ ID NO: 263          moltype = AA  length = 121
FEATURE                 Location/Qualifiers
source                  1..121
                        mol_type = protein
                        note = 1G6 VHH2 single binder
                        organism = synthetic construct
SEQUENCE: 263
QLVESGGCSV QPGESLELSC AASGRIFSLN VMGWYRQVPG KQRELVARIS SGGSTSYADS  60
VKGRFTISRG NARDNALNTV FLQMNSVKPE DTAVYYCKLE DFTGGYAMDY WGKGTLVTVS  120
S                                                                  121

SEQ ID NO: 264          moltype = AA  length = 122
FEATURE                 Location/Qualifiers
source                  1..122
                        mol_type = protein
                        note = 1E2 VHH2 single binder
                        organism = synthetic construct
SEQUENCE: 264
EVQLVESVGG SVQAGGSLRL SCAASGRTFS TYAMGWFRQA PGKEREFVAS ISWGGRATYY  60
ADSVKGRFTI SRDNSKNTAY LQMNSLKPED TAVYYCAAAD LPTRVSTAYT FWGQGTQVTV  120
SS                                                                 122

SEQ ID NO: 265          moltype = AA  length = 114
FEATURE                 Location/Qualifiers
source                  1..114
                        mol_type = protein
                        note = 1B12 VHH1 single binder
                        organism = synthetic construct
SEQUENCE: 265
EVQLVESGGG SVQAGGSLRL SCAASGSIFI LNVMGWYRQA PGNQRELVAL MSSGGSTKYA  60
DSVKGRFTIS RDNVRNTVYL QMNSLKPEDT AVYYCTLRTE NDYWGQGTQV TVSS        114

SEQ ID NO: 266          moltype = AA  length = 118
FEATURE                 Location/Qualifiers
source                  1..118
                        mol_type = protein
                        note = 1C3 VHH2 single binder
                        organism = synthetic construct
SEQUENCE: 266
QLVESGGGSV QAGGSLILSC AASGDIPSIQ AMGWYRQAPG KQRELVAAIT SGGRTHYRDS  60
VKGRFTISGS NDKSALYLQM NSLKPEDTAV YYCAADRGLT AVGEYDYWGQ GTQVTVSS    118

SEQ ID NO: 267          moltype = AA  length = 118
FEATURE                 Location/Qualifiers
source                  1..118
                        mol_type = protein
                        note = 21A4 VHH1 single binder
                        organism = synthetic construct
SEQUENCE: 267
EVQLVESGGG SVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSS    118

SEQ ID NO: 268          moltype = AA  length = 5
FEATURE                 Location/Qualifiers
source                  1..5
                        mol_type = protein
                        note = 21A4 VHH1 CDR1 (Kabat numbering)
                        organism = synthetic construct
SEQUENCE: 268
SYTMG                                                              5

SEQ ID NO: 269          moltype = AA  length = 17
FEATURE                 Location/Qualifiers
source                  1..17
                        mol_type = protein
                        note = 21A4 VHH1 CDR2 (Kabat numbering)
                        organism = synthetic construct
SEQUENCE: 269
```

```
GISSSGYVMY NSESMKG                                              17

SEQ ID NO: 270          moltype = AA  length = 9
FEATURE                 Location/Qualifiers
source                  1..9
                        mol_type = protein
                        note = 21A4 VHH1 CDR3 (Kabat numbering)
                        organism = synthetic construct
SEQUENCE: 270
GTIGRPYDY                                                       9

SEQ ID NO: 271          moltype = AA  length = 115
FEATURE                 Location/Qualifiers
source                  1..115
                        mol_type = protein
                        note = 21A4 VHH2 single binder
                        organism = synthetic construct
SEQUENCE: 271
VQLVESGGGL VQPGGSLRLS CAASGSIFRL NVMGWYRQAP GEQRELVAAI STGGSTKYAD  60
SVKGRFTISR DNVKNTVYLE MNSLKPEDAA VYFCNVRLVG AYDYWGQGTL VTVSS       115

SEQ ID NO: 272          moltype = AA  length = 5
FEATURE                 Location/Qualifiers
source                  1..5
                        mol_type = protein
                        note = 21A4 VHH2  CDR1 (Kabat numbering)
                        organism = synthetic construct
SEQUENCE: 272
LNVMG                                                           5

SEQ ID NO: 273          moltype = AA  length = 16
FEATURE                 Location/Qualifiers
source                  1..16
                        mol_type = protein
                        note = 21A4 VHH2  CDR2 (Kabat numbering)
                        organism = synthetic construct
SEQUENCE: 273
AISTGGSTKY ADSVKG                                               16

SEQ ID NO: 274          moltype = AA  length = 8
FEATURE                 Location/Qualifiers
source                  1..8
                        mol_type = protein
                        note = 21A4 VHH2  CDR3 (Kabat numbering)
                        organism = synthetic construct
SEQUENCE: 274
RLVGAYDY                                                        8

SEQ ID NO: 275          moltype = AA  length = 118
FEATURE                 Location/Qualifiers
source                  1..118
                        mol_type = protein
                        note = 21C11 VHH1 single binder
                        organism = synthetic construct
SEQUENCE: 275
EVQLVESGGG LVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSS    118

SEQ ID NO: 276          moltype = AA  length = 5
FEATURE                 Location/Qualifiers
source                  1..5
                        mol_type = protein
                        note = 21C11 VHH1 CDR1 (Kabat numbering)
                        organism = synthetic construct
SEQUENCE: 276
SYTMG                                                           5

SEQ ID NO: 277          moltype = AA  length = 17
FEATURE                 Location/Qualifiers
source                  1..17
                        mol_type = protein
                        note = 21C11 VHH1 CDR2 (Kabat numbering)
                        organism = synthetic construct
SEQUENCE: 277
GISSSGYVMY NSESMKG                                              17

SEQ ID NO: 278          moltype = AA  length = 9
FEATURE                 Location/Qualifiers
source                  1..9
```

```
                        mol_type = protein
                        note = 21C11 VHH1 CDR3 (Kabat numbering)
                        organism = synthetic construct
SEQUENCE: 278
GTIGRPYDY                                                      9

SEQ ID NO: 279          moltype = AA  length = 121
FEATURE                 Location/Qualifiers
source                  1..121
                        mol_type = protein
                        note = 21C11 VHH2 single binder
                        organism = synthetic construct
SEQUENCE: 279
VQLVESGGDL VQAGGSLRLS CAASGRTFST YIIGWFRQAP GKEREFVTAI SWGGRGTYYA  60
DSVKGRFTIS RDNAKNTVYL QMNSLRPEDT AVYFCAAGDL MVSTRSQYDY WGQGTLVTVS  120
S                                                              121

SEQ ID NO: 280          moltype = AA  length = 5
FEATURE                 Location/Qualifiers
source                  1..5
                        mol_type = protein
                        note = 21C11 VHH2 CDR1 (Kabat numbering)
                        organism = synthetic construct
SEQUENCE: 280
TYIIG                                                          5

SEQ ID NO: 281          moltype = AA  length = 17
FEATURE                 Location/Qualifiers
source                  1..17
                        mol_type = protein
                        note = 21C11 VHH2 CDR2 (Kabat numbering)
                        organism = synthetic construct
SEQUENCE: 281
AISWGGRGTY YADSVKG                                             17

SEQ ID NO: 282          moltype = AA  length = 13
FEATURE                 Location/Qualifiers
source                  1..13
                        mol_type = protein
                        note = 21C11 VHH2 CDR3 (Kabat numbering)
                        organism = synthetic construct
SEQUENCE: 282
GDLMVSTRSQ YDY                                                 13

SEQ ID NO: 283          moltype = AA  length = 118
FEATURE                 Location/Qualifiers
source                  1..118
                        mol_type = protein
                        note = 21C8 VHH1 single binder
                        organism = synthetic construct
SEQUENCE: 283
EVQLVESGGG SVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTLVTVSS    118

SEQ ID NO: 284          moltype = AA  length = 5
FEATURE                 Location/Qualifiers
source                  1..5
                        mol_type = protein
                        note = 21C8 VHH1 CDR1 (Kabat numbering)
                        organism = synthetic construct
SEQUENCE: 284
SYTMG                                                          5

SEQ ID NO: 285          moltype = AA  length = 17
FEATURE                 Location/Qualifiers
source                  1..17
                        mol_type = protein
                        note = 21C8 VHH1 CDR2 (Kabat numbering)
                        organism = synthetic construct
SEQUENCE: 285
GISSSGYVMY NSESMKG                                             17

SEQ ID NO: 286          moltype = AA  length = 9
FEATURE                 Location/Qualifiers
source                  1..9
                        mol_type = protein
                        note = 21C8 VHH1 CDR3 (Kabat numbering)
                        organism = synthetic construct
SEQUENCE: 286
```

```
GTIGRPYDY                                                      9

SEQ ID NO: 287          moltype = AA  length = 121
FEATURE                 Location/Qualifiers
source                  1..121
                        mol_type = protein
                        note = 21C8 VHH2 single binder
                        organism = synthetic construct
SEQUENCE: 287
QLVESGGDLV QPGGSLRLSC AASGRTFSTY AMGWFRQAPG KEREFVAAIS WGGRGTYYAD  60
SVRGRFTISR DNPKNTVFLQ MNSLKPDDTA VYYCAAGDLP GGRRALDYDY WGQGTQVTVS  120
S                                                              121

SEQ ID NO: 288          moltype = AA  length = 5
FEATURE                 Location/Qualifiers
source                  1..5
                        mol_type = protein
                        note = 21C8 VHH2 CDR1 (Kabat numbering)
                        organism = synthetic construct
SEQUENCE: 288
TYAMG                                                          5

SEQ ID NO: 289          moltype = AA  length = 17
FEATURE                 Location/Qualifiers
source                  1..17
                        mol_type = protein
                        note = 21C8 VHH2 CDR2 (Kabat numbering)
                        organism = synthetic construct
SEQUENCE: 289
AISWGGRGTY YADSVRG                                             17

SEQ ID NO: 290          moltype = AA  length = 14
FEATURE                 Location/Qualifiers
source                  1..14
                        mol_type = protein
                        note = 21C8 VHH2 CDR3 (Kabat numbering)
                        organism = synthetic construct
SEQUENCE: 290
GDLPGGRRAL DYDY                                                14

SEQ ID NO: 291          moltype = AA  length = 120
FEATURE                 Location/Qualifiers
source                  1..120
                        mol_type = protein
                        note = 21B11 VHH1 single binder
                        organism = synthetic construct
SEQUENCE: 291
EVQLVESGGG LVQPGGSLSL SCTASGSITS IVAMGWYRQT PGKQRELVAA ITSGGRTHYR  60
DSVKGRFTIS GNNDNSALYL HMNSLKPEDT AVYYCAADRG WTSVGEYDYW GQGTLVTVSS  120

SEQ ID NO: 292          moltype = AA  length = 5
FEATURE                 Location/Qualifiers
source                  1..5
                        mol_type = protein
                        note = 21B11 VHH1 CDR1 (Kabat numbering)
                        organism = synthetic construct
SEQUENCE: 292
IVAMG                                                          5

SEQ ID NO: 293          moltype = AA  length = 16
FEATURE                 Location/Qualifiers
source                  1..16
                        mol_type = protein
                        note = 21B11 VHH1 CDR2 (Kabat numbering)
                        organism = synthetic construct
SEQUENCE: 293
AITSGGRTHY RDSVKG                                              16

SEQ ID NO: 294          moltype = AA  length = 12
FEATURE                 Location/Qualifiers
source                  1..12
                        mol_type = protein
                        note = 21B11 VHH1 CDR3 (Kabat numbering)
                        organism = synthetic construct
SEQUENCE: 294
DRGWTSVGEY DY                                                  12

SEQ ID NO: 295          moltype = AA  length = 123
FEATURE                 Location/Qualifiers
```

```
source                  1..123
                        mol_type = protein
                        note = 21B11 VHH2 single binder
                        organism = synthetic construct
SEQUENCE: 295
QLVESGGGSV QAGASLRLSC VSSGPTYGFY VTAWFRQAPG KEREFVAAVR GIASRVNYAD  60
SVKGRFTISR DNAANTIFLQ MNSLKPEDTA VYYCALRRQY STNYDSSTAY DVWGQGTLVT  120
VSS                                                              123

SEQ ID NO: 296          moltype = AA  length = 5
FEATURE                 Location/Qualifiers
source                  1..5
                        mol_type = protein
                        note = 21B11 VHH2 CDR1 (Kabat numbering)
                        organism = synthetic construct
SEQUENCE: 296
FYVTA                                                            5

SEQ ID NO: 297          moltype = AA  length = 17
FEATURE                 Location/Qualifiers
source                  1..17
                        mol_type = protein
                        note = 21B11 VHH2 CDR2 (Kabat numbering)
                        organism = synthetic construct
SEQUENCE: 297
AVRGIASRVN YADSVKG                                               17

SEQ ID NO: 298          moltype = AA  length = 16
FEATURE                 Location/Qualifiers
source                  1..16
                        mol_type = protein
                        note = 21B11 VHH2 CDR3 (Kabat numbering)
                        organism = synthetic construct
SEQUENCE: 298
RRQYSTNYDS STAYDV                                                16

SEQ ID NO: 299          moltype = AA  length = 125
FEATURE                 Location/Qualifiers
source                  1..125
                        mol_type = protein
                        note = 21G5 VHH1 single binder
                        organism = synthetic construct
SEQUENCE: 299
EVQLVESGGG SVQAGASLRL SCVSSGPTYG FYVTAWFRQA PGKEREFVAA VRGIASRVNY  60
ADSVKGRFTI SRDNAANTIF LQMNSLKPED TAVYYCALRR QYSTNYDSST AYDVWGQGTL  120
VTVSS                                                            125

SEQ ID NO: 300          moltype = AA  length = 5
FEATURE                 Location/Qualifiers
source                  1..5
                        mol_type = protein
                        note = 21G5 VHH1 CDR1 (Kabat numbering)
                        organism = synthetic construct
SEQUENCE: 300
FYVTA                                                            5

SEQ ID NO: 301          moltype = AA  length = 17
FEATURE                 Location/Qualifiers
source                  1..17
                        mol_type = protein
                        note = 21G5 VHH1 CDR2 (Kabat numbering)
                        organism = synthetic construct
SEQUENCE: 301
AVRGIASRVN YADSVKG                                               17

SEQ ID NO: 302          moltype = AA  length = 16
FEATURE                 Location/Qualifiers
source                  1..16
                        mol_type = protein
                        note = 21G5 VHH1 CDR3 (Kabat numbering)
                        organism = synthetic construct
SEQUENCE: 302
RRQYSTNYDS STAYDV                                                16

SEQ ID NO: 303          moltype = AA  length = 117
FEATURE                 Location/Qualifiers
source                  1..117
                        mol_type = protein
                        note = 21G5 VHH2 single binder
```

```
                         organism = synthetic construct
SEQUENCE: 303
LEESGGGLVQ PGGSLILSCA ASGDIPSIVA MGWYRQAPGK QRELVAAITS GGRTHYRDSV  60
KGRFTISGNN DNSALYLHMN SLKPEDTAVY YCAADRGLTA VGEYDYWGQG TQVTVSS     117

SEQ ID NO: 304           moltype = AA  length = 5
FEATURE                  Location/Qualifiers
source                   1..5
                         mol_type = protein
                         note = 21G5 VHH2 CDR1 (Kabat numbering)
                         organism = synthetic construct
SEQUENCE: 304
IVAMG                                                              5

SEQ ID NO: 305           moltype = AA  length = 16
FEATURE                  Location/Qualifiers
source                   1..16
                         mol_type = protein
                         note = 21G5 VHH2 CDR2 (Kabat numbering)
                         organism = synthetic construct
SEQUENCE: 305
AITSGGRTHY RDSVKG                                                  16

SEQ ID NO: 306           moltype = AA  length = 12
FEATURE                  Location/Qualifiers
source                   1..12
                         mol_type = protein
                         note = 21G5 VHH2 CDR3 (Kabat numbering)
                         organism = synthetic construct
SEQUENCE: 306
DRGLTAVGEY DY                                                      12

SEQ ID NO: 307           moltype = AA  length = 115
FEATURE                  Location/Qualifiers
source                   1..115
                         mol_type = protein
                         note = 21G7 VHH1 single binder
                         organism = synthetic construct
SEQUENCE: 307
EVQLVESGGG LVQPGGSLRL SCAASGSGFG IGRMGWYRQA PGKQRELVAI ISSLTGTTYA  60
DSVKGRFTGS RDSAKNMVYL RMDSLKPEDT AVYYCYANRF TVDYWGQGTL VTVSS       115

SEQ ID NO: 308           moltype = AA  length = 5
FEATURE                  Location/Qualifiers
source                   1..5
                         mol_type = protein
                         note = 21G7 VHH1 CDR1 (Kabat numbering)
                         organism = synthetic construct
SEQUENCE: 308
IGRMG                                                              5

SEQ ID NO: 309           moltype = AA  length = 16
FEATURE                  Location/Qualifiers
source                   1..16
                         mol_type = protein
                         note = 21G7 VHH1 CDR2 (Kabat numbering)
                         organism = synthetic construct
SEQUENCE: 309
IISSLTGTTY ADSVKG                                                  16

SEQ ID NO: 310           moltype = AA  length = 7
FEATURE                  Location/Qualifiers
source                   1..7
                         mol_type = protein
                         note = 21G7 VHH1 CDR3 (Kabat numbering)
                         organism = synthetic construct
SEQUENCE: 310
NRFTVDY                                                            7

SEQ ID NO: 311           moltype = AA  length = 120
FEATURE                  Location/Qualifiers
source                   1..120
                         mol_type = protein
                         note = 21G7 VHH2 single binder
                         organism = synthetic construct
SEQUENCE: 311
EVQLVESGGG LVQAGGSLRL SCAASGDIPS IVAMGWYRQA PGKQRELVAA ITSGGRTHYR  60
DSVKGRFTIS GNNDNSALYL HMNSLKPEDT AVYYCAADRG LTAVGEYDYW GQGTLVTVSS  120
```

```
SEQ ID NO: 312          moltype = AA  length = 5
FEATURE                 Location/Qualifiers
source                  1..5
                        mol_type = protein
                        note = 21G7 VHH2 CDR1 (Kabat numbering)
                        organism = synthetic construct
SEQUENCE: 312
IVAMG                                                                5

SEQ ID NO: 313          moltype = AA  length = 16
FEATURE                 Location/Qualifiers
source                  1..16
                        mol_type = protein
                        note = 21G7 VHH2 CDR2 (Kabat numbering)
                        organism = synthetic construct
SEQUENCE: 313
AITSGGRTHY RDSVKG                                                    16

SEQ ID NO: 314          moltype = AA  length = 12
FEATURE                 Location/Qualifiers
source                  1..12
                        mol_type = protein
                        note = 21G7 VHH2 CDR3 (Kabat numbering)
                        organism = synthetic construct
SEQUENCE: 314
DRGLTAVGEY DY                                                        12

SEQ ID NO: 315          moltype = AA  length = 125
FEATURE                 Location/Qualifiers
source                  1..125
                        mol_type = protein
                        note = 21H2 VHH1 single binder
                        organism = synthetic construct
SEQUENCE: 315
EVQLVESGGG LVQAGGSLRL SCAASGRTSS VFSTAWFRRA PGKEREFVGN IRGIADRTDY  60
ADSVKGRFTI SRDNAKNTVY LQMNTLKPED TAVYYCAAKR SYTRDYVTDY NYDYWGQGTL  120
VTVSS                                                                125

SEQ ID NO: 316          moltype = AA  length = 5
FEATURE                 Location/Qualifiers
source                  1..5
                        mol_type = protein
                        note = 21H2 VHH1 CDR1 (Kabat numbering)
                        organism = synthetic construct
SEQUENCE: 316
VFSTA                                                                5

SEQ ID NO: 317          moltype = AA  length = 17
FEATURE                 Location/Qualifiers
source                  1..17
                        mol_type = protein
                        note = 21H2 VHH1 CDR2 (Kabat numbering)
                        organism = synthetic construct
SEQUENCE: 317
NIRGIADRTD YADSVKG                                                   17

SEQ ID NO: 318          moltype = AA  length = 16
FEATURE                 Location/Qualifiers
source                  1..16
                        mol_type = protein
                        note = 21H2 VHH1 CDR3 (Kabat numbering)
                        organism = synthetic construct
SEQUENCE: 318
KRSYTRDYVT DYNYDY                                                    16

SEQ ID NO: 319          moltype = AA  length = 117
FEATURE                 Location/Qualifiers
source                  1..117
                        mol_type = protein
                        note = 21H2 VHH2 single binder
                        organism = synthetic construct
SEQUENCE: 319
LVESGGGLVQ AGGSLILSCA ASGDISSIVA MGWYRQAPGK QRELVAAITS GGRTHYRDSV  60
KGRFTISGNN DNSALYLHMN SLKPEDTAVY YCAADRGWTS VGEYDYWGQG TLVTVSS     117

SEQ ID NO: 320          moltype = AA  length = 5
FEATURE                 Location/Qualifiers
source                  1..5
                        mol_type = protein
```

```
                        note = 21H2 VHH2 CDR1 (Kabat numbering)
                        organism = synthetic construct
SEQUENCE: 320
IVAMG                                                         5

SEQ ID NO: 321          moltype = AA  length = 16
FEATURE                 Location/Qualifiers
source                  1..16
                        mol_type = protein
                        note = 21H2 VHH2 CDR2 (Kabat numbering)
                        organism = synthetic construct
SEQUENCE: 321
AITSGGRTHY RDSVKG                                             16

SEQ ID NO: 322          moltype = AA  length = 12
FEATURE                 Location/Qualifiers
source                  1..12
                        mol_type = protein
                        note = 21H2 VHH2 CDR3 (Kabat numbering)
                        organism = synthetic construct
SEQUENCE: 322
DRGWTSVGEY DY                                                 12

SEQ ID NO: 323          moltype = AA  length = 115
FEATURE                 Location/Qualifiers
source                  1..115
                        mol_type = protein
                        note = 19B5 VHH1 single binder
                        organism = synthetic construct
SEQUENCE: 323
EVQLVESGGG LVQPGGSLRL SCAASGSGFG IGRMGWYRQA PGKQRELVAI ISSLSGTTYT  60
DSVKGRFTIS RDIAKNMVYL RMDSLKPEDT AVYYCYANRF TVDYWGQGTQ VTVSS       115

SEQ ID NO: 324          moltype = AA  length = 5
FEATURE                 Location/Qualifiers
source                  1..5
                        mol_type = protein
                        note = 19B5 VHH1 CDR1 (Kabat numbering)
                        organism = synthetic construct
SEQUENCE: 324
IGRMG                                                         5

SEQ ID NO: 325          moltype = AA  length = 16
FEATURE                 Location/Qualifiers
source                  1..16
                        mol_type = protein
                        note = 19B5 VHH1 CDR2 (Kabat numbering)
                        organism = synthetic construct
SEQUENCE: 325
IISSLSGTTY TDSVKG                                             16

SEQ ID NO: 326          moltype = AA  length = 7
FEATURE                 Location/Qualifiers
source                  1..7
                        mol_type = protein
                        note = 19B5 VHH1 CDR3 (Kabat numbering)
                        organism = synthetic construct
SEQUENCE: 326
NRFTVDY                                                       7

SEQ ID NO: 327          moltype = AA  length = 119
FEATURE                 Location/Qualifiers
source                  1..119
                        mol_type = protein
                        note = 19B5 VHH2 single binder
                        organism = synthetic construct
SEQUENCE: 327
VQLVESVGGL VQAGGSLRLS CAASGDIPSI QAMGWYRQAP GKQRELVAAI TSGGRTHYRD  60
SVKGRFTISG SNDKSALYLQ MNSLKPEDTA VYYCAADRGL TAVGEYDYWG QGTLVTVSS   119

SEQ ID NO: 328          moltype = AA  length = 5
FEATURE                 Location/Qualifiers
source                  1..5
                        mol_type = protein
                        note = 19B5 VHH2 CDR1 (Kabat numbering)
                        organism = synthetic construct
SEQUENCE: 328
IQAMG                                                         5
```

```
SEQ ID NO: 329          moltype = AA  length = 16
FEATURE                 Location/Qualifiers
source                  1..16
                        mol_type = protein
                        note = 19B5 VHH2 CDR2 (Kabat numbering)
                        organism = synthetic construct
SEQUENCE: 329
AITSGGRTHY RDSVKG                                                 16

SEQ ID NO: 330          moltype = AA  length = 12
FEATURE                 Location/Qualifiers
source                  1..12
                        mol_type = protein
                        note = 19B5 VHH2 CDR3 (Kabat numbering)
                        organism = synthetic construct
SEQUENCE: 330
DRGLTAVGEY DY                                                     12

SEQ ID NO: 331          moltype = AA  length = 115
FEATURE                 Location/Qualifiers
source                  1..115
                        mol_type = protein
                        note = 22D1 VHH1 single binder
                        organism = synthetic construct
SEQUENCE: 331
EVQLVESGGG SVQPGGSLRL SCAASGSGFG VGRMGWYRQA PGNKRELVAI VSSLTGTTYA  60
DSAKGRFTIS RDSAKNMVYL RMDSLKPEDT AVYYCYANRF TVDYWGQGTL VTVSS       115

SEQ ID NO: 332          moltype = AA  length = 5
FEATURE                 Location/Qualifiers
source                  1..5
                        mol_type = protein
                        note = 22D1 VHH1 CDR1 (Kabat numbering)
                        organism = synthetic construct
SEQUENCE: 332
VGRMG                                                             5

SEQ ID NO: 333          moltype = AA  length = 16
FEATURE                 Location/Qualifiers
source                  1..16
                        mol_type = protein
                        note = 22D1 VHH1 CDR2 (Kabat numbering)
                        organism = synthetic construct
SEQUENCE: 333
IVSSLTGTTY ADSAKG                                                 16

SEQ ID NO: 334          moltype = AA  length = 7
FEATURE                 Location/Qualifiers
source                  1..7
                        mol_type = protein
                        note = 22D1 VHH1 CDR3 (Kabat numbering)
                        organism = synthetic construct
SEQUENCE: 334
NRFTVDY                                                           7

SEQ ID NO: 335          moltype = AA  length = 120
FEATURE                 Location/Qualifiers
source                  1..120
                        mol_type = protein
                        note = 22D1 VHH2 single binder
                        organism = synthetic construct
SEQUENCE: 335
EVQLVESGGG LVQPGGSLTL SCAASGDILS IVAMGWYRQA PGKQRELVAA ITSGGRTHYR  60
DSVKGRFTIS GNNDNSALYL HMNSLKPEDT AVYYCAADRG LTAVGEYDYW GQGTQVTVSS  120

SEQ ID NO: 336          moltype = AA  length = 5
FEATURE                 Location/Qualifiers
source                  1..5
                        mol_type = protein
                        note = 22D1 VHH2 CDR1 (Kabat numbering)
                        organism = synthetic construct
SEQUENCE: 336
IVAMG                                                             5

SEQ ID NO: 337          moltype = AA  length = 16
FEATURE                 Location/Qualifiers
source                  1..16
                        mol_type = protein
                        note = 22D1 VHH2 CDR2 (Kabat numbering)
```

```
                         organism = synthetic construct
SEQUENCE: 337
AITSGGRTHY RDSVKG                                                  16

SEQ ID NO: 338           moltype = AA  length = 12
FEATURE                  Location/Qualifiers
source                   1..12
                         mol_type = protein
                         note = 22D1 VHH2 CDR3 (Kabat numbering)
                         organism = synthetic construct
SEQUENCE: 338
DRGLTAVGEY DY                                                      12

SEQ ID NO: 339           moltype = AA  length = 125
FEATURE                  Location/Qualifiers
source                   1..125
                         mol_type = protein
                         note = 22D8 VHH1 single binder
                         organism = synthetic construct
SEQUENCE: 339
EVQLVESGGG SVQAGASLRL SCVSSGPTYG FYVTAWFRQA PGKEREFVAA VRGIASRVNY  60
ADSVKGRFTI SRDNAANTIF LQMNSLKPED TAVYYCALRR QYSTNYDSST AYDVWGQGTL  120
VTVSS                                                              125

SEQ ID NO: 340           moltype = AA  length = 5
FEATURE                  Location/Qualifiers
source                   1..5
                         mol_type = protein
                         note = 22D8 VHH1 CDR1 (Kabat numbering)
                         organism = synthetic construct
SEQUENCE: 340
FYVTA                                                              5

SEQ ID NO: 341           moltype = AA  length = 17
FEATURE                  Location/Qualifiers
source                   1..17
                         mol_type = protein
                         note = 22D8 VHH1 CDR2 (Kabat numbering)
                         organism = synthetic construct
SEQUENCE: 341
AVRGIASRVN YADSVKG                                                 17

SEQ ID NO: 342           moltype = AA  length = 16
FEATURE                  Location/Qualifiers
source                   1..16
                         mol_type = protein
                         note = 22D8 VHH1 CDR3 (Kabat numbering)
                         organism = synthetic construct
SEQUENCE: 342
RRQYSTNYDS STAYDV                                                  16

SEQ ID NO: 343           moltype = AA  length = 117
FEATURE                  Location/Qualifiers
source                   1..117
                         mol_type = protein
                         note = 22D8 VHH2 single binder
                         organism = synthetic construct
SEQUENCE: 343
LVESGGGLVQ AGGSLILSCA ASGDIPSIVA MGWYRQAPGK QRELVAAITS GGRTHYRDSV  60
KGRFTISGNN DNSALYLHMN SLKPEDTAVY YCAADRGLTA VGEYDYWGQG TLVTVSS     117

SEQ ID NO: 344           moltype = AA  length = 5
FEATURE                  Location/Qualifiers
source                   1..5
                         mol_type = protein
                         note = 22D8 VHH2 CDR1 (Kabat numbering)
                         organism = synthetic construct
SEQUENCE: 344
IVAMG                                                              5

SEQ ID NO: 345           moltype = AA  length = 16
FEATURE                  Location/Qualifiers
source                   1..16
                         mol_type = protein
                         note = 22D8 VHH2 CDR2 (Kabat numbering)
                         organism = synthetic construct
SEQUENCE: 345
AITSGGRTHY RDSVKG                                                  16
```

-continued

```
SEQ ID NO: 346          moltype = AA  length = 12
FEATURE                 Location/Qualifiers
source                  1..12
                        mol_type = protein
                        note = 22D8 VHH2 CDR3 (Kabat numbering)
                        organism = synthetic construct
SEQUENCE: 346
DRGLTAVGEY DY                                                              12
```

IL31-BINDING POLYPEPTIDES AND USES THEREOF

CROSS-REFERENCE TO RELATED APPLICATIONS

This application claims the benefit of U.S. provisional patent application Ser. No. 63/637,775, filed Apr. 23, 2024, U.S. provisional patent application Ser. No. 63/690,297, filed Sep. 3, 2024, and U.S. provisional patent application Ser. No. 63/770,198, filed Mar. 11, 2025, each of which is incorporated herein by reference in its entirety.

REFERENCE TO SEQUENCE LISTING SUBMITTED ELECTRONICALLY

The content of the electronically submitted sequence listing (Name: 5614_0020004_SequenceListing_ST26.xml; Size: 843,079 bytes; and Date of Creation: Apr. 23, 2025), filed with the application, is incorporated herein by reference in its entirety.

FIELD

The present disclosure relates to IL31-binding polypeptides, and methods of using IL31-binding polypeptides to modulate the biological activity of IL31. Such methods include, but are not limited to, methods of treating pruritic conditions, atopic dermatitis, prurigo nodularis, and chronic spontaneous urticaria.

BACKGROUND

Interleukin 31 (IL31) is a cytokine mostly produced by Th2 cells and has been implicated in the pathophysiology of several skin disorders, such as pruritic conditions, allergic diseases, and other inflammatory conditions. IL31 functions by binding IL31 receptor A (IL31RA)/oncostatin M receptor beta (OSMRβ) and activation of downstream JAK/STAT and PI3K/AKT pathways, which mediates inflammatory responses, initiating immunoregulatory circuits, stimulating itch, and neuronal outgrowth. Many of the clinical problems associated with dermatitis and other skin disorders are thought to be associated with IL31 activity.

Chronic inflammatory skin diseases such as atopic dermatitis (AD) and prurigo nodularis (PN) lead to intensely pruritic skin lesions resulting in severe scratching. Topical steroids and calcineurin inhibitors are not sufficient to manage symptoms in AD or PN patients. Nemolizumab, an antibody that targets IL31RA, has shown promising anti-pruritic efficacy, validating the IL31-IL31RA pathway in providing symptom relief in AD and PN patients. Overall, however, there remains a strong need for improved therapies for treating IL31-associated conditions, including therapies that have the potential to induce fast and prolonged control of symptoms in patients with chronic inflammatory skin disease.

SUMMARY

Provided herein are high affinity and potent biparatopic polypeptides that bind to the IL31 ligand, which has the potential to induce fast and prolonged control of pruritus in patients with chronic inflammatory skin disease.

The polypeptides disclosed herein provide for multiple advantages and improvements over standard-of-care treatments and/or treatments still in development. Such advantages and improvements include, but are not limited to, greater efficacy against lesions and itches, greater safety (e.g., less conjunctivitis), rapid itch relief (days to weeks), extended half-life, avoidance of target-mediated drug disposition (TMDD), and more convenient and/or less frequent dosing, which leads to reduced injection burden. Such advantages and improvements allow the polypeptides disclosed herein to be used as treatment options for nonresponding and/or relapsed patients who received standard-of-care treatments and/or treatments still in development.

In some aspects, polypeptides that bind IL31 comprising one or more IL31 binder are provided herein.

In some aspects, provided herein is a polypeptide that binds IL31 comprising two or more IL31 binders, wherein the first IL31 binder comprises a VHH1 which comprises a CDR1 comprising the amino acid sequence of SEQ ID NO: 59; a CDR2 comprising the amino acid sequence of SEQ ID NO: 63; and a CDR3 comprising the amino acid sequence of SEQ ID NO: 64 and the second IL31 binder comprises a VHH2 that binds to IL31.

In some aspects, provided herein is a polypeptide that binds IL31 comprising two or more IL31 binders, wherein the first IL31 binder comprises a VHH1 which comprises a CDR1 comprising the amino acid sequence of SEQ ID NO: 59; a CDR2 comprising the amino acid sequence of SEQ ID NO: 60 or SEQ ID NO: 63; and a CDR3 comprising the amino acid sequence of SEQ ID NO: 61 or SEQ ID NO: 64 and the second IL31 binder comprising a VHH2 which binds to IL31. In some aspects, the VHH1 comprises a CDR1 comprising the amino acid sequence of SEQ ID NO: 59; a CDR2 comprising the amino acid sequence of SEQ ID NO: 63; and a CDR3 comprising the amino acid sequence of SEQ ID NO: 61. In some aspects, the VHH1 comprises a CDR1 comprising the amino acid sequence of SEQ ID NO: 59; a CDR2 comprising the amino acid sequence of SEQ ID NO: 60; and a CDR3 comprising the amino acid sequence of SEQ ID NO: 61. In some aspects, the VHH1 comprises a CDR1 comprising the amino acid sequence of SEQ ID NO: 59; a CDR2 comprising the amino acid sequence of SEQ ID NO: 60; and a CDR3 comprising the amino acid sequence of SEQ ID NO: 64.

In some aspects, the polypeptide that binds IL31 comprises a first IL31 binder and a second IL31 binder.

In some aspects, the first IL31 binder comprises a VHH1 comprising a CDR1 comprising the amino acid sequence of SEQ ID NO: 5, SEQ ID NO: 19, SEQ ID NO: 33, SEQ ID NO: 47, SEQ ID NO: 78, SEQ ID NO: 81, or SEQ ID NO: 59; a CDR2 comprising the amino acid sequence of SEQ ID NO: 6, SEQ ID NO: 20, SEQ ID NO: 34, SEQ ID NO: 48, SEQ ID NO: 79, SEQ ID NO: 82, SEQ ID NO: 60, or SEQ ID NO: 63; and a CDR3 comprising the amino acid sequence of SEQ ID NO: 7, SEQ ID NO: 21, SEQ ID NO: 35, SEQ ID NO: 49, SEQ ID NO: 80, SEQ ID NO: 83, SEQ ID NO: 61, or SEQ ID NO: 64.

In some aspects, the first IL31 binder comprises a VHH1 comprising a CDR1 comprising the amino acid sequence of SEQ ID NO: 268, SEQ ID NO: 276, SEQ ID NO: 284, SEQ ID NO: 292, SEQ ID NO: 300, SEQ ID NO: 308, SEQ ID NO: 316, SEQ ID NO: 324, SEQ ID NO: 332, and SEQ ID NO: 340; a CDR2 comprising the amino acid sequence of SEQ ID NO: 269, SEQ ID NO: 277, SEQ ID NO: 285, SEQ ID NO: 293, SEQ ID NO: 301, SEQ ID NO: 309, SEQ ID NO: 317, SEQ ID NO: 325, SEQ ID NO: 333, and SEQ ID NO: 341; and a CDR3 comprising the amino acid sequence of SEQ ID NO: 270; SEQ ID NO: 278, SEQ ID NO: 286, SEQ ID NO: 294, SEQ ID NO: 302, SEQ ID NO: 310, SEQ ID NO: 318, SEQ ID NO: 326, SEQ ID NO: 334, and SEQ ID NO: 342.

In some aspects, the second IL31 binder comprises a VHH2 comprising a CDR1 comprising the amino acid sequence of SEQ ID NO: 10, SEQ ID NO: 24, SEQ ID NO: 38, SEQ ID NO: 52, SEQ ID NO: 84, SEQ ID NO: 87, or SEQ ID NO: 251; a CDR2 comprising the amino acid sequence of SEQ ID NO: 11, SEQ ID NO: 25, SEQ ID NO: 39, SEQ ID NO: 53, SEQ ID NO: 85, SEQ ID NO: 88, or SEQ ID NO: 252; and a CDR3 comprising the amino acid sequence of SEQ ID NO: 12, SEQ ID NO: 26, SEQ ID NO: 40, SEQ ID NO: 54, SEQ ID NO: 86, SEQ ID NO: 89, or SEQ ID NO: 253.

In some aspects, the second IL31 binder comprises a VHH2 comprising a CDR1 comprising the amino acid sequence of SEQ ID NO: 272, SEQ ID NO: 280, SEQ ID NO: 288, SEQ ID NO: 296, SEQ ID NO: 304, SEQ ID NO: 312, SEQ ID NO: 320, SEQ ID NO: 328, SEQ ID NO: 336, SEQ ID NO: 344; a CDR2 comprising the amino acid sequence of SEQ ID NO: 273, SEQ ID NO: 281, SEQ ID NO: 289, SEQ ID NO: 297, SEQ ID NO: 305, SEQ ID NO: 313, SEQ ID NO: 321, SEQ ID NO: 329, SEQ ID NO: 337, and SEQ ID NO: 345; and a CDR3 comprising the amino acid sequence of SEQ ID NO: 274, SEQ ID NO: 282, SEQ ID NO: 290, SEQ ID NO: 298, SEQ ID NO: 306, SEQ ID NO: 314, SEQ ID NO: 322, SEQ ID NO: 330, SEQ ID NO: 338, and SEQ ID NO: 346.

In some aspects, a) the first IL31 binder comprises a VHH1 comprising a CDR1 comprising the amino acid sequence of SEQ ID NO: 5, SEQ ID NO: 19, SEQ ID NO: 33, SEQ ID NO: 47, SEQ ID NO: 78, SEQ ID NO: 81, or SEQ ID NO: 59; a CDR2 comprising the amino acid sequence of SEQ ID NO: 6, SEQ ID NO: 20, SEQ ID NO: 34, SEQ ID NO: 48, SEQ ID NO: 79, SEQ ID NO: 82, SEQ ID NO: 60, or SEQ ID NO: 63; and a CDR3 comprising the amino acid sequence of SEQ ID NO: 7, SEQ ID NO: 21, SEQ ID NO: 35, SEQ ID NO: 49, SEQ ID NO: 80, SEQ ID NO: 83, SEQ ID NO: 61, or SEQ ID NO: 64; and b) the second IL31 binder comprises a VHH2 comprising a CDR1 comprising the amino acid sequence of SEQ ID NO: 10, SEQ ID NO: 24, SEQ ID NO: 38, SEQ ID NO: 52, SEQ ID NO: 84, SEQ ID NO: 87, SEQ ID NO: 251; a CDR2 comprising the amino acid sequence of SEQ ID NO: 11, SEQ ID NO: 25, SEQ ID NO: 39, SEQ ID NO: 53, SEQ ID NO: 85, SEQ ID NO: 88, or SEQ ID NO: 252; and a CDR3 comprising the amino acid sequence of SEQ ID NO: 12, SEQ ID NO: 26, SEQ ID NO: 40, SEQ ID NO: 54, SEQ ID NO: 86, SEQ ID NO: 89, or SEQ ID NO: 253.

In some aspects, a) the first IL31 binder comprises a VHH1 comprising a CDR1 comprising the amino acid sequence of SEQ ID NO: 268, SEQ ID NO: 276, SEQ ID NO: 284, SEQ ID NO: 292, SEQ ID NO:300, SEQ ID NO: 308, SEQ ID NO:316, SEQ ID NO:324, SEQ ID NO: 332, and SEQ ID NO:340; a CDR2 comprising the amino acid sequence of SEQ ID NO: 269, SEQ ID NO: 277, SEQ ID NO: 285, SEQ ID NO: 293, SEQ ID NO:301, SEQ ID NO:309, SEQ ID NO: 317, SEQ ID NO:325, SEQ ID NO:333, and SEQ ID NO:341; and a CDR3 comprising the amino acid sequence of SEQ ID NO: 270; SEQ ID NO: 278, SEQ ID NO: 286, SEQ ID NO: 294, SEQ ID NO:302, SEQ ID NO:310, SEQ ID NO:318, SEQ ID NO:326, SEQ ID NO:334, and SEQ ID NO: 342; and b) the second IL31 binder comprises a VHH2 comprising a CDR1 comprising the amino acid sequence of SEQ ID NO: 272, SEQ ID NO: 280, SEQ ID NO: 288, SEQ ID NO: 296, SEQ ID NO:304, SEQ ID NO:312, SEQ ID NO:320, SEQ ID NO:328, SEQ ID NO:336, SEQ ID NO: 344; a CDR2 comprising the amino acid sequence of SEQ ID NO: 273, SEQ ID NO: 281, SEQ ID NO: 289, SEQ ID NO: 297, SEQ ID NO:305, SEQ ID NO:313, SEQ ID NO:321, SEQ ID NO: 329, SEQ ID NO:337, and SEQ ID NO:345; and a CDR3 comprising the amino acid sequence of SEQ ID NO: 274, SEQ ID NO: 282, SEQ ID NO: 290, SEQ ID NO: 298, SEQ ID NO:306, SEQ ID NO: 314, SEQ ID NO:322, SEQ ID NO:330, SEQ ID NO:338, and SEQ ID NO:346.

In some aspects, the VHH1 comprises: a) a CDR1 comprising the amino acid sequence of SEQ ID NO: 5, a CDR2 comprising the amino acid sequence of SEQ ID NO: 6, and a CDR3 comprising the amino acid sequence of SEQ ID NO: 7; b) a CDR1 comprising the amino acid sequence of SEQ ID NO: 19, a CDR2 comprising the amino acid sequence of SEQ ID NO: 20, and a CDR3 comprising the amino acid sequence of SEQ ID NO: 21; c) a CDR1 comprising the amino acid sequence of SEQ ID NO: 33, a CDR2 comprising the amino acid sequence of SEQ ID NO: 34, and a CDR3 comprising the amino acid sequence of SEQ ID NO: 35; d) a CDR1 comprising the amino acid sequence of SEQ ID NO: 47, a CDR2 comprising the amino acid sequence of SEQ ID NO: 48, and a CDR3 comprising the amino acid sequence of SEQ ID NO: 49; e) a CDR1 comprising the amino acid sequence of SEQ ID NO: 78, a CDR2 comprising the amino acid sequence of SEQ ID NO: 79, and a CDR3 comprising the amino acid sequence of SEQ ID NO: 80; or f) a CDR1 comprising the amino acid sequence of SEQ ID NO: 81, a CDR2 comprising the amino acid sequence of SEQ ID NO: 82, and a CDR3 comprising the amino acid sequence of SEQ ID NO: 83.

In some aspects, provided herein is a polypeptide that binds IL31 comprising two or more IL31 binders, wherein the first IL31 binder comprises a VHH1 binding to IL31, and the second IL31 binder comprises a VHH2 which comprises:

a. a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12;
b. a CDR1 comprising the amino acid sequence of SEQ ID NO: 24, a CDR2 comprising the amino acid sequence of SEQ ID NO: 25, and a CDR3 comprising the amino acid sequence of SEQ ID NO: 26;
c. a CDR1 comprising the amino acid sequence of SEQ ID NO: 38, a CDR2 comprising the amino acid sequence of SEQ ID NO: 39, and a CDR3 comprising the amino acid sequence of SEQ ID NO: 40;
d. a CDR1 comprising the amino acid sequence of SEQ ID NO: 52, a CDR2 comprising the amino acid sequence of SEQ ID NO: 53, and a CDR3 comprising the amino acid sequence of SEQ ID NO: 54;
e. a CDR1 comprising the amino acid sequence of SEQ ID NO: 84, a CDR2 comprising the amino acid sequence of SEQ ID NO: 85, and a CDR3 comprising the amino acid sequence of SEQ ID NO: 86; or
f. a CDR1 comprising the amino acid sequence of SEQ ID NO: 87, a CDR2 comprising the amino acid sequence of SEQ ID NO: 88, and a CDR3 comprising the amino acid sequence of SEQ ID NO: 89.

In some aspects, provided herein is a polypeptide that binds IL31 comprising two or more IL31 binders, wherein the first IL31 binder comprises a VHH1 binding to IL31, and the second IL31 binder comprises a VHH2 which comprises a CDR1 comprising the amino acid sequence of SEQ ID NO: 251, a CDR2 comprising the amino acid sequence of SEQ ID NO: 252, and a CDR3 comprising the amino acid sequence of SEQ ID NO: 253.

In some aspects, the VHH2 comprises: a) a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12; b) a CDR1 comprising the amino acid sequence of SEQ ID NO: 24, a CDR2 comprising the amino acid sequence of SEQ ID NO: 25, and a CDR3 comprising the amino acid sequence of SEQ ID NO: 26; c) a CDR1 comprising the amino acid sequence of SEQ ID NO: 38, a CDR2 comprising the amino acid sequence of SEQ ID NO: 39, and a CDR3 comprising the amino acid sequence of SEQ ID NO: 40; d) a CDR1 comprising the amino acid sequence of SEQ ID NO: 52, a CDR2 comprising the amino acid sequence of SEQ ID NO: 53, and a CDR3 comprising the amino acid sequence of SEQ ID NO: 54; e) a CDR1 comprising the amino acid sequence of SEQ ID NO: 84, a CDR2 comprising the amino acid sequence of SEQ ID NO: 85, and a CDR3 comprising the amino acid sequence of SEQ ID NO: 86; or f) a CDR1 comprising the amino acid sequence of SEQ ID NO: 87, a CDR2 comprising the amino acid sequence of SEQ ID NO: 88, and a CDR3 comprising the amino acid sequence of SEQ ID NO: 89. In some aspects, the VHH2 comprises a CDR1 comprising the amino acid sequence of SEQ ID NO: 251, a CDR2 comprising the amino acid sequence of SEQ ID NO: 252, and a CDR3 comprising the amino acid sequence of SEQ ID NO: 253.

In some aspects, the VHH1 comprises a CDR1 comprising the amino acid sequence of SEQ ID NO: 5, a CDR2 comprising the amino acid sequence of SEQ ID NO: 6, and a CDR3 comprising the amino acid sequence of SEQ ID NO: 7; and the VHH2 comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12.

In some aspects, the VHH1 comprises a CDR1 comprising the amino acid sequence of SEQ ID NO: 19, a CDR2 comprising the amino acid sequence of SEQ ID NO: 20, and a CDR3 comprising the amino acid sequence of SEQ ID NO: 21; and the VHH2 comprises a CDR1 comprising the amino acid sequence of SEQ ID NO: 24, a CDR2 comprising the amino acid sequence of SEQ ID NO: 25, and a CDR3 comprising the amino acid sequence of SEQ ID NO: 26.

In some aspects, the VHH1 comprises a CDR1 comprising the amino acid sequence of SEQ ID NO: 33, a CDR2 comprising the amino acid sequence of SEQ ID NO: 34, and a CDR3 comprising the amino acid sequence of SEQ ID NO: 35; and the VHH2 comprises a CDR1 comprising the amino acid sequence of SEQ ID NO: 38, a CDR2 comprising the amino acid sequence of SEQ ID NO: 39, and a CDR3 comprising the amino acid sequence of SEQ ID NO: 40.

In some aspects, the VHH1 comprises a CDR1 comprising the amino acid sequence of SEQ ID NO: 47, a CDR2 comprising the amino acid sequence of SEQ ID NO: 48, and a CDR3 comprising the amino acid sequence of SEQ ID NO: 49; and the VHH2 comprises a CDR1 comprising the amino acid sequence of SEQ ID NO: 52, a CDR2 comprising the amino acid sequence of SEQ ID NO: 53, and a CDR3 comprising the amino acid sequence of SEQ ID NO: 54.

In some aspects, the VHH1 comprises a CDR1 comprising the amino acid sequence of SEQ ID NO: 78, a CDR2 comprising the amino acid sequence of SEQ ID NO: 79, and a CDR3 comprising the amino acid sequence of SEQ ID NO: 80; and the VHH2 comprises a CDR1 comprising the amino acid sequence of SEQ ID NO: 84, a CDR2 comprising the amino acid sequence of SEQ ID NO: 85, and a CDR3 comprising the amino acid sequence of SEQ ID NO: 86.

In some aspects, the VHH1 comprises a CDR1 comprising the amino acid sequence of SEQ ID NO: 81, a CDR2 comprising the amino acid sequence of SEQ ID NO: 82, and a CDR3 comprising the amino acid sequence of SEQ ID NO: 83; and the VHH2 comprises a CDR1 comprising the amino acid sequence of SEQ ID NO: 87, a CDR2 comprising the amino acid sequence of SEQ ID NO: 88, and a CDR3 comprising the amino acid sequence of SEQ ID NO: 89.

In some aspects, the VHH1 and/or the VHH2 are humanized.

In some aspects, the VHH1 comprises an amino acid sequence at least 85%, at least 90%, at least 95%, at least 96%, at least 97%, at least 98%, or at least 99% identical to the amino acid sequence of SEQ ID NO: 3, SEQ ID NO: 17, SEQ ID NO: 31, or SEQ ID NO: 45. In some aspects, the VHH1 comprises the amino acid sequence of SEQ ID NO: 3, SEQ ID NO: 17, SEQ ID NO: 31, or SEQ ID NO: 45.

In some aspects, the VHH1 comprises an amino acid sequence at least 85%, at least 90%, at least 95%, at least 96%, at least 97%, at least 98%, or at least 99% identical to the amino acid sequence of SEQ ID NO: 4, SEQ ID NO: 18, SEQ ID NO: 32, or SEQ ID NO: 46. In some aspects, the VHH1 comprises the amino acid sequence of SEQ ID NO: 4, SEQ ID NO: 18, SEQ ID NO: 32, or SEQ ID NO: 46.

In some aspects, the VHH2 comprises an amino acid sequence at least 85%, at least 90%, at least 95%, at least 96%, at least 97%, at least 98%, or at least 99% identical to the amino acid sequence of SEQ ID NO: 8, SEQ ID NO: 22, SEQ ID NO: 36, or SEQ ID NO: 50. In some aspects, the VHH2 comprises the amino acid sequence of SEQ ID NO: 8, SEQ ID NO: 22, SEQ ID NO: 36, or SEQ ID NO: 50.

In some aspects, the VHH2 comprises an amino acid sequence at least 85%, at least 90%, at least 95%, at least 96%, at least 97%, at least 98%, or at least 99% identical to the amino acid sequence of SEQ ID NO: 9, SEQ ID NO: 23, SEQ ID NO: 37, or SEQ ID NO: 51. In some aspects, the VHH2 comprises the amino acid sequence of SEQ ID NO: 9, SEQ ID NO: 23, SEQ ID NO: 37, or SEQ ID NO: 51.

In some aspects, the VHH1 comprises the amino acid sequence of SEQ ID NO: 4 and the VHH2 comprises the amino acid sequence of SEQ ID NO: 9. In some aspects, the VHH1 comprises the amino acid sequence of SEQ ID NO: 18 and the VHH2 comprises the amino acid sequence of SEQ ID NO: 23. In some aspects, the VHH1 comprises the amino acid sequence of SEQ ID NO: 32 and the VHH2 comprises the amino acid sequence of SEQ ID NO: 37. In some aspects, the VHH1 comprises the amino acid sequence of SEQ ID NO: 46 and the VHH2 comprises the amino acid sequence of SEQ ID NO: 51.

In some aspects, the VHH1 comprises: an amino acid sequence at least 85%, at least 90%, at least 95%, at least 96%, at least 97%, at least 98%, or at least 99% identical to the amino acid sequence of SEQ ID NO:3, SEQ ID NO:4, SEQ ID NO: 17, SEQ ID NO: 18, SEQ ID NO:31, SEQ ID NO: 32, SEQ ID NO:45, SEQ ID NO:46, SEQ ID NO:65, SEQ ID NO: 68, SEQ ID NO:69, SEQ ID NO: 70, SEQ ID NO: 71, SEQ ID NO: 72, SEQ ID NO: 73, SEQ ID NO: 74, SEQ ID NO: 75, SEQ ID NO: 77, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 140, SEQ ID NO: 141, SEQ ID NO: 142, SEQ ID NO: 143, SEQ ID NO: 144, SEQ ID NO: 145, SEQ ID NO: 177, SEQ ID NO: 178, SEQ ID NO: 179, SEQ ID NO: 180, SEQ ID NO:181, SEQ ID NO:182, SEQ ID NO:183, SEQ ID NO:184, SEQ ID NO: 221, SEQ ID NO: 222, SEQ ID NO: 223, SEQ ID NO: 224, SEQ ID NO: 225, SEQ ID NO: 226, SEQ ID NO: 255, SEQ ID NO: 256, SEQ ID NO: 265, SEQ ID NO: 267, SEQ ID NO: 275, SEQ ID NO: 283, SEQ ID NO: 291, SEQ ID NO: 299, SEQ ID NO: 307, SEQ ID NO:315, SEQ ID NO: 323, SEQ ID NO:331, or SEQ ID NO:339.

In some aspects, the VHH1 comprises the amino acid sequence of SEQ ID NO:3, SEQ ID NO: 4, SEQ ID NO: 17, SEQ ID NO: 18, SEQ ID NO:31, SEQ ID NO:32, SEQ ID NO:45, SEQ ID NO: 46, SEQ ID NO:65, SEQ ID NO:68, SEQ ID NO: 69, SEQ ID NO: 70, SEQ ID NO:71, SEQ ID NO: 72, SEQ ID NO:73, SEQ ID NO:74, SEQ ID NO:75, SEQ ID NO:77, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 140, SEQ ID NO: 141, SEQ ID NO: 142, SEQ ID NO: 143, SEQ ID NO: 144, SEQ ID NO: 145, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 221, SEQ ID NO: 222, SEQ ID NO: 223, SEQ ID NO: 224, SEQ ID NO: 225, SEQ ID NO: 226, SEQ ID NO: 255, SEQ ID NO: 256, SEQ ID NO: 265, SEQ ID NO: 267, SEQ ID NO: 275, SEQ ID NO: 283, SEQ ID NO: 291, SEQ ID NO: 299, SEQ ID NO: 307, SEQ ID NO:315, SEQ ID NO:323, SEQ ID NO:331, or SEQ ID NO:339. In some aspects, the VHH2 comprises the amino acid sequence of SEQ ID NO:8, SEQ ID NO:9, SEQ ID NO: 22, SEQ ID NO: 23, SEQ ID NO:36, SEQ ID NO: 37, SEQ ID NO:50, SEQ ID NO:51, SEQ ID NO: 66, SEQ ID NO:67, SEQ ID NO: 76, SEQ ID NO: 101, SEQ ID NO: 102, SEQ ID NO: 103, SEQ ID NO: 146, SEQ ID NO:185, SEQ ID NO: 186, SEQ ID NO:187, SEQ ID NO: 254, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 266, SEQ ID NO: 271, SEQ ID NO: 279, SEQ ID NO: 287, SEQ ID NO: 295, SEQ ID NO: 303, SEQ ID NO:311, SEQ ID NO:319, SEQ ID NO:327, SEQ ID NO:335, or SEQ ID NO: 343.

In some aspects, the VHH1 comprises: an amino acid sequence at least 85%, at least 90%, at least 95%, at least 96%, at least 97%, at least 98%, or at least 99% identical to the amino acid sequence of SEQ ID NO:3, SEQ ID NO:4, SEQ ID NO:17, SEQ ID NO: 18, SEQ ID NO:31, SEQ ID NO: 32, SEQ ID NO:45, SEQ ID NO:46, SEQ ID NO:65, SEQ ID NO: 68, SEQ ID NO:69, SEQ ID NO: 70, SEQ ID NO:71, SEQ ID NO: 72, SEQ ID NO: 73, SEQ ID NO: 74, SEQ ID NO: 75, SEQ ID NO: 77, SEQ ID NO:93, SEQ ID NO:94, SEQ ID NO:95, SEQ ID NO: 96, SEQ ID NO:97, SEQ ID NO: 98, SEQ ID NO: 99, SEQ ID NO: 100, SEQ ID NO: 140, SEQ ID NO: 141, SEQ ID NO: 142, SEQ ID NO: 143, SEQ ID NO: 144, SEQ ID NO: 145, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 221, SEQ ID NO: 222, SEQ ID NO: 223, SEQ ID NO: 224, SEQ ID NO: 225, SEQ ID NO: 226, SEQ ID NO: 255, SEQ ID NO: 256, SEQ ID NO: 265, SEQ ID NO: 267, SEQ ID NO: 275, SEQ ID NO: 283, SEQ ID NO: 291, SEQ ID NO: 299, SEQ ID NO:307, SEQ ID NO: 315, SEQ ID NO:323, SEQ ID NO:331, or SEQ ID NO:339. In some aspects, the VHH2 comprises: an amino acid sequence at least 85%, at least 90%, at least 95%, at least 96%, at least 97%, at least 98%, or at least 99% identical to the amino acid sequence of SEQ ID NO:8, SEQ ID NO: 9, SEQ ID NO: 22, SEQ ID NO: 23, SEQ ID NO:36, SEQ ID NO:37, SEQ ID NO:50, SEQ ID NO: 51, SEQ ID NO:66, SEQ ID NO:67, SEQ ID NO:76, SEQ ID NO: 101, SEQ ID NO: 102, SEQ ID NO: 103, SEQ ID NO:146, SEQ ID NO: 185, SEQ ID NO: 186, SEQ ID NO: 187, SEQ ID NO: 254, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 266, SEQ ID NO: 271, SEQ ID NO: 279, SEQ ID NO: 287, SEQ ID NO: 295, SEQ ID NO:303, SEQ ID NO:311, SEQ ID NO:319, SEQ ID NO:327, SEQ ID NO:335, or SEQ ID NO:343.

In some aspects, the VHH1 comprises the amino acid sequence of SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 221, SEQ ID NO: 222, SEQ ID NO: 223, SEQ ID NO: 224, SEQ ID NO: 225, SEQ ID NO: 226, SEQ ID NO: 255, SEQ ID NO: 256, SEQ ID NO: 265, SEQ ID NO: 267, SEQ ID NO: 275, SEQ ID NO: 283, SEQ ID NO: 291, SEQ ID NO: 299, SEQ ID NO: 307, SEQ ID NO:315, SEQ ID NO:323, SEQ ID NO:331, or SEQ ID NO:339. In some aspects, the VHH2 comprises the amino acid sequence of SEQ ID NO:8, SEQ ID NO:9, SEQ ID NO: 22, SEQ ID NO: 23, SEQ ID NO:36, SEQ ID NO:37, SEQ ID NO:50, SEQ ID NO:51, SEQ ID NO: 66, SEQ ID NO:67, SEQ ID NO: 76, SEQ ID NO: 101, SEQ ID NO: 102, SEQ ID NO: 103, SEQ ID NO: 146, SEQ ID NO: 185, SEQ ID NO: 186, SEQ ID NO: 187, SEQ ID NO: 254, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 266, SEQ ID NO: 271, SEQ ID NO: 279, SEQ ID NO: 287, SEQ ID NO: 295, SEQ ID NO:303, SEQ ID NO:311, SEQ ID NO:319, SEQ ID NO:327, SEQ ID NO:335, or SEQ ID NO:343.

In some aspects, the VHH1 comprises: an amino acid sequence at least 85%, at least 90%, at least 95%, at least 96%, at least 97%, at least 98%, or at least 99% identical to the amino acid sequence of SEQ ID NO:3, SEQ ID NO:4, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 140, SEQ ID NO: 141, SEQ ID NO: 142, SEQ ID NO: 143, SEQ ID NO: 144, or SEQ ID NO: 145. In some aspects, the VHH2 comprises an amino acid sequence at least 85%, at least 90%, at least 95%, at least 96%, at least 97%, at least 98%, or at least 99% identical to the amino acid sequence of SEQ ID NO:8, SEQ ID NO:9, SEQ ID NO: 101, SEQ ID NO: 102, SEQ ID NO: 103, or SEQ ID NO: 146.

In some aspects, provided herein is a polypeptide that binds IL31 comprising two or more IL31 binders, wherein the first IL31 binder comprises a VHH1 which comprises the amino acid sequence of SEQ ID NO:3, SEQ ID NO:4, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 140, SEQ ID NO: 141, SEQ ID NO: 142, SEQ ID NO: 143, SEQ ID NO: 144, SEQ ID NO: 145, and the second IL31 binder comprises a VHH2 that binds to IL31.

In some aspects, provided herein is a polypeptide that binds IL31 comprising two or more IL31 binders, wherein the first IL31 binder comprises a VHH1 that binds to IL31 and the second IL31 binder comprises a VHH2 comprising the amino acid sequence of SEQ ID NO: 8, SEQ ID NO: 9, SEQ ID NO: 101, SEQ ID NO: 102, SEQ ID NO: 103, or SEQ ID NO: 146.

In some aspects, provided herein is a polypeptide that binds IL31 comprising two or more IL31 binders, wherein the first IL31 binder comprises a VHH1 comprising the amino acid sequence of SEQ ID NO:3, SEQ ID NO:4, SEQ ID NO: 93, SEQ ID NO: 94, SEQ ID NO: 95, SEQ ID NO:

96, SEQ ID NO: 97, SEQ ID NO: 98, SEQ ID NO: 99, SEQ ID NO: 100, SEQ ID NO: 140, SEQ ID NO: 141, SEQ ID NO: 142, SEQ ID NO: 143, SEQ ID NO: 144, or SEQ ID NO: 145 and the second IL31 binder comprises a VHH2 comprising the amino acid sequence of SEQ ID NO:8, SEQ ID NO:9, SEQ ID NO: 101, SEQ ID NO: 102, SEQ ID NO: 103, or SEQ ID NO: 146.

In some aspects, the polypeptide has the structure: [VHH1]-linker-[VHH2].

In some aspects, the linker is from about 5 to about 50 amino acids in length. In some aspects, the linker is from about 8 to about 40 amino acids in length. In some aspects, the linker is from about 12 to about 37 amino acids in length. In some aspects, the linker is a flexible linker. In some aspects, the linker is a rigid linker.

In some aspects, the linker comprises an amino acid sequence having at least 85%, at least 90%, at least 95%, at least 96%, at least 97%, at least 98%, at least 99%, or about 100% sequence identity to SEQ ID NO: 104 or SEQ ID NO: 188.

In some aspects, the polypeptide comprises an amino acid sequence at least 85%, at least 90%, at least 95%, at least 96%, at least 97%, at least 98%, or at least 99% identical to the amino acid sequence of SEQ ID NO: 13, SEQ ID NO: 27, SEQ ID NO: 41, SEQ ID NO: 55, SEQ ID NO: 14, SEQ ID NO: 28, SEQ ID NO: 42, or SEQ ID NO: 56. In some aspects, the polypeptide comprises the amino acid sequence of SEQ ID NO: 13, SEQ ID NO: 27, SEQ ID NO: 41, SEQ ID NO: 55, SEQ ID NO: 14, SEQ ID NO: 28, SEQ ID NO: 42, or SEQ ID NO: 56. In some aspects, the polypeptide comprises the amino acid sequence of SEQ ID NO: 14, SEQ ID NO: 28, SEQ ID NO: 42, or SEQ ID NO: 56. In some aspects, the polypeptide comprises the amino acid sequence of SEQ ID NO: 14. In some aspects, the polypeptide comprises the amino acid sequence of SEQ ID NO: 28. In some aspects, the polypeptide comprises the amino acid sequence of SEQ ID NO: 42. In some aspects, the polypeptide comprises the amino acid sequence of SEQ ID NO: 56.

In some aspects, the polypeptide comprises an amino acid sequence having at least 85%, at least 90%, at least 95%, at least 96%, at least 97%, at least 98%, at least 99%, or about 100% sequence identity to the amino acid sequence of SEQ ID NO:13, SEQ ID NO:14, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, or SEQ ID NO: 176.

In some aspects, the polypeptide comprises the amino acid sequence of SEQ ID NO: 13, SEQ ID NO:14, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, or SEQ ID NO: 176.

In some aspects, the polypeptide comprises an amino acid sequence having at least 85%, at least 90%, at least 95%, at least 96%, at least 97%, at least 98%, at least 99%, or about 100% sequence identity to the amino acid sequence of SEQ ID NO:55, SEQ ID NO:56, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO: 211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249 or SEQ ID NO: 250.

In some aspects, the polypeptide comprises the amino acid sequence of SEQ ID NO:55, SEQ ID NO:56, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO:200, SEQ ID NO:201, SEQ ID NO:202, SEQ ID NO:203, SEQ ID NO: 204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO: 215, SEQ ID NO:216, SEQ ID NO:217, SEQ ID NO:218, SEQ ID NO:219, SEQ ID NO:220, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249 or SEQ ID NO: 250.

In some aspects, the polypeptide further comprises an Fc region. In some aspects, the polypeptide has the structure: [VHH1]-linker-[VHH2]-Fc region.

In some aspects, the polypeptide of the present disclosure binds to an antigen comprising at least two binding moieties that comprise VHH1, VHH2, and a linker, wherein the polypeptide has the structure: [VHH1]-linker-[VHH2], wherein the linker comprises an amino acid sequence comprising (X)n-G, and the VHH2 comprises at the N-terminus Xa, Xb, and Xc, wherein X is an amino acid, G is glycine, n is any integer between 0 and 100, Xa is E (Glutamic acid), Q (Glutamine), or missing, Xb is V (Valine) or missing, and Xc is Q (Glutamine), K (Lysine), or missing. In some aspects, the VHH1 comprises any VHH1 disclosed herein. In some aspects, the VHH2 comprises any VHH2 disclosed herein.

In some aspects, the polypeptide further comprises an Fc region. In some aspects, the X in the linker comprises (G2S)n, (G3S)n, (G4S)n, (G5S)n, or any combination thereof, and n is an integer between 1 and 10. In some aspects, the X in the linker comprises (G4S)n, and n is 4, 5, or 6. In some aspects, the linker comprises the amino acid sequence of SEQ ID NO: 104 or SEQ ID NO: 188.

In some aspects, the polypeptide comprises an IgG1, IgG2, IgG3, or IgG4 Fc region. In some aspects, the polypeptide comprises a human Fc region. In some aspects, the Fc region comprises one or more substitutions, deletions, insertions, or any combination thereof. In some aspects, the one or more substitutions comprise C220S (hinge region), M252Y (CH2 region), S254T (CH2 region), T256E (CH2 region), L234A (CH2 region), L235A (CH2 region), M428L (CH3 region), N434S (CH3 region), or any combination thereof, according to the EU numbering system. In some aspects, the C terminus of the Fc region is Lysine. In some aspects, the C terminus of the Fc region is not Lysine. In some aspects, the C terminal Lysine of the Fc region has been removed, e.g., enzymatically removed during upstream production process.

In some aspects, the polypeptide comprises an Fc region with a modified effector function. In some aspects, the polypeptide comprises an effector null Fc region. In some aspects, the polypeptide comprises an Fc region comprising a full or partial hinge, no CH1 region, a full or partial CH2 region, and a full or partial CH3 region. In some aspects, the polypeptide comprises an Fc region comprising a full hinge region, no CH1 region, full CH2 region and full CH3 region. In some aspects, the full or partial hinge region comprises a cysteine (C) to serine(S) mutation at position 220 according to EU numbering (C220S). In some aspects, the Fc region comprises the amino acid sequence of SEQ ID NO: 62 or the amino acid residues 1-231 of SEQ ID NO: 62. In some aspects, the Fc region comprises the amino acid sequence of SEQ ID NO: 90 or the amino acid residues 1-231 of SEQ ID NO: 90.

In some aspects, the polypeptide disclosed herein is monospecific. In some aspects, the polypeptide disclosed herein is bispecific. In some aspects, the polypeptide disclosed herein is trispecific. In some aspects, the polypeptide disclosed herein is tetraspecific.

In some aspects, the polypeptide further comprises a binder that binds to a protein, but does not bind to IL31 ("third binder). In some aspects, the polypeptide further comprises a binder that binds to the same protein as the third binder or a different protein from the third binder or IL31 ("fourth binder"). In some aspects, the third binder comprises a VHH (VHH3). In some aspects, the fourth binder comprises a VHH (VHH4). In some aspects, the VHH3 and the VHH4 are different. In some aspects, the VHH3 and the VHH4 are the same. In some aspects, the VHH3 and VHH4 single binders bind to the same target antigen biparatopically or recognize two different epitopes on the same target antigen. In some aspects, the biparatopic VHH3 and VHH4 single binders bind the same target antigen at nonoverlapping epitopes, which allows both VHH3 and VHH4 single binders to bind the same target antigen simultaneously.

In some aspects, the polypeptide comprises an amino acid sequence at least 85%, at least 90%, at least 95%, at least 96%, at least 97%, at least 98%, or at least 99% identical to the amino acid sequence of SEQ ID NO: 15 or the amino acid residues 1-506 of SEQ ID NO: 15, SEQ ID NO: 29 or the amino acid residues 1-496 of SEQ ID NO: 29, SEQ ID NO: 43 or the amino acid residues 1-487 of SEQ ID NO: 43, SEQ ID NO: 57 or the amino acid residues 1-507 of SEQ ID NO: 57, SEQ ID NO: 16 or the amino acid residues 1-506 of SEQ ID NO: 16, SEQ ID NO: 30 or the amino acid residues 1-496 of SEQ ID NO: 30, SEQ ID NO: 44 or the amino acid residues 1-487 of SEQ ID NO: 44, SEQ ID NO: 58 or the amino acid residues 1-507 of SEQ ID NO: 58, SEQ ID NO: 91 or the amino acid residues 1-506 of SEQ ID NO: 91, or SEQ ID NO: 92 or the amino acid residues 1-506 of SEQ ID NO: 92. In some aspects, the polypeptide comprises the amino acid sequence of SEQ ID NO: 15 or the amino acid residues 1-506 of SEQ ID NO: 15, SEQ ID NO: 29 or the amino acid residues 1-496 of SEQ ID NO: 29, SEQ ID NO: 43 or the amino acid residues 1-487 of SEQ ID NO: 43, SEQ ID NO: 57 or the amino acid residues 1-507 of SEQ ID NO: 57, SEQ ID NO: 91 or the amino acid residues 1-506 of SEQ ID NO: 91, SEQ ID NO: 16 or the amino acid residues 1-506 of SEQ ID NO: 16, SEQ ID NO: 30 or the amino acid residues 1-496 of SEQ ID NO: 30, SEQ ID NO: 44 or the amino acid residues 1-487 of SEQ ID NO: 44, SEQ ID NO: 58 or the amino acid residues 1-507 of SEQ ID NO: 58, or SEQ ID NO: 92 or the amino acid residues 1-506 of SEQ ID NO: 92. In some aspects, the polypeptide comprises the amino acid sequence of SEQ ID NO: 16 or the amino acid residues 1-506 of SEQ ID NO: 16, SEQ ID NO: 30 or the amino acid residues 1-496 of SEQ ID NO: 30, SEQ ID NO: 44 or the amino acid residues 1-487 of SEQ ID NO: 44, SEQ ID NO: 58 or the amino acid residues 1-507 of SEQ ID NO: 58, or SEQ ID NO: 92 or the amino acid residues 1-506 of SEQ ID NO: 92. In some aspects, the polypeptide comprises the amino acid sequence of SEQ ID NO: 16 or the amino acid residues 1-506 of SEQ ID NO: 16. In some aspects, the polypeptide comprises the amino acid sequence of SEQ ID NO: 30 or the amino acid residues 1-496 of SEQ ID NO: 30. In some aspects, the polypeptide comprises the amino acid sequence of SEQ ID NO: 44 or the amino acid residues 1-487 of SEQ ID NO: 44. In some aspects, the polypeptide comprises the amino acid sequence of SEQ ID NO: 58 or the amino acid residues 1-507 of SEQ ID NO: 58. In some aspects, the polypeptide comprises the amino acid sequence of SEQ ID NO: 92 or the amino acid residues 1-506 of SEQ ID NO: 92.

In some aspects, the polypeptide binds to human IL31. In some aspects, the human IL31 comprises the amino acid sequence of SEQ ID NO: 1 or SEQ ID NO: 2.

In some aspects, the polypeptide binds to human IL31 at a kD of less than or equal to $1\times10^{-9}$ M, less than or equal to $5\times10^{-10}$ M, less than or equal to $1\times10^{-10}$ M, less than or equal to $5\times10^{-11}$ M, less than or equal to $1\times10^{-11}$ M, less than or equal to $5\times10^{-12}$ M, or less than or equal to $1\times10^{-12}$ M, as measured by surface plasmon resonance. In some aspects, the polypeptide binds to human IL31 with a koff rate of less than or equal to $5\times10^{-4}$ M per second, less than or equal to $1\times10^{-4}$ M per second, less than or equal to $5\times10^{-5}$ M per second, less than or equal to $1\times10^{-5}$ M per second, less than or equal to $5\times10^{-6}$ M per second, or less than or equal to $1\times10^{-6}$ M per second, as measured by surface plasmon resonance.

In some aspects, polypeptides comprising a Fc region are provided herein. In some aspects, the Fc region comprises an amino acid sequence at least 85%, at least 90%, at least 95%, at least 96%, at least 97%, at least 98%, or at least 99% identical to the amino acid sequence of SEQ ID NO: 62 or the amino acid residues 1-231 of SEQ ID NO: 62. In some aspects, the Fc region comprises an amino acid sequence at least 85%, at least 90%, at least 95%, at least 96%, at least 97%, at least 98%, or at least 99% identical to the amino acid sequence of SEQ ID NO: 62 or the amino acid residues 1-231 of SEQ ID NO: 62, and wherein position 5 is serine, position 37 is tyrosine, position 39 is threonine, and position 41 is glutamate according to SEQ ID NO: 62 or the amino acid residues 1-231 of SEQ ID NO: 62. In some aspects, the polypeptide and/or the Fc region comprises the amino acid sequence of SEQ ID NO: 62 or the amino acid residues 1-231 of SEQ ID NO: 62.

In some aspects, polypeptides comprising a Fc region are provided herein. In some aspects, the Fc region comprises an amino acid sequence at least 85%, at least 90%, at least 95%, at least 96%, at least 97%, at least 98%, or at least 99% identical to the amino acid sequence of SEQ ID NO: 90 or the amino acid residues 1-231 of SEQ ID NO: 90. In some aspects, the Fc region comprises an amino acid sequence at least 85%, at least 90%, at least 95%, at least 96%, at least 97%, at least 98%, or at least 99% identical to the amino acid sequence of SEQ ID NO: 90 or the amino acid residues 1-231 of SEQ ID NO: 90, and wherein position 5 is serine, position 37 is tyrosine, position 39 is threonine, and position 41 is glutamate according to SEQ ID NO: 90 or the amino acid residues 1-231 of SEQ ID NO: 90. In some aspects, the polypeptide and/or the Fc region comprises the amino acid sequence of SEQ ID NO: 90 or the amino acid residues 1-231 of SEQ ID NO: 90.

Also provided herein are multimeric polypeptides, each comprising two or more of any one of the polypeptides provided herein.

Also provided herein are pharmaceutical compositions comprising any one or more of the polypeptides or any one or more of the multimeric polypeptides described herein and a pharmaceutically acceptable carrier.

Also provided herein are isolated nucleic acids encoding any one or more of the polypeptides or any one or more of the multimeric polypeptides described herein. Further provided herein are vectors comprising any one or more of the nucleic acids described herein. Further provided herein are in vitro or ex vivo cells comprising any one or more of the nucleic acids described herein. Further provided herein are in vitro or ex vivo cells comprising any one or more of the vectors described herein.

Also provided herein are methods of producing any one or more of the polypeptides or any one or more of the multimeric polypeptides described herein. In some aspects, the method comprises culturing an in vitro or ex vivo cell comprising any one or more of the nucleic acids described herein under conditions suitable for expression of the polypeptide(s). In some aspects, the method comprises culturing an in vitro or ex vivo cell comprising any one or more of the vectors described herein under conditions suitable for expression of the polypeptide(s) or multimeric polypeptide(s). In some aspects, the method further comprises isolating the polypeptide(s) or multimeric polypeptide(s).

Also provided herein are methods for treating a subject having an IL31-associated condition comprising administering to the subject a therapeutically effective amount of any one or more the polypeptides or any one or more of the multimeric polypeptides described herein or a pharmaceutical composition thereof.

In some aspects, the subject is a human subject.

In some aspects, the IL31-associated condition is a pruritic condition. In some aspects, the IL31-associated condition is atopic dermatitis, prurigo nodularis, or chronic spontaneous urticaria.

In some aspects, the polypeptide, the multimeric polypeptide, or the pharmaceutical composition is administered parenterally. In some aspects, the polypeptide, the multimeric polypeptide, or the pharmaceutical composition is administered by an intravenous route, a subcutaneous route, an intramuscular route, or an intraperitoneal route. In some aspects, the polypeptide, the multimeric polypeptide, or the pharmaceutical composition is administered by intravenous route. In some aspects, the polypeptide, the multimeric polypeptide, or the pharmaceutical composition is administered by subcutaneous route.

In some aspects, the method comprises administering one or more therapeutic agent in combination with the polypeptide, the multimeric polypeptide, or the pharmaceutical composition. In some aspects, the one or more therapeutic agent is an antibody, a small molecule inhibitor, and/or a systemic immunosuppressant agent. In some aspects, the one or more therapeutic agent is a topical corticosteroid, a calcineurin inhibitor, an anti-IL4RA antibody, an anti-IL13RA antibody, an anti-OSMR antibody, an anti-Ox40 antibody, an anti-Ox40L antibody, an anti-TSLP antibody an anti-IL17 antibody, an anti-TNFα antibody, an anti-CD20 antibody, an anti-CD19 antibody, an anti-CD25 antibody, an anti-IL4 antibody, an anti-IL13 antibody, an anti-IL23 antibody, anti-IL23p19 antibody, an anti-IL31RA antibody, an anti-IgE antibody, an anti-CD11α antibody, anti-IL6R antibody, anti-α4-Intergrin antibody, an anti-IL12 antibody, an anti-IL1β antibody, an anti-BlyS antibody, an anti-CKIT antibody, an anti-MRGPRX2 antibody, an anti-Fc epsilon receptor (FcεRI) antibody, an anti-SIGLEC-6 antibody, and/or an anti-SIGLEC-8 antibody. In some aspects, the one or more therapeutic agent is a small molecule inhibitor of IL4RA, IL13RA, IL13, IL31RA, OSMR, Ox40, Ox40L, TSLP, IL17, TNFα, CD20, CD19, CD25, IL4, IL23, IgE, CD11a, IL6R, α4-Intergrin, IL12, IL1β, BlyS, CKIT, MRGPRX2, Fc epsilon receptor (FcεRI), and/or SIGLEC-6. In some aspects, the one or more therapeutic agent is a STAT inhibitor, a JAK inhibitor, a PI3K inhibitor, an AKT inhibitor, a MAPK inhibitor, a MRGPRX2 inhibitor, a topical corticosteroid, a calcineurin inhibitor, and/or a fusion protein comprising a portion of CTLA-4 and an Fc region of an immunoglobulin, optionally wherein the fusion protein is abatacept or belatacept.

Also provided herein are methods of detecting human IL31 in a biological sample comprising contacting the biological sample with any one or more of the polypeptides or multimeric polypeptides described herein under conditions permissive for binding of the polypeptide or multimeric polypeptide to a human IL31 and detecting whether a complex is formed between the polypeptide or multimeric polypeptide and the human IL31 in the biological sample. In some aspects, wherein the biological sample is a serum sample.

MACS eluates for 0 nM IL31 and 100 nM IL31 stained samples. Round 2 (R2) FACS and round 3 (R3), FACS images represent flow plots for sorting human IL31 specific single binder displaying yeast cells at 100 nM and 30 nM human IL31 concentrations, respectively.

Figure 2:
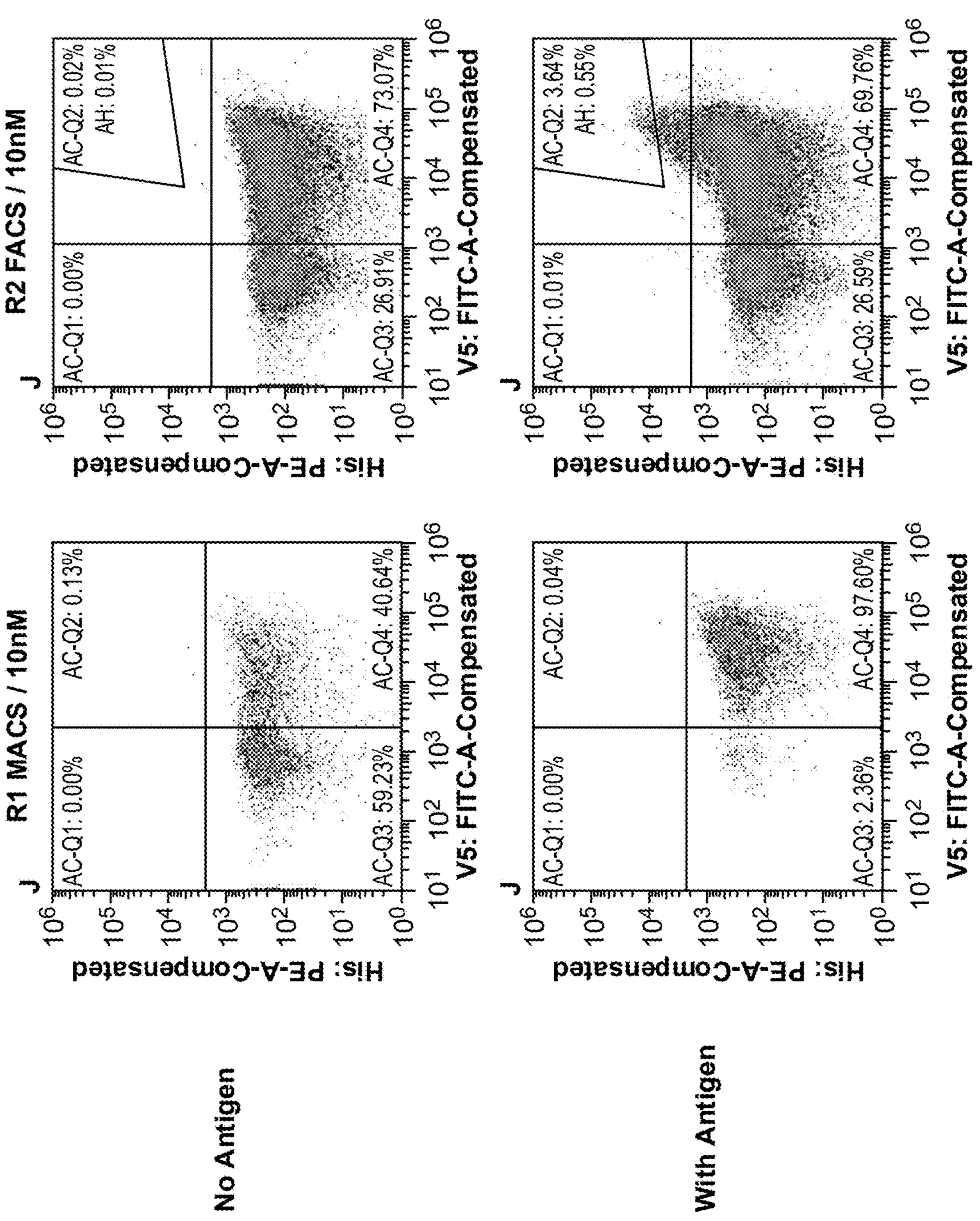
Figure 2:
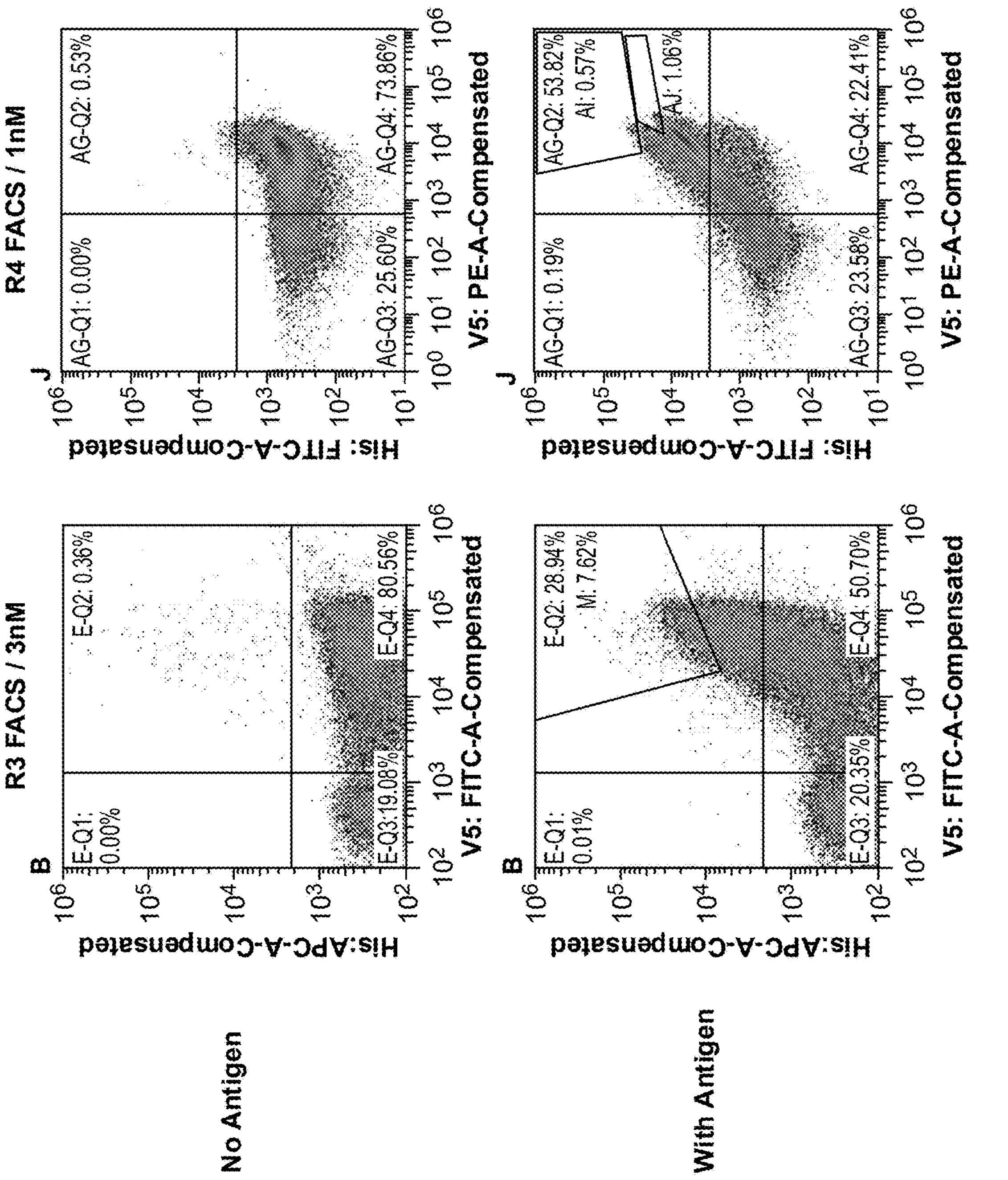

FIG. 2 shows flow cytometry plots for Campaign 1 anti-IL31 co-binder selection. Round 1 (R1) MACS flow plot images were taken from flow cytometry analysis of R1 MACS eluates for 0 nM IL31 and 10 nM IL31 stained samples. Round 2 (R2) FACS, round 3 (R3) FACS, round 4 (R4) FACS images represent flow plots for sorting human IL31 specific co-binder displaying yeast cells at 10 nM, 3 nM, and 1 nM human IL31 concentrations, respectively. In R4 FACS plot, AI gate represents populations with higher affinity to human IL31 than AJ gate.

Figure 3:
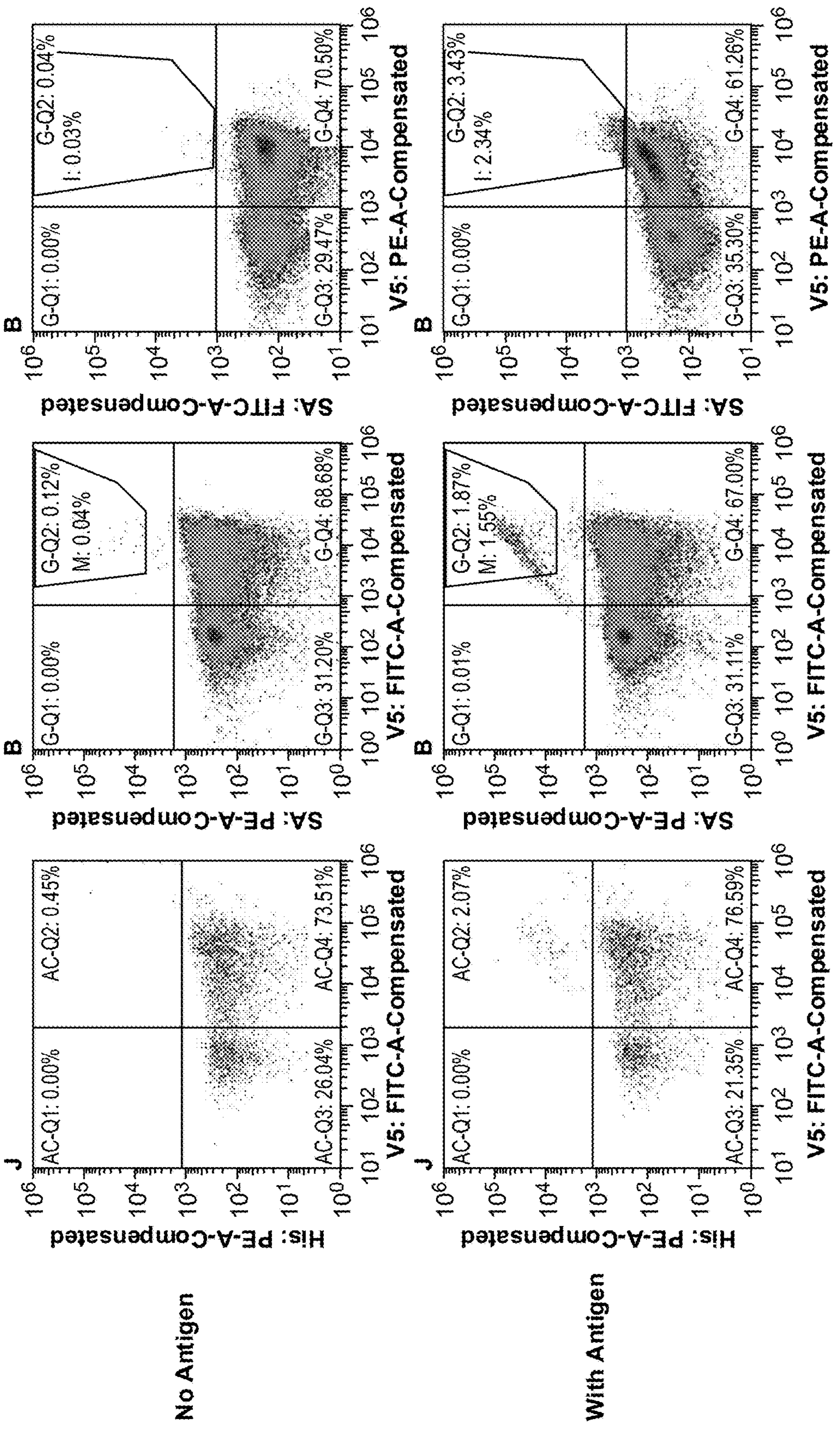
Figure 3:
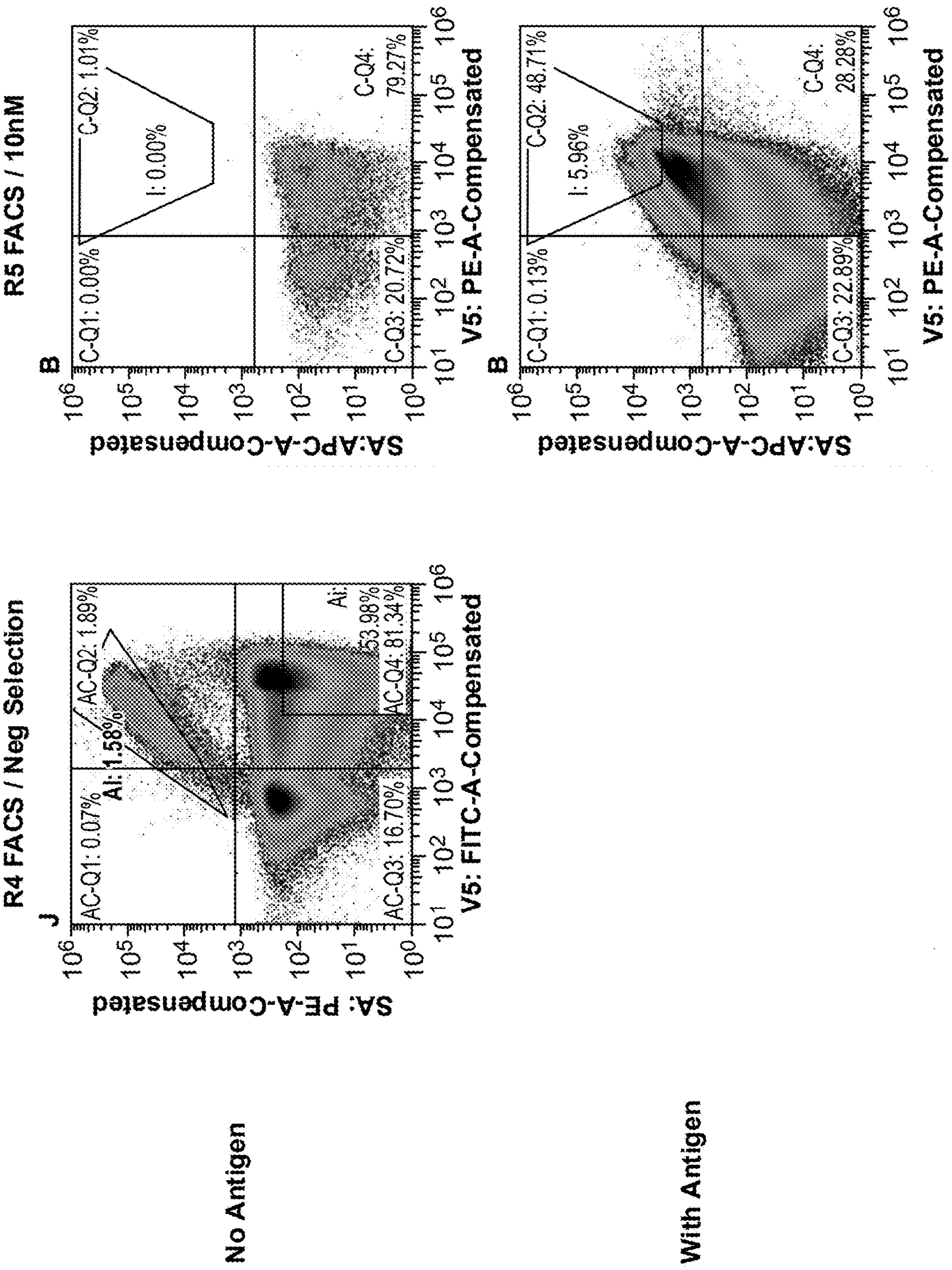

FIG. 3 shows flow cytometry plots for Campaign 2 anti-IL31 single binder selection. Round 1 (R1) MACS flow plot images were taken from flow cytometry analysis of R1 MACS eluates for 0 nM IL31 and 30 nM IL31 stained samples. Round 2 (R2) FACS and round 3 (R3) FACS images represent flow plots for sorting human anti-IL31 VHH displaying yeast cells at 30 nM and 10 nM human IL31 concentrations, respectively. A negative selection was performed in round 4 (R4) FACS to avoid potential non-specific binding. Round 5 (R5) FACS was performed for positive selection of anti-IL31 VHH displaying cells with 10 nM IL31 concentration.

Figure 4:
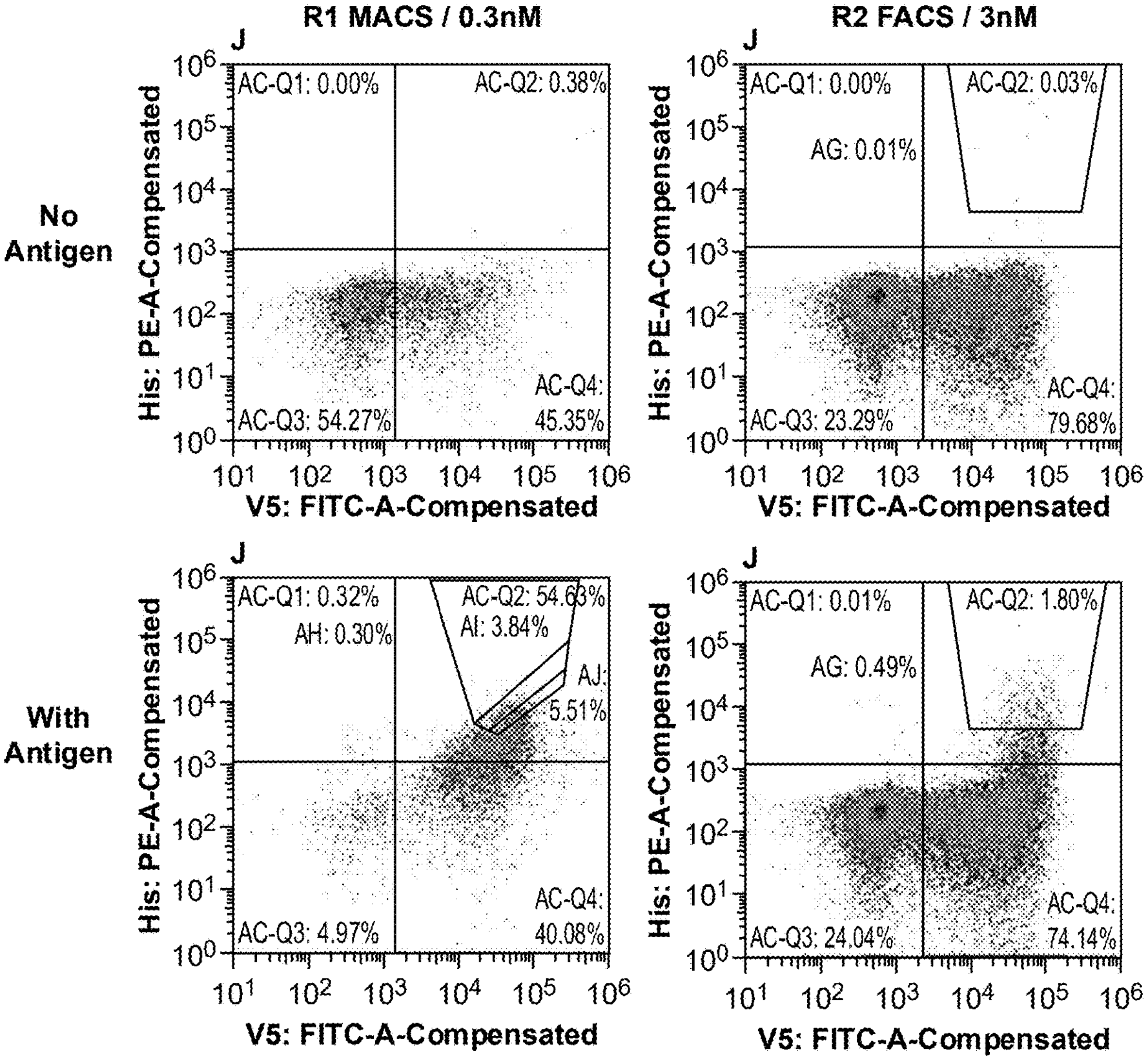

FIG. 4 shows flow cytometry plots for Campaign 2 anti-IL31 co-binder selection. Round 1 (R1) MACS flow plot images were taken from flow cytometry analysis of R1 MACS eluates for 0 nM IL31 and 0.3 nM IL31 stained samples. Round 2 (R2) FACS was performed for sorting human anti-IL31 single-binder displaying yeast cells at 3 nM human IL31 concentrations. A negative selection was performed in round 3 (R3) FACS to avoid potential non-specific binding. Round 4 (R4) and round 5 (R5) FACS were performed for positive selection of anti-IL31 VHH displaying cells with 1 nM and 0.1 nM human IL31 concentrations, respectively.

FIG. 5 is a sequence alignment of VHH1 or VHH2 regions of certain co-binder clone candidates.

Figure 6A:
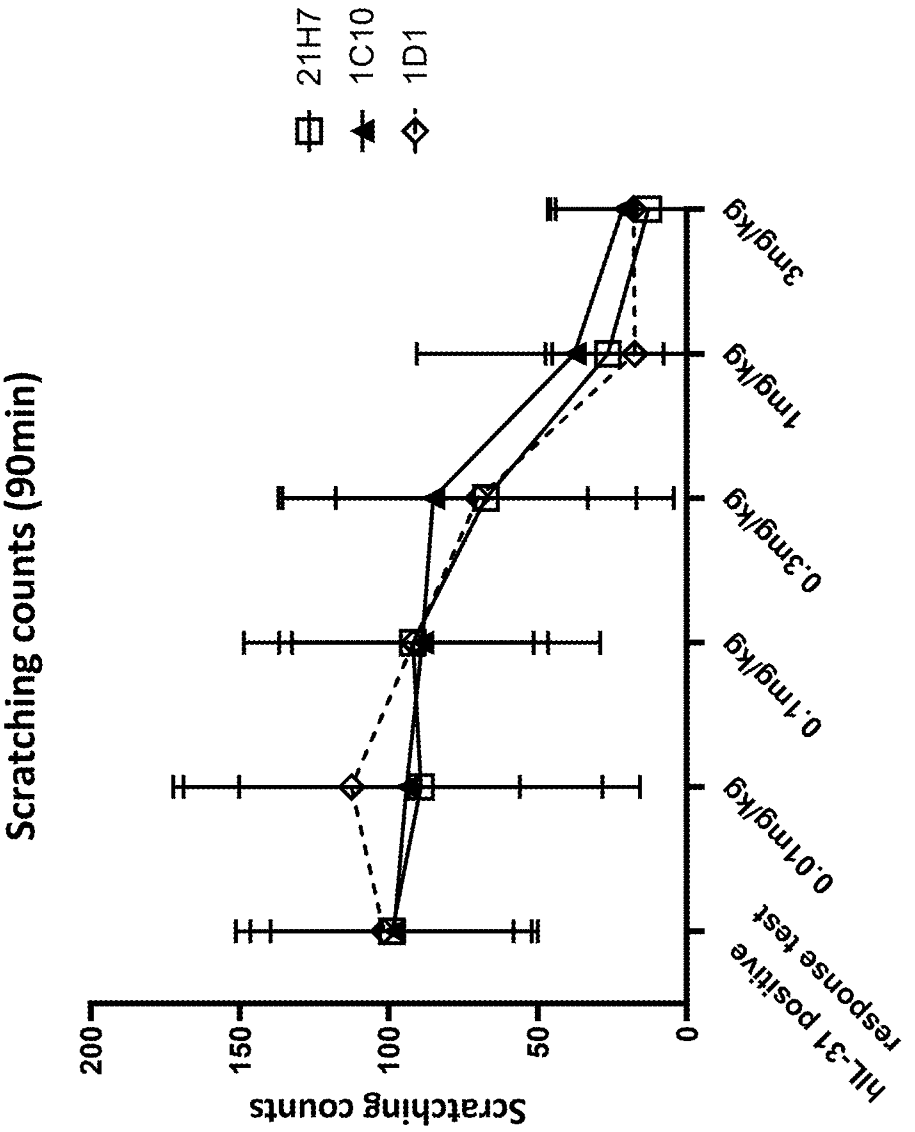
Figure 6B:
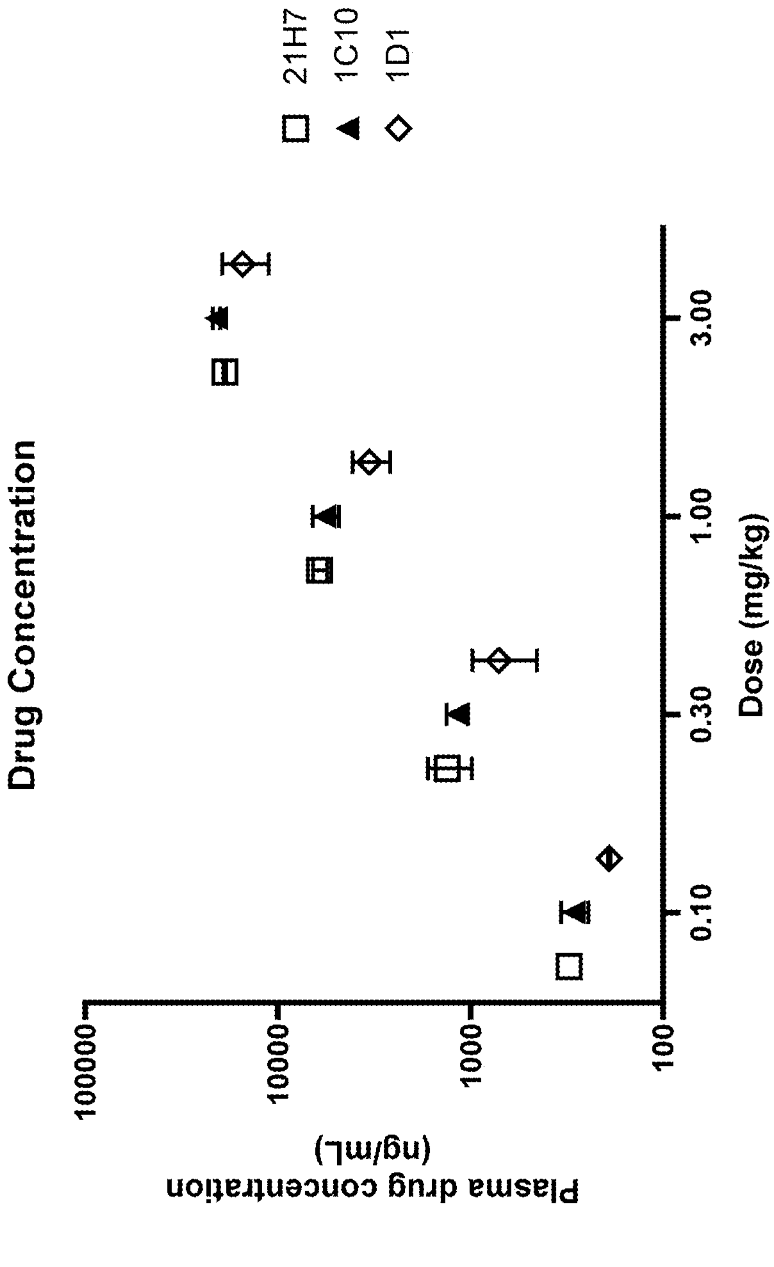

FIGS. 6A-6B are plots showing anti-pruritic activity in mice. Female transgenic hIL31/hIL31RA/hOSMR mice were administered 21H7, 1C10, or 1D1 at increasing dose ranging from 0.3 to 3 mg/kg levels then treated intravenously with hIL31 after 24 hours. FIG. 6A is a plot showing pruritic activity as percent scratching counts relative to pre-study treatment with IL31. FIG. 6B is a plot showing plasma concentrations of co-binders as assessed on the day of hIL31 administration.

Figure 7A:
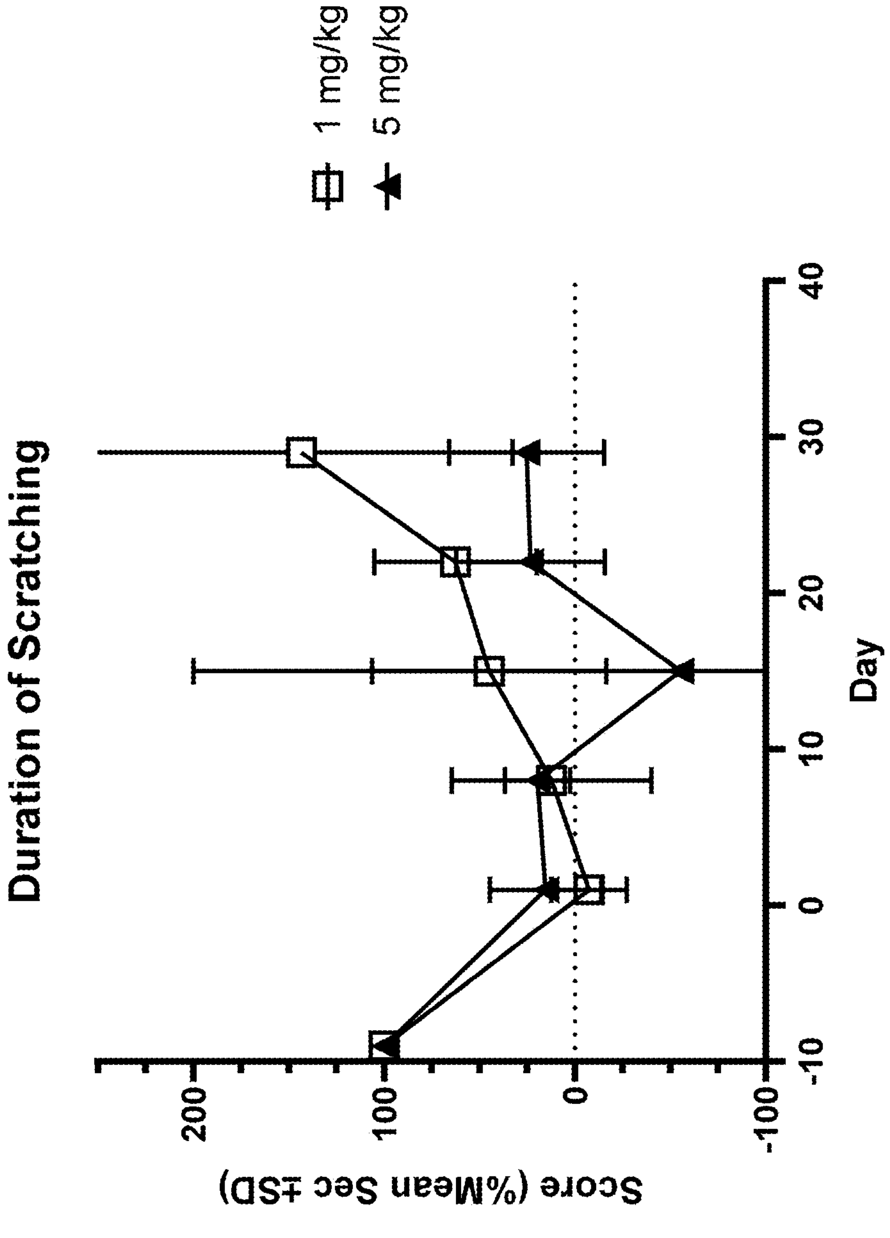
Figure 7B:
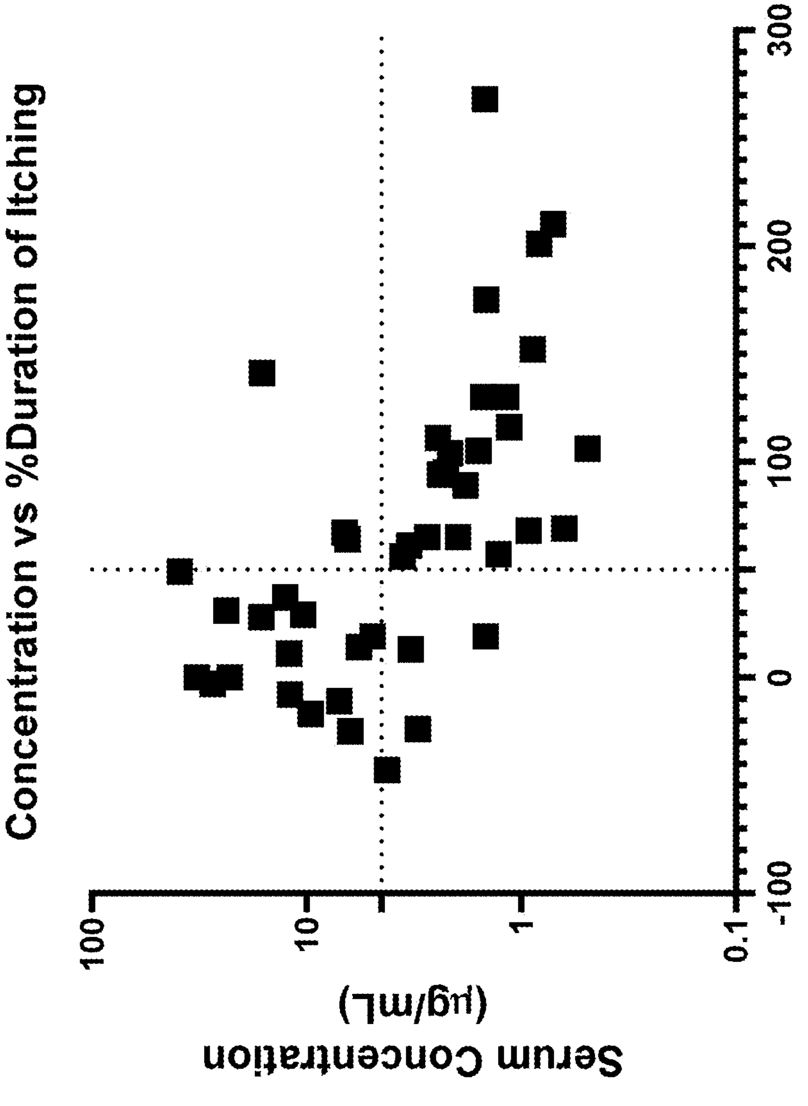

FIGS. 7A-7B are plots showing anti-pruritic activity in non-human primates. Healthy male cynomolgus monkeys were administered co-binder 1C10 at either 1 or 5 mg/kg. Animals were then treated intravenously with cynomolgus IL31 after 24 hours. FIG. 7A is a plot showing pruritic activity as percent duration of scratching relative to pre-study treatment with IL31. FIG. 7B is a plot showing the relative duration of pruritic activity to the calculated serum drug concentration.

DESCRIPTION OF THE SEQUENCES

Table 1 provides a listing of certain sequences referenced herein.

TABLE 1

Description of Certain Sequences

Description of Certain Sequences

| SEQ ID NO | Sequence | Description |
|---|---|---|
| 1 | MASHSGPSTSVLFLFCCLGGWLASHTLPVRLLRPSDDVQKIVEEL QSLSKMLLKDVEEEKGVLVSQNYTLPCLSPDAQPPNNIHSPAIRA YLKTIRQLDNKSVIDEIIEHLDKLIFQDAPETNISVPTDTHECKR FILTISQQFSECMDLALKSLTSGAQQATT | Human IL31 with signal sequence |
| 2 | SHTLPVRLLRPSDDVQKIVEELQSLSKMLLKDVEEEKGVLVSQNY TLPCLSPDAQPPNNIHSPAIRAYLKTIRQLDNKSVIDEIIEHLDK LIFQDAPETNISVPTDTHECKRFILTISQQFSECMDLALKSLTSG AQQATT | Human IL31 without signal sequence |
| 3 | EVQLVESGGGLVQAGGSLRLSCAASGGTFSSYTMGWFRQAPGKER EYVGGISSSGYVMYNSESMKGRFTISRENAKNMVYLQMNSLKPED TAVYYCAAGTIGRPYDYWGQGTQVTVSS | 1C10 VHH1 single binder |
| 4 | EVQLVESGGGLVQPGGSLRLSCAASGGTFSSYTMGWFRQAP GKEREYVGGISSSGYVMYNSESMKGRFTISRDNAKNTLYLQ MNSLRAEDTAVYYCAAGTIGRPYDYWGQGTQVTVSS | Humanized 1C10 VHH1 single binder |
| 5 | SYTMG | 1C10 VHH1 CDR1 (Kabat numbering) |
| 6 | GISSSGYVMYNSESMKG | 1C10 VHH1 CDR2 (Kabat numbering) |
| 7 | GTIGRPYDY | 1C10 VHH1 CDR3 (Kabat numbering) |
| 8 | VKLEESGGGLVQPGGSLILSCAASGDISSIVAMGWYRQAPGKQRE LVAAITSGGRTHYRDSVKGRFTISGNNDNSALYLHMNSLKPEDTA VYYCAADRGWTSVGEYDYWGKGTLVTVSS | 1C10 VHH2 single binder |

TABLE 1-continued

Description of Certain Sequences
Description of Certain Sequences

| SEQ ID NO | Sequence | Description |
|---|---|---|
| 9 | VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS | Humanized 1C10 VHH2 single binder |
| 10 | IVAMG | 1C10 VHH2 CDR1 (Kabat numbering) |
| 11 | AITSGGRTHYRDSVKG | 1C10 VHH2 CDR2 (Kabat numbering) |
| 12 | DRGWTSVGEYDY | 1C10 VHH2 CDR3 (Kabat numbering) |
| 13 | EVQLVESGGGLVQAGGSLRLSCAASGGTFSSYTMGWFRQAPGKEREYVGGISSSGYVMYNSESMKGRFTISRENAKNMVYLQMNSLKPEDTAVYYCAAGTIGRPYDYWGQGTQVTVSSGGGGSGGGGSGGGGSGGGGSGGGGSGGGGSGGGGSGMTGVKLEESGGGLVQPGGSLILSCAASGDISSIVAMGWYRQAPGKQRELVAAITSGGRTHYRDSVKGRFTISGNNDNSALYLHMNSLKPEDTAVYYCAADRGWTSVGEYDYWGKGTLVTVSS | 1C10 co-binder |
| 14 | EVQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS | Humanized 1C10 co-binder |
| 15 | EVQLVESGGGLVQAGGSLRLSCAASGGTFSSYTMGWFRQAPGKEREYVGGISSSGYVMYNSESMKGRFTISRENAKNMVYLQMNSLKPEDTAVYYCAAGTIGRPYDYWGQGTQVTVSSGGGGSGGGGSGGGGSGGGGSGGGGSGGGGSGGGGSGMTGVKLEESGGGLVQPGGSLILSCAASGDISSIVAMGWYRQAPGKQRELVAAITSGGRTHYRDSVKGRFTISGNNDNSALYLHMNSLKPEDTAVYYCAADRGWTSVGEYDYWGKGTLVTVSSEPKSSDKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 1C10 co-binder + huIgG1Fc_YTE_C→S |
| 16 | EVQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSSEPKSSDKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | Humanized 1C10 co-binder + huIgG1Fc_YTE_C→S |
| 17 | EVQLVESGGGLVQAGGSLRLSCAASGGTFSSYAMAWFRQAPGKEREYVAGISSSGYTLYKSDSMKGRFTISRENAKNMVYLQMNSLKPEDTAVYSCAAGIFGRPYEYWGQGTLVTVSS | 1D1 VHH1 single binder |
| 18 | EVQLVESGGGLVQPGGSLRLSCAASGGTFSSYAMAWFRQAPGKEREYVAGISSSGYTLYKSDSMKGRFTISRDNAKNTLYLQMNSLRAEDTAVYYCAAGIFGRPYEYWGQGTLVTVSS | Humanized 1D1 VHH1 single binder |
| 19 | SYAMA | 1D1 VHH1 CDR1 |
| 20 | GISSSGYTLYKSDSMKG | 1D1 VHH1 CDR2 |
| 21 | GIFGRPYEY | 1D1 VHH1 CDR3 |

TABLE 1-continued

Description of Certain Sequences
Description of Certain Sequences

| SEQ ID NO | Sequence | Description |
|---|---|---|
| 22 | VKLEESGGGLVQAGGSLILSCAASGDIPSIVAMGWYRQAPGKQRE LVAAITSGGRTHYRDSVKGRFTISGNNDNSALYLHMNSLKPEDTA VYYCAADMGLTAVGEYDYWGQGTQVTVSS | 1D1 VHH2 single binder |
| 23 | VQLVESGGGLVQPGGSLRLSCAASGDIPSIVAMGWYRQAPG KQRELVSAITSGGRTHYRDSVKGRFTISRDNSKNTLYLQMN SLRAEDTAVYYCAADMGLTAVGEYDYWGQGTQVTVSS | Humanized 1D1 VHH2 single binder |
| 24 | IVAMG | 1D1 VHH2 CDR1 |
| 25 | AITSGGRTHYRDSVKG | 1D1 VHH2 CDR2 |
| 26 | DMGLTAVGEYDY | 1D1 VHH2 CDR3 |
| 27 | EVQLVESGGGLVQAGGSLRLSCAASGGTFSSYAMAWFRQAPGKER EYVAGISSSGYTLYKSDSMKGRFTISRENAKNMVYLQMNSLKPED TAVYSCAAGIFGRPYEYWGQGTLVTVSSGGGSGGGGSGGGGSGGG GSGGGGSPSMGVKLEESGGGLVQAGGSLILSCAASGDIPSIVAMG WYRQAPGKQRELVAAITSGGRTHYRDSVKGRFTISGNNDNSALYL HMNSLKPEDTAVYYCAADMGLTAVGEYDYWGQGTQVTVSS | 1D1 co-binder |
| 28 | EVQLVESGGGLVQPGGSLRLSCAASGGTFSSYAMAWFRQAPGKER EYVAGISSSGYTLYKSDSMKGRFTISRDNAKNTLYLQMNSLRAED TAVYYCAAGIFGRPYEYWGQGTLVTVSSGGGSGGGGSGGGGSGGG GSGGGGSPSMGVQLVESGGGLVQPGGSLRLSCAASGDIPSIVAMG WYRQAPGKQRELVSAITSGGRTHYRDSVKGRFTISRDNSKNTLYL QMNSLRAEDTAVYYCAADMGLTAVGEYDYWGQGTQVTVSS | Humanized 1D1 co-binder |
| 29 | EVQLVESGGGLVQAGGSLRLSCAASGGTFSSYAMAWFRQAPGKER EYVAGISSSGYTLYKSDSMKGRFTISRENAKNMVYLQMNSLKPED TAVYSCAAGIFGRPYEYWGQGTLVTVSSGGGSGGGGSGGGGSGGG GSGGGGSPSMGVKLEESGGGLVQAGGSLILSCAASGDIPSIVAMG WYRQAPGKQRELVAAITSGGRTHYRDSVKGRFTISGNNDNSALYL HMNSLKPEDTAVYYCAADMGLTAVGEYDYWGQGTQVTVSSEPKSS DKTHTCPPCPAPELLGGPSVFLFPPKPKDTLYITREPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSR DELTKNQVSLTCLVKGFYPSDIAVEWESNGQPENNYKTTPPVLDS DGSFFLYSKLTVDKSRWQQGNVFSCSVMHEALHNHYTQKSLSLSP GK | 1D1 co-binder + huIgG1Fc_YTE_C→S |
| 30 | EVQLVESGGGLVQPGGSLRLSCAASGGTFSSYAMAWFRQAPGKER EYVAGISSSGYTLYKSDSMKGRFTISRDNAKNTLYLQMNSLRAED TAVYYCAAGIFGRPYEYWGQGTLVTVSSGGGSGGGGSGGGGSGGG GSGGGGSPSMGVQLVESGGGLVQPGGSLRLSCAASGDIPSIVAMG WYRQAPGKQRELVSAITSGGRTHYRDSVKGRFTISRDNSKNTLYL QMNSLRAEDTAVYYCAADMGLTAVGEYDYWGQGTQVTVSSEPKSS DKTHTCPPCPAPELLGGPSVFLFPPKPKDTLYITREPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSR DELTKNQVSLTCLVKGFYPSDIAVEWESNGQPENNYKTTPPVLDS DGSFFLYSKLTVDKSRWQQGNVFSCSVMHEALHNHYTQKSLSLSP GK | Humanized 1D1 co-binder + huIgG1Fc_YTE_C→S |
| 31 | EVQLVESGGGSVQAGGSLRLSCAASGGTFSSYAMAWFRQAPGKER EYVAGISSSGYTLYKSDSMKGRFTISRENAKNMVYLQMNSLKPED TAVYSCAAGIFGRPYEYWGQGTQVTVSS | 1H5 VHH1 single binder |
| 32 | EVQLVESGGGLVQPGGSLRLSCAASGGTFSSYAMAWFRQAPGKER EYVAGISSSGYTLYKSDSMKGRFTISRDNAKNTLYLQMNSLRAED TAVYYCAAGIFGRPYEYWGQGTQVTVSS | Humanized 1H5 VHH1 |
| 33 | SYAMA | 1H5 VHH1 CDR1 |
| 34 | GISSSGYTLYKSDSMKG | 1H5 VHH1 CDR2 |
| 35 | GIFGRPYEY | 1H5 VHH1 CDR3 |
| 36 | VQLVESGGGLVQAGGSLRLSCAASGSISSIHAMGWYRQAPGKQRE LIAAITSGGRRHYRDSVKGRFTISGDNAKTNLYLQMNSLKPEDTA VYYCAADTGRVAVGEYDYWGQGTLVTVSS | 1H5 VHH2 single binder |

TABLE 1-continued

| SEQ ID NO | Sequence | Description |
|---|---|---|
| | Description of Certain Sequences | |
| | Description of Certain Sequences | |
| 37 | VQLVESGGGLVQPGGSLRLSCAASGSISSIHAMGWYRQAPGKQRE LIAAITSGGRRHYRDSVKGRFTISRDNSKNTLYLQMNSLRAEDTA VYYCAADTGRVAVGEYDYWGQGTLVTVSS | Humanized 1H5 VHH2 |
| 38 | IHAMG | 1H5 VHH2 CDR1 |
| 39 | AITSGGRRHYRDSVKG | 1H5 VHH2 CDR2 |
| 40 | DTGRVAVGEYDY | 1H5 VHH2 CDR3 |
| 41 | EVQLVESGGGSVQAGGSLRLSCAASGGTFSSYAMAWFRQAPGKER EYVAGISSSGYTLYKSDSMKGRFTISRENAKNMVYLQMNSLKPED TAVYSCAAGIFGRPYEYWGQGTQVTVSSGGGGSGGGGSGGGGSRS VGVQLVESGGGLVQAGGSLRLSCAASGSISSIHAMGWYRQAPGKQ RELIAAITSGGRRHYRDSVKGRFTISGDNAKTNLYLQMNSLKPED TAVYYCAADTGRVAVGEYDYWGQGTLVTVSS | 1H5 co-binder |
| 42 | EVQLVESGGGLVQPGGSLRLSCAASGGTFSSYAMAWFRQAPGKER EYVAGISSSGYTLYKSDSMKGRFTISRDNAKNTLYLQMNSLRAED TAVYYCAAGIFGRPYEYWGQGTQVTVSSGGGGSGGGGSGGGGSRS VGVQLVESGGGLVQPGGSLRLSCAASGSISSIHAMGWYRQAPGKQ RELIAAITSGGRRHYRDSVKGRFTISRDNSKNTLYLQMNSLRAED TAVYYCAADTGRVAVGEYDYWGQGTLVTVSS | Humanized 1H5 co-binder |
| 43 | EVQLVESGGGSVQAGGSLRLSCAASGGTFSSYAMAWFRQAPGKER EYVAGISSSGYTLYKSDSMKGRFTISRENAKNMVYLQMNSLKPED TAVYSCAAGIFGRPYEYWGQGTQVTVSSGGGGSGGGGSGGGGSRS VGVQLVESGGGLVQAGGSLRLSCAASGSISSIHAMGWYRQAPGKQ RELIAAITSGGRRHYRDSVKGRFTISGDNAKTNLYLQMNSLKPED TAVYYCAADTGRVAVGEYDYWGQGTLVTVSSEPKSSDKTHTCPPC PAPELLGGPSVFLFPPKPKDTLYITREPEVTCVVVDVSHEDPEVK FNWYVDGVEVHNAKTKPREEQYNSTYRVVSVLTVLHQDWLNGKEY KCKVSNKALPAPIEKTISKAKGQPREPQVYTLPPSRDELTKNQVS LTCLVKGFYPSDIAVEWESNGQPENNYKTTPPVLDSDGSFFLYSK LTVDKSRWQQGNVFSCSVMHEALHNHYTQKSLSLSPGK | 1H5 co-binder + huIgG1Fc_YTE_C→S |
| 44 | EVQLVESGGGLVQPGGSLRLSCAASGGTFSSYAMAWFRQAPGKER EYVAGISSSGYTLYKSDSMKGRFTISRDNAKNTLYLQMNSLRAED TAVYYCAAGIFGRPYEYWGQGTQVTVSSGGGGSGGGGSGGGGSRS VGVQLVESGGGLVQPGGSLRLSCAASGSISSIHAMGWYRQAPGKQ RELIAAITSGGRRHYRDSVKGRFTISRDNSKNTLYLQMNSLRAED TAVYYCAADTGRVAVGEYDYWGQGTLVTVSSEPKSSDKTHTCPPC PAPELLGGPSVFLFPPKPKDTLYITREPEVTCVVVDVSHEDPEVK FNWYVDGVEVHNAKTKPREEQYNSTYRVVSVLTVLHQDWLNGKEY KCKVSNKALPAPIEKTISKAKGQPREPQVYTLPPSRDELTKNQVS LTCLVKGFYPSDIAVEWESNGQPENNYKTTPPVLDSDGSFFLYSK LTVDKSRWQQGNVFSCSVMHEALHNHYTQKSLSLSPGK | Humanized 1H5 co-binder + huIgG1Fc_YTE_C→S |
| 45 | EVQLVESGGGLVQAGGSLRLSCAASGGTFSSYTMGWFRQAPGKER EYVGGISSSGYVMYNSESMKGRFTISRENAKNMVYLQMNSLKPED TAVYYCAAGTIGRPYDYWGQGTQVTVSS | 21H7 VHH1 single binder |
| 46 | EVQLVESGGGLVQPGGSLRLSCAASGGTFSSYTMGWFRQAP GKEREYVGGISSSGYVMYNSESMKGRFTISRDNAKNTLYLQ MNSLRAEDTAVYYCAAGTIGRPYDYWGQGTQVTVSS | Humanized 21H7 VHH1 |
| 47 | SYTMG | 21H7 VHH1 CDR1 |
| 48 | GISSSGYVMYNSESMKG | 21H7 VHH1 CDR2 |
| 49 | GTIGRPYDY | 21H7 VHH1 CDR3 |
| 50 | LVESGGGSVQAGDSLRLSCAASGRTFSTYIIGWFRQAPGKEREFV ASISWGGRGTYYADSVKDRFTISRDNP KNMVYLQMNSLKPEDTAV YYCAAGDLPGGRRALDYDYWGQGTLVTVSS | 21H7 VHH2 single binder |
| 51 | LVESGGGLVQPGGSLRLSCAASGRTFSTYIIGWFRQAPGKE REFVASISWGGRGTYYADSVKDRFTISRDNPKNMVYLQMNS LRAEDTAVYYCAAGDLPGGRRALDYDYWGQGTLVTVSS | Humanized 21H7 VHH2 |

TABLE 1-continued

Description of Certain Sequences
Description of Certain Sequences

| SEQ ID NO | Sequence | Description |
|---|---|---|
| 52 | TYIIG | 21H7 VHH2 CDR1 |
| 53 | SISWGGRGTYYADSVKD | 21H7 VHH2 CDR2 |
| 54 | GDLPGGRRALDYDY | 21H7 VHH2 CDR3 |
| 55 | EVQLVESGGGLVQAGGSLRLSCAASGGTFSSYTMGWFRQAPGKER<br>EYVGGISSSGYVMYNSESMKGRFTISRENAKNMVYLQMNSLKPED<br>TAVYYCAAGTIGRPYDYWGQGTQVTVSSGGGGSGGGGSGGGGSGGG<br>GSGGGGSGGGGSGGGGSEGVGLVESGGGSVQAGDSLRLSCAASGR<br>TFSTYIIGWFRQAPGKEREFVASISWGGRGTYYADSVKDRFTISR<br>DNPKNMVYLQMNSLKPEDTAVYYCAAGDLPGGRRALDYDYWGQGT<br>LVTVSS | 21H7 co-binder |
| 56 | EVQLVESGGGLVQPGGSLRLSCAASGGTFSSYTMGWFRQAPGKER<br>EYVGGISSSGYVMYNSESMKGRFTISRDNAKNTLYLQMNSLRAED<br>TAVYYCAAGTIGRPYDYWGQGTQVTVSSGGGGSGGGGSGGGGSGGG<br>GSGGGGSGGGGSGGGGSEGVGLVESGGGLVQPGGSLRLSCAASGR<br>TFSTYIIGWFRQAPGKEREFVASISWGGRGTYYADSVKDRFTISR<br>DNPKNMVYLQMNSLRAEDTAVYYCAAGDLPGGRRALDYDYWGQGT<br>LVTVSS | Humanized 21H7 co-binder |
| 57 | EVQLVESGGGLVQAGGSLRLSCAASGGTFSSYTMGWFRQAPGKER<br>EYVGGISSSGYVMYNSESMKGRFTISRENAKNMVYLQMNSLKPED<br>TAVYYCAAGTIGRPYDYWGQGTQVTVSSGGGGSGGGGSGGGGSGGG<br>GSGGGGSGGGGSGGGGSEGVGLVESGGGSVQAGDSLRLSCAASGR<br>TFSTYIIGWFRQAPGKEREFVASISWGGRGTYYADSVKDRFTISR<br>DNPKNMVYLQMNSLKPEDTAVYYCAAGDLPGGRRALDYDYWGQGT<br>LVTVSSEPKSSDKTHTCPPCPAPELLGGPSVFLFPPKPKDTLYIT<br>REPEVTCVVVDVSHEDPEVKFNWYVDGVEVHNAKTKPREEQYNST<br>YRVVSVLTVLHQDWLNGKEYKCKVSNKALPAPIEKTISKAKGQPR<br>EPQVYTLPPSRDELTKNQVSLTCLVKGFYPSDIAVEWESNGQPEN<br>NYKTTPPVLDSDGSFFLYSKLTVDKSRWQQGNVFSCSVMHEALHN<br>HYTQKSLSLSPGK | 21H7 co-binder + huIgG1Fc_YTE_C→S |
| 58 | EVQLVESGGGLVQPGGSLRLSCAASGGTFSSYTMGWFRQAPGKER<br>EYVGGISSSGYVMYNSESMKGRFTISRDNAKNTLYLQMNSLRAED<br>TAVYYCAAGTIGRPYDYWGQGTQVTVSSGGGGSGGGGSGGGGSGGG<br>GSGGGGSGGGGSGGGGSEGVGLVESGGGLVQPGGSLRLSCAASGR<br>TFSTYIIGWFRQAPGKEREFVASISWGGRGTYYADSVKDRFTISR<br>DNPKNMVYLQMNSLRAEDTAVYYCAAGDLPGGRRALDYDYWGQGT<br>LVTVSSEPKSSDKTHTCPPCPAPELLGGPSVFLFPPKPKDTLYIT<br>REPEVTCVVVDVSHEDPEVKFNWYVDGVEVHNAKTKPREEQYNST<br>YRVVSVLTVLHQDWLNGKEYKCKVSNKALPAPIEKTISKAKGQPR<br>EPQVYTLPPSRDELTKNQVSLTCLVKGFYPSDIAVEWESNGQPEN<br>NYKTTPPVLDSDGSFFLYSKLTVDKSRWQQGNVFSCSVMHEALHN<br>HYTQKSLSLSPGK | Humanized 21H7 co-binder + huIgG1Fc_YTE_C→S |
| 59 | SY$X_1$M$X_2$<br>Wherein $X_1$ is A or T, and $X_2$ is A or G. | Exemplary VHH1 CDR1 consensus sequence (Kabat numbering) |
| 60 | GISSSGY$X_3X_4$ Y$X_5$S$X_6$ SMKG<br>wherein $X_3$ is T or V, $X_4$ is L or M, $X_5$ is K or N, and $X_6$ is D or E. | Exemplary VHH1 CDR2 consensus sequence (Kabat numbering) |
| 61 | G$X_7X_8$GRPYX, Y<br>wherein $X_7$ is I or T, $X_8$ is F or I, and $X_9$ is E or D. | Exemplary VHH1 CDR3 consensus sequence (Kabat numbering) |
| 62 | EPKSSDKTHTCPPCPAPELLGGPSVFLFPPKPKDTLYITREPEVT<br>CVVVDVSHEDPEVKFNWYVDGVEVHNAKTKPREEQYNSTYRVVSV<br>LTVLHQDWLNGKEYKCKVSNKALPAPIEKTISKAKGQPREPQVYT<br>LPPSRDELTKNQVSLTCLVKGFYPSDIAVEWESNGQPENNYKTTP<br>PVLDSDGSFFLYSKLTVDKSRWQQGNVFSCSVMHEALHNHYTQKS<br>LSLSPGK | huIgG1Fc_YTE_C→S |

TABLE 1-continued

| SEQ ID NO | Sequence | Description |
|---|---|---|
| | Description of Certain Sequences | |
| | Description of Certain Sequences | |
| 63 | GISSSGY$X_{10}$$X_{11}$Y$X_{12}$$X_{13}$$X_{14}$ SMKG wherein $X_{10}$ is T or V, $X_{11}$ is L or M, $X_{12}$ is K or N, $X_{13}$ is S or A, and $X_{14}$ is D or E. | Exemplary VHH CDR2 consensus sequence (Kabat numbering) |
| 64 | G$X_{15}$$X_{16}$GRPY$X_{17}$$X_{18}$ wherein $X_{15}$ is I, T, or V, $X_{16}$ is F or I, and $X_{17}$ is E or D, and $X_{18}$ is Y or F. | Exemplary VHH CDR3 consensus sequence (Kabat numbering) |
| 65 | EVQLVESGGGSVQAGDSLRLSCAASGGTFSSYTMGWFRQAPGKER EYVGGISSSGYVMYNSESMKGRFTISRENAKNMVYLQMNSLKPED TAVYYCAAGTIGRPYDYWGQGTLVTVSS | 20C7 VHH1 single binder |
| 66 | EVQLVESGGDLVQAGGSLRLSCAASGGTFSSYAMAWFRQAPGKER EYVAGISSSGYTLYKADSMKGRFTISRENAKNMVYLQMNSLKPED TAVYSCAAGVFGRPYEYWGRGTQVTVSS | 1H4 VHH2 single binder |
| 67 | EVQLVESGGGSVQAGGSLRLSCAASGGTFSSYTMGWFRQAPGKER EYVGGISSSGYVMYNSESMKGRFTISRENAKNMVYLQMNSLKPED TAVYYCAAGTIGRPYDYWGQGTQVTVSS | 1C2 VHH2 single binder |
| 68 | EVQLVESGGGSVQAGGSLRLSCAASGGTFSSYAMAWFRQAPGKER EYVAGISSSGYTLYKSDSMKGRFTISRENAKNMVYLQMNSLKPED TAVYSCAAGIFGRPYEYWGQGTLVTVSS | 1E3 VHH1 single binder |
| 69 | EVQLVESGGGSVQPGGSLRLSCAASGGTFSSYTMGWFRQAPGKER EYVGGISSSGYVMYNSDSMKGRFTISRENAKNMVYLQMNSLKPED TAVYYCAAGTIGRPYDFWGQGTLVTVSS | 1D12 VHH1 single binder |
| 70 | EVQLVESGGGSVQPGGSLRLSCAASGGTFSSYTMGWFRQAPGKER EYVGGISSSGYVMYNSESMKGRFTISRENAKNMVYLQMNSLKPED TAVYYCAAGTIGRPYDYWGQGTLVTVSS | 2H2 VHH1 single binder |
| 71 | EVQLVESGGGSVQAGGSLRLSCAASGGTFSSYTMGWFRQAPGKER EYVGGISSSGYVMYNSESMKGRFTISRENAKNMVYLQMNSLKPED TAVYYCAAGTIGRPYDYWGQGTQVTVSS | 1H2 VHH1 single binder |
| 72 | EVQLVESGGGSVQPGGSLRLSCAASGGTFSSYTMGWFRQAPGKER EYVGGISSSGYVMYNSESMKGRFTISRENAKNMVYLQMNSLKPED TAVYYCAAGTIGRPYDYWGQGTQVTVSS | 1C7 VHH1 single binder |
| 73 | EVQLVESGGGSVQPGGSLRLSCAASGGTFSSYTMGWFRQAPGKER EYVGGISSSGYVMYNSDSMKGRFTISRENAKNMVYLQMNSLKPED TAVYYCAAGTIGRPYDFWGQGTLVTVSS | 1B10 VHH1 single binder |
| 74 | EVQLVESGGGSVQAGGSLRLSCAASGGTFSSYAMAWFRQAPGKER EYVAGISSSGYTLYKSDSMKGRFTISRENAKNMVYLQMNSLKPED TAVYSCAAGIFGRPYEYWGQGTQVTVSS | 1G6 VHH1 single binder |
| 75 | EVQLVESGGGSVQAGGSLRLSCAASGGTFSSYTMGWFRQAPGKER EYVGGISSSGYVMYNSESMKGRFTISRENAKNMVYLQMNSLKPED TAVYYCAAGTIGRPYDYWGQGTQVTVSS | 1E2 VHH1 single binder |
| 76 | QVKLEESGGGSVQAGGSLRLSCAASGGTFSSYTMGWFRQAPGKER EYVGGISSSGYVMYNSESMKGRFTISRENAKNMVYLQMNSLKPED TAVYYCAAGTIGRPYDYWGQGTLVTVSS | 1B12 VHH2 single binder |
| 77 | EVQLVESGGGSVQAGGSLRLSCAASGGTFSSYAMAWFRQAPGKER EYVAGISSSGYTLYKSDSMKGRFTISRENAKNMVYLQMNSLKPED TAVYSCAAGIFGRPYEYWGQGTQVTVSS | 1C3 VHH1 single binder |
| 78 | GGTFSSYT | 1C10 VHH1 CDR1 (IMGT numbering) |
| 79 | ISSSGYVM | 1C10 VHH1 CDR2 (IMGT numbering) |
| 80 | AAGTIGRPYDY | 1C10 VHH1 CDR3 (IMGT numbering) |

TABLE 1-continued

Description of Certain Sequences
Description of Certain Sequences

| SEQ ID NO | Sequence | Description |
|---|---|---|
| 81 | GGTFSSY | 1C10 VHH1 CDR1 (Chothia numbering) |
| 82 | SSSGYV | 1C10 VHH1 CDR2 (Chothia numbering) |
| 83 | GTIGRPYDY | 1C10 VHH1 CDR3 (Chothia numbering) |
| 84 | GDISSIVA | 1C10 VHH2 CDR1 (IMGT numbering) |
| 85 | ITSGGRT | 1C10 VHH2 CDR2 (IMGT numbering) |
| 86 | AADRGWTSVGEYDY | 1C10 VHH2 CDR3 (IMGT numbering) |
| 87 | GDISSIV | 1C10 VHH2 CDR1 (Chothia numbering) |
| 88 | TSGGR | 1C10 VHH2 CDR2 (Chothia numbering) |
| 89 | DRGWTSVGEYDY | 1C10 VHH2 CDR3 (Chothia numbering) |
| 90 | EPKSSDKTHT CPPCPAPEAA GGPSVFLFPP KPKDTLYITR EPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK | huIgG1Fc_YTE_LALA_C-S |
| 91 | EVQLVESGGGLVQAGGSLRLSCAASGGTFSSYTMGWFRQAPGKER EYVGGISSSGYVMYNSESMKGRFTISRENAKNMVYLQMNSLKPED TAVYYCAAGTIGRPYDYWGQGTQVTVSSGGGSGGGGSGGGGSGGG GSGGGGSGGGGSGGGGSGMTGVKLEESGGGLVQPGGSLILSCAAS GDISSIVAMGWYRQAPGKQRELVAAITSGGRTHYRDSVKGRFTIS GNNDNSALYLHMNSLKPEDTAVYYCAADRGWTSVGEYDYWGKGTL VTVSSEPKSSDKTHTCPPCPAPEAAGGPSVFLFPPKPKDTLYITR EPEVTCVVVDVSHEDPEVKFNWYVDGVEVHNAKTKPREEQYNSTY RVVSVLTVLHQDWLNGKEYKCKVSNKALPAPIEKTISKAKGQPRE PQVYTLPPSRDELTKNQVSLTCLVKGFYPSDIAVEWESNGQPENN YKTTPPVLDSDGSFFLYSKLTVDKSRWQQGNVFSCSVMHEALHNH YTQKSLSLSPGK | 1C10 co-binder + huIgG1Fc_ YTE_LALA_C→S |
| 92 | EVQLVESGGGLVQPGGSLRLSCAASGGTFSSYTMGWFRQAPGKER EYVGGISSSGYVMYNSESMKGRFTISRDNAKNTLYLQMNSLRAED TAVYYCAAGTIGRPYDYWGQGTQVTVSSGGGSGGGGSGGGGSGGG GSGGGGSGGGGSGGGGSGMTGVQLVESGGGLVQPGGSLRLSCAAS GDISSIVAMGWYRQAPGKQRELVSAITSGGRTHYRDSVKGRFTIS RDNAKNTLYLQMNSLRAEDTAVYYCAADRGWTSVGEYDYWGQGTQ VTVSSEPKSSDKTHTCPPCPAPEAAGGPSVFLFPPKPKDTLYITR EPEVTCVVVDVSHEDPEVKFNWYVDGVEVHNAKTKPREEQYNSTY RVVSVLTVLHQDWLNGKEYKCKVSNKALPAPIEKTISKAKGQPRE | Humanized 1C10 co-binder + huIgG1Fc_ YTE_LALA_C→S |

TABLE 1-continued

| Description of Certain Sequences | | |
|---|---|---|
| Description of Certain Sequences | | |
| SEQ ID NO | Sequence | Description |
| | PQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | |
| 93 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSS wherein $X_{19}$ is E or Q | Humanized 1C10 VHH1 with N-terminal consensus residue |
| 94 | $X_{19}$VQLVESGGGLVQPGGSLRLSCAASGGTFSSYX$_1$MX$_2$WFRQAPGKEREYVGGISSSGYVMYNSESMKGRFTISRDNAKNTLYLQMNSLRAEDTAVYYCAAGTIGRPYDYWGQGTQVTVSS wherein $X_1$ is A or T, $X_2$ is A or G, and $X_{19}$ is E or Q | Humanized 1C10 VHH1 with N-terminal consensus residue, and consensus CDR1 |
| 95 | $X_{19}$VQLVESGGGLVQPGGSLRLSCAASGGTFSSYTMGWFRQAPGKEREYVGGISSSGYX$_3$X$_4$YX$_5$SX$_6$SMKGRFTISRDNAKNTLYLQMNSLRAEDTAVYYCAAGTIGRPYDYWGQGTQVTVSS wherein $X_3$ is T or V, $X_4$ is L or M, $X_5$ is K or N, $X_6$ is D or E, and $X_{19}$ is E or Q | Humanized 1C10 VHH1 with N-terminal consensus residue, and consensus CDR2A |
| 96 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGX$_7$X$_8$GRPYX$_9$YWGQGTQVTVSS wherein $X_7$ is I or T, $X_8$ is F or I, $X_9$ is E or D, and $X_{19}$ is E or Q | Humanized 1C10 VHH1 with N-terminal consensus residue, and consensus CDR3A |
| 97 | $X_{19}$VQLVESGGGLVQPGGSLRLSCAASGGTFSSYX$_1$MX$_2$WFRQAPGKEREYVGGISSSGYX$_3$X$_4$YX$_5$X$_6$SMKGRFTISRDNAKNTLYLQMNSLRAEDTAVYYCAAGTIGRPYDYWGQGTQVTVSS wherein $X_1$ is A or T, $X_2$ is A or G, $X_3$ is T or V, $X_4$ is L or M, $X_5$ is K or N, $X_6$ is D or E, and $X_{19}$ is E or a | Humanized 1C10 VHH1 with N-terminal consensus residue, and consensus CDRs1 and 2A |
| 98 | $X_{19}$VQLVESGGGLVQPGGSLRLSCAASGGTFSSYX$_1$MX$_2$WFRQAPGKEREYVGGISSSGYVMYNSESMKGRFTISRDNAKNTLYLQMNSLRAEDTAVYYCAAGX$_7$X$_8$GRPYX$_9$YWGQGTQVTVSS wherein $X_1$ is A or T, $X_2$ is A or G, $X_7$ is I or T, $X_8$ is F or I, Xe is E or D, and $X_{19}$ is E or Q | Humanized 1C10 VHH1 with N-terminal consensus residue, and consensus CDRs1 and 3A |
| 99 | $X_{19}$VQLVESGGGLVQPGGSLRLSCAASGGTFSSYTMGWFRQAPGKEREYVGGISSSGYX$_3$X$_4$YX$_5$SX$_6$SMKGRFTISRDNAKNTLYLQMNSLRAEDTAVYYCAAGX$_7$X$_8$GRPYX$_9$YWGQGTQVTVSS wherein $X_3$ is T or V, $X_4$ is L or M, $X_5$ is K or N, $X_6$ is D or E, $X_7$ is I or T, $X_8$ is F or I, Xe is E or D, and $X_{19}$ is E or Q | Humanized 1C10 VHH1 with N-terminal consensus residue, and consensus CDRs2A and 3A |
| 100 | $X_{19}$VQLVESGGGLVQPGGSLRLSCAASGGTFSSYX$_1$MX$_2$WFRQAPGKEREYVGGISSSGYX$_3$X$_4$YX$_5$X$_6$SMKGRFTISRDNAKNTLYLQMNSLRAEDTAVYYCAAGX$_7$X$_8$GRPYX$_9$YWGQGTQVTVSS wherein $X_1$ is A or T, $X_2$ is A or G, $X_3$ is T or V, $X_4$ is L or M, $X_5$ is K or N, $X_6$ is D or E, $X_7$ is I or T, $X_8$ is F or I, $X_9$ is E or D, and $X_{19}$ is E or Q | Humanized 1C10 VHH1 with N-terminal consensus residue, and consensus CDRs1, 2A and 3A |
| 101 | $X_{20}$VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{20}$ is E or Q | Humanized 1C10 VHH2 with one amino acid consensus addition at N-terminus |
| 102 | QLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS | Humanized 1C10 VHH2 with one amino acid deletion at N-terminus |
| 103 | LVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS | Humanized 1C10 VHH2 with two amino acid deletion at N-terminus |

TABLE 1-continued

Description of Certain Sequences
Description of Certain Sequences

| SEQ ID NO | Sequence | Description |
|---|---|---|
| 104 | GGGSGGGGSGGGGSGGGGSGGGGSGGGGSGGGGSGMTG | Humanized 1C10 linker connecting VHH1 and VHH2 |
| 105 | EVQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTG$X_{20}$VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{20}$ is E or Q | Humanized 1C10 co-binder with VHH2 having one amino acid consensus addition at N-terminus |
| 106 | EVQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS | Humanized 1C10 co-binder with VHH2 having one amino acid deletion at N-terminus |
| 107 | EVQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS | Humanized 1C10 co-binder with VHH2 having two amino acid deletion at N-terminus |
| 108 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{19}$ is E or Q | Humanized 1C10 co-binder with VHH1 N-terminal consensus residue |
| 109 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTG$X_{20}$VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{19}$ is E or Q, and $X_{20}$ is E or Q | Humanized 1C10 co-binder with VHH1 N-terminal consensus residue, and VHH2 with one amino acid consensus addition at N-terminus |
| 110 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{19}$ is E or Q | Humanized 1C10 co-binder with VHH1 N-terminal consensus residue, and VHH2 with one amino acid deletion at N-terminus |
| 111 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{19}$ is E or Q | Humanized 1C10 co-binder with VHH1 N-terminal consensus residue, and VHH2 with two amino acid deletion at N-terminus |
| 112 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, and $X_{19}$ is E or Q | Humanized 1C10 co-binder with VHH1 N-terminal consensus residue and consensus CDR1 |

TABLE 1-continued

Description of Certain Sequences
Description of Certain Sequences

| SEQ ID NO | Sequence | Description |
|---|---|---|
| 113 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTG$X_{20}$VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, $X_{19}$ is E or Q, and $X_{20}$ is E or Q | Humanized 1C10 co-binder with VHH1 N-terminal consensus residue and consensus CDR1, and VHH2 with one amino acid consensus addition at N-terminus |
| 114 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, and $X_{19}$ is E or Q | Humanized 1C10 co-binder with VHH1 N-terminal consensus residue and consensus CDR1, and VHH2 with one amino acid deletion at N-terminus |
| 115 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, and $X_{19}$ is E or Q | Humanized 1C10 co-binder with VHH1 N-terminal consensus residue and consensus CDR1, and VHH2 with two amino acid deletion at N-terminus |
| 116 | $X_{19}$VQLVESGGGLVQPGGSLRLSCAASGGTFSSYTMGWFRQAPGKEREYVGGISSSGY$X_3X_4$Y$X_5X_6$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_3$ is T or V, $X_4$ is L or M, $X_5$ is K or N, $X_6$ is D or E, and $X_{19}$ is E or Q | Humanized 1C10 co-binder with VHH1 N-terminal consensus residue and consensus CDR2A |
| 117 | $X_{19}$VQLVESGGGLVQPGGSLRLSCAASGGTFSSYTMGWFRQAPGKEREYVGGISSSGY$X_3X_4$Y$X_5$S$X_6$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTG$X_{20}$VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_3$ is T or V, $X_4$ is L or M, $X_5$ is K or N, $X_6$ is D or E, $X_{19}$ is E or Q, and $X_{20}$ is E or Q | Humanized 1C10 co-binder with VHH1 N-terminal consensus residue and consensus CDR2A, and VHH2 with one amino acid consensus addition at N-terminus |
| 118 | $X_{19}$VQLVESGGGLVQPGGSLRLSCAASGGTFSSYTMGWFRQAPGKEREYVGGISSSGY$X_3X_4$Y$X_5$S$X_6$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_3$ is T or V, $X_4$ is L or M, $X_5$ is K or N, $X_6$ is D or E, and $X_{19}$ is E or Q | Humanized 1C10 co-binder with VHH1 N-terminal consensus residue and consensus CDR2A, and VHH2 with one amino acid deletion at N-terminus |
| 119 | $X_{19}$VQLVESGGGLVQPGGSLRLSCAASGGTFSSYTMGWFRQAPGKEREYVGGISSSGY$X_3X_4$Y$X_5X_6$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_3$ is T or V, $X_4$ is L or M, $X_5$ is K or N, $X_6$ is D or E, and $X_{19}$ is E or Q | Humanized 1C10 co-binder with VHH1 N-terminal consensus residue and consensus CDR2A, and VHH2 with two amino acid deletion at N-terminus |

TABLE 1-continued

Description of Certain Sequences

Description of Certain Sequences

| SEQ ID NO | Sequence | Description |
|---|---|---|
| 120 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_7X_8$GRPY$X_9$YWGQGTQVTVSSGGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_7$ is I or T, $X_8$ is F or I, $X_9$ is E or D, and $X_{19}$ is E or Q | Humanized 1C10 co-binder with VHH1 N-terminal consensus residue and consensus CDR3A |
| 121 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_7X_8$GRPY$X_9$YWGQGTQVTVSSGGGGSGGGGSGGGGSGGGGSGGGGSGGGGSGGGGSGMTG$X_{20}$VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_7$ is I or T, $X_8$ is F or I, $X_9$ is E or D, $X_{19}$ is E or Q, and $X_{20}$ is E or Q | Humanized 1C10 co-binder with VHH1 N-terminal consensus residue and consensus CDR3A, and VHH2 with one amino acid consensus addition at N-terminus |
| 122 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_7X_8$GRPY$X_9$YWGQGTQVTVSSGGGGSGGGGSGGGGSGGGGSGGGGSGGGGSGMTGQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_7$ is I or T, $X_8$ is F or I, $X_9$ is E or D, and $X_{19}$ is E or Q | Humanized 1C10 co-binder with VHH1 N-terminal consensus residue and consensus CDR3A, and VHH2 with one amino acid deletion at N-terminus |
| 123 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_7X_8$GRPY$X_9$YWGQGTQVTVSSGGGGSGGGGSGGGGSGGGGSGGGGSGGGGSGGGGSGMTGLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_7$ is I or T, $X_8$ is F or I, $X_9$ is E or D, and $X_{19}$ is E or Q | Humanized 1C10 co-binder with VHH1 N-terminal consensus residue and consensus CDR3A, and VHH2 with two amino acid deletion at N-terminus |
| 124 | $X_{19}$VQLVESGGGLVQPGGSLRLSCAASGGTFSSY$X_1$M$X_2$WFRQAPGKEREYVGGISSSGY$X_3X_4$Y$X_5X_6$SMKGRFTISRDNAKNTLYLQMNSLRAEDTAVYYCAAGTIGRPYDYWGQGTQVTVSSGGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, $X_3$ is T or V, $X_4$ is L or M, $X_5$ is K or N, $X_6$ is D or E, and $X_{19}$ is E or Q | Humanized 1C10 co-binder with VHH1 N-terminal consensus residue and consensus CDRs1 and 2A |
| 125 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAGTIGRPYDYWGQGTQVTVSSGGGGSGGGGSGGGGSGGGGSGGGGSGGGGSGGGGSGMTG$X_{20}$VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, and $X_2$ is A or G, $X_3$ is T or V, $X_4$ is L or M, $X_5$ is K or N, $X_6$ is D or E, $X_{19}$ is E or Q, and $X_{20}$ is E or Q | Humanized 1C10 co-binder with VHH1 N-terminal consensus residue and consensus CDRs1 and 2A, and VHH2 with one amino acid consensus addition at N-terminus |
| 126 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAGTIGRPYDYWGQGTQVTVSSGGGGSGGGGSGGGGSGGGGSGGGGSGGGGSGGGGSGMTGQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, $X_3$ is T or V, $X_4$ is L or M, $X_5$ is K or N, $X_6$ is D or E, and $X_{19}$ is E or Q | Humanized 1C10 co-binder with VHH1 N-terminal consensus residue and consensus CDRs1 and 2A, and VHH2 with one amino acid deletion at N-terminus |

TABLE 1-continued

Description of Certain Sequences
Description of Certain Sequences

| SEQ ID NO | Sequence | Description |
|---|---|---|
| 127 | $X_{19}$VQLVESGGGLVQPGGSLRLSCAASGGTFSSY$X_1$M$X_2$WFRQAPG KEREYVGGISSSGY$X_3$$X_4$Y$X_5$S$X_6$SMKGRFTISRDNAKNTLYLQMN SLRAEDTAVYYCAAGTIGRPYDYWGQGTQVTVSSGGGSGGGGSGG GGSGGGGSGGGGSGGGGSGGGGSGMTGLVESGGGLVQPGGSLRLS CAASGDISSIVAMGWYRQAPGKQRELVSAITSGGRTHYRDSVKGR FTISRDNAKNTLYLQMNSLRAEDTAVYYCAADRGWTSVGEYDYWG QGTQVTVSS wherein $X_1$ is A or T, $X_2$ is A or G, $X_3$ is T or V, $X_4$ is L or M, $X_5$ is K or N, $X_6$ is D or E, and $X_{19}$ is E or Q | Humanized 1C10 co-binder with VHH1 N-terminal consensus residue and consensus CDRs1 and 2A, and VHH2 with two amino acid deletion at N-terminus |
| 128 | $X_{19}$VQLVESGGGLVQPGGSLRLSCAASGGTFSSY$X_1$M$X_2$WFRQAPG KEREYVGGISSSGYVMYNSESMKGRFTISRDNAKNTLYLQMNSLR AEDTAVYYCAAG$X_7$$X_8$GRPY$X_9$YWGQGTQVTVSSGGGSGGGGSGGG GSGGGGSGGGGSGGGGSGGGGSGMTGVQLVESGGGLVQPGGSLRL SCAASGDISSIVAMGWYRQAPGKQRELVSAITSGGRTHYRDSVKG RFTISRDNAKNTLYLQMNSLRAEDTAVYYCAADRGWTSVGEYDYW GQGTQVTVSS wherein $X_1$ is A or T, $X_2$ is A or G, $X_7$ is I or T, $X_8$ is F or I, X, is E or D, and $X_{19}$ is E or Q | Humanized 1C10 co-binder with VHH1 N-terminal consensus residue and consensus CDRs1 and 3A |
| 129 | $X_{19}$VQLVESGGGLVQPGGSLRLSCAASGGTFSSY$X_1$M$X_2$WFRQAPG KEREYVGGISSSGYVMYNSESMKGRFTISRDNAKNTLYLQMNSLR AEDTAVYYCAAG$X_7$$X_8$GRPY$X_9$YWGQGTQVTVSSGGGSGGGGSGGG GSGGGGSGGGGSGGGGSGGGGSGMTG$X_{20}$VQLVESGGGLVQPGGSL RLSCAASGDISSIVAMGWYRQAPGKQRELVSAITSGGRTHYRDSV KGRFTISRDNAKNTLYLQMNSLRAEDTAVYYCAADRGWTSVGEYD YWGQGTQVTVSS wherein $X_1$ is A or T, $X_2$ is A or G, $X_7$ is I or T, $X_8$ is F or I, $X_9$ is E or D, $X_{19}$ is E or Q, and $X_{20}$ is E or Q | Humanized 1C10 co-binder with VHH1 N-terminal consensus residue and consensus CDRs1 and 3A, and VHH2 with one amino acid consensus addition at N-terminus |
| 130 | $X_{19}$VQLVESGGGLVQPGGSLRLSCAASGGTFSSY$X_1$M$X_2$WFRQAPG KEREYVGGISSSGYVMYNSESMKGRFTISRDNAKNTLYLQMNSLR AEDTAVYYCAAG$X_7$$X_8$GRPY$X_9$YWGQGTQVTVSSGGGSGGGGSGGG GSGGGGSGGGGSGGGGSGGGGSGMTGQLVESGGGLVQPGGSLRLS CAASGDISSIVAMGWYRQAPGKQRELVSAITSGGRTHYRDSVKGR FTISRDNAKNTLYLQMNSLRAEDTAVYYCAADRGWTSVGEYDYWG QGTQVTVSS wherein $X_1$ is A or T, $X_2$ is A or G, $X_7$ is I or T, $X_8$ is F or I, $X_9$ is E or D, and $X_{19}$ is E or Q | Humanized 1C10 co-binder with VHH1 N-terminal consensus residue and consensus CDRs1 and 3A, and VHH2 with one amino acid deletion at N-terminus |
| 131 | $X_{19}$VQLVESGGGLVQPGGSLRLSCAASGGTFSSY$X_1$M$X_2$WFRQAPG KEREYVGGISSSGYVMYNSESMKGRFTISRDNAKNTLYLQMNSLR AEDTAVYYCAAG$X_7$$X_8$GRPY$X_9$YWGQGTQVTVSSGGGSGGGGSGGG GSGGGGSGGGGSGGGGSGGGGSGMTGLVESGGGLVQPGGSLRLSC AASGDISSIVAMGWYRQAPGKQRELVSAITSGGRTHYRDSVKGRF TISRDNAKNTLYLQMNSLRAEDTAVYYCAADRGWTSVGEYDYWGQ GTQVTVSS wherein $X_1$ is A or T, $X_2$ is A or G, $X_7$ is I or T, $X_8$ is F or I, $X_9$ is E or D, and $X_{19}$ is E or Q | Humanized 1C10 co-binder with VHH1 N-terminal consensus residue and consensus CDRs1 and 3A, and VHH2 with two amino acid deletion at N-terminus |
| 132 | $X_{19}$VQLVESGGGLVQPGGSLRLSCAASGGTFSSYTMGWFRQAPGKE REYVGGISSSGY$X_3$$X_4$Y$X_5$S$X_6$SMKGRFTISRDNAKNTLYLQMNSL RAEDTAVYYCAAG$X_7$$X_8$GRPY$X_9$YWGQGTQVTVSSGGGSGGGGSGG GGSGGGGSGGGGSGGGGSGGGGSGMTGVQLVESGGGLVQPGGSLR LSCAASGDISSIVAMGWYRQAPGKQRELVSAITSGGRTHYRDSVK GRFTISRDNAKNTLYLQMNSLRAEDTAVYYCAADRGWTSVGEYDY WGQGTQVTVSS wherein $X_3$ is T or V, $X_4$ is L or M, $X_5$ is K or N, and $X_6$ is D or E, $X_7$ is I or T, $X_8$ is F or I, X, is E or D, and $X_{19}$ is E or Q | Humanized 1C10 co-binder with VHH1 N-terminal consensus residue and consensus CDRs2A and 3A |
| 133 | $X_{19}$VQLVESGGGLVQPGGSLRLSCAASGGTFSSYTMGWFRQAPGKE REYVGGISSSGY$X_3$$X_4$Y$X_5$S$X_6$SMKGRFTISRDNAKNTLYLQMNSL RAEDTAVYYCAAG$X_7$$X_8$GRPY$X_9$YWGQGTQVTVSSGGGSGGGGSGG GGSGGGGSGGGGSGGGGSGGGGSGMTG$X_{20}$VQLVESGGGLVQPGGS LRLSCAASGDISSIVAMGWYRQAPGKQRELVSAITSGGRTHYRDS VKGRFTISRDNAKNTLYLQMNSLRAEDTAVYYCAADRGWTSVGEY | Humanized 1C10 co-binder with VHH1 N-terminal consensus residue and consensus CDRs2A and 3A, |

TABLE 1-continued

Description of Certain Sequences
Description of Certain Sequences

| SEQ ID NO | Sequence | Description |
|---|---|---|
| | DYWGQGTQVTVSS wherein $X_3$ is T or V, $X_4$ is L or M, $X_5$ is K or N, $X_6$ is D or E, $X_7$ is I or T, $X_8$ is F or I, $X_9$ is E or D, $X_{19}$ is E or Q, and $X_{20}$ is E or Q | and VHH2 with one amino acid consensus addition at N-terminus |
| 134 | $X_{19}$VQLVESGGGLVQPGGSLRLSCAASGGTFSSYTMGWFRQAPGKEREYVGGISSSGY$X_3X_4$Y$X_5$S$X_6$SMKGRFTISRDNAKNTLYLQMNSLRAEDTAVYYCAAG$X_7X_8$GRPY$X_9$YWGQGTQVTVSSGGGSGGGGSGGGGSGGGGSGGGGSGGGGSGGGGSGMTGQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_3$ is T or V, $X_4$ is L or M, $X_5$ is K or N, $X_6$ is D or E, $X_7$ is I or T, $X_8$ is F or I, $X_9$ is E or D, and $X_{19}$ is E or Q | Humanized 1C10 co-binder with VHH1 N-terminal consensus residue and consensus CDRs2A and 3A, and VHH2 with one amino acid deletion at N-terminus |
| 135 | $X_{19}$VQLVESGGGLVQPGGSLRLSCAASGGTFSSYTMGWFRQAPGKEREYVGGISSSGY$X_3X_4$Y$X_5$S$X_6$SMKGRFTISRDNAKNTLYLQMNSLRAEDTAVYYCAAG$X_7X_8$GRPY$X_9$YWGQGTQVTVSSGGGSGGGGSGGGGSGGGGSGGGGSGGGGSGGGGSGMTGLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_3$ is T or V, $X_4$ is L or M, $X_5$ is K or N, $X_6$ is D or E, $X_7$ is I or T, $X_8$ is F or I, $X_9$ is E or D, and $X_{19}$ is E or Q | Humanized 1C10 co-binder with VHH1 N-terminal consensus residue and consensus CDRs2A and 3A, and VHH2 with two amino acid deletion at N-terminus |
| 136 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAG$X_7X_8$GRPY$X_9$YWGQGTQVTVSSGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, $X_3$ is T or V, $X_4$ is L or M, $X_5$ is K or N, $X_6$ is D or E, $X_7$ is I or T, $X_8$ is F or I, $X_9$ is E or D, and $X_{19}$ is E or Q | Humanized 1C10 co-binder with VHH1 N-terminal consensus residue and consensus CDRs1, 2A and 3A |
| 137 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAG$X_7X_8$GRPY$X_9$YWGQGTQVTVSSGGGSGGGGSGGGGSGGGGSGGGGSGGGGSGGGGSGMTG$X_{20}$VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, $X_3$ is T or V, $X_4$ is L or M, $X_5$ is K or N, $X_6$ is D or E, $X_7$ is I or T, $X_8$ is F or I, $X_9$ is E or D, $X_{19}$ is E or Q, and $X_{20}$ is E or Q | Humanized 1C10 co-binder with VHH1 N-terminal consensus residue and consensus CDRs1, 2A and 3A, and VHH2 with one amino acid consensus addition at N-terminus |
| 138 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAG$X_7X_8$GRPY$X_7$YWGQGTQVTVSSGGGSGGGGSGGGGSGGGGSGGGGSGGGGSGGGGSGMTGQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, $X_3$ is T or V, $X_4$ is L or M, X, is K or N, $X_6$ is D or E, $X_7$ is I or T, $X_8$ is F or I, $X_9$ is E or D, and $X_{19}$ is E or Q | Humanized 1C10 co-binder with VHH1 N-terminal consensus residue and consensus CDRs1, 2A and 3A, and VHH2 with one amino acid deletion at N-terminus |
| 139 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAG$X_7X_8$GRPY$X_9$YWGQGTQVTVSSGGGSGGGGSGGGGSGGGGSGGGGSGGGGSGGGGSGMTGLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, $X_3$ is T or V, $X_4$ is L or M, $X_5$ is K or N, $X_6$ is D or E, $X_7$ is I or T, $X_8$ is F or I, $X_9$ is E or D, and $X_{19}$ is E or Q | Humanized 1C10 co-binder with VHH1 N-terminal consensus residue and consensus CDRs1, 2A and 3A, and VHH2 with two amino acid deletion at N-terminus |
| 140 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQM | Humanized 1C10 VHH1 with N- |

TABLE 1-continued

Description of Certain Sequences
Description of Certain Sequences

| SEQ ID NO | Sequence | Description |
|---|---|---|
| | NSLRAEDTAVYYCAAGTIGRPYDYWGQGTQVTVSS wherein $X_{10}$ is T or V, $X_{11}$ is L or M, $X_{12}$ is K or N, $X_{13}$ is S or A, $X_{14}$ is D or E, and $X_{19}$ is E or Q | terminal consensus residue, and consensus CDR2B |
| 141 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSS wherein $X_{15}$ is I, T, or V, $X_{16}$ is F or I, $X_{17}$ is E or D, $X_{18}$ is Y or F, and $X_{19}$ is E or Q | Humanized 1C10 VHH1 with N-terminal consensus residue, and consensus CDR3B |
| 142 | $X_{19}$VQLVESGGGLVQPGGSLRLSCAASGGTFSSY$X_1$M$X_2$WFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, and $X_{19}$ is E or Q | Humanized 1C10 VHH1 with N-terminal consensus residue, and consensus CDRs1 and 2B |
| 143 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSS wherein $X_1$ is A or T, $X_2$ is A or G, $X_{15}$ is I, T, or V, $X_{16}$ is F or I, $X_{17}$ is E or D, $X_{18}$ is Y or F, and $X_{19}$ is E or Q | Humanized 1C10 VHH1 with N-terminal consensus residue, and consensus CDRs1 and 3B |
| 144 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSS wherein $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, and $X_{19}$ is E or Q | Humanized 1C10 VHH1 with N-terminal consensus residue, and consensus CDRs2B and 3B |
| 145 | $X_{19}$VQLVESGGGLVQPGGSLRLSCAASGGTFSSYXM$X_2$WFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSS wherein $X_1$ is A or T, $X_2$ is A or G, $X_{10}$ is T or V, Xm is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, and $X_{19}$ is E or Q | Humanized 1C10 VHH1 with N-terminal consensus residue, and consensus CDRs1, 2B and 3B |
| 146 | $X_{20}$V$X_{21}$LVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{20}$ is E or Q, and $X_{21}$ is Q or K | Humanized 1C10 VHH2 with N-terminal consensus residues at position 1 and 3 |
| 147 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{10}$ is T or V, $X_{11}$ is L or M, $X_{12}$ is K or N, $X_{13}$ is S or A, $X_{14}$ is D or E, and $X_{19}$ is E or Q | Humanized 1C10 co-binder with VHH1 N-terminal consensus residue, and consensus CDR2B |
| 148 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTG$X_{20}$VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{10}$ is T or V, $X_{11}$ is L or M, $X_{12}$ is K or N, $X_{13}$ is S or A, $X_{14}$ is D or E, $X_{19}$ is E or Q, and $X_{20}$ is E or Q | Humanized 1C10 co-binder with VHH1 N-terminal consensus residue and consensus CDR2B, and VHH2 with one amino acid consensus addition at N-terminus |
| 149 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDY | Humanized 1C10 co-binder with VHH1 N-terminal consensus residue and consensus CDR2B, and |

TABLE 1-continued

| SEQ ID NO | Sequence | Description |
|---|---|---|
| | Description of Certain Sequences | |
| | Description of Certain Sequences | |
| | WGQGTQVTVSS wherein $X_{10}$ is T or V, $X_{11}$ is L or M, $X_{12}$ is K or N, $X_{13}$ is S or A, $X_{14}$ is D or E, and $X_{19}$ is E or Q | VHH2 with one amino acid deletion at N-terminus |
| 150 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{10}$ is T or V, Xm is L or M, $X_{12}$ is K or N, $X_{13}$ is S or A, $X_{14}$ is D or E, and $X_{19}$ is E or Q | Humanized 1C10 co-binder with VHH1 N-terminal consensus residue and consensus CDR2B, and VHH2 with two amino acid deletion at N-terminus |
| 151 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTG$X_{20}$V$X_{21}$LVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{10}$ is T or V, $X_{11}$ is L or M, $X_{12}$ is K or N, $X_{13}$ is S or A, $X_{14}$ is D or E, $X_{19}$ is E or Q, $X_{20}$ is E or Q, and $X_{21}$ is Q or K | Humanized 1C10 co-binder with VHH1 N-terminal consensus residue and consensus CDR2B, and VHH2 with N-terminal consensus residues at position 1 and 3 |
| 152 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{15}$ is I, T, or V, $X_{16}$ is F or I, $X_{17}$ is E or D, $X_{18}$ is Y or F, and $X_{19}$ is E or Q | Humanized 1C10 co-binder with VHH1 N-terminal consensus residue, and consensus CDR3B |
| 153 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSGMTG$X_{20}$VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{15}$ is I, T, or V, $X_{16}$ is F or I, $X_{17}$ is E or D, $X_{18}$ is Y or F, $X_{19}$ is E or Q, and $X_{20}$ is E or Q | Humanized 1C10 co-binder with VHH1 N-terminal consensus residue and consensus CDR3B, and VHH2 with one amino acid consensus addition at N-terminus |
| 154 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSGMTGQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{15}$ is I, T, or V, $X_{16}$ is F or I, $X_{17}$ is E or D, $X_{18}$ is Y or F, and $X_{19}$ is E or Q | Humanized 1C10 co-binder with VHH1 N-terminal consensus residue and consensus CDR3B, and VHH2 with one amino acid deletion at N-terminus |
| 155 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSGMTGLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{15}$ is I, T, or V, $X_{16}$ is F or I, $X_{17}$ is E or D, $X_{18}$ is Y or F, and $X_{19}$ is E or Q | Humanized 1C10 co-binder with VHH1 N-terminal consensus residue and consensus CDR3B, and VHH2 with two amino acid deletion at N-terminus |
| 156 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSGMTG$X_{20}$V$X_{21}$LVESGGGLVQPG | Humanized 1C10 co-binder with VHH1 N-terminal consensus residue |

TABLE 1-continued

Description of Certain Sequences
Description of Certain Sequences

| SEQ ID NO | Sequence | Description |
|---|---|---|
| | GSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{15}$ is I, T, or V, $X_{16}$ is F or I, $X_{17}$ is E or D, $X_{18}$ is Y or F, $X_{19}$ is E or Q, $X_{20}$ is E or Q, and $X_{21}$ is Q or K | and consensus CDR3B, and VHH2 with N-terminal consensus residues at position 1 and 3 |
| 157 | $X_{19}$VQLVESGGGLVQPGGSLRLSCAASGGTFSSY$X_{1}$M$X_{2}$WFRQAPGKEREYVGGISSSGY$X_{10}$$X_{11}$Y$X_{12}$$X_{13}$$X_{14}$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{1}$ is A or T, $X_{2}$ is A or G, $X_{10}$ is T or V, $X_{11}$ is L or M, $X_{12}$ is K or N, $X_{13}$ is S or A, $X_{14}$ is D or E, and $X_{19}$ is E or Q | Humanized 1C10 co-binder with VHH1 N-terminal consensus residue, and consensus CDRs1 and 2B |
| 158 | $X_{19}$VQLVESGGGLVQPGGSLRLSCAASGGTFSSY$X_{1}$M$X_{2}$WFRQAPGKEREYVGGISSSGY$X_{10}$$X_{11}$Y$X_{12}$$X_{13}$$X_{14}$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTG$X_{20}$VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{1}$ is A or T, $X_{2}$ is A or G, $X_{10}$ is T or V, $X_{11}$ is L or M, $X_{12}$ is K or N, $X_{13}$ is S or A, $X_{14}$ is D or E, $X_{19}$ is E or Q, and $X_{20}$ is E or Q | Humanized 1C10 co-binder with VHH1 N-terminal consensus residue and consensus CDRs1 and 2B, and VHH2 with one amino acid consensus addition at N-terminus |
| 159 | $X_{19}$VQLVESGGGLVQPGGSLRLSCAASGGTFSSY$X_{1}$M$X_{2}$WFRQAPGKEREYVGGISSSGY$X_{10}$$X_{11}$Y$X_{12}$$X_{13}$$X_{14}$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{1}$ is A or T, $X_{2}$ is A or G, $X_{10}$ is T or V, $X_{11}$ is L or M, $X_{12}$ is K or N, $X_{13}$ is S or A, $X_{14}$ is D or E, and $X_{19}$ is E or Q | Humanized 1C10 co-binder with VHH1 N-terminal consensus residue and consensus CDRs1 and 2B, and VHH2 with one amino acid deletion at N-terminus |
| 160 | $X_{19}$VQLVESGGGLVQPGGSLRLSCAASGGTFSSY$X_{1}$M$X_{2}$WFRQAPGKEREYVGGISSSGY$X_{10}$$X_{11}$Y$X_{12}$$X_{13}$$X_{14}$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{1}$ is A or T, $X_{2}$ is A or G, $X_{10}$ is T or V, $X_{11}$ is L or M, $X_{12}$ is K or N, $X_{13}$ is S or A, $X_{14}$ is D or E, and $X_{19}$ is E or Q | Humanized 1C10 co-binder with VHH1 N-terminal consensus residue and consensus CDRs1 and 2B, and VHH2 with two amino acid deletion at N-terminus |
| 161 | $X_{19}$VQLVESGGGLVQPGGSLRLSCAASGGTFSSY$X_{1}$M$X_{2}$WFRQAPGKEREYVGGISSSGY$X_{10}$$X_{11}$Y$X_{12}$$X_{13}$$X_{14}$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTG$X_{20}$V$X_{21}$LVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{1}$ is A or T, $X_{2}$ is A or G, $X_{10}$ is T or V, $X_{11}$ is L or M, $X_{12}$ is K or N, $X_{13}$ is S or A, $X_{14}$ is D or E, $X_{19}$ is E or Q, $X_{20}$ is E or Q, and $X_{21}$ is Q or K | Humanized 1C10 co-binder with VHH1 N-terminal consensus residue and consensus CDRs1 and 2B, and VHH2 with N-terminal consensus residues at position 1 and 3 |
| 162 | $X_{19}$VQLVESGGGLVQPGGSLRLSCAASGGTFSSY$X_{1}$M$X_{2}$WFRQAPGKEREYVGGISSSGYVMYNSESMKGRFTISRDNAKNTLYLQMNSLRAEDTAVYYCAAG$X_{15}$$X_{16}$GRPY$X_{17}$$X_{18}$WGQGTQVTVSSGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{1}$ is A or T, $X_{2}$ is A or G, $X_{15}$ is I, T, or V, $X_{16}$ is F or I, $X_{17}$ is E or D, $X_{18}$ is Y or F, and $X_{19}$ is E or Q | Humanized 1C10 co-binder with VHH1 N-terminal consensus residue, and consensus CDRs1 and 3B |
| 163 | $X_{19}$VQLVESGGGLVQPGGSLRLSCAASGGTFSSY$X_{1}$M$X_{2}$WFRQAPGKEREYVGGISSSGYVMYNSESMKGRFTISRDNAKNTLYLQMNSLR | Humanized 1C10 co-binder with |

TABLE 1-continued

Description of Certain Sequences
Description of Certain Sequences

| SEQ ID NO | Sequence | Description |
|---|---|---|
| | AEDTAVYYCAAG$X_{15}X_{16}$GRPY$X_{17}X_{18}$WGQGTQVTVSSGGGGSGGGGSGGGGSGGGGSGGGGSGGGGSGGGGSGGGGSGMTG$X_{20}$VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, $X_{15}$ is I, T, or V, $X_{16}$ is F or I, $X_{17}$ is E or D, $X_{18}$ is Y or F, $X_{19}$ is E or Q, and $X_{20}$ is E or Q | VHH1 N-terminal consensus residue, and consensus CDRs1 and 3B, and VHH2 with one amino acid consensus addition at N-terminus |
| 164 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGGSGGGGSGGGGSGGGGSGGGGSGGGGSGGGGSGGGGSGMTGQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, $X_{15}$ is I, T, or V, $X_{16}$ is F or I, $X_{17}$ is E or D, $X_{18}$ is Y or F, and $X_{19}$ is E or Q | Humanized 1C10 co-binder with VHH1 N-terminal consensus residue, and consensus CDRs1 and 3B, and VHH2 with one amino acid deletion at N-terminus |
| 165 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGGSGGGGSGGGGSGGGGSGGGGSGGGGSGGGGSGGGGSGMTGLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, $X_{15}$ is I, T, or V, $X_{16}$ is F or I, $X_{17}$ is E or D, $X_{18}$ is Y or F, and $X_{19}$ is E or Q | Humanized 1C10 co-binder with VHH1 N-terminal consensus residue, and consensus CDRs1 and 3B, and VHH2 with two amino acid deletion at N-terminus |
| 166 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGGSGGGGSGGGGSGGGGSGGGGSGGGGSGGGGSGGGGSGMTG$X_{20}$V$X_{21}$LVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, $X_{15}$ is I, T, or V, $X_{16}$ is F or I, $X_{17}$ is E or D, $X_{18}$ is Y or F, $X_{19}$ is E or Q, $X_{20}$ is E or Q, and $X_{21}$ is Q or K | Humanized 1C10 co-binder with VHH1 N-terminal consensus residue, and consensus CDRs1 and 3B, and VHH2 with N-terminal consensus residues at position 1 and 3 |
| 167 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSSGGGGSGGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, and $X_{19}$ is E or Q | Humanized 1C10 co-binder with VHH1 N-terminal consensus residue, and consensus CDRs2B and 3B |
| 168 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSSGGGGSGGGGSGGGGSGGGGSGGGGSGGGGSGGGGSGGGGSGMTG$X_{20}$VQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, $X_{19}$ is E or Q, and $X_{20}$ is E or Q | Humanized 1C10 co-binder with VHH1 N-terminal consensus residue, and consensus CDRs2B and 3B, and VHH2 with one amino acid consensus addition at N-terminus |
| 169 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSSGGGGSGGGGSGGGGSGGGGSGGGGSGGGGSGGGGSGGGGSGMTGQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_{10}$ is T or V, Xm is | Humanized 1C10 co-binder with VHH1 N-terminal consensus residue, and consensus CDRs2B and 3B, and VHH2 with |

TABLE 1-continued

Description of Certain Sequences
Description of Certain Sequences

| SEQ ID NO | Sequence | Description |
|---|---|---|
| | L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, and $X_{19}$ is E or Q | one amino acid deletion at N-terminus |
| 170 | $X_{19}$VQLVESGGGLVQPGGSLRLSCAASGGTFSSYTMGWFRQAPGKE REYVGGISSSGY$X_{10}X_{11}$Y$X_{12}X_{13}X_{14}$SMKGRFTISRDNAKNTLYLQM NSLRAEDTAVYYCAAG$X_{15}X_{16}$GRPY$X_{17}X_{18}$WGQGTQVTVSSGGGSG GGGSGGGGSGGGGSGGGGSGGGGSGGGGSGMTGLVESGGGLVQPG GSLRLSCAASGDISSIVAMGWYRQAPGKQRELVSAITSGGRTHYR DSVKGRFTISRDNAKNTLYLQMNSLRAEDTAVYYCAADRGWTSVG EYDYWGQGTQVTVSS wherein $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, and $X_{19}$ is E or Q | Humanized 1C10 co-binder with VHH1 N-terminal consensus residue, and consensus CDRs2B and 3B, and VHH2 with two amino acid deletion at N-terminus |
| 171 | $X_{19}$VQLVESGGGLVQPGGSLRLSCAASGGTFSSYTMGWFRQAPGKE REYVGGISSSGY$X_{10}X_{11}$Y$X_{12}X_{13}X_{14}$SMKGRFTISRDNAKNTLYLQM NSLRAEDTAVYYCAAG$X_{15}X_{16}$GRPY$X_{17}X_{18}$WGQGTQVTVSSGGGSG GGGSGGGGSGGGGSGGGGSGGGGSGGGGSGMTG$X_{20}$V$X_{21}$LVESGG GLVQPGGSLRLSCAASGDISSIVAMGWYRQAPGKQRELVSAITSG GRTHYRDSVKGRFTISRDNAKNTLYLQMNSLRAEDTAVYYCAADR GWTSVGEYDYWGQGTQVTVSS wherein $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, $X_{19}$ is E or Q, $X_{20}$ is E or Q, and $X_{21}$ is Q or K | Humanized 1C10 co-binder with VHH1 N-terminal consensus residue, and consensus CDRs2B and 3B, and VHH2 with N-terminal consensus residues at position 1 and 3 |
| 172 | $X_{19}$VQLVESGGGLVQPGGSLRLSCAASGGTFSSY$X_1$M$X_2$WFRQAPG KEREYVGGISSSGY$X_{10}X_{11}$Y$X_{12}X_{13}X_{14}$SMKGRFTISRDNAKNTLYL QMNSLRAEDTAVYYCAAG$X_{15}X_{16}$GRPY$X_{17}X_{18}$WGQGTQVTVSSGGG SGGGGSGGGGSGGGGSGGGGSGGGGSGGGGSGMTGVQLVESGGGL VQPGGSLRLSCAASGDISSIVAMGWYRQAPGKQRELVSAITSGGR THYRDSVKGRFTISRDNAKNTLYLQMNSLRAEDTAVYYCAADRGW TSVGEYDYWGQGTQVTVSS wherein $X_1$ is A or T, $X_2$ is A or G, $X_{10}$ is T or V, Xm is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, and $X_{19}$ is E or Q | Humanized 1C10 co-binder with VHH1 N-terminal consensus residue, and consensus CDRs1, 2B and 3B |
| 173 | $X_{19}$VQLVESGGGLVQPGGSLRLSCAASGGTFSSY$X_1$M$X_2$WFRQAPG KEREYVGGISSSGY$X_{10}X_{11}$Y$X_{12}X_{13}X_{14}$SMKGRFTISRDNAKNTLYL QMNSLRAEDTAVYYCAAG$X_{15}X_{16}$GRPY$X_{17}X_{18}$WGQGTQVTVSSGGG SGGGGSGGGGSGGGGSGGGGSGGGGSGGGGSGMTG$X_{20}$VQLVESGG GLVQPGGSLRLSCAASGDISSIVAMGWYRQAPGKQRELVSAITSG GRTHYRDSVKGRFTISRDNAKNTLYLQMNSLRAEDTAVYYCAADR GWTSVGEYDYWGQGTQVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, $X_{19}$ is E or Q, and $X_{20}$ is E or Q | Humanized 1C10 co-binder with VHH1 N-terminal consensus residue, and consensus CDRs1, 2B and 3B, and VHH2 with one amino acid consensus addition at N-terminus |
| 174 | $X_{19}$VQLVESGGGLVQPGGSLRLSCAASGGTFSSY$X_1$M$X_2$WFRQAPG KEREYVGGISSSGY$X_{10}X_{11}$Y$X_{12}X_{13}X_{14}$SMKGRFTISRDNAKNTLYL QMNSLRAEDTAVYYCAAG$X_{15}X_{16}$GRPY$X_{17}X_{18}$WGQGTQVTVSSGGG SGGGGSGGGGSGGGGSGGGGSGGGGSGGGGSGMTGQLVESGGGLV QPGGSLRLSCAASGDISSIVAMGWYRQAPGKQRELVSAITSGGRT HYRDSVKGRFTISRDNAKNTLYLQMNSLRAEDTAVYYCAADRGWT SVGEYDYWGQGTQVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, and $X_{19}$ is E or Q | Humanized 1C10 co-binder with VHH1 N-terminal consensus residue, and consensus CDRs1, 2B and 3B, and VHH2 with one amino acid deletion at N-terminus |
| 175 | $X_{19}$VQLVESGGGLVQPGGSLRLSCAASGGTFSSY$X_1$M$X_2$WFRQAPG KEREYVGGISSSGY$X_{10}X_{11}$Y$X_{12}X_{13}X_{14}$SMKGRFTISRDNAKNTLYL QMNSLRAEDTAVYYCAAG$X_{15}X_{16}$GRPY$X_{17}X_{18}$WGQGTQVTVSSGGG SGGGGSGGGGSGGGGSGGGGSGGGGSGGGGSGMTGLVESGGGLVQ PGGSLRLSCAASGDISSIVAMGWYRQAPGKQRELVSAITSGGRTH YRDSVKGRFTISRDNAKNTLYLQMNSLRAEDTAVYYCAADRGWTS VGEYDYWGQGTQVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, and $X_{19}$ is E or Q | Humanized 1C10 co-binder with VHH1 N-terminal consensus residue, and consensus CDRs1, 2B and 3B, and VHH2 with two amino acid deletion at N-terminus |

TABLE 1-continued

Description of Certain Sequences
Description of Certain Sequences

| SEQ ID NO | Sequence | Description |
|---|---|---|
| 176 | $X_{19}$VQLVESGGGLVQPGGSLRLSCAASGGTFSSY$X_1$M$X_2$WFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSGMTG$X_{20}$V$X_{21}$LVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, $X_{19}$ is E or Q, $X_{20}$ is E or Q, and $X_{21}$ is Q or K | Humanized 1C10 co-binder with VHH1 N-terminal consensus residue, and consensus CDRs1, 2B and 3B, and VHH2 with N-terminal consensus residues at position 1 and 3 |
| 177 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSS wherein $X_{19}$ is E or Q | Humanized 21H7 VHH1 with N-terminal consensus residue |
| 178 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAGTIGRPYDYWGQGTQVTVSS wherein $X_1$ is A or T, $X_2$ is A or G, and $X_{19}$ is E or Q | Humanized 21H7 VHH1 with N-terminal consensus residue, and consensus CDR1 |
| 179 | $X_{19}$VQLVESGGGLVQPGGSLRLSCAASGGTFSSYTMGWFRQAPGKEREYVGGISSSGY$X_3X_4$Y$X_5$S$X_6$SMKGRFTISRDNAKNTLYLQMNSLRAEDTAVYYCAAGTIGRPYDYWGQGTQVTVSS wherein $X_3$ is T or V, $X_4$ is L or M, $X_5$ is K or N, $X_6$ is D or E, and $X_{19}$ is E or Q | Humanized 21H7 VHH1 with N-terminal consensus residue, and consensus CDR2A |
| 180 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_7X_8$GRPY$X_9$YWGQGTQVTVSS wherein $X_7$ is I or T, $X_8$ is F or I, X, is E or D, and $X_{19}$ is E or Q | Humanized 21H7 VHH1 with N-terminal consensus residue, and consensus CDR3A |
| 181 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAGTIGRPYDYWGQGTQVTVSS wherein $X_1$ is A or T, $X_2$ is A or G, $X_3$ is T or V, $X_4$ is L or M, $X_5$ is K or N, $X_6$ is D or E, and $X_{19}$ is E or Q | Humanized 21H7 VHH1 with N-terminal consensus residue, and consensus CDRs1 and 2A |
| 182 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_7X_8$GRPY$X_9$YWGQGTQVTVSS wherein $X_1$ is A or T, $X_2$ is A or G, $X_7$ is I or T, $X_8$ is F or I, $X_9$ is E or D, and $X_{19}$ is E or Q | Humanized 21H7 VHH1 with N-terminal consensus residue, and consensus CDRs1 and 3A |
| 183 | $X_{19}$VQLVESGGGLVQPGGSLRLSCAASGGTFSSYTMGWFRQAPGKEREYVGGISSSGY$X_3X_4$Y$X_5$S$X_6$SMKGRFTISRDNAKNTLYLQMNSLRAEDTAVYYCAAG$X_7X_8$GRPY$X_9$YWGQGTQVTVSS wherein $X_3$ is T or V, $X_4$ is L or M, $X_5$ is K or N, $X_6$ is D or E, $X_7$ is I or T, $X_8$ is F or I, $X_9$ is E or D, and $X_{19}$ is E or Q | Humanized 21H7 VHH1 with N-terminal consensus residue, and consensus CDRs2A and 3A |
| 184 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAG$X_7X_8$GRPY$X_9$YWGQGTQVTVSS wherein $X_1$ is A or T, $X_2$ is A or G, $X_3$ is T or V, $X_4$ is L or M, $X_5$ is K or N, $X_6$ is D or E, $X_7$ is I or T, $X_8$ is F or I, $X_9$ is E or D, and $X_{19}$ is E or Q | Humanized 21H7 VHH1 with N-terminal consensus residue, and consensus CDRs1, 2A and 3A |
| 185 | $X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{21}$ is Q or K | Humanized 21H7 VHH2 with one amino acid consensus addition at N-terminus |
| 186 | $X_{22}X_{21}$LVESGGGLVQPGGSLRLSCAASGRTFSTYIIGWFRQAPGKEREFVASISWGGRGTYYADSVKDRFTISRDNPKNMVYLQMNSLRA | Humanized 21H7 VHH2 with two |

TABLE 1-continued

Description of Certain Sequences
Description of Certain Sequences

| SEQ ID NO | Sequence | Description |
|---|---|---|
| | EDTAVYYCAAGDLPGGRRALDYDYWGQGTLVTVSS wherein $X_{21}$ is Q or K, and $X_{22}$ is V | amino acid consensus addition at N-terminus |
| 187 | $X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{20}$ is E or Q, $X_{21}$ is Q or K, and $X_{22}$ is V | Humanized 21H7 VHH2 with three amino acid consensus addition at N-terminus |
| 188 | GGGSGGGGSGGGGSGGGGSGGGGSGGGGSGGGGSEGVG | Humanized 21H7 linker connecting VHH1 and VHH2 |
| 189 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{19}$ is E or Q | Humanized 21H7 co-binder with VHH1 N-terminal consensus residue |
| 190 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVG$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{19}$ is E or Q, and $X_{21}$ is Q or K | Humanized 21H7 co-binder with VHH1 N-terminal consensus residue, and VHH2 with one amino acid consensus addition at N-terminus |
| 191 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVG$X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{19}$ is E or Q, $X_{21}$ is Q or K, and $X_{22}$ is V | Humanized 21H7 co-binder with VHH1 N-terminal consensus residue, and VHH2 with two amino acid consensus addition at N-terminus |
| 192 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVG$X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{19}$ is E or Q, $X_{20}$ is E or Q, $X_{21}$ is Q or K, and $X_{22}$ is V | Humanized 21H7 co-binder with VHH1 N-terminal consensus residue, and VHH2 with three amino acid consensus addition at N-terminus |
| 193 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, and $X_{19}$ is E or Q | Humanized 21H7 co-binder with VHH1 N-terminal consensus residue and consensus CDR1 |
| 194 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVG$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{19}$ is E or Q, and $X_{21}$ is Q or K | Humanized 21H7 co-binder with VHH1 N-terminal consensus residue and consensus CDR1, and VHH2 with one amino acid consensus addition at N-terminus |
| 195 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVG$X_{22}X_{21}$LVESGGGLVQPGGSLRLSCAASGRTFSTYIIGWFRQAPGKEREFVASISWGGRGTYYADSV | Humanized 21H7 co-binder with VHH1 N-terminal consensus residue and consensus |

TABLE 1-continued

Description of Certain Sequences
Description of Certain Sequences

| SEQ ID NO | Sequence | Description |
|---|---|---|
| | KDRFTISRDNPKNMVYLQMNSLRAEDTAVYYCAAGDLPGGRRALDYDYWGQGTLVTVSS wherein $X_1$ is A or T, $X_2$ is A or G, $X_{19}$ is E or Q, $X_{21}$ is Q or K, and $X_{22}$ is V | CDR1, and VHH2 with two amino acid consensus addition at N-terminus |
| 196 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVG$X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{19}$ is E or Q, $X_{20}$ is E or Q, $X_{21}$ is Q or K, and $X_{22}$ is V | Humanized 21H7 co-binder with VHH1 N-terminal consensus residue and consensus CDR1, and VHH2 with three amino acid consensus addition at N-terminus |
| 197 | $X_{19}$VQLVESGGGLVQPGGSLRLSCAASGGTFSSYTMGWFRQAPGKEREYVGGISSSGY$X_3X_4$Y$X_5$S$X_6$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_3$ is T or V, $X_4$ is L or M, $X_5$ is K or N, $X_6$ is D or E, and $X_{19}$ is E or Q | Humanized 21H7 co-binder with VHH1 N-terminal consensus residue and consensus CDR2A |
| 198 | $X_{19}$VQLVESGGGLVQPGGSLRLSCAASGGTFSSYTMGWFRQAPGKEREYVGGISSSGY$X_3X_4$Y$X_5X_6$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVG$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_3$ is T or V, $X_4$ is L or M, $X_5$ is K or N, $X_6$ is D or E, $X_{19}$ is E or Q, and $X_{21}$ is Q or K | Humanized 21H7 co-binder with VHH1 N-terminal consensus residue and consensus CDR2A, and VHH2 with one amino acid consensus addition at N-terminus |
| 199 | $X_{19}$VQLVESGGGLVQPGGSLRLSCAASGGTFSSYTMGWFRQAPGKEREYVGGISSSGY$X_3X_4$Y$X_5$S$X_6$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVG$X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_3$ is T or V, $X_4$ is L or M, $X_5$ is K or N, $X_6$ is D or E, $X_{19}$ is E or Q, $X_{21}$ is Q or K , and $X_{22}$ is V | Humanized 21H7 co-binder with VHH1 N-terminal consensus residue and consensus CDR2A, and VHH2 with two amino acid consensus addition at N-terminus |
| 200 | $X_{19}$VQLVESGGGLVQPGGSLRLSCAASGGTFSSYTMGWFRQAPGKEREYVGGISSSGY$X_3X_4$Y$X_5$S$X_6$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVG$X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_3$ is T or V, $X_4$ is L or M, $X_5$ is K or N, $X_6$ is D or E, $X_{19}$ is E or Q, $X_{20}$ is E or Q, $X_{21}$ is Q or K, and $X_{22}$ is V | Humanized 21H7 co-binder with VHH1 N-terminal consensus residue and consensus CDR2A, and VHH2 with three amino acid consensus addition at N-terminus |
| 201 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_7X_8$GRPY$X_9$YWGQGTQVTVSSGGGSGGGGSGGGGSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_7$ is I or T, $X_8$ is F or I, $X_9$ is E or D, and $X_{19}$ is E or Q | Humanized 21H7 co-binder with VHH1 N-terminal consensus residue and consensus CDR3A |
| 202 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_7X_8$GRPY$X_9$YWGQGTQVTVSSGGGSGGGGSGGGGSGGGGSGGGGGGGGSGGGGSEGVG$X_{21}$LVESGGGLVQPGGSLRLSCAASGRTFSTYIIGWFRQAPGKEREFVASISWGGRGTYYADSVKDR | Humanized 21H7 co-binder with VHH1 N-terminal consensus residue and consensus |

TABLE 1-continued

Description of Certain Sequences
Description of Certain Sequences

| SEQ ID NO | Sequence | Description |
|---|---|---|
| | FTISRDNPKNMVYLQMNSLRAEDTAVYYCAAGDLPGGRRALDYDYWGQGTLVTVSS wherein $X_7$ is I or T, $X_8$ is F or I, $X_9$ is E or D, $X_{19}$ is E or Q, and $X_{21}$ is Q or K | CDR3A, and VHH2 with one amino acid consensus addition at N-terminus |
| 203 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_7X_8$GRPY$X_9$YWGQGTQVTVSSGGGSGGGGSGGGGSGGGGSGGGGSGGGGSGGGGSEGVG$X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_7$ is I or T, $X_8$ is F or I, $X_9$ is E or D, $X_{19}$ is E or Q, $X_{21}$ is Q or K, and $X_{22}$ is V | Humanized 21H7 co-binder with VHH1 N-terminal consensus residue and consensus CDR3A, and VHH2 with two amino acid consensus addition at N-terminus |
| 204 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_7X_8$GRPYX, YWGQGTQVTVSSGGGSGGGGSGGGGSGGGGSGGGGSGGGGSGGGGSEGVG$X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDL PGGRRALDYDYWGQGTLVTVSS wherein $X_7$ is I or T, $X_8$ is F or I, $X_9$ is E or D, $X_{19}$ is E or Q, $X_{20}$ is E or Q, $X_{21}$ is Q or K, and $X_{22}$ is V | Humanized 21H7 co-binder with VHH1 N-terminal consensus residue and consensus CDR3A, and VHH2 with three amino acid consensus addition at N-terminus |
| 205 | $X_{19}$VQLVESGGGLVQPGGSLRLSCAASGGTFSSY$X_1$M$X_2$WFRQAPGKEREYVGGISSSGY$X_3X_4$Y$X_5X_6$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_3$ is T or V, $X_4$ is L or M, $X_5$ is K or N, $X_6$ is D or E, and $X_{19}$ is E or Q | Humanized 21H7 co-binder with VHH1 N-terminal consensus residue and consensus CDRs1 and 2A |
| 206 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVG$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_3$ is T or V, $X_4$ is L or M, $X_5$ is K or N, $X_6$ is D or E, $X_{19}$ is E or Q, and $X_{21}$ is Q or K | Humanized 21H7 co-binder with VHH1 N-terminal consensus residue and consensus CDRs1 and 2A, and VHH2 with one amino acid consensus addition at N-terminus |
| 207 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVG$X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_3$ is T or V, $X_4$ is L or M, $X_5$ is K or N, $X_6$ is D or E, $X_{19}$ is E or Q, $X_{21}$ is Q or K, and $X_{22}$ is V | Humanized 21H7 co-binder with VHH1 N-terminal consensus residue and consensus CDRs1 and 2A, and VHH2 with two amino acid consensus addition at N-terminus |
| 208 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAGTIGRPYDYWGQGTQVTVSSGGGSGGGGSGGGGSGGGGSGGGGSGGGGSGGGGSEGVG$X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_3$ is T or V, $X_4$ is L or M, $X_5$ is K or N, $X_6$ is D or E, $X_{19}$ is E or Q, $X_{20}$ is E or Q, $X_{21}$ is Q or K, and $X_{22}$ is V | Humanized 21H7 co-binder with VHH1 N-terminal consensus residue and consensus CDRs1 and 2A, and VHH2 with three amino acid consensus addition at N-terminus |
| 209 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_7X_8$GRPY$X_9$YWGQGTQVTVSSGGGSGGGGSGGG | Humanized 21H7 co-binder with VHH1 N-terminal |

TABLE 1-continued

Description of Certain Sequences
Description of Certain Sequences

| SEQ ID NO | Sequence | Description |
|---|---|---|
| | GSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_7$ is I or T, $X_8$ is F or I, $X_9$ is E or D, and $X_{19}$ is E or Q | consensus residue and consensus CDRs1 and 3A |
| 210 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_7$$X_8$GRPY$X_9$YWGQGTQVTVSSGGGGSGGGGSGGGGSGGGGSGGGGSGGGGSGGGGSEGVG$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_7$ is I or T, $X_8$ is F or I, Xe is E or D, $X_{19}$ is E or Q, and $X_{21}$ is Q or K | Humanized 21H7 co-binder with VHH1 N-terminal consensus residue and consensus CDRs1 and 3A, and VHH2 with one amino acid consensus addition at N-terminus |
| 211 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_7$$X_8$GRPY$X_9$YWGQGTQVTVSSGGGGSGGGGSGGGGSGGGGSGGGGSGGGGSGGGGSEGVG$X_{22}$$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_7$ is I or T, $X_8$ is F or I, X, is E or D, $X_{19}$ is E or Q, $X_{21}$ is Q or K, and $X_{22}$ is V | Humanized 21H7 co-binder with VHH1 N-terminal consensus residue and consensus CDRs1 and 3A, and VHH2 with two amino acid consensus addition at N-terminus |
| 212 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_7$$X_8$GRPY$X_9$YWGQGTQVTVSSGGGGSGGGGSGGGGSGGGGSGGGGSGGGGSGGGGSEGVG$X_{20}$$X_{22}$$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_7$ is I or T, $X_8$ is F or I, $X_9$ is E or D, $X_{19}$ is E or Q, $X_{20}$ is E or Q, $X_{21}$ is Q or K, and $X_{22}$ is V | Humanized 21H7 co-binder with VHH1 N-terminal consensus residue and consensus CDRs1 and 3A, and VHH2 with three amino acid consensus addition at N-terminus |
| 213 | $X_{19}$VQLVESGGGLVQPGGSLRLSCAASGGTFSSYTMGWFRQAPGKEREYVGGISSSGY$X_3$$X_4$Y$X_5$S$X_6$SMKGRFTISRDNAKNTLYLQMNSLRAEDTAVYYCAAG$X_7$$X_8$GRPY$X_7$YWGQGTQVTVSSGGGGSGGGGSGGGGSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_3$ is T or V, $X_4$ is L or M, $X_5$ is K or N, $X_6$ is D or E, $X_7$ is I or T, $X_8$ is F or I, $X_9$ is E or D, and $X_{19}$ is E or Q | Humanized 21H7 co-binder with VHH1 N-terminal consensus residue and consensus CDRs2A and 3A |
| 214 | $X_{19}$VQLVESGGGLVQPGGSLRLSCAASGGTFSSYTMGWFRQAPGKEREYVGGISSSGY$X_3$$X_4$Y$X_5$SX&SMKGRFTISRDNAKNTLYLQMNSLRAEDTAVYYCAAG$X_7$$X_8$GRPY$X_9$YWGQGTQVTVSSGGGGSGGGGSGGGGSGGGGSGGGGSGGGGSGGGGSEGVG$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_3$ is T or V, $X_4$ is L or M, $X_5$ is K or N, $X_6$ is D or E, $X_7$ is I or T, $X_8$ is F or I, $X_9$ is E or D, $X_{19}$ is E or Q, and $X_{21}$ is Q or K | Humanized 21H7 co-binder with VHH1 N-terminal consensus residue and consensus CDRs2A and 3A, and VHH2 with one amino acid consensus addition at N-terminus |
| 215 | $X_{19}$VQLVESGGGLVQPGGSLRLSCAASGGTFSSYTMGWFRQAPGKEREYVGGISSSGY$X_3$$X_4$Y$X_5$S$X_6$SMKGRFTISRDNAKNTLYLQMNSLRAEDTAVYYCAAG$X_7$$X_8$GRPY$X_9$YWGQGTQVTVSSGGGGSGGGGSGGGGSGGGGSGGGGSGGGGSGGGGSEGVG$X_{22}$$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_3$ is T or V, $X_4$ is L or M, $X_5$ is K or N, $X_6$ is D or E, $X_7$ is I or T, $X_8$ is F or I, $X_9$ is E or D, $X_{19}$ is E or Q, $X_{21}$ is Q or K, and $X_{22}$ is V | Humanized 21H7 co-binder with VHH1 N-terminal consensus residue and consensus CDRs2A and 3A, and VHH2 with two amino acid consensus addition at N-terminus |
| 216 | $X_{19}$VQLVESGGGLVQPGGSLRLSCAASGGTFSSYTMGWFRQAPGKEREYVGGISSSGY$X_3$$X_4$Y$X_5$S$X_6$SMKGRFTISRDNAKNTLYLQMNSL | Humanized 21H7 co-binder with |

TABLE 1-continued

Description of Certain Sequences
Description of Certain Sequences

| SEQ ID NO | Sequence | Description |
|---|---|---|
| | RAEDTAVYYCAAG$X_7X_8$GRPY$X_9$YWGQGTQVTVSSGGGSGGGGSGGGGSGGGGSGGGGSGGGGSGGGGSEGVG$X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_3$ is T or V, $X_4$ is L or M, $X_5$ is K or N, $X_6$ is D or E, $X_7$ is I or T, $X_8$ is F or I, $X_9$ is E or D, $X_{19}$ is E or Q, $X_{20}$ is E or Q, $X_{21}$ is Q or K, and $X_{22}$ is V | VHH1 N-terminal consensus residue and consensus CDRs2A and 3A, and VHH2 with three amino acid consensus addition at N-terminus |
| 217 | $X_{19}$VQLVESGGGLVQPGGSLRLSCAASGGTFSSY$X_1$M$X_2$WFRQAPGKEREYVGGISSSGY$X_3X_4$Y$X_5X_6$SMKGRFTISRDNAKNTLYLQMNSLRAEDTAVYYCAAG$X_7X_8$GRPY$X_9$YWGQGTQVTVSSGGGSGGGGSGGGGSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_3$ is T or V, $X_4$ is L or M, $X_5$ is K or N, $X_6$ is D or E, $X_7$ is I or T, $X_8$ is F or I, $X_9$ is E or D, and $X_{19}$ is E or Q | Humanized 21H7 co-binder with VHH1 N-terminal consensus residue and consensus CDRs1, 2A and 3A |
| 218 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAG$X_7X_8$GRPY$X_9$YWGQGTQVTVSSGGGSGGGGSGGGGSGGGGSGGGGSGGGGSGGGGSEGVG$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_3$ is T or V, $X_4$ is L or M, $X_5$ is K or N, $X_6$ is D or E, $X_7$ is I or T, $X_8$ is F or I, $X_9$ is E or D, $X_{19}$ is E or Q, and $X_{21}$ is Q or K | Humanized 21H7 co-binder with VHH1 N-terminal consensus residue and consensus CDRs1, 2A and 3A, and VHH2 with one amino acid consensus addition at N-terminus |
| 219 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAG$X_7X_8$GRPY$X_9$YWGQGTQVTVSSGGGSGGGGSGGGGSGGGGSGGGGSGGGGSGGGGSEGVG$X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_3$ is T or V, $X_4$ is L or M, $X_5$ is K or N, $X_6$ is D or E, $X_7$ is I or T, $X_8$ is F or I, $X_9$ is E or D, $X_{19}$ is E or Q, $X_{21}$ is Q or K, and $X_{22}$ is V | Humanized 21H7 co-binder with VHH1 N-terminal consensus residue and consensus CDRs1, 2A and 3A, and VHH2 with two amino acid consensus addition at N-terminus |
| 220 | $X_{19}$VQLVESGGGLVQPGGSLRLSCAASGGTFSSY$X_1$M$X_2$WFRQAPGKEREYVGGISSSGY$X_3X_4$Y$X_5$S$X_6$SMKGRFTISRDNAKNTLYLQMNSLRAEDTAVYYCAAG$X_7X_8$GRPY$X_9$YWGQGTQVTVSSGGGSGGGGSGGGGGGGGSGGGGSGGGGSGGGGSGGGGSEGVG$X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_3$ is T or V, $X_4$ is L or M, $X_5$ is K or N, $X_6$ is D or E, $X_7$ is I or T, $X_8$ is F or I, $X_9$ is E or D, $X_{19}$ is E or Q, $X_{20}$ is E or Q, $X_{21}$ is Q or K, and $X_{22}$ is V | Humanized 21H7 co-binder with VHH1 N-terminal consensus residue and consensus CDRs1, 2A and 3A, and VHH2 with three amino acid consensus addition at N-terminus |
| 221 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSS wherein $X_{10}$ is T or V, $X_{11}$ is L or M, $X_{12}$ is K or N, $X_{13}$ is S or A, $X_{14}$ is D or E, and $X_{19}$ is E or Q | Humanized 21H7 VHH1 with N-terminal consensus residue, and consensus CDR2B |
| 222 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSS wherein $X_{15}$ is I, T, or V, $X_{16}$ is F or I, $X_{17}$ is E or D, $X_{18}$ is Y or F, and $X_{19}$ is E or Q | Humanized 21H7 VHH1 with N-terminal consensus residue, and consensus CDR3B |
| 223 | $X_{19}$VQLVESGGGLVQPGGSLRLSCAASGGTFSSY$X_1$M$X_2$WFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, and $X_{19}$ is E or Q | Humanized 21H7 VHH1 with N-terminal consensus residue, and consensus CDRs1 and 2B |

TABLE 1-continued

Description of Certain Sequences
Description of Certain Sequences

| SEQ ID NO | Sequence | Description |
|---|---|---|
| 224 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSS wherein $X_1$ is A or T, $X_2$ is A or G, $X_{15}$ is I, T, or V, $X_{16}$ is F or I, $X_{17}$ is E or D, $X_{18}$ is Y or F, and $X_{19}$ is E or Q | Humanized 21H7 VHH1 with N-terminal consensus residue, and consensus CDRs1 and 3B |
| 225 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSS wherein $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, and $X_{19}$ is E or Q | Humanized 21H7 VHH1 with N-terminal consensus residue, and consensus CDRs2B and 3B |
| 226 | $X_{19}$VQLVESGGGLVQPGGSLRLSCAASGGTFSSY$X_1$M$X_2$WFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, and $X_{19}$ is E or Q | Humanized 21H7 VHH1 with N-terminal consensus residue, and consensus CDRs1, 2B and 3B |
| 227 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSSGGGGSGGGGSGGGGSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{10}$ is T or V, $X_{11}$ is L or M, $X_{12}$ is K or N, $X_{13}$ is S or A, $X_{14}$ is D or E, and $X_{19}$ is E or Q | Humanized 21H7 co-binder with VHH1 N-terminal consensus residue, and consensus CDR2B |
| 228 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSSGGGGSGGGGSGGGGSGGGGSGGGGSGGGGSGGGGSEGVG$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{10}$ is T or V, $X_{11}$ is L or M, $X_{12}$ is K or N, $X_{13}$ is S or A, $X_{14}$ is D or E, $X_{19}$ is E or Q, and $X_{21}$ is Q or K | Humanized 21H7 co-binder with VHH1 N-terminal consensus residue, and consensus CDR2B, and VHH2 with one amino acid consensus addition at N-terminus |
| 229 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSSGGGGSGGGGSGGGGSGGGGSGGGGSGGGGSGGGGSEGVG$X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{10}$ is T or V, $X_{11}$ is L or M, $X_{12}$ is K or N, $X_{13}$ is S or A, $X_{14}$ is D or E, $X_{19}$ is E or Q, $X_{21}$ is Q or K, and $X_{22}$ is V | Humanized 21H7 co-binder with VHH1 N-terminal consensus residue, and consensus CDR2B, and VHH2 with two amino acid consensus addition at N-terminus |
| 230 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSSGGGGSGGGGSGGGGSGGGGSGGGGSGGGGGGGGSEGVG$X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{10}$ is T or V, $X_{11}$ is L or M, $X_{12}$ is K or N, $X_{13}$ is S or A, $X_{14}$ is D or E, $X_{19}$ is E or Q, $X_{20}$ is E or Q, $X_{21}$ is Q or K, and $X_{22}$ is V | Humanized 21H7 co-binder with VHH1 N-terminal consensus residue, and consensus CDR2B, and VHH2 with three amino acid consensus addition at N-terminus |
| 231 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGGSGGGGSGGGGSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYD | Humanized 21H7 co-binder with VHH1 N-terminal consensus residue, and consensus CDR3B |

TABLE 1-continued

Description of Certain Sequences
Description of Certain Sequences

| SEQ ID NO | Sequence | Description |
|---|---|---|
| | YWGQGTLVTVSS wherein $X_{15}$ is I, T, or V, $X_{16}$ is F or I, $X_{17}$ is E or D, $X_{18}$ is Y or F, and $X_{19}$ is E or Q | |
| 232 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGGSGGGGSGGGGSGGGGSGGGGSGGGGSGGGGSGGGGSEGVG$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{15}$ is I, T, or V, $X_{16}$ is F or I, $X_{17}$ is E or D, $X_{18}$ is Y or F, $X_{19}$ is E or Q, and $X_{21}$ is Q or K | Humanized 21H7 co-binder with VHH1 N-terminal consensus residue, and consensus CDR3B, and VHH2 with one amino acid consensus addition at N-terminus |
| 233 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGGSGGGGSGGGGSGGGGSGGGGSGGGGSGGGGSGGGGSEGVG$X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{15}$ is I, T, or V, $X_{16}$ is F or I, $X_{17}$ is E or D, $X_{18}$ is Y or F, $X_{19}$ is E or Q, $X_{21}$ is Q or K, and $X_{22}$ is V | Humanized 21H7 co-binder with VHH1 N-terminal consensus residue, and consensus CDR3B, and VHH2 with two amino acid consensus addition at N-terminus |
| 234 | $X_{19}$VQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGGSGGGGSGGGGSGGGGSGGGGSGGGGSGGGGSGGGGSEGVG$X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{15}$ is I, T, or V, $X_{16}$ is F or I, $X_{17}$ is E or D, $X_{18}$ is Y or F, $X_{19}$ is E or Q, $X_{20}$ is E or Q, $X_{21}$ is Q or K, and $X_{22}$ is V | Humanized 21H7 co-binder with VHH1 N-terminal consensus residue, and consensus CDR3B, and VHH2 with three amino acid consensus addition at N-terminus |
| 235 | $X_{19}$VQLVESGGGLVQPGGSLRLSCAASGGTFSSY$X_1$M$X_2$WFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSSGGGGSGGGGSGGGGSGGGGSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, and $X_{19}$ is E or Q | Humanized 21H7 co-binder with VHH1 N-terminal consensus residue, and consensus CDRs1 and 2B |
| 236 | $X_{19}$VQLVESGGGLVQPGGSLRLSCAASGGTFSSY$X_1$M$X_2$WFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSSGGGGSGGGGSGGGGSGGGGSGGGGSGGGGSGGGGSGGGGSEGVG$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, $X_{19}$ is E or Q, and $X_{21}$ is Q or K | Humanized 21H7 co-binder with VHH1 N-terminal consensus residue, and consensus CDRs1 and 2B, and VHH2 with one amino acid consensus addition at N-terminus |
| 237 | $X_{19}$VQLVESGGGLVQPGGSLRLSCAASGGTFSSY$X_1$M$X_2$WFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSSGGGGSGGGGSGGGGSGGGGSGGGGSGGGGSGGGGSGGGGSEGVG$X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, $X_{19}$ is E or Q, $X_{21}$ is Q or K, and $X_{22}$ is V | Humanized 21H7 co-binder with VHH1 N-terminal consensus residue, and consensus CDRs1 and 2B, and VHH2 with two amino acid consensus addition at N-terminus |
| 238 | $X_{19}$VQLVESGGGLVQPGGSLRLSCAASGGTFSSY$X_1$M$X_2$WFRQAPGKEREYVGGISSSGY$X_{10}X_{11}$Y$X_{12}X_{13}X_{14}$SMKGRFTISRDNAKNTLYLQMNSLRAEDTAVYYCAAGTIGRPYDYWGQGTQVTVSSGGGGSGGGG | Humanized 21H7 co-binder with VHH1 N-terminal |

TABLE 1-continued

Description of Certain Sequences
Description of Certain Sequences

| SEQ ID NO | Sequence | Description |
|---|---|---|
| | SGGGGSGGGGSGGGGSGGGGSGGGGSEGVG$X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, $X_{19}$ is E or Q, $X_{20}$ is E or Q, $X_{21}$ is Q or K, and $X_{22}$ is V | consensus residue, and consensus CDRs1 and 2B, and VHH2 with three amino acid consensus addition at N-terminus |
| 239 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{15}$ is I, T, or V, $X_{16}$ is F or I, $X_{17}$ is E or D, $X_{18}$ is Y or F, and $X_{19}$ is E or Q | Humanized 21H7 co-binder with VHH1 N-terminal consensus residue, and consensus CDRs1 and 3B |
| 240 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSEGVG$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{15}$ is I, T, or V, $X_{16}$ is F or I, $X_{17}$ is E or D, $X_{18}$ is Y or F, $X_{19}$ is E or Q, and $X_{21}$ is Q or K | Humanized 21H7 co-binder with VHH1 N-terminal consensus residue, and consensus CDRs1 and 3B, and VHH2 with one amino acid consensus addition at N-terminus |
| 241 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSEGVG$X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{15}$ is I, T, or V, $X_{16}$ is F or I, $X_{17}$ is E or D, $X_{18}$ is Y or F, $X_{19}$ is E or Q, $X_{21}$ is Q or K, and $X_{22}$ is V | Humanized 21H7 co-binder with VHH1 N-terminal consensus residue, and consensus CDRs1 and 3B, and VHH2 with two amino acid consensus addition at N-terminus |
| 242 | $X_{19}$VQLVESGGGLVQPGGSLRLSCAASGGTFSSY$X_1$M$X_2$WFRQAPGKEREYVGGISSSGYVMYNSESMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSEGVG$X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{15}$ is I, T, or V, $X_{16}$ is F or I, $X_{17}$ is E or D, $X_{18}$ is Y or F, $X_{19}$ is E or Q, $X_{20}$ is E or Q, $X_{21}$ is Q or K, and $X_{22}$ is V | Humanized 21H7 co-binder with VHH1 N-terminal consensus residue, and consensus CDRs1 and 3B, and VHH2 with three amino acid consensus addition at N-terminus |
| 243 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, and $X_{19}$ is E or Q | Humanized 21H7 co-binder with VHH1 N-terminal consensus residue, and consensus CDRs2B and 3B |
| 244 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSEGVG$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{10}$ is T or V, $X_{11}$ is L or M, $X_{12}$ is K or N, $X_{13}$ is S or A, $X_{14}$ | Humanized 21H7 co-binder with VHH1 N-terminal consensus residue, and consensus CDRs2B and 3B, and VHH2 with one amino acid |

TABLE 1-continued

| Description of Certain Sequences | | |
|---|---|---|
| Description of Certain Sequences | | |
| SEQ ID NO | Sequence | Description |
| | is D or E, $X_{15}$ is I, T, or V, $X_{16}$ is F or I, and $X_{17}$ is E or D, $X_{18}$ is Y or F, $X_{19}$ is E or Q, and $X_{21}$ is Q or K | consensus addition at N-terminus |
| 245 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSEGVG$X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, $X_{19}$ is E or Q, $X_{21}$ is Q or K, and $X_{22}$ is V | Humanized 21H7 co-binder with VHH1 N-terminal consensus residue, and consensus CDRs2B and 3B, and VHH2 with two amino acid consensus addition at N-terminus |
| 246 | $X_{19}$VQLVESGGGLVQPGGSLRLSCAASGGTFSSYTMGWFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSEGVG$X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, $X_{19}$ is E or Q, $X_{20}$ is E or Q, $X_{21}$ is Q or K, and $X_{22}$ is V | Humanized 21H7 co-binder with VHH1 N-terminal consensus residue, and consensus CDRs2B and 3B, and VHH2 with three amino acid consensus addition at N-terminus |
| 247 | $X_{19}$VQLVESGGGLVQPGGSLRLSCAASGGTFSSY$X_1$M$X_2$WFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSEGVGLVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, and $X_{19}$ is E or Q | Humanized 21H7 co-binder with VHH1 N-terminal consensus residue, and consensus CDRs1, 2B and 3B |
| 248 | $X_{19}$VQLVESGGGLVQPGGSLRLSCAASGGTFSSY$X_1$M$X_2$WFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSEGVG$X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, $X_{19}$ is E or Q, and $X_{21}$ is Q or K | Humanized 21H7 co-binder with VHH1 N-terminal consensus residue, and consensus CDRs1, 2B and 3B, VHH2 with one amino acid consensus addition at N-terminus Humanized 21H7 |
| 249 | $X_{19}$VQLVESGGGLVQPGGSLRLSCAASGGTFSSY$X_1$M$X_2$WFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSEGVG$X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, $X_{15}$ is I, T, or V, $X_{16}$ is F or I, $X_{17}$ is E or D, $X_{18}$ is Y or F, $X_{19}$ is E or Q, $X_{21}$ is Q or K, and $X_{22}$ is V | co-binder with VHH1 N-terminal consensus residue, and consensus CDRs1, 2B and 3B, and VHH2 with two amino acid consensus addition at N-terminus |
| 250 | $X_{19}$VQLVESGGGLVQPGGSLRLSCAASGGTFSSY$X_1$M$X_2$WFRQAPGKEREYVGGISSSGY$X_{10}X_{11}$Y$X_{12}X_{13}X_{14}$SMKGRFTISRDNAKNTLYLQMNSLRAEDTAVYYCAAG$X_{15}X_{16}$GRPY$X_{17}X_{18}$WGQGTQVTVSSGGGSGGGGSGGGGSGGGGSGGGGSGGGGSGGGGSEGVG$X_{20}X_{22}X_{21}$LVESGGGLVQPGGSLRLSCAASGRTFSTYIIGWFRQAPGKEREFVASISWGGRGTYYADSVKDRFTISRDNPKNMVYLQMNSLRAEDTAVYYCAAGDLPGGRRALDYDYWGQGTLVTVSS wherein $X_1$ is A or T, $X_2$ is A or G, $X_{10}$ is T or V, $X_{11}$ is L or M, $X_{12}$ is K or N, $X_{13}$ is S or A, $X_{14}$ is D or E, | Humanized 21H7 co-binder with VHH1 N-terminal consensus residue, and consensus CDRs1, 2B and 3B, and VHH2 with three amino acid consensus |

TABLE 1-continued

| SEQ ID NO | Sequence | Description |
|---|---|---|
| | Description of Certain Sequences | |
| | Description of Certain Sequences | |
| | $X_{15}$ is I, T, or V, $X_{16}$ is F or I, $X_{17}$ is E or D, $X_{18}$ is Y or F, $X_{19}$ is E or Q, $X_{20}$ is E or Q, $X_{21}$ is Q or K, and $X_{22}$ is V | addition at N-terminus |
| 251 | I$X_{23}$AMG, $X_{23}$ is V, H, or Q. | Exemplary VHH2 consensus CDR1 (Kabat numbering) |
| 252 | AITSGGR$X_{24}$HYRDSVKG, $X_{24}$ is T or R. | Exemplary VHH2 consensus CDR2 (Kabat numbering) |
| 253 | D$X_{25}$G$X_{26}X_{27}X_{28}$VGEYDY<br>$X_{25}$ is R, M, or T<br>$X_{26}$ is W, L, or R<br>$X_{27}$ is T or V<br>$X_{28}$ is S or A | Exemplary VHH2 consensus CDR3 (Kabat numbering) |
| 254 | VQLVESGGGLVQAGGSLRLSCAASGSISSIYAMGWYRQAPGKQRELVAAITYGGRSHYRDSVKGRFTISGNSDNSALYLHMNSLKPEDTAVYYCAADRGLTAVGEYDYWGQGTQVTVSS | 20C7 VHH2 single binder |
| 255 | EVQLVESGGGSVQPGGSLRLSCAASGSIFILNVMGWYRQAPGNQRELVALMSSGGSTKYADSVKGRFTISRDNVRDTVYLQMNSLKPEDTAVYYCTLRTENDYWGQGTQVTVSS | 1H4 VHH1 single binder |
| 256 | QVQLVESGGGLVQAGGSLRLSCAASGRTFSSYAMGWFRQGPGKEREFVAAISWSGGGTYYADSVKGRFTISRDNAKNTVYLQMNSLKPEDTAVYYCAAGDLPWSRSDLEYDYWGQGTLVTVSS | 1C2 VHH1 single binder |
| 257 | LEESGGGSVQAGGSLRLSCAASGRTFSTYAMGWLRQAPGKEREFVAGISWGGGRTDYADSVKDRFTISRDNPKNTVYLQMNSLKPEDTAVYYCAAKDLPSGWGRTSEYDYWGQGTQVTVSS | 1E3 VHH2 single binder |
| 258 | EVQLVESGGGSVQPGGSLRLSCAGSGSIFPLNVMGWYRQAPGKEREFIALITSGGSTKHADSVKGRFTISRDNFKNTVYLQMNSLKPEDTAVYYCYLDQSRQYWGQGTLVTVSS | 1D12 VHH2 single binder |
| 259 | LVESGGGSVQPGGSLRLSCAASGSIFVLNSMGWYREAPGKERELVAVSTSGGSTGYADSVKGRFTISRENFKNTVYLQMNSLKPEDTAVYYCYLETDRRFWGQGTLVTVSS | 2H2 VHH2 single binder |
| 260 | LVESGGGSVQAGGSLRLSCAASGRTFSSYAMGWFRLAPGKEREFVAAISWGGRGTYYADSVKGRFTISRDNAKNTVYLQMNSLKPEDTAVYYCAAGDLPVVAGTEYEYWGQGTQVTVSS | 1H2 VHH2 single binder |
| 261 | VQLVESGGGLVQPGGSLRLSCAASGFTFSTYAMGWFRQAPGKEREFVAAISWGGRGTYYADFAKGRFTISRDNAKNTVYLQMNSLKPEDTAAYYCGAGDLPGATVQEEYNYWGQGTQVTVSS | 1C7 VHH2 single binder |
| 262 | EVQLVESGGGSVQPGGSLRLSCAGSGSIFPLNVMGWYRQAPGKEREFIALITSGGSTKHADSVKGRFTISRDNFKNTVYLQMNSLKPEDTAVYYCYLDQSRQYWGQGTLVTVSS | 1B10 VHH2 single binder |
| 263 | QLVESGGCSVQPGESLELSCAASGRIFSLNVMGWYRQVPGKQRELVARISSGGSTSYADSVKGRFTISRGNARDNALNTVFLQMNSVKPEDTAVYYCKLEDFTGGYAMDYWGKGTLVTVSS | 1G6 VHH2 single binder |
| 264 | EVQLVESVGGSVQAGGSLRLSCAASGRTFSTYAMGWFRQAPGKEREFVASISWGGRATYYADSVKGRFTISRDNSKNTAYLQMNSLKPEDTAVYYCAAADLPTRVSTAYTFWGQGTQVTVSS | 1E2 VHH2 single binder |
| 265 | EVQLVESGGGSVQAGGSLRLSCAASGSIFILNVMGWYRQAPGNQRELVALMSSGGSTKYADSVKGRFTISRDNVRNTVYLQMNSLKPEDTAVYYCTLRTENDYWGQGTQVTVSS | 1B12 VHH1 single binder |
| 266 | QLVESGGGSVQAGGSLILSCAASGDIPSIQAMGWYRQAPGKQRELVAAITSGGRTHYRDSVKGRFTISGSNDKSALYLQMNSLKPEDTAVYYCAADRGLTAVGEYDYWGQGTQVTVSS | 1C3 VHH2 single binder |
| 267 | EVQLVESGGG SVQAGGSLRL SCAASGGTFS SYTMGWFRQA PGKEREYVGG ISSSGYVMYN SESMKGRFTI SRENAKNMVY LQMNSLKPED TAVYYCAAGT IGRPYDYWGQ GTQVTVSS | 21A4 VHH1 single binder |

TABLE 1-continued

Description of Certain Sequences
Description of Certain Sequences

| SEQ ID NO | Sequence | Description |
|---|---|---|
| 268 | SYTMG | 21A4 VHH1 CDR1 (Kabat numbering) |
| 269 | GISSSGYVMY NSESMKG | 21A4 VHH1 CDR2 (Kabat numbering) |
| 270 | GTIGRPYDY | 21A4 VHH1 CDR3 (Kabat numbering) |
| 271 | VQLVESGGGL VQPGGSLRLS CAASGSIFRL NVMGWYRQAP GEQRELVAAI STGGSTKYAD SVKGRFTISR DNVKNTVYLE MNSLKPEDAA VYFCNVRLVG AYDYWGQGTL VTVSS | 21A4 VHH2 single binder |
| 272 | LNVMG | 21A4 VHH2 CDR1 (Kabat numbering) |
| 273 | AISTGGSTKY ADSVKG | 21A4 VHH2 CDR2 (Kabat numbering) |
| 274 | RLVGAYDY | 21A4 VHH2 CDR3 (Kabat numbering) |
| 275 | EVQLVESGGG LVQAGGSLRL SCAASGGTFS SYTMGWFRQA PGKEREYVGG ISSSGYVMYN SESMKGRFTI SRENAKNMVY LQMNSLKPED TAVYYCAAGT IGRPYDYWGQ GTQVTVSS | 21C11 VHH1 single binder |
| 276 | SYTMG | 21C11 VHH1 CDR1 (Kabat numbering) |
| 277 | GISSSGYVMY NSESMKG | 21C11 VHH1 CDR2 (Kabat numbering) |
| 278 | GTIGRPYDY | 21C11 VHH1 CDR3 (Kabat numbering) |
| 279 | VQLVESGGDL VQAGGSLRLS CAASGRTFST YIIGWFRQAP GKEREFVTAI SWGGRGTYYA DSVKGRFTIS RDNAKNTVYL QMNSLRPEDT AVYFCAAGDL MVSTRSQYDY WGQGTLVTVS S | 21C11 VHH2 single binder |
| 280 | TYIIG | 21C11 VHH2 CDR1 (Kabat numbering) |
| 281 | AISWGGRGTY YADSVKG | 21C11 VHH2 CDR2 (Kabat numbering) |
| 282 | GDLMVSTRSQ YDY | 21C11 VHH2 CDR3 (Kabat numbering) |
| 283 | EVQLVESGGG SVQAGGSLRL SCAASGGTFS SYTMGWFRQA PGKEREYVGG ISSSGYVMYN SESMKGRFTI SRENAKNMVY LQMNSLKPED TAVYYCAAGT IGRPYDYWGQ GTLVTVSS | 21C8 VHH1 single binder |
| 284 | SYTMG | 21C8 VHH1 CDR1 (Kabat numbering) |
| 285 | GISSSGYVMY NSESMKG | 21C8 VHH1 CDR2 (Kabat numbering) |

TABLE 1-continued

Description of Certain Sequences
Description of Certain Sequences

| SEQ ID NO | Sequence | Description |
|---|---|---|
| 286 | GTIGRPYDY | 21C8 VHH1 CDR3 (Kabat numbering) |
| 287 | QLVESGGDLV QPGGSLRLSC AASGRTESTY AMGWFRQAPG KEREFVAAIS WGGRGTYYAD SVRGRFTISR DNPKNTVFLQ MNSLKPDDTA VYYCAAGDLP GGRRALDYDY WGQGTQVTVS S | 21C8 VHH2 single binder |
| 288 | TYAMG | 21C8 VHH2 CDR1 (Kabat numbering) |
| 289 | AISWGGRGTY YADSVRG | 21C8 VHH2 CDR2 (Kabat numbering) |
| 290 | GDLPGGRRAL DYDY | 21C8 VHH2 CDR3 (Kabat numbering) |
| 291 | EVQLVESGGG LVQPGGSLSL SCTASGSITS IVAMGWYRQT PGKQRELVAA ITSGGRTHYR DSVKGRFTIS GNNDNSALYL HMNSLKPEDT AVYYCAADRG WTSVGEYDYW GQGTLVTVSS | 21B11 VHH1 single binder |
| 292 | IVAMG | 21B11 VHH1 CDR1 (Kabat numbering) |
| 293 | AITSGGRTHY RDSVKG | 21B11 VHH1 CDR2 (Kabat numbering) |
| 294 | DRGWTSVGEY DY | 21B11 VHH1 CDR3 (Kabat numbering) |
| 295 | QLVESGGGSV QAGASLRLSC VSSGPTYGFY VTAWFRQAPG KEREFVAAVR GIASRVNYAD SVKGRFTISR DNAANTIFLQ MNSLKPEDTA VYYCALRRQY STNYDSSTAY DVWGQGTLVT VSS | 21B11 VHH2 single binder |
| 296 | FYVTA | 21B11 VHH2 CDR1 (Kabat numbering) |
| 297 | AVRGIASRVN YADSVKG | 21B11 VHH2 CDR2 (Kabat numbering) |
| 298 | RRQYSTNYDS STAYDV | 21B11 VHH2 CDR3 (Kabat numbering) |
| 299 | EVQLVESGGG SVQAGASLRL SCVSSGPTYG FYVTAWFRQA PGKEREFVAA VRGIASRVNY ADSVKGRFTI SRDNAANTIF LQMNSLKPED TAVYYCALRR QYSTNYDSST AYDVWGQGTL VTVSS | 21G5 VHH1 single binder |
| 300 | FYVTA | 21G5 VHH1 CDR1 (Kabat numbering) |
| 301 | AVRGIASRVN YADSVKG | 21G5 VHH1 CDR2 (Kabat numbering) |
| 302 | RRQYSTNYDS STAYDV | 21G5 VHH1 CDR3 (Kabat numbering) |

TABLE 1-continued

Description of Certain Sequences
Description of Certain Sequences

| SEQ ID NO | Sequence | Description |
|---|---|---|
| 303 | LEESGGGLVQ PGGSLILSCA ASGDIPSIVA MGWYRQAPGK QRELVAAITS GGRTHYRDSV KGRFTISGNN DNSALYLHMN SLKPEDTAVY YCAADRGLTA VGEYDYWGQG TQVTVSS | 21G5 VHH2 single binder |
| 304 | IVAMG | 21G5 VHH2 CDR1 (Kabat numbering) |
| 305 | AITSGGRTHY RDSVKG | 21G5 VHH2 CDR2 (Kabat numbering) |
| 306 | DRGLTAVGEY DY | 21G5 VHH2 CDR3 (Kabat numbering) |
| 307 | EVQLVESGGG LVQPGGSLRL SCAASGSGFG IGRMGWYRQA PGKQRELVAI ISSLTGTTYA DSVKGRFTGS RDSAKNMVYL RMDSLKPEDT AVYYCYANRF TVDYWGQGTL VTVSS | 21G7 VHH1 single binder |
| 308 | IGRMG | 21G7 VHH1 CDR1 (Kabat numbering) |
| 309 | IISSLTGTTY ADSVKG | 21G7 VHH1 CDR2 (Kabat numbering) |
| 310 | NRFTVDY | 21G7 VHH1 CDR3 (Kabat numbering) |
| 311 | EVQLVESGGG LVQAGGSLRL SCAASGDIPS IVAMGWYRQA PGKQRELVAA ITSGGRTHYR DSVKGRFTIS GNNDNSALYL HMNSLKPEDT AVYYCAADRG LTAVGEYDYW GQGTLVTVSS | 21G7 VHH2 single binder |
| 312 | IVAMG | 21G7 VHH2 CDR1 (Kabat numbering) |
| 313 | AITSGGRTHY RDSVKG | 21G7 VHH2 CDR2 (Kabat numbering) |
| 314 | DRGLTAVGEY DY | 21G7 VHH2 CDR3 (Kabat numbering) |
| 315 | EVQLVESGGG LVQAGGSLRL SCAASGRTSS VFSTAWFRRA PGKEREFVGN IRGIADRTDY ADSVKGRFTI SRDNAKNTVY LQMNTLKPED TAVYYCAAKR SYTRDYVTDY NYDYWGQGTL VTVSS | 21H2 VHH1 single binder |
| 316 | VFSTA | 21H2 VHH1 CDR1 (Kabat numbering) |
| 317 | NIRGIADRTD YADSVKG | 21H2 VHH1 CDR2 (Kabat numbering) |
| 318 | KRSYTRDYVT DYNYDY | 21H2 VHH1 CDR3 (Kabat numbering) |
| 319 | LVESGGGLVQ AGGSLILSCA ASGDISSIVA MGWYRQAPGK QRELVAAITS GGRTHYRDSV KGRFTISGNN DNSALYLHMN SLKPEDTAVY YCAADRGWTS VGEYDYWGQG TLVTVSS | 21H2 VHH2 single binder |
| 320 | IVAMG | 21H2 VHH2 CDR1 (Kabat numbering) |

TABLE 1-continued

Description of Certain Sequences
Description of Certain Sequences

| SEQ ID NO | Sequence | Description |
|---|---|---|
| 321 | AITSGGRTHY RDSVKG | 21H2 VHH2 CDR2 (Kabat numbering) |
| 322 | DRGWTSVGEY DY | 21H2 VHH2 CDR3 (Kabat numbering) |
| 323 | EVQLVESGGG LVQPGGSLRL SCAASGSGFG IGRMGWYRQA PGKQRELVAI ISSLSGTTYT DSVKGRFTIS RDIAKNMVYL RMDSLKPEDT AVYYCYANRF TVDYWGQGTQ VTVSS | 19B5 VHH1 single binder |
| 324 | IGRMG | 19B5 VHH1 CDR1 (Kabat numbering) |
| 325 | IISSLSGTTY TDSVKG | 19B5 VHH1 CDR2 (Kabat numbering) |
| 326 | NRFTVDY | 19B5 VHH1 CDR3 (Kabat numbering) |
| 327 | VQLVESVGGL VQAGGSLRLS CAASGDIPSI QAMGWYRQAP GKQRELVAAI TSGGRTHYRD SVKGRFTISG SNDKSALYLQ MNSLKPEDTA VYYCAADRGL TAVGEYDYWG QGTLVTVSS | 19B5 VHH2 single binder |
| 328 | IQAMG | 19B5 VHH2 CDR1 (Kabat numbering) |
| 329 | AITSGGRTHY RDSVKG | 19B5 VHH2 CDR2 (Kabat numbering) |
| 330 | DRGLTAVGEY DY | 19B5 VHH2 CDR3 (Kabat numbering) |
| 331 | EVQLVESGGG SVQPGGSLRL SCAASGSGFG VGRMGWYRQA PGNKRELVAI VSSLTGTTYA DSAKGRFTIS RDSAKNMVYL RMDSLKPEDT AVYYCYANRF TVDYWGQGTL VTVSS | 22D1 VHH1 single binder |
| 332 | VGRMG | 22D1 VHH1 CDR1 (Kabat numbering) |
| 333 | IVSSLTGTTY ADSAKG | 22D1 VHH1 CDR2 (Kabat numbering) |
| 334 | NRFTVDY | 22D1 VHH1 CDR3 (Kabat numbering) |
| 335 | EVQLVESGGG LVQPGGSLTL SCAASGDILS IVAMGWYRQA PGKQRELVAA ITSGGRTHYR DSVKGRFTIS GNNDNSALYL HMNSLKPEDT AVYYCAADRG LTAVGEYDYW GQGTQVTVSS | 22D1 VHH2 single binder |
| 336 | IVAMG | 22D1 VHH2 CDR1 (Kabat numbering) |
| 337 | AITSGGRTHY RDSVKG | 22D1 VHH2 CDR2 (Kabat numbering) |
| 338 | DRGLTAVGEY DY | 22D1 VHH2 CDR3 (Kabat numbering) |

TABLE 1-continued

Description of Certain Sequences
Description of Certain Sequences

| SEQ ID NO | Sequence | Description |
|---|---|---|
| 339 | EVQLVESGGG SVQAGASLRL SCVSSGPTYG FYVTAWFRQA PGKEREFVAA VRGIASRVNY ADSVKGRFTI SRDNAANTIF LQMNSLKPED TAVYYCALRR QYSTNYDSST AYDVWGQGTL VTVSS | 22D8 VHH1 single binder |
| 340 | FYVTA | 22D8 VHH1 CDR1 (Kabat numbering) |
| 341 | AVRGIASRVN YADSVKG | 22D8 VHH1 CDR2 (Kabat numbering) |
| 342 | RRQYSTNYDS STAYDV | 22D8 VHH1 CDR3 (Kabat numbering) |
| 343 | LVESGGGLVQ AGGSLILSCA ASGDIPSIVA MGWYRQAPGK QRELVAAITS GGRTHYRDSV KGRFTISGNN DNSALYLHMN SLKPEDTAVY YCAADRGLTA VGEYDYWGQG TLVTVSS | 22D8 VHH2 single binder |
| 344 | IVAMG | 22D8 VHH2 CDR1 (Kabat numbering) |
| 345 | AITSGGRTHY RDSVKG | 22D8 VHH2 CDR2 (Kabat numbering) |
| 346 | DRGLTAVGEY DY | 22D8 VHH2 CDR3 (Kabat numbering) |

DESCRIPTION

I. Definitions

The section headings used herein are for organizational purposes only and are not to be construed as limiting the subject matter described.

The complete disclosures of all publications cited herein are incorporated herein by reference in their entireties as if each were individually set forth in full herein and incorporated.

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

In general, the numbering of the residues in an antibody heavy chain is that of the EU index as in Kabat et al., Sequences of Proteins of Immunological Interest, 5th Ed. Public Health Service, National Institutes of Health, Bethesda, Md. (1991). Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The terms "multimer" and "multimeric" refer to a complex of two or more component molecules, such as two or more polypeptides. A multimer includes, but is not limited to, a dimer or a trimer. Within a multimer, the two or more component molecules may be the same (i.e., the multimer is a homomultimer), or one or more of the two or more component molecules may be different from the other component molecules (i.e., the multimer is a heteromultimer).

The terms "IL31," and "interleukin-31" as used herein refer to any native, mature IL31 that results from processing of an IL31 precursor in a cell. The term includes IL31 from any vertebrate source, including mammals such as primates (e.g., humans and cynomolgus or rhesus monkeys) and rodents (e.g., mice and rats), unless otherwise indicated. The term also includes naturally occurring variants of IL31, such as splice variants or allelic variants. Nonlimiting exemplary human IL31 amino acid sequences are shown in Table 1 (see SEQ ID NOs: 1 and 2; signal sequence is underlined). See also UniProtKB/Swiss-Prot Accession: Q6EBC2.

The term “specifically binds” to an antigen or epitope is a term that is well understood in the art, and methods to determine such specific binding are also well known in the art. A molecule is said to exhibit “specific binding” or “preferential binding” if it reacts or associates more frequently, more rapidly, with greater duration and/or with greater affinity with a particular cell or substance than it does with alternative cells or substances. A single-domain antibody (sdAb) or VHH-containing polypeptide “specifically binds” or “preferentially binds” to a target if it binds with greater affinity, avidity, more readily, and/or with greater duration than it binds to other substances. For example, a sdAb or VHH-containing polypeptide that specifically or preferentially binds to a IL31 epitope is a sdAb or VHH-containing polypeptide that binds this epitope with greater affinity, avidity, more readily, and/or with greater duration than it binds to other IL31 epitopes or non-IL31 epitopes. It is also understood by reading this definition that; for example, a sdAb or VHH-containing polypeptide that specifically or preferentially binds to a first target may or may not specifically or preferentially bind to a second target. As such, “specific binding” or “preferential binding” does not necessarily require (although it can include) exclusive binding. Generally, but not necessarily, reference to binding means preferential binding. “Specificity” refers to the ability of a binding protein to selectively bind an antigen.

The terms “inhibition” or “inhibit” refer to a decrease or cessation of any phenotypic characteristic or to the decrease or cessation in the incidence, degree, or likelihood of that characteristic. To “reduce” or “inhibit” is to decrease, reduce or arrest an activity, function, and/or amount as compared to a reference. In some aspects, by “reduce” or “inhibit” is meant the ability to cause an overall decrease of 10% or greater. In some aspects, by “reduce” or “inhibit” is meant the ability to cause an overall decrease of 50% or greater. In some aspects, by “reduce” or “inhibit” is meant the ability to cause an overall decrease of 75%, 85%, 90%, 95%, or greater. In some aspects, the amount noted above is inhibited or decreased over a period of time, relative to a control over the same period of time.

The term “antibody” is used in the broadest sense and encompasses various polypeptides that comprise antibody-like antigen-binding domains, including but not limited to conventional antibodies (typically comprising at least one heavy chain and at least one light chain), single-domain antibodies (sdAbs, comprising at least one variable heavy domain of heavy chain or “VHH” domain and an Fc region), VHH-containing polypeptides (polypeptides comprising at least one VHH domain), and fragments or multimers of any of the foregoing so long as they exhibit the desired antigen-binding activity. In some aspects, an antibody comprises a dimerization domain. Such dimerization domains include, but are not limited to, heavy chain constant domains (comprising CH1, hinge, CH2, and CH3 domains, where CH1 typically pairs with a light chain constant domain, CL, and where the hinge mediates dimerization) and Fc regions (comprising hinge, CH2, and CH3, where the hinge mediates dimerization).

As used herein, the term “binder” refers to a molecule or a portion of a molecule which binds a specific target molecule. A binder can comprise a protein, peptide, nucleic acid, carbohydrate, lipid, or small molecular weight compound. In some aspects, a binder comprises an antibody. In some aspects, a binder comprises an antigen-binding domain of an antibody. In some aspects, a binder comprises an antibody or an antigen-binding domain. In some aspects, a binder comprises a heavy chain variable region of an antibody. In some aspects, a binder comprises a light chain variable region of an antibody. In some aspects, a binder comprises a variable region of an antibody. In some aspects, a binder comprises an antibody mimetic. In some aspects, a binder comprises a small molecular weight component. In some aspects, a binding molecule (e.g., a polypeptide) has only one binder. In some aspects, a binding molecule (e.g., a polypeptide) has two binding moieties. In some aspects, a binding molecule (e.g., a polypeptide) has three or more binding moieties. In some aspects, the two or more binding moieties on one binding molecule (e.g., a polypeptide) are the same. In some aspects, the two or more binding moieties on one binding molecule (e.g., a polypeptide) are different. For example, a binding molecule (e.g., a polypeptide) can have two binding moieties, both being antigen binding domains, such as VHHs. For another example, a binding molecule (e.g., a polypeptide) can also have two binding moieties, one being a variable heavy domain of heavy chain “VHH”, and the other being scFv.

The term “antigen-binding domain” as used herein refers to a portion of an antibody sufficient to bind an antigen. In some aspects, an antigen binding domain of a conventional antibody comprises three heavy chain CDRs and three light chain CDRs. Thus, in some aspects, an antigen binding domain comprises a heavy chain variable region comprising CDR1-FR2-CDR2-FR3-CDR3, and any portions of FRI and/or FR4 required to maintain binding to antigen, and a light chain variable region comprising CDR1-FR2-CDR2-FR3-CDR3, and any portions of FRI and/or FR4 required to maintain binding to antigen. In some aspects, an antigen-binding domain of an sdAb or VHH-containing polypeptide comprises three CDRs of a VHH domain (e.g., CDR1, CDR2, and CDR3). Thus, in some aspects, an antigen binding domain of an sdAb or VHH-containing polypeptide comprises a VHH domain comprising CDR1-FR2-CDR2-FR3-CDR3, and any portions of FRI and/or FR4 required to maintain binding to antigen.

The term “VHH” or “VHH domain” or “VHH antigen-binding domain” as used herein refers to the Variable Heavy domain of a Heavy chain, or the antigen-binding portion of a single-domain antibody, such as a camelid antibody or shark antibody. In some aspects, a VHH comprises three CDRs and four framework regions, designated FRI, CDR1, FR2, CDR2, FR3, CDR3, and FR4. In some aspects, a VHH may be truncated at the N-terminus or C-terminus such that it comprises only a partial FRI and/or FR4, or lacks one or both of those framework regions, so long as the VHH substantially maintains antigen binding and specificity.

The terms “single domain antibody” and “sdAb” are used interchangeably herein to refer to an antibody comprising at least one monomeric domain, such as a VHH domain, without a light chain, and an Fc region. Single domain antibodies may be derived, for example, from a Camelid species, such as llamas, alpacas and camels. In some aspects, an sdAb is a dimer of two polypeptides wherein each polypeptide comprises at least one VHH domain and an Fc region. As used herein, the terms “single domain antibody” and “sdAb” encompass polypeptides that comprise multiple VHH domains, such as a polypeptide having the structure VHH1-VHH2-Fc or VHH1-linker-VHH2-Fc, wherein VHH1 and VHH2 may be the same or different.

The term "VHH-containing polypeptide" refers to a polypeptide that comprises at least one VHH domain. In some aspects, a VHH polypeptide comprises two, three, or four or more VHH domains, wherein each VHH domain may be the same or different. In some aspects, a VHH-containing polypeptide comprises an Fc region. In some such aspects, the VHH-containing polypeptide may be referred to as an sdAb. Further, in some such aspects, the VHH polypeptide may form a dimer. Nonlimiting structures of VHH-containing polypeptides, which are also sdAbs, include VHH1-VHH2-Fc, wherein VHH1 and VHH2 may be the same or different. In some aspects of such structures, one VHH may be connected to another VHH by a linker, or one VHH may be connected to the Fc by a linker. In some such aspects, the linker comprises 5-50 amino acids. In some such aspects, the linker comprises 8 to 40 amino acids. In some aspects, the linker comprises 12 to 37 amino acids. In some aspects, the linker is composed of glycine and serine. In some aspects, the linker is composed of glycine, serine, and other amino acids. Some examples of polypeptide linkers are described in WO2022147463, which is incorporated herein by reference in its entirety. In some aspects, when a VHH-containing polypeptide comprises an Fc, it forms a dimer. Thus, the structure VHH1-VHH2-Fc, if it forms a dimer, is considered to be tetravalent (i.e., the dimer has four VHH domains).

The term "single binder" refers to a single domain binder, e.g., VHH, capable of specifically binding a target antigen. A general structure, for example, of a single binder is as follows: FR1-CDR1-FR2-CDR2-FR3-CDR3-FR4, in which FRI to FR4 refer to framework regions 1 to 4, respectively, and in which CDR1 to CDR3 refer to the complementarity determining regions 1 to 3, respectively.

The term "co-binder" refers to two single domain binding moieties, e.g., VHHs, joined together by an optional linker peptide in which each single binder is capable of simultaneously binding the same target antigen, e.g., IL-31, as the other single binder. A co-binder may comprise two biparatopic single binders. For example, each single binder is capable of specifically binding to the same target antigen (e.g., bind at a non-overlapping epitope) allowing each single binder to simultaneously bind the target. A general structure, for example, of a co-binder is as follows: 1st Single Binder-Linker-2nd Single Binder, wherein the N-terminal region of the 2nd single binder may be truncated, see WO 2022/147463. In some aspects, a IL31 co-binder is capable of binding to IL31 at a binding affinity at least about 2 folds, 3 folds, 4 folds, 5 folds, 6 folds, 7 folds, 8 folds, 9 folds, 10 folds, 11 folds, 12 folds, 13 folds, 14 folds, 15 folds 16 folds, 17 folds, 18 folds, 19 folds, or 20 folds stronger than each of the first IL31 and the second IL31 binders.

The term "biparatopic" refers to two or more antibodies, two or more "single binders", one or more "co-binder(s)" that recognize and bind two different epitopes of the same target antigen. For example, each single binder, such as a VHH, of a co-binder binds to the same target antigen at nonoverlapping epitopes, which allows both single binders to bind the same target antigen simultaneously.

The term "monoclonal antibody" refers to an antibody (including an sdAb or VHH-containing polypeptide) of a substantially homogeneous population of antibodies, that is, the individual antibodies comprising the population are identical except for possible naturally-occurring mutations that may be present in minor amounts.

The term "CDR" denotes a complementarity determining region as defined by at least one manner of identification to one of skill in the art. In some aspects, CDRs can be defined in accordance with any of the IMGT numbering scheme, the Chothia numbering scheme, the Kabat numbering scheme, a combination of Kabat and Chothia, the AbM definition, and/or the contact definition. A VHH comprises three CDRs, designated CDR1, CDR2, and CDR3.

The term "heavy chain constant region" as used herein refers to a region comprising at least three heavy chain constant domains, CH1, hinge, CH2, and CH3. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an a constant region is an IgA antibody. Further, an antibody comprising a u constant region is an IgM antibody, and an antibody comprising an ε constant region is an IgE antibody. Certain isotypes can be further subdivided into subclasses. For example, IgG antibodies include, but are not limited to, IgG1 (comprising a γ1 constant region), IgG2 (comprising a γ2 constant region), IgG3 (comprising a γ3 constant region), and IgG4 (comprising a γ4 constant region) antibodies; IgA antibodies include, but are not limited to, IgA1 (comprising an al constant region) and IgA2 (comprising an α2 constant region) antibodies; and IgM antibodies include, but are not limited to, IgM1 and IgM2.

A "Fc region" as used herein refers to a portion of a heavy chain constant region comprising CH2 and CH3. In some aspects, an Fc region comprises a hinge, CH2, and CH3, i.e., no CH1. In various aspects, when an Fc region comprises a hinge, wherein the hinge mediates dimerization between two Fc-containing polypeptides. In some aspects, the hinge region comprises a cysteine (C) to serine(S) mutation at position 220 as determined by EU numbering. An Fc region may be of any antibody heavy chain constant region isotype discussed herein. In some aspects, an Fc region is an IgG1, IgG2, IgG3, or IgG4.

An "acceptor human framework" as used herein is a framework comprising the amino acid sequence of a heavy chain variable domain (VH) framework derived from a human immunoglobulin framework or a human consensus framework, as discussed herein. An acceptor human framework derived from a human immunoglobulin framework or a human consensus framework can comprise the same amino acid sequence thereof, or it can contain amino acid sequence changes. In some aspects, the number of amino acid changes are fewer than 10, or fewer than 9, or fewer than 8, or fewer than 7, or fewer than 6, or fewer than 5, or fewer than 4, or fewer than 3, across all the human frameworks in a single antigen binding domain, such as a VHH.

A "humanized VHH" as used herein refers to a VHH in which one or more framework regions have been substantially replaced with human framework regions. In some instances, certain framework region (FR) residues of the human immunoglobulin are replaced by corresponding non-human residues. Furthermore, the humanized VHH can comprise residues that are found neither in the original VHH nor in the human framework sequences, but are included to remove any potential liabilities (e.g., immunogenicity or safety concerns in administering the polypeptide to a subject, or polypeptide stability), or further refine and optimize sdAb VHH-containing polypeptide performance. In some aspects, a humanized sdAb or VHH-containing polypeptide comprises a human Fc region. As will be appreciated, a humanized sequence can be identified by its primary sequence and does not necessarily denote the process by which the antibody was created.

The terms "label" and "detectable label" mean a moiety attached to an antibody or its analyte to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some aspects, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

"Affinity" refers to the strength of the sum total of noncovalent interactions between a single binding site of a molecule (for example, an antibody, such as an sdAb, or VHH-containing polypeptide) and its binding partner (for example, an antigen). The affinity or the apparent affinity of a molecule X for its partner Y can generally be represented by the dissociation constant (kD) or the kD-apparent, respectively. Affinity can be measured by common methods known in the art (such as, for example, ELISA KD, KinExA, flow cytometry, and/or surface plasmon resonance (SPR) devices), including those described herein. Such methods include, but are not limited to, methods involving BIAcore®, Octet®, or flow cytometry.

The terms "kD," "$K_D$," "$K_d$," "Kd" or "Kd value" as used interchangeably to refer to the equilibrium dissociation constant of an antigen-binding molecule (e.g., an antibody or VHH) and antigen interaction. When the term "kD" is used herein, it includes kD and kD-apparent. The equilibrium dissociation constant ($K_d$) is calculated as the ratio of $k_{off}/k_{on}$. The term "$k_{on}$" refers to the rate constant for association of an antibody to an antigen and the term "$k_{off}$" refers to the rate constant for dissociation of an antibody from the antibody/antigen complex.

The term "binds" to an antigen or epitope is a term that is well understood in the art, and methods to determine such binding are also well known in the art. A molecule is said to exhibit "binding" if it reacts, associates with, or has affinity for a particular cell or substance and the reaction, association, or affinity is detectable by one or more methods known in the art, such as, for example, immunoblot, ELISA KD, KinEx A, surface plasmon resonance devices, or biolayer interferometry (BLI).

"Surface plasmon resonance" denotes an optical phenomenon that allows for the analysis of real-time biospecific interactions by detection of alterations in protein concentrations within a biosensor matrix, for example using the BIAcore™ system (BIAcore International AB, a GE Healthcare company, Uppsala, Sweden and Piscataway, N.J.). For further descriptions, see Jonsson et al. (1993) *Ann. Biol. Clin.* 51:19-26.

An "effector-positive Fc region" possesses an effector function of a native sequence Fc region.

An "effector null Fc region" lacks one or more effector function(s) of a native sequence Fc region.

Exemplary "effector functions" include Fc receptor binding; Clq binding and complement dependent cytotoxicity (CDC); Fc receptor binding; antibody-dependent cell-mediated cytotoxicity (ADCC); phagocytosis; down regulation of cell surface receptors (for example B-cell receptor); and B-cell activation, etc. Such effector functions generally require the Fc region to be combined with a binding domain (for example, an antibody variable domain) and can be assessed using various assays.

A "variant Fc region" comprises an amino acid sequence which differs from that of a native sequence Fc region by virtue of at least one amino acid modification. In some aspects, a "variant Fc region" comprises an amino acid sequence which differs from that of a native sequence Fc region by virtue of at least one amino acid modification, yet retains at least one effector function of the native sequence Fc region. In some aspects, a "variant Fc region" comprises an amino acid sequence which differs from that of a native sequence Fc region by virtue of at least one amino acid modification, and the variant Fc region has a modified effector function. In some aspects, a "variant Fc region" comprises an amino acid sequence which differs from that of a native sequence Fc region by virtue of at least one amino acid modification, and the variant Fc region is an effector null Fc region. In some aspects, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some aspects, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 2. Amino acid substitutions may be introduced into a polypeptide of interest and the products screened for a desired activity, for example, retained/improved antigen binding, decreased immunogenicity, or improved ADCC or CDC.

TABLE 2

| Amino acid residues | |
|---|---|
| Original Residue | Exemplary Substitutions |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E, CHO-DG44, CHO-K1, CHO-S, and CHO-DS cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) as provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" and "subject" are used interchangeably herein to refer to an animal; for example, a mammal. In some aspects, methods of treating mammals, including, but not limited to, humans, rodents, and simians, are provided. In some examples, an "individual" or "subject" refers to an individual or subject in need of treatment for a disease or disorder. In some aspects, the subject to receive the treatment can be a patient, designating the fact that the subject has been identified as having a disease or disorder of relevance to the treatment, or being at adequate risk of contracting the disease or disorder.

A "disease" or "disorder" as used herein refers to a condition where treatment is needed and/or desired.

As used herein, "IL31-associated condition" refers to any condition, disorder, or disease that involves aberrant expression, activity, or function of the IL31 protein within a biological context, such as in vivo in a subject. For example, an IL31-associated condition may involve increased IL31 expression, excessive IL31 activity, and/or any IL31 dysfunction that results in a condition where treatment is needed and/or desired.

As used herein, "treatment" is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

A "therapeutically effective amount" of a substance/molecule, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

The terms "pharmaceutical formulation" and "pharmaceutical composition" are used interchangeably and refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and are compatible with other ingredients of the formulation. The pharmaceutically acceptable carrier is appropriate for the formulation employed.

II. Exemplary IL31 Binding Polypeptides

Provided herein are polypeptides that bind IL31. In some aspects, the polypeptide that binds IL31 comprises one or more IL31 binders. In some aspects, the one or more IL31 binder comprises a VHH1. In some aspects, the two or more IL31 binders comprise a VHH1 and a VHH2. In some aspects, the polypeptide comprising a first IL31 binder (e.g., VHH1) and a second IL31 binder (e.g., VHH2) are referred to as a IL31 co-binder. Therefore, provided herein are various single binders (e.g., VHH1 or VHH2 disclosed herein) or co-binders (VHH1 and VHH2 in combination, optionally linked by a linker). Also provided herein is a polypeptide comprising a single IL31 binder (e.g., any VHH1 or VHH2 disclosed herein) and another binder that binds to IL31, but is not disclosed herein. In some aspects, provided herein is a polypeptide comprising a single IL31 binder (e.g., any VHH1 or VHH2 disclosed herein) and another binder that binds to an antigen other than IL31.

In some aspects, the VHH1 comprises a CDR1 comprising the amino acid sequence of SEQ ID NO:59; a CDR2 comprising the amino acid sequence of SEQ ID NO:63; and a CDR3 comprising the amino acid sequence of SEQ ID NO: 64. In some aspects, the VHH1 comprises a CDR1 comprising the amino acid sequence of SEQ ID NO: 59; a CDR2 comprising the amino acid sequence of SEQ ID NO: 63; and a CDR3 comprising the amino acid sequence of SEQ ID NO:64. In some aspects, the IL31 binder comprises a VHH comprising a CDR1 comprising the amino acid sequence $SYX_1MX_2$, wherein $X_1$ is A or T, and $X_2$ is A or G (SEQ ID NO:59); a CDR2 comprising the amino acid sequence $GISSSGYX_{10}X_{11}YX_{12}X_{13}X_{14}SMKG$, wherein $X_{10}$ is T or V, $X_{11}$ is L or M, $X_{12}$ is K or N, $X_{13}$ is S or A, and $X_{14}$ is D or E (SEQ ID NO:63); and a CDR3 comprising the amino acid sequence $GX_{15}X_{16}GRPYX_{17}X_{18}$, wherein $X_{15}$ is I, T, or V, $X_{16}$ is F or I, and $X_{17}$ is E or D, and $X_{18}$ is Y or F (SEQ ID NO:64).

In some aspects, the VHH1 comprises a CDR1 comprising the amino acid sequence of SEQ ID NO:59; a CDR2 comprising the amino acid sequence of SEQ ID NO:63; and a CDR3 comprising the amino acid sequence of SEQ ID NO:61. In some aspects, the VHH1 comprises a CDR1 comprising the amino acid sequence of SEQ ID NO:59; a CDR2 comprising the amino acid sequence of SEQ ID NO:63; and a CDR3 comprising the amino acid sequence of SEQ ID NO:61. In some aspects, the IL31 binder comprises a VHH comprising a CDR1 comprising the amino acid sequence $SYX_1MX_2$, wherein $X_1$ is A or T, and $X_2$ is A or G (SEQ ID NO:59); a CDR2 comprising the amino acid sequence $GISSSGYX_{10}X_{11}YX_{12}X_{13}X_{14}SMKG$, wherein $X_{10}$ is T or V, $X_{11}$ is L or M, $X_{12}$ is K or N, $X_{13}$ is S or A, and $X_{14}$ is D or E (SEQ ID NO:63); and a CDR3 comprising the amino acid sequence $GX_7X_8GRPYX_9Y$, wherein $X_7$ is I or T, $X_8$ is F or I, and $X_9$ is E or D (SEQ ID NO: 61).

In some aspects, the VHH1 comprises a CDR1 comprising the amino acid sequence of SEQ ID NO:59; a CDR2 comprising the amino acid sequence of SEQ ID NO:60; and a CDR3 comprising the amino acid sequence of SEQ ID NO:61. In some aspects, the VHH1 comprises a CDR1 comprising the amino acid sequence of SEQ ID NO:59; a CDR2 comprising the amino acid sequence of SEQ ID NO:60; and a CDR3 comprising the amino acid sequence of SEQ ID NO:61. In some aspects, the IL31 binder comprises a VHH comprising a CDR1 comprising the amino acid sequence $SYX_1MX_2$, wherein $X_1$ is A or T, and $X_2$ is A or G (SEQ ID NO:59); a CDR2 comprising the amino acid sequence $GISSSGYX_3X_4YX_5SX_6SMKG$, wherein $X_3$ is T or V, $X_4$ is L or M, $X_5$ is K or N, and $X_6$ is D or E (SEQ ID NO:60); and a CDR3 comprising the amino acid sequence $GX_7X_8GRPYX_9Y$, wherein $X_7$ is I or T, $X_8$ is F or I, and $X_9$ is E or D (SEQ ID NO:61).

In some aspects, the VHH1 comprises a CDR1 comprising the amino acid sequence of SEQ ID NO:59; a CDR2 comprising the amino acid sequence of SEQ ID NO:60; and a CDR3 comprising the amino acid sequence of SEQ ID NO:64. In some aspects, the VHH1 comprises a CDR1 comprising the amino acid sequence of SEQ ID NO:59; a CDR2 comprising the amino acid sequence of SEQ ID NO:60; and a CDR3 comprising the amino acid sequence of SEQ ID NO:64. In some aspects, the IL31 binder comprises a VHH comprising a CDR1 comprising the amino acid sequence $SYX_1MX_2$, wherein $X_1$ is A or T, and $X_2$ is A or G (SEQ ID NO: 59); a CDR2 comprising the amino acid sequence $GISSSGYX_3X_4YX_5SX_6SMKG$, wherein $X_3$ is T or V, $X_4$ is L or M, $X_5$ is K or N, and $X_6$ is D or E (SEQ ID NO:60); and a CDR3 comprising the amino acid sequence $GX_{15}X_{16}GRPYX_{17}X_{18}$ wherein $X_{15}$ is I, T, or V, $X_{16}$ is F or I, and $X_{17}$ is E or D, and $X_{18}$ is Y or F (SEQ ID NO:64).

In some aspects, the polypeptide that binds IL31 comprises a first IL31 binder and a second IL31 binder. In some aspects, the first IL31 binder comprises a VHH1 comprising a CDR1 comprising the amino acid sequence of SEQ ID NO: 5, SEQ ID NO: 19, SEQ ID NO: 33, SEQ ID NO: 47, SEQ ID NO: 78, SEQ ID NO: 81, or SEQ ID NO: 59; a CDR2 comprising the amino acid sequence of SEQ ID NO: 6, SEQ ID NO: 20, SEQ ID NO: 34, SEQ ID NO: 48, SEQ ID NO: 79, SEQ ID NO: 82, SEQ ID NO: 60, or SEQ ID NO:63; and a CDR3 comprising the amino acid sequence of SEQ ID NO: 7, SEQ ID NO: 21, SEQ ID NO: 35, SEQ ID NO: 49, SEQ ID NO: 80, SEQ ID NO: 83, SEQ ID NO: 61 or SEQ ID NO:64, wherein one or more of the CDR1, CDR2, and CDR3 comprises 1, 2, 3, 4, or 5 amino acid substitutions, insertions or deletions. In some aspects, the first IL31 binder comprises a VHH1 comprising a CDR1 comprising the amino acid sequence of SEQ ID NO: 5, SEQ ID NO: 19, SEQ ID NO: 33, SEQ ID NO: 47, SEQ ID NO: 78, SEQ ID NO: 81, or SEQ ID NO: 59; a CDR2 comprising the amino acid sequence of SEQ ID NO: 6, SEQ ID NO: 20, SEQ ID NO: 34, SEQ ID NO: 48, SEQ ID NO: 79, SEQ ID NO: 82, SEQ ID NO: 60, or SEQ ID NO:63; and a CDR3 comprising the amino acid sequence of SEQ ID NO: 7, SEQ ID NO: 21, SEQ ID NO: 35, SEQ ID NO: 49, SEQ ID NO: 80, SEQ ID NO: 83, SEQ ID NO: 61, or SEQ ID NO:64. In some aspects, the second IL31 binder comprises a VHH2 comprising a CDR1 comprising the amino acid sequence of SEQ ID NO: 10, SEQ ID NO: 24, SEQ ID NO: 38, SEQ ID NO: 52, SEQ ID NO: 84, SEQ ID NO: 87, or SEQ ID NO:59; a CDR2 comprising the amino acid sequence of SEQ ID NO: 11, SEQ ID NO: 25, SEQ ID NO: 39, SEQ ID NO: 53, SEQ ID NO: 85, SEQ ID NO: 88, SEQ ID NO:60, or SEQ ID NO:63; and a CDR3 comprising the amino acid sequence of SEQ ID NO: 12, SEQ ID NO: 26, SEQ ID NO: 40, SEQ ID NO: 54, SEQ ID NO: 86, SEQ ID NO: 89, SEQ ID NO: 61, or SEQ ID NO: 64, wherein one or more of the CDR1, CDR2, and CDR3 comprises 1, 2, 3, 4, or 5 amino acid substitutions, insertions or deletions. In some aspects, the second IL31 binder comprises a VHH2 comprising a CDR1 comprising the amino acid sequence of SEQ ID NO: 10, SEQ ID NO: 24, SEQ ID NO: 38, SEQ ID NO: 52, SEQ ID NO: 84, SEQ ID NO: 87, or SEQ ID NO:59; a CDR2 comprising the amino acid sequence of SEQ ID NO: 11, SEQ ID NO: 25, SEQ ID NO: 39, SEQ ID NO: 53, SEQ ID NO: 85, SEQ ID NO: 88, SEQ ID NO: 60, or SEQ ID NO:63; and a CDR3 comprising the amino acid sequence of SEQ ID NO: 12, SEQ ID NO: 26, SEQ ID NO: 40, SEQ ID NO: 54, SEQ ID NO: 86, SEQ ID NO: 89, SEQ ID NO: 61, or SEQ ID NO:64.

In some aspects, the VHH1 comprises a CDR1 comprising the amino acid sequence of SEQ ID NO: 5, a CDR2 comprising the amino acid sequence of SEQ ID NO: 6, and a CDR3 comprising the amino acid sequence of SEQ ID NO: 7, wherein one or more of the CDR1, CDR2, and CDR3 comprises 1, 2, 3, 4, or 5 amino acid substitutions, insertions or deletions. In some aspects, the VHH1 comprises a CDR1 comprising the amino acid sequence of SEQ ID NO: 5, a CDR2 comprising the amino acid sequence of SEQ ID NO: 6, and a CDR3 comprising the amino acid sequence of SEQ ID NO: 7. In some aspects, the VHH1 comprises a CDR1 comprising the amino acid sequence of SEQ ID NO: 19, a CDR2 comprising the amino acid sequence of SEQ ID NO: 20, and a CDR3 comprising the amino acid sequence of SEQ ID NO: 21, wherein one or more of the CDR1, CDR2, and CDR3 comprises 1, 2, 3, 4, or 5 amino acid substitutions, insertions or deletions. In some aspects, the VHH1 comprises a CDR1 comprising the amino acid sequence of SEQ ID NO: 19, a CDR2 comprising the amino acid sequence of SEQ ID NO: 20, and a CDR3 comprising the amino acid sequence of SEQ ID NO: 21. In some aspects, the VHH1 comprises a CDR1 comprising the amino acid sequence of SEQ ID NO: 33, a CDR2 comprising the amino acid sequence of SEQ ID NO: 34, and a CDR3 comprising the amino acid sequence of SEQ ID NO: 35, wherein one or more of the CDR1, CDR2, and CDR3 comprises 1, 2, 3, 4, or 5 amino acid substitutions, insertions or deletions. In some aspects, the VHH1 comprises a CDR1 comprising the amino acid sequence of SEQ ID NO: 33, a CDR2 comprising the amino acid sequence of SEQ ID NO: 34, and a CDR3 comprising the amino acid sequence of SEQ ID NO: 35. In some aspects, the VHH1 comprises a CDR1 comprising the amino acid sequence of SEQ ID NO: 47, a CDR2 comprising the amino acid sequence of SEQ ID NO: 48, and a CDR3 comprising the amino acid sequence of SEQ ID NO: 49, wherein one or more of the CDR1, CDR2, and CDR3 comprises 1, 2, 3, 4, or 5 amino acid substitutions, insertions or deletions. In some aspects, the VHH1 comprises a CDR1 comprising the amino acid sequence of SEQ ID NO: 47, a CDR2 comprising the amino acid sequence of SEQ ID NO: 48, and a CDR3 comprising the amino acid sequence of SEQ ID NO: 49. In some aspects, the VHH1 comprises a CDR1 comprising the amino acid sequence of SEQ ID NO: 78, a CDR2 comprising the amino acid sequence of SEQ ID NO: 79, and a CDR3 comprising the amino acid sequence of SEQ ID NO: 80, wherein one or more of the CDR1, CDR2, and CDR3 comprises 1, 2, 3, 4, or 5 amino acid substitutions, insertions or deletions. In some aspects, the VHH1 comprises a CDR1 comprising the amino acid sequence of SEQ ID NO: 78, a CDR2 comprising the amino acid sequence of SEQ ID NO: 79, and a CDR3 comprising the amino acid sequence of SEQ ID NO: 80. In some aspects, the VHH1 comprises a CDR1 comprising the amino acid sequence of SEQ ID NO: 81, a CDR2 comprising the amino acid sequence of SEQ ID NO: 82, and a CDR3 comprising the amino acid sequence of SEQ ID NO: 83, wherein one or more of the CDR1, CDR2, and CDR3 comprises 1, 2, 3, 4, or 5 amino acid substitutions, insertions or deletions. In some aspects, the VHH1 comprises a CDR1 comprising the amino acid sequence of SEQ ID NO: 81, a CDR2 comprising the amino acid sequence of SEQ ID NO: 82, and a CDR3 comprising the amino acid sequence of SEQ ID NO: 83. In some aspects, the VHH1 comprises a CDR1 comprising the amino acid sequence of SEQ ID NO: 59, a CDR2 comprising the amino acid sequence of SEQ ID NO: 60 or SEQ ID NO:63, and a CDR3 comprising the amino acid sequence of SEQ ID NO: 61 or SEQ ID NO:64, wherein one or more of the CDR1, CDR2, and CDR3 comprises 1, 2, 3, 4, or 5 amino acid substitutions, insertions or deletions. In some aspects, the VHH1 comprises a CDR1 comprising the amino acid sequence of SEQ ID NO: 59, a CDR2 comprising the amino acid sequence of SEQ ID NO: 60 or SEQ ID NO: 63, and a CDR3 comprising the amino acid sequence of SEQ ID NO: 61 or SEQ ID NO:64. In some aspects, the first IL31 binder comprises a VHH1 comprising a CDR1 comprising the amino acid sequence $SYX_1MX_2$, wherein $X_1$ is A or T, and $X_2$ is A or G (SEQ ID NO: 59); a CDR2 comprising the amino acid sequence $GISSSGYX_3X_4YX_5SX_6SMKG$, wherein $X_3$ is T or V, $X_4$ is L or M, $X_5$ is K or N, and $X_6$ is D or E (SEQ ID NO: 60), or $GISSSGYX_{10}X_{11}YX_{12}X_{13}X_{14}SMKG$, wherein $X_{10}$ is T or V, $X_{11}$ is L or M, $X_{12}$ is K or N, $X_{13}$ is S or A, and $X_{14}$ is D or E (SEQ ID NO:63); and a CDR3 comprising the amino acid sequence $GX_7X_8GRPYX_9Y$, wherein $X_7$ is I or T, and $X_8$ is F or I, and $X_9$ is E or D (SEQ ID NO: 61), or $GX_{15}X_{16}GRPYX_{17}X_{18}$, wherein $X_{15}$ is I, T, or V, $X_{16}$ is F or I, and $X_{17}$ is E or D, and $X_{18}$ is Y or F.

In some aspects, the VHH2 comprises a CDR1 comprising the amino acid sequence of $IX_{23}AMG$, $X_{23}$ is V or H (SEQ ID NO: 251), a CDR2 comprising the amino acid sequence of $AITSGGRX_{24}HYRDSVKG$, $X_{24}$ is T or R (SEQ ID NO: 252), and a CDR3 comprising the amino acid sequence of $DX_{25}GX_{26}X_{27}X_{28}$ VGEYDY, $X_{25}$ is R, M, or T, $X_{26}$ is W, L, or R, $X_{27}$ is T or V, and $X_{28}$ is S or A (SEQ ID NO: 253).

In some aspects, the VHH2 comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12, wherein one or more of the CDR1, CDR2, and CDR3 comprises 1, 2, 3, 4, or 5 amino acid substitutions, insertions or deletions. In some aspects, the VHH2 comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12. In some aspects, the VHH2 comprises a CDR1 comprising the amino acid sequence of SEQ ID NO: 24, a CDR2 comprising the amino acid sequence of SEQ ID NO: 25, and a CDR3 comprising the amino acid sequence of SEQ ID NO: 26, wherein one or more of the CDR1, CDR2, and CDR3 comprises 1, 2, 3, 4, or 5 amino acid substitutions, insertions or deletions. In some aspects, the VHH2 comprises a CDR1 comprising the amino acid sequence of SEQ ID NO: 24, a CDR2 comprising the amino acid sequence of SEQ ID NO:25, and a CDR3 comprising the amino acid sequence of SEQ ID NO: 26. In some aspects, the VHH2 comprises a CDR1 comprising the amino acid sequence of SEQ ID NO: 38, a CDR2 comprising the amino acid sequence of SEQ ID NO: 39, and a CDR3 comprising the amino acid sequence of SEQ ID NO: 40, wherein one or more of the CDR1, CDR2, and CDR3 comprises 1, 2, 3, 4, or 5 amino acid substitutions, insertions or deletions. In some aspects, the VHH2 comprises a CDR1 comprising the amino acid sequence of SEQ ID NO: 38, a CDR2 comprising the amino acid sequence of SEQ ID NO: 39, and a CDR3 comprising the amino acid sequence of SEQ ID NO: 40. In some aspects, the VHH2 comprises a CDR1 comprising the amino acid sequence of SEQ ID NO: 52, a CDR2 comprising the amino acid sequence of SEQ ID NO: 53, and a CDR3 comprising the amino acid sequence of SEQ ID NO: 54, wherein one or more of the CDR1, CDR2, and CDR3 comprises 1, 2, 3, 4, or 5 amino acid substitutions, insertions or deletions. In some aspects, the VHH2 comprises a CDR1 comprising the amino acid sequence of SEQ ID NO: 52, a CDR2 comprising the amino acid sequence of SEQ ID NO: 53, and a CDR3 comprising the amino acid sequence of SEQ ID NO: 54. In some aspects, the VHH2 comprises a CDR1 comprising the amino acid sequence of SEQ ID NO: 84, a CDR2 comprising the amino acid sequence of SEQ ID NO: 85, and a CDR3 comprising the amino acid sequence of SEQ ID NO: 86, wherein one or more of the CDR1, CDR2, and CDR3 comprises 1, 2, 3, 4, or 5 amino acid substitutions, insertions or deletions. In some aspects, the VHH2 comprises a CDR1 comprising the amino acid sequence of SEQ ID NO: 84, a CDR2 comprising the amino acid sequence of SEQ ID NO: 85, and a CDR3 comprising the amino acid sequence of SEQ ID NO: 86. In some aspects, the VHH2 comprises a CDR1 comprising the amino acid sequence of SEQ ID NO: 87, a CDR2 comprising the amino acid sequence of SEQ ID NO: 88, and a CDR3 comprising the amino acid sequence of SEQ ID NO: 89, wherein one or more of the CDR1, CDR2, and CDR3 comprises 1, 2, 3, 4, or 5 amino acid substitutions, insertions or deletions. In some aspects, the VHH2 comprises a CDR1 comprising the amino acid sequence of SEQ ID NO: 87, a CDR2 comprising the amino acid sequence of SEQ ID NO: 88, and a CDR3 comprising the amino acid sequence of SEQ ID NO: 89.

In some aspects, (i) the VHH1 comprises a CDR1 comprising the amino acid sequence of SEQ ID NO: 59, a CDR2 comprising the amino acid sequence of SEQ ID NO: 60 or SEQ ID NO: 63, and a CDR3 comprising the amino acid sequence of SEQ ID NO: 61 or SEQ ID NO:64; and (ii) the VHH2 comprises a CDR1 comprising the amino acid sequence of SEQ ID NO: 10, SEQ ID NO: 24, SEQ ID NO: 38, SEQ ID NO: 52, SEQ ID NO: 84, SEQ ID NO: 87 or SEQ ID NO: 251, a CDR2 comprising the amino acid sequence of SEQ ID NO: 11, SEQ ID NO: 25, SEQ ID NO: 39, SEQ ID NO: 53, SEQ ID NO: 85, SEQ ID NO: 88, or SEQ ID NO:252, and a CDR3 comprising the amino acid sequence of SEQ ID NO: 12, SEQ ID NO: 26, SEQ ID NO: 40, SEQ ID NO: 54, SEQ ID NO: 86, SEQ ID NO: 89, or SEQ ID NO:253.

In some aspects, (i) the VHH1 comprises a CDR1 comprising the amino acid sequence of SEQ ID NO: 5, a CDR2 comprising the amino acid sequence of SEQ ID NO: 6, and a CDR3 comprising the amino acid sequence of SEQ ID NO: 7; and (ii) the VHH2 comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12. In some aspects, (i) the VHH1 comprises a CDR1 comprising the amino acid sequence of SEQ ID NO: 19, a CDR2 comprising the amino acid sequence of SEQ ID NO: 20, and a CDR3 comprising the amino acid sequence of SEQ ID NO: 21; and (ii) the VHH2 comprises a CDR1 comprising the amino acid sequence of SEQ ID NO: 24, a CDR2 comprising the amino acid sequence of SEQ ID NO: 25, and a CDR3 comprising the amino acid sequence of SEQ ID NO: 26. In some aspects, (i) the VHH1 comprises a CDR1 comprising the amino acid sequence of SEQ ID NO: 33, a CDR2 comprising the amino acid sequence of SEQ ID NO: 34, and a CDR3 comprising the amino acid sequence of SEQ ID NO: 35; and (ii) the VHH2 comprises a CDR1 comprising the amino acid sequence of SEQ ID NO: 38, a CDR2 comprising the amino acid sequence of SEQ ID NO: 39, and a CDR3 comprising the amino acid sequence of SEQ ID NO: 40. In some aspects, (i) the VHH1 comprises a CDR1 comprising the amino acid sequence of SEQ ID NO: 47, a CDR2 comprising the amino acid sequence of SEQ ID NO: 48, and a CDR3 comprising the amino acid sequence of SEQ ID NO: 49; and (ii) the VHH2 comprises a CDR1 comprising the amino acid sequence of SEQ ID NO: 52, a CDR2 comprising the amino acid sequence of SEQ ID NO: 53, and a CDR3 comprising the amino acid sequence of SEQ ID NO: 54. In some aspects, (i) the VHH1 comprises a CDR1 comprising the amino acid sequence of SEQ ID NO: 78, a CDR2 comprising the amino acid sequence of SEQ ID NO: 79, and a CDR3 comprising the amino acid sequence of SEQ ID NO: 80; and (ii) the VHH2 comprises a CDR1 comprising the amino acid sequence of SEQ ID NO: 84, a CDR2 comprising the amino acid sequence of SEQ ID NO: 85, and a CDR3 comprising the amino acid sequence of SEQ ID NO: 86. In some aspects, (i) the VHH1 comprises a CDR1 comprising the amino acid sequence of SEQ ID NO: 81, a CDR2 comprising the amino acid sequence of SEQ ID NO: 82, and a CDR3 comprising the amino acid sequence of SEQ ID NO: 83; and (ii) the VHH2 comprises a CDR1 comprising the amino acid sequence of SEQ ID NO: 87, a CDR2 comprising the amino acid sequence of SEQ ID NO: 88, and a CDR3 comprising the amino acid sequence of SEQ ID NO: 89. In some aspects, one or more of the VHH1 and the VHH2 are VHH domains. In some aspects, the VHH1 and the VHH2 are VHH domains.

In some aspects, (i) the VHH1 comprises a CDR1 comprising the amino acid sequence of SEQ ID NO:268, a CDR2 comprising the amino acid sequence of SEQ ID NO:269, and a CDR3 comprising the amino acid sequence of SEQ ID NO:270; and (ii) the VHH2 comprises a CDR1 comprising the amino acid sequence of SEQ ID NO:272, a CDR2 comprising the amino acid sequence of SEQ ID NO:273, and a CDR3 comprising the amino acid sequence of SEQ ID NO: 275. In some aspects, (i) the VHH1 comprises a CDR1 comprising the amino acid sequence of SEQ ID NO:276, a CDR2 comprising the amino acid sequence of SEQ ID NO:277, and a CDR3 comprising the amino acid sequence of SEQ ID NO:278; and (ii) the VHH2 comprises a CDR1 comprising the amino acid sequence of SEQ ID NO:280, a CDR2 comprising the amino acid sequence of SEQ ID NO:281, and a CDR3 comprising the amino acid sequence of SEQ ID NO: 282. In some aspects, (i) the VHH1 comprises a CDR1 comprising the amino acid sequence of SEQ ID NO:284, a CDR2 comprising the amino acid sequence of SEQ ID NO:285, and a CDR3 comprising the amino acid sequence of SEQ ID NO:286; and (ii) the VHH2 comprises a CDR1 comprising the amino acid sequence of SEQ ID NO:288, a CDR2 comprising the amino acid sequence of SEQ ID NO:289, and a CDR3 comprising the amino acid sequence of SEQ ID NO: 290. In some aspects, (i) the VHH1 comprises a CDR1 comprising the amino acid sequence of SEQ ID NO:292, a CDR2 comprising the amino acid sequence of SEQ ID NO:293, and a CDR3 comprising the amino acid sequence of SEQ ID NO:294; and (ii) the VHH2 comprises a CDR1 comprising the amino acid sequence of SEQ ID NO:296, a CDR2 comprising the amino acid sequence of SEQ ID NO:297, and a CDR3 comprising the amino acid sequence of SEQ ID NO: 298. In some aspects, (i) the VHH1 comprises a CDR1 comprising the amino acid sequence of SEQ ID NO:300, a CDR2 comprising the amino acid sequence of SEQ ID NO:301, and a CDR3 comprising the amino acid sequence of SEQ ID NO:302; and (ii) the VHH2 comprises a CDR1 comprising the amino acid sequence of SEQ ID NO:304, a CDR2 comprising the amino acid sequence of SEQ ID NO:305, and a CDR3 comprising the amino acid sequence of SEQ ID NO: 306. In some aspects, (i) the VHH1 comprises a CDR1 comprising the amino acid sequence of SEQ ID NO:308, a CDR2 comprising the amino acid sequence of SEQ ID NO:309, and a CDR3 comprising the amino acid sequence of SEQ ID NO:310; and (ii) the VHH2 comprises a CDR1 comprising the amino acid sequence of SEQ ID NO:312, a CDR2 comprising the amino acid sequence of SEQ ID NO:313, and a CDR3 comprising the amino acid sequence of SEQ ID NO: 314. In some aspects, (i) the VHH1 comprises a CDR1 comprising the amino acid sequence of SEQ ID NO:316, a CDR2 comprising the amino acid sequence of SEQ ID NO:317, and a CDR3 comprising the amino acid sequence of SEQ ID NO:318; and (ii) the VHH2 comprises a CDR1 comprising the amino acid sequence of SEQ ID NO:320, a CDR2 comprising the amino acid sequence of SEQ ID NO:321, and a CDR3 comprising the amino acid sequence of SEQ ID NO: 322. In some aspects, (i) the VHH1 comprises a CDR1 comprising the amino acid sequence of SEQ ID NO:324, a CDR2 comprising the amino acid sequence of SEQ ID NO:325, and a CDR3 comprising the amino acid sequence of SEQ ID NO:326; and (ii) the VHH2 comprises a CDR1 comprising the amino acid sequence of SEQ ID NO:328, a CDR2 comprising the amino acid sequence of SEQ ID NO:329, and a CDR3 comprising the amino acid sequence of SEQ ID NO: 330. In some aspects, (i) the VHH1 comprises a CDR1 comprising the amino acid sequence of SEQ ID NO:332, a CDR2 comprising the amino acid sequence of SEQ ID NO:333, and a CDR3 comprising the amino acid sequence of SEQ ID NO:334; and (ii) the VHH2 comprises a CDR1 comprising the amino acid sequence of SEQ ID NO:336, a CDR2 comprising the amino acid sequence of SEQ ID NO:337, and a CDR3 comprising the amino acid sequence of SEQ ID NO: 338. In some aspects, (i) the VHH1 comprises a CDR1 comprising the amino acid sequence of SEQ ID NO:340, a CDR2 comprising the amino acid sequence of SEQ ID NO:341, and a CDR3 comprising the amino acid sequence of SEQ ID NO:342; and (ii) the VHH2 comprises a CDR1 comprising the amino acid sequence of SEQ ID NO:344, a CDR2 comprising the amino acid sequence of SEQ ID NO:345, and a CDR3 comprising the amino acid sequence of SEQ ID NO: 346.

In some aspects, the polypeptide that binds IL31 (e.g., VHH domain) may be humanized. Humanized binding molecules (such as sdAbs or VHH-containing polypeptides) are useful as therapeutic molecules because they reduce or eliminate the human immune response to non-human binding molecules. For example, a humanized antibody can comprise one or more variable domains in which CDRs, (or portions thereof) are derived from a non-human antibody, and FRs (or portions thereof) are derived from human antibody sequences. A humanized antibody optionally may also comprise at least a portion of a human constant region. In some aspects, some FR residues in a humanized binding molecule are substituted with corresponding residues from a non-human binding molecule (for example, the antibody from which the CDR residues are derived), for example, to restore or improve antibody specificity or affinity.

Humanized binding molecules and methods of making them are reviewed, for example, in Almagro and Fransson, (2008) Front. Biosci. 13:1619-1633, and are further described, for example, in Riechmann et al., (1988) Nature 332:323-329; Queen et al., (1989) Proc. Natl Acad. Sci. USA 86:10029-10033; U.S. Pat. Nos. 5,821,337, 7,527,791, 6,982,321, and 7,087,409; Kashmiri et al., (2005) Methods 36:25-34; Padlan, (1991) Mol. Immunol. 28:489-498 (describing "resurfacing"); Dall'Acqua et al., (2005) Methods 36:43-60 (describing "FR shuffling"); and Osbourn et al., (2005) Methods 36:61-68 and Klimka et al., (2000) Br. J. Cancer, 83:252-260 (describing the "guided selection" approach to FR shuffling).

Human framework regions that can be used for humanization include but are not limited to: framework regions selected using the "best-fit" method (see, for example, Sims et al. (1993) J. Immunol. 151:2296); framework regions derived from the consensus sequence of human antibodies of a particular subgroup of heavy chain variable regions (see, for example, Carter et al. (1992) Proc. Natl. Acad. Sci. USA, 89:4285; and Presta et al. (1993) J. Immunol, 151:2623); human mature (somatically mutated) framework regions or human germline framework regions (see, for example, Almagro and Fransson, (2008) Front. Biosci. 13:1619-1633); and framework regions derived from screening FR libraries (see, for example, Baca et al., (1997) J. Biol. Chem. 272:10678-10684 and Rosok et al., (1996) J. Biol. Chem. 271:22611-22618). Typically, the FR regions of a VHH are replaced with human FR regions to make a humanized VHH. In some aspects, certain FR residues of the human FR are replaced in order to improve one or more properties of the humanized VHH. VHH domains with such replaced residues are still referred to herein as "humanized."

In some aspects, the VHH1 comprises an amino acid sequence at least 85%, at least 90%, at least 95%, at least 96%, at least 97%, at least 98%, or at least 99% identical to the amino acid sequence of SEQ ID NO: 3, SEQ ID NO: 17, SEQ ID NO: 31, or SEQ ID NO: 45. In some aspects, the VHH1 comprises an amino acid sequence at least 85%, at least 90%, at least 95%, at least 96%, at least 97%, at least 98%, or at least 99% identical to the amino acid sequence of SEQ ID NO: 4, SEQ ID NO: 18, SEQ ID NO: 32, or SEQ ID NO: 46.

In some aspects, the VHH2 comprises an amino acid sequence at least 85%, at least 90%, at least 95%, at least 96%, at least 97%, at least 98%, or at least 99% identical to the amino acid sequence of SEQ ID NO: 8, SEQ ID NO: 22, SEQ ID NO: 36, or SEQ ID NO: 50. In some aspects, the VHH2 comprises an amino acid sequence at least 85%, at least 90%, at least 95%, at least 96%, at least 97%, at least 98%, or at least 99% identical to the amino acid sequence of SEQ ID NO: 9, SEQ ID NO: 23, SEQ ID NO: 37, or SEQ ID NO: 51.

In some aspects, the VHH1 comprises a CDR1 comprising the amino acid sequence of SEQ ID NO: 5, a CDR2 comprising the amino acid sequence of SEQ ID NO: 6, and a CDR3 comprising the amino acid sequence of SEQ ID NO: 7, wherein the VHH1 comprises an amino acid sequence at least 85%, at least 90%, at least 95%, at least 96%, at least 97%, at least 98%, or at least 99% identical to the amino acid sequence of SEQ ID NO: 3. In some aspects, the VHH1 comprises a CDR1 comprising the amino acid sequence of SEQ ID NO: 5, a CDR2 comprising the amino acid sequence of SEQ ID NO: 6, and a CDR3 comprising the amino acid sequence of SEQ ID NO: 7, wherein the VHH1 comprises an amino acid sequence at least 85%, at least 90%, at least 95%, at least 96%, at least 97%, at least 98%, or at least 99% identical to the amino acid sequence of SEQ ID NO: 4.

In some aspects, the VHH1 comprises a CDR1 comprising the amino acid sequence of SEQ ID NO: 19, a CDR2 comprising the amino acid sequence of SEQ ID NO: 20, and a CDR3 comprising the amino acid sequence of SEQ ID NO: 21, wherein the VHH1 comprises an amino acid sequence at least 85%, at least 90%, at least 95%, at least 96%, at least 97%, at least 98%, or at least 99% identical to the amino acid sequence of SEQ ID NO: 17. In some aspects, the VHH1 comprises a CDR1 comprising the amino acid sequence of SEQ ID NO: 19, a CDR2 comprising the amino acid sequence of SEQ ID NO: 20, and a CDR3 comprising the amino acid sequence of SEQ ID NO: 21, wherein the VHH1 comprises an amino acid sequence at least 85%, at least 90%, at least 95%, at least 96%, at least 97%, at least 98%, or at least 99% identical to the amino acid sequence of SEQ ID NO: 18.

In some aspects, the VHH1 comprises a CDR1 comprising the amino acid sequence of SEQ ID NO: 33, a CDR2 comprising the amino acid sequence of SEQ ID NO: 34, and a CDR3 comprising the amino acid sequence of SEQ ID NO: 35, wherein the VHH1 comprises an amino acid sequence at least 85%, at least 90%, at least 95%, at least 96%, at least 97%, at least 98%, or at least 99% identical to the amino acid sequence of SEQ ID NO: 31. In some aspects, the VHH1 comprises a CDR1 comprising the amino acid sequence of SEQ ID NO: 33, a CDR2 comprising the amino acid sequence of SEQ ID NO: 34, and a CDR3 comprising the amino acid sequence of SEQ ID NO: 35, wherein the VHH1 comprises an amino acid sequence at least 85%, at least 90%, at least 95%, at least 96%, at least 97%, at least 98%, or at least 99% identical to the amino acid sequence of SEQ ID NO: 32.

In some aspects, the VHH1 comprises a CDR1 comprising the amino acid sequence of SEQ ID NO: 47, a CDR2 comprising the amino acid sequence of SEQ ID NO: 48, and a CDR3 comprising the amino acid sequence of SEQ ID NO: 49, wherein the VHH1 comprises an amino acid sequence at least 85%, at least 90%, at least 95%, at least 96%, at least 97%, at least 98%, or at least 99% identical to the amino acid sequence of SEQ ID NO: 45. In some aspects, the VHH1 comprises a CDR1 comprising the amino acid sequence of SEQ ID NO: 47, a CDR2 comprising the amino acid sequence of SEQ ID NO: 48, and a CDR3 comprising the amino acid sequence of SEQ ID NO: 49, wherein the VHH1 comprises an amino acid sequence at least 85%, at least 90%, at least 95%, at least 96%, at least 97%, at least 98%, or at least 99% identical to the amino acid sequence of SEQ ID NO: 46.

In some aspects, the VHH1 comprises a CDR1 comprising the amino acid sequence of SEQ ID NO: 78, a CDR2 comprising the amino acid sequence of SEQ ID NO: 79, and a CDR3 comprising the amino acid sequence of SEQ ID NO: 80, wherein the VHH1 comprises an amino acid sequence at least 85%, at least 90%, at least 95%, at least 96%, at least 97%, at least 98%, or at least 99% identical to the amino acid sequence of SEQ ID NO: 3. In some aspects, the VHH1 comprises a CDR1 comprising the amino acid sequence of SEQ ID NO: 78, a CDR2 comprising the amino acid sequence of SEQ ID NO: 79, and a CDR3 comprising the amino acid sequence of SEQ ID NO: 80, wherein the VHH1 comprises an amino acid sequence at least 85%, at least 90%, at least 95%, at least 96%, at least 97%, at least 98%, or at least 99% identical to the amino acid sequence of SEQ ID NO: 4.

In some aspects, the VHH1 comprises a CDR1 comprising the amino acid sequence of SEQ ID NO: 81, a CDR2 comprising the amino acid sequence of SEQ ID NO: 82, and a CDR3 comprising the amino acid sequence of SEQ ID NO: 83, wherein the VHH1 comprises an amino acid sequence at least 85%, at least 90%, at least 95%, at least 96%, at least 97%, at least 98%, or at least 99% identical to the amino acid sequence of SEQ ID NO: 3. In some aspects, the VHH1 comprises a CDR1 comprising the amino acid sequence of SEQ ID NO: 81, a CDR2 comprising the amino acid sequence of SEQ ID NO: 82, and a CDR3 comprising the amino acid sequence of SEQ ID NO: 83, wherein the VHH1 comprises an amino acid sequence at least 85%, at least 90%, at least 95%, at least 96%, at least 97%, at least 98%, or at least 99% identical to the amino acid sequence of SEQ ID NO: 4.

In some aspects, the VHH2 comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12, wherein the VHH2 comprises an amino acid sequence at least 85%, at least 90%, at least 95%, at least 96%, at least 97%, at least 98%, or at least 99% identical to the amino acid sequence of SEQ ID NO: 8. In some aspects, the VHH2 comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12, wherein the VHH2 comprises an amino acid sequence at least 85%, at least 90%, at least 95%, at least 96%, at least 97%, at least 98%, or at least 99% identical to the amino acid sequence of SEQ ID NO: 9.

In some aspects, the VHH2 comprises a CDR1 comprising the amino acid sequence of SEQ ID NO: 24, a CDR2 comprising the amino acid sequence of SEQ ID NO: 25, and a CDR3 comprising the amino acid sequence of SEQ ID NO: 26, wherein the VHH2 comprises an amino acid sequence at least 85%, at least 90%, at least 95%, at least 96%, at least 97%, at least 98%, or at least 99% identical to the amino acid sequence of SEQ ID NO: 22. In some aspects, the VHH2 comprises a CDR1 comprising the amino acid sequence of SEQ ID NO: 24, a CDR2 comprising the amino acid sequence of SEQ ID NO: 25, and a CDR3 comprising the amino acid sequence of SEQ ID NO: 26, wherein the VHH2 comprises an amino acid sequence at least 85%, at least 90%, at least 95%, at least 96%, at least 97%, at least 98%, or at least 99% identical to the amino acid sequence of SEQ ID NO: 23.

In some aspects, the VHH2 comprises a CDR1 comprising the amino acid sequence of SEQ ID NO: 38, a CDR2 comprising the amino acid sequence of SEQ ID NO: 39, and a CDR3 comprising the amino acid sequence of SEQ ID NO: 40, wherein the VHH2 comprises an amino acid sequence at least 85%, at least 90%, at least 95%, at least 96%, at least 97%, at least 98%, or at least 99% identical to the amino acid sequence of SEQ ID NO: 36. In some aspects, the VHH2 comprises a CDR1 comprising the amino acid sequence of SEQ ID NO: 38, a CDR2 comprising the amino acid sequence of SEQ ID NO: 39, and a CDR3 comprising the amino acid sequence of SEQ ID NO: 40, wherein the VHH2 comprises an amino acid sequence at least 85%, at least 90%, at least 95%, at least 96%, at least 97%, at least 98%, or at least 99% identical to the amino acid sequence of SEQ ID NO: 37.

In some aspects, the VHH2 comprises a CDR1 comprising the amino acid sequence of SEQ ID NO: 52, a CDR2 comprising the amino acid sequence of SEQ ID NO: 53, and a CDR3 comprising the amino acid sequence of SEQ ID NO: 54, wherein the VHH2 comprises an amino acid sequence at least 85%, at least 90%, at least 95%, at least 96%, at least 97%, at least 98%, or at least 99% identical to the amino acid sequence of SEQ ID NO: 50. In some aspects, the VHH2 comprises a CDR1 comprising the amino acid sequence of SEQ ID NO: 52, a CDR2 comprising the amino acid sequence of SEQ ID NO: 53, and a CDR3 comprising the amino acid sequence of SEQ ID NO: 54, wherein the VHH2 comprises an amino acid sequence at least 85%, at least 90%, at least 95%, at least 96%, at least 97%, at least 98%, or at least 99% identical to the amino acid sequence of SEQ ID NO: 51.

In some aspects, the VHH2 comprises a CDR1 comprising the amino acid sequence of SEQ ID NO: 84, a CDR2 comprising the amino acid sequence of SEQ ID NO: 85, and a CDR3 comprising the amino acid sequence of SEQ ID NO: 86, wherein the VHH2 comprises an amino acid sequence at least 85%, at least 90%, at least 95%, at least 96%, at least 97%, at least 98%, or at least 99% identical to the amino acid sequence of SEQ ID NO: 8. In some aspects, the VHH2 comprises a CDR1 comprising the amino acid sequence of SEQ ID NO: 84, a CDR2 comprising the amino acid sequence of SEQ ID NO: 85, and a CDR3 comprising the amino acid sequence of SEQ ID NO: 86, wherein the VHH2 comprises an amino acid sequence at least 85%, at least 90%, at least 95%, at least 96%, at least 97%, at least 98%, or at least 99% identical to the amino acid sequence of SEQ ID NO: 9.

In some aspects, the VHH2 comprises a CDR1 comprising the amino acid sequence of SEQ ID NO: 87, a CDR2 comprising the amino acid sequence of SEQ ID NO: 88, and a CDR3 comprising the amino acid sequence of SEQ ID NO: 89, wherein the VHH2 comprises an amino acid sequence at least 85%, at least 90%, at least 95%, at least 96%, at least 97%, at least 98%, or at least 99% identical to the amino acid sequence of SEQ ID NO: 8. In some aspects, the VHH2 comprises a CDR1 comprising the amino acid sequence of SEQ ID NO: 87, a CDR2 comprising the amino acid sequence of SEQ ID NO: 88, and a CDR3 comprising the amino acid sequence of SEQ ID NO: 89, wherein the VHH2 comprises an amino acid sequence at least 85%, at least 90%, at least 95%, at least 96%, at least 97%, at least 98%, or at least 99% identical to the amino acid sequence of SEQ ID NO: 9.

In some aspects, the VHH1 comprises the amino acid sequence of SEQ ID NO: 3, SEQ ID NO: 17, SEQ ID NO: 31, or SEQ ID NO: 45. In some aspects, the VHH1 comprises the amino acid sequence of SEQ ID NO: 4, SEQ ID NO: 18, SEQ ID NO: 32, or SEQ ID NO: 46.

In some aspects, the VHH2 comprises the amino acid sequence of SEQ ID NO: 8, SEQ ID NO: 22, SEQ ID NO: 36, or SEQ ID NO: 50. In some aspects, the VHH2 comprises the amino acid sequence of SEQ ID NO: 9, SEQ ID NO: 23, or SEQ ID NO: 37, or SEQ ID NO: 51.

In some aspects, the VHH1 comprises a CDR1 comprising the amino acid sequence of SEQ ID NO: 5, a CDR2 comprising the amino acid sequence of SEQ ID NO: 6, and a CDR3 comprising the amino acid sequence of SEQ ID NO: 7, wherein the VHH1 comprises an amino acid sequence at least 85%, at least 90%, at least 95%, at least 96%, at least 97%, at least 98%, or at least 99% identical to the amino acid sequence of SEQ ID NO: 3; and the VHH2 comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12, wherein the VHH2 comprises an amino acid sequence at least 85%, at least 90%, at least 95%, at least 96%, at least 97%, at least 98%, or at least 99% identical to the amino acid sequence of SEQ ID NO: 8.

In some aspects, the VHH1 comprises a CDR1 comprising the amino acid sequence of SEQ ID NO: 5, a CDR2 comprising the amino acid sequence of SEQ ID NO: 6, and a CDR3 comprising the amino acid sequence of SEQ ID NO: 7, wherein the VHH1 comprises an amino acid sequence at least 85%, at least 90%, at least 95%, at least 96%, at least 97%, at least 98%, or at least 99% identical to the amino acid sequence of SEQ ID NO: 4; and the VHH2 comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12, wherein the VHH2 comprises an amino acid sequence at least 85%, at least 90%, at least 95%, at least 96%, at least 97%, at least 98%, or at least 99% identical to the amino acid sequence of SEQ ID NO: 9. In some aspects, provided herein is a polypeptide, wherein the VHH1 comprises the amino acid sequence of SEQ ID NO: 4 and the VHH2 comprises the amino acid sequence of SEQ ID NO: 9.

In some aspects, the VHH1 comprises a CDR1 comprising the amino acid sequence of SEQ ID NO: 19, a CDR2 comprising the amino acid sequence of SEQ ID NO: 20, and a CDR3 comprising the amino acid sequence of SEQ ID NO: 21, wherein the VHH1 comprises an amino acid sequence at least 85%, at least 90%, at least 95%, at least 96%, at least 97%, at least 98%, or at least 99% identical to the amino acid sequence of SEQ ID NO: 17; and the VHH2 comprises a CDR1 comprising the amino acid sequence of SEQ ID NO: 24, a CDR2 comprising the amino acid sequence of SEQ ID NO: 25, and a CDR3 comprising the amino acid sequence of SEQ ID NO: 26, wherein the VHH2 comprises an amino acid sequence at least 85%, at least 90%, at least 95%, at least 96%, at least 97%, at least 98%, or at least 99% identical to the amino acid sequence of SEQ ID NO: 22.

In some aspects, the VHH1 comprises a CDR1 comprising the amino acid sequence of SEQ ID NO: 19, a CDR2 comprising the amino acid sequence of SEQ ID NO: 20, and a CDR3 comprising the amino acid sequence of SEQ ID NO: 21, wherein the VHH1 comprises an amino acid sequence at least 85%, at least 90%, at least 95%, at least 96%, at least 97%, at least 98%, or at least 99% identical to the amino acid sequence of SEQ ID NO: 18; and the VHH2 comprises a CDR1 comprising the amino acid sequence of SEQ ID NO: 24, a CDR2 comprising the amino acid sequence of SEQ ID NO: 25, and a CDR3 comprising the amino acid sequence of SEQ ID NO: 26, wherein the VHH2 comprises an amino acid sequence at least 85%, at least 90%, at least 95%, at least 96%, at least 97%, at least 98%, or at least 99% identical to the amino acid sequence of SEQ ID NO: 23. In some aspects, the VHH1 comprises the amino acid sequence of SEQ ID NO: 18 and the VHH2 comprises the amino acid sequence of SEQ ID NO: 23.

In some aspects, the VHH1 comprises a CDR1 comprising the amino acid sequence of SEQ ID NO: 33, a CDR2 comprising the amino acid sequence of SEQ ID NO: 34, and a CDR3 comprising the amino acid sequence of SEQ ID NO: 35, wherein the VHH1 comprises an amino acid sequence at least 85%, at least 90%, at least 95%, at least 96%, at least 97%, at least 98%, or at least 99% identical to the amino acid sequence of SEQ ID NO: 31; and the VHH2 comprises a CDR1 comprising the amino acid sequence of SEQ ID NO: 38, a CDR2 comprising the amino acid sequence of SEQ ID NO: 39, and a CDR3 comprising the amino acid sequence of SEQ ID NO: 40, wherein the VHH2 comprises an amino acid sequence at least 85%, at least 90%, at least 95%, at least 96%, at least 97%, at least 98%, or at least 99% identical to the amino acid sequence of SEQ ID NO: 36.

In some aspects, the VHH1 comprises a CDR1 comprising the amino acid sequence of SEQ ID NO: 33, a CDR2 comprising the amino acid sequence of SEQ ID NO: 34, and a CDR3 comprising the amino acid sequence of SEQ ID NO: 35, wherein the VHH1 comprises an amino acid sequence at least 85%, at least 90%, at least 95%, at least 96%, at least 97%, at least 98%, or at least 99% identical to the amino acid sequence of SEQ ID NO: 32; and the VHH2 comprises a CDR1 comprising the amino acid sequence of SEQ ID NO: 38, a CDR2 comprising the amino acid sequence of SEQ ID NO: 39, and a CDR3 comprising the amino acid sequence of SEQ ID NO: 40, wherein the VHH2 comprises an amino acid sequence at least 85%, at least 90%, at least 95%, at least 96%, at least 97%, at least 98%, or at least 99% identical to the amino acid sequence of SEQ ID NO: 37. In some aspects, the VHH1 comprises the amino acid sequence of SEQ ID NO: 32 and the VHH2 comprises the amino acid sequence of SEQ ID NO: 37.

In some aspects, the VHH1 comprises a CDR1 comprising the amino acid sequence of SEQ ID NO: 47, a CDR2 comprising the amino acid sequence of SEQ ID NO: 48, and a CDR3 comprising the amino acid sequence of SEQ ID NO: 49, wherein the VHH1 comprises an amino acid sequence at least 85%, at least 90%, at least 95%, at least 96%, at least 97%, at least 98%, or at least 99% identical to the amino acid sequence of SEQ ID NO: 45; and the VHH2 comprises a CDR1 comprising the amino acid sequence of SEQ ID NO: 52, a CDR2 comprising the amino acid sequence of SEQ ID NO: 53, and a CDR3 comprising the amino acid sequence of SEQ ID NO: 54, wherein the VHH2 comprises an amino acid sequence at least 85%, at least 90%, at least 95%, at least 96%, at least 97%, at least 98%, or at least 99% identical to the amino acid sequence of SEQ ID NO: 50.

In some aspects, the VHH1 comprises a CDR1 comprising the amino acid sequence of SEQ ID NO: 47, a CDR2 comprising the amino acid sequence of SEQ ID NO: 48, and a CDR3 comprising the amino acid sequence of SEQ ID NO: 49, wherein the VHH1 comprises an amino acid sequence at least 85%, at least 90%, at least 95%, at least 96%, at least 97%, at least 98%, or at least 99% identical to the amino acid sequence of SEQ ID NO: 46; and the VHH2 comprises a CDR1 comprising the amino acid sequence of SEQ ID NO: 52, a CDR2 comprising the amino acid sequence of SEQ ID NO: 53, and a CDR3 comprising the amino acid sequence of SEQ ID NO: 54, wherein the VHH2 comprises an amino acid sequence at least 85%, at least 90%, at least 95%, at least 96%, at least 97%, at least 98%, or at least 99% identical to the amino acid sequence of SEQ ID NO: 51. In some aspects, the VHH1 comprises the amino acid sequence of SEQ ID NO: 46 and the VHH2 comprises the amino acid sequence of SEQ ID NO: 51.

In some aspects, disclosed herein is a polypeptide comprising a VHH1 which comprises: an amino acid sequence at least 85%, at least 90%, at least 95%, at least 96%, at least 97%, at least 98%, or at least 99% identical to the amino acid sequence of SEQ ID NO:3, SEQ ID NO:4, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 140, SEQ ID NO: 141, SEQ ID NO: 142, SEQ ID NO: 143, SEQ ID NO: 144, or SEQ ID NO: 145. In some aspects, disclosed herein is a polypeptide comprising a VHH2 which comprises an amino acid sequence at least 85%, at least 90%, at least 95%, at least 96%, at least 97%, at least 98%, or at least 99% identical to the amino acid sequence of SEQ ID NO:8, SEQ ID NO:9, SEQ ID NO: 101, SEQ ID NO: 102, SEQ ID NO: 103, or SEQ ID NO: 146. In some aspects, disclosed herein is a polypeptide comprising both the VHH1 and the VHH2.

In some aspects, disclosed herein is a polypeptide comprising a VHH1 which comprises the amino acid sequence of SEQ ID NO:3, SEQ ID NO:4, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 140, SEQ ID NO: 141, SEQ ID NO: 142, SEQ ID NO: 143, SEQ ID NO: 144, or SEQ ID NO: 145. In some aspects, disclosed herein is a polypeptide comprising a VHH2 which comprises the amino acid sequence of SEQ ID NO:8, SEQ ID NO:9, SEQ ID NO: 101, SEQ ID NO: 102, SEQ ID NO: 103, or SEQ ID NO: 146. In some aspects, disclosed herein is a polypeptide comprising (i) a VHH1 which comprises the amino acid sequence of SEQ ID NO:3, SEQ ID NO:4, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 140, SEQ ID NO: 141, SEQ ID NO: 142, SEQ ID NO: 143, SEQ ID NO: 144, or SEQ ID NO: 145 and a VHH2 which comprises the amino acid sequence of SEQ ID NO:8, SEQ ID NO:9, SEQ ID NO: 101, SEQ ID NO: 102, SEQ ID NO: 103, or SEQ ID NO: 146.

In some aspects, disclosed herein is a polypeptide comprising a VHH1 which comprises an amino acid sequence at least 85%, at least 90%, at least 95%, at least 96%, at least 97%, at least 98%, or at least 99% identical to the amino acid sequence of SEQ ID NO:45, SEQ ID NO:46, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 221, SEQ ID NO: 222, SEQ ID NO: 223, SEQ ID NO: 224, SEQ ID NO: 225, or SEQ ID NO: 226. In some aspects, disclosed herein is a polypeptide comprising a VHH2 which comprises an amino acid sequence at least 85%, at least 90%, at least 95%, at least 96%, at least 97%, at least 98%, or at least 99% identical to the amino acid sequence of SEQ ID NO:50, SEQ ID NO:51, SEQ ID NO: 185, SEQ ID NO: 186, or SEQ ID NO: 187.

In some aspects, disclosed herein is a polypeptide comprising a VHH1 which comprises the amino acid sequence of SEQ ID NO:45, SEQ ID NO:46, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 221, SEQ ID NO: 222, SEQ ID NO: 223, SEQ ID NO: 224, SEQ ID NO: 225, or SEQ ID NO: 226 and a VHH2 which comprises the amino acid sequence of SEQ ID NO: 50, SEQ ID NO:51, SEQ ID NO: 185, SEQ ID NO: 186, or SEQ ID NO: 187.

In some aspects, disclosed herein is a polypeptide comprising a VHH1 which comprises a CDR1 comprising the amino acid sequence of SEQ ID NO: 78, a CDR2 comprising the amino acid sequence of SEQ ID NO: 79, and a CDR3 comprising the amino acid sequence of SEQ ID NO: 80, wherein the VHH1 comprises an amino acid sequence at least 85%, at least 90%, at least 95%, at least 96%, at least 97%, at least 98%, or at least 99% identical to the amino acid sequence of SEQ ID NO: 3; and a VHH2 which comprises a CDR1 comprising the amino acid sequence of SEQ ID NO: 84, a CDR2 comprising the amino acid sequence of SEQ ID NO: 85, and a CDR3 comprising the amino acid sequence of SEQ ID NO: 86, wherein the VHH2 comprises an amino acid sequence at least 85%, at least 90%, at least 95%, at least 96%, at least 97%, at least 98%, or at least 99% identical to the amino acid sequence of SEQ ID NO: 8.

In some aspects, the VHH1 comprises a CDR1 comprising the amino acid sequence of SEQ ID NO: 78, a CDR2 comprising the amino acid sequence of SEQ ID NO: 79, and a CDR3 comprising the amino acid sequence of SEQ ID NO: 80, wherein the VHH1 comprises an amino acid sequence at least 85%, at least 90%, at least 95%, at least 96%, at least 97%, at least 98%, or at least 99% identical to the amino acid sequence of SEQ ID NO: 4; and the VHH2 comprises a CDR1 comprising the amino acid sequence of SEQ ID NO: 84, a CDR2 comprising the amino acid sequence of SEQ ID NO: 85, and a CDR3 comprising the amino acid sequence of SEQ ID NO: 86, wherein the VHH2 comprises an amino acid sequence at least 85%, at least 90%, at least 95%, at least 96%, at least 97%, at least 98%, or at least 99% identical to the amino acid sequence of SEQ ID NO: 9. In some aspects, provided herein is a polypeptide, wherein the VHH1 comprises the amino acid sequence of SEQ ID NO: 4 and the VHH2 comprises the amino acid sequence of SEQ ID NO: 9.

In some aspects, the VHH1 comprises a CDR1 comprising the amino acid sequence of SEQ ID NO: 81, a CDR2 comprising the amino acid sequence of SEQ ID NO: 82, and a CDR3 comprising the amino acid sequence of SEQ ID NO: 83, wherein the VHH1 comprises an amino acid sequence at least 85%, at least 90%, at least 95%, at least 96%, at least 97%, at least 98%, or at least 99% identical to the amino acid sequence of SEQ ID NO: 3; and the VHH2 comprises a CDR1 comprising the amino acid sequence of SEQ ID NO: 87, a CDR2 comprising the amino acid sequence of SEQ ID NO: 88, and a CDR3 comprising the amino acid sequence of SEQ ID NO: 89, wherein the VHH2 comprises an amino acid sequence at least 85%, at least 90%, at least 95%, at least 96%, at least 97%, at least 98%, or at least 99% identical to the amino acid sequence of SEQ ID NO: 8.

In some aspects, the VHH1 comprises a CDR1 comprising the amino acid sequence of SEQ ID NO: 81, a CDR2 comprising the amino acid sequence of SEQ ID NO: 82, and a CDR3 comprising the amino acid sequence of SEQ ID NO: 83, wherein the VHH1 comprises an amino acid sequence at least 85%, at least 90%, at least 95%, at least 96%, at least 97%, at least 98%, or at least 99% identical to the amino acid sequence of SEQ ID NO:4; and the VHH2 comprises a CDR1 comprising the amino acid sequence of SEQ ID NO: 87, a CDR2 comprising the amino acid sequence of SEQ ID NO: 88, and a CDR3 comprising the amino acid sequence of SEQ ID NO: 89, wherein the VHH2 comprises an amino acid sequence at least 85%, at least 90%, at least 95%, at least 96%, at least 97%, at least 98%, or at least 99% identical to the amino acid sequence of SEQ ID NO: 9. In some aspects, provided herein is a polypeptide, wherein the VHH1 comprises the amino acid sequence of SEQ ID NO: 4 and the VHH2 comprises the amino acid sequence of SEQ ID NO: 9.

In some aspects, the polypeptide provided herein comprises a linker. In some aspects, the linker is an amino acid linker. In some aspects, the amino acid linker connects two or more antibody variable domains together. In some aspects, the VHH1 is connected to the VHH2 by a linker. In some aspects, the polypeptide has the structure: [first IL31 binder]-linker-[second IL31 binder]. In some aspects, the first and second IL31 binding moieties are the same. In some aspects, the first and second IL31 binding moieties are different. In some aspects, the polypeptide has the structure: [VHH1]-linker-[VHH2]. In some aspects, VHH1 and VHH2 are the same. In some aspects, VHH1 and VHH2 are different.

In some aspects, the linker is from 5 to 50 amino acids long. In some aspects, the linker is between about 1-50, 8-40, 12-37, or 16-30 amino acids in length. In some aspects, the linker is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In some aspects, the linker is between about 8 to 40 amino acids in length. In some aspects, the linker is between about 12 to 37 amino acids in length. In some aspect, the linker is a flexible linker. In some aspects, the linker is a rigid linker. In some aspects, the linker is a charged linker. In some aspects, the linker comprises glycine and/or serine residues. In some aspects, the linker comprises an amino acid sequence having at least 85%, at least 90%, at least 95%, at least 96%, at least 97%, at least 98%, at least 99%, or about 100% sequence identity to SEQ ID NO: 104 or SEQ ID NO: 188.

In some aspects, the polypeptide comprises an amino acid sequence at least 85%, at least 90%, at least 95%, at least 96%, at least 97%, at least 98%, or at least 99% identical to the amino acid sequence of SEQ ID NO: 13, SEQ ID NO: 27, SEQ ID NO: 41, SEQ ID NO: 55, SEQ ID NO: 14, SEQ ID NO: 28, SEQ ID NO: 42, or SEQ ID NO: 56. In some aspects, the polypeptide comprises an amino acid sequence at least 85%, at least 90%, at least 95%, at least 96%, at least 97%, at least 98%, or at least 99% identical to the amino acid sequence of SEQ ID NO: 13. In some aspects, the polypeptide comprises an amino acid sequence at least 85%, at least 90%, at least 95%, at least 96%, at least 97%, at least 98%, or at least 99% identical to the amino acid sequence of SEQ ID NO: 27. In some aspects, the polypeptide comprises an amino acid sequence at least 85%, at least 90%, at least 95%, at least 96%, at least 97%, at least 98%, or at least 99% identical to the amino acid sequence of SEQ ID NO: 41. In some aspects, the polypeptide comprises an amino acid sequence at least 85%, at least 90%, at least 95%, at least 96%, at least 97%, at least 98%, or at least 99% identical to the amino acid sequence of SEQ ID NO: 55. In some aspects, the polypeptide comprises an amino acid sequence at least 85%, at least 90%, at least 95%, at least 96%, at least 97%, at least 98%, or at least 99% identical to the amino acid sequence of SEQ ID NO: 14. In some aspects, the polypeptide comprises an amino acid sequence at least 85%, at least 90%, at least 95%, at least 96%, at least 97%, at least 98%, or at least 99% identical to the amino acid sequence of SEQ ID NO: 28. In some aspects, the polypeptide comprises an amino acid sequence at least 85%, at least 90%, at least 95%, at least 96%, at least 97%, at least 98%, or at least 99% identical to the amino acid sequence of SEQ ID NO: 42. In some aspects, the polypeptide comprises an amino acid sequence at least 85%, at least 90%, at least 95%, at least 96%, at least 97%, at least 98%, or at least 99% identical to the amino acid sequence of SEQ ID NO: 56.

In some aspects, the polypeptide comprises an amino acid sequence having at least 85%, at least 90%, at least 95%, at least 96%, at least 97%, at least 98%, at least 99%, or about 100% sequence identity to the amino acid sequence of SEQ ID NO:13, SEQ ID NO:14, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, or SEQ ID NO: 176.

In some aspects, the polypeptide comprises the amino acid sequence of SEQ ID NO:13, SEQ ID NO:14, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, or SEQ ID NO: 176.

In some aspects, the polypeptide comprises an amino acid sequence having at least 85%, at least 90%, at least 95%, at least 96%, at least 97%, at least 98%, at least 99%, or about 100% sequence identity to the amino acid sequence of SEQ ID NO:55, SEQ ID NO:56, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO: 211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249 or SEQ ID NO: 250.

In some aspects, the polypeptide comprises the amino acid sequence of SEQ ID NO:55, SEQ ID NO:56, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO:200, SEQ ID NO:201, SEQ ID NO:202, SEQ ID NO:203, SEQ ID NO: 204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO: 215, SEQ ID NO:216, SEQ ID NO:217, SEQ ID NO:218, SEQ ID NO:219, SEQ ID NO:220, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249 or SEQ ID NO: 250.

In some aspects, the polypeptide comprises an amino acid sequence at least 85% identical to the amino acid sequence of SEQ ID NO: 13. In some aspects, the polypeptide comprises an amino acid sequence at least 90% identical to the amino acid sequence of SEQ ID NO: 13. In some aspects, the polypeptide comprises an amino acid sequence at least 95% identical to the amino acid sequence of SEQ ID NO: 13. In some aspects, the polypeptide comprises an amino acid sequence at least 96% identical to the amino acid sequence of SEQ ID NO: 13. In some aspects, the polypeptide comprises an amino acid sequence at least 97% identical to the amino acid sequence of SEQ ID NO: 13. In some aspects, the polypeptide comprises an amino acid sequence at least 98% identical to the amino acid sequence of SEQ ID NO: 13. In some aspects, the polypeptide comprises an amino acid sequence at least 99% identical to the amino acid sequence of SEQ ID NO: 13.

In some aspects, the polypeptide comprises an amino acid sequence at least 85% identical to the amino acid sequence of SEQ ID NO: 27. In some aspects, the polypeptide comprises an amino acid sequence at least 90% identical to the amino acid sequence of SEQ ID NO: 27. In some sequence of SEQ ID NO: 27. In some aspects, the polypeptide comprises an amino acid sequence at least 96% identical to the amino acid sequence of SEQ ID NO: 27. In some aspects, the polypeptide comprises an amino acid sequence at least 97% identical to the amino acid sequence of SEQ ID NO: 27. In some aspects, the polypeptide comprises an amino acid sequence at least 98% identical to the amino acid sequence of SEQ ID NO: 27. In some aspects, the polypeptide comprises an amino acid sequence at least 99% identical to the amino acid sequence of SEQ ID NO: 27.

In some aspects, the polypeptide comprises an amino acid sequence at least 85% identical to the amino acid sequence of SEQ ID NO: 41. In some aspects, the polypeptide comprises an amino acid sequence at least 90% identical to the amino acid sequence of SEQ ID NO: 41. In some aspects, the polypeptide comprises an amino acid sequence at least 95% identical to the amino acid sequence of SEQ ID NO: 41. In some aspects, the polypeptide comprises an amino acid sequence at least 96% identical to the amino acid sequence of SEQ ID NO: 41. In some aspects, the polypeptide comprises an amino acid sequence at least 97% identical to the amino acid sequence of SEQ ID NO: 41. In some aspects, the polypeptide comprises an amino acid sequence at least 98% identical to the amino acid sequence of SEQ ID NO: 41. In some aspects, the polypeptide comprises an amino acid sequence at least 99% identical to the amino acid sequence of SEQ ID NO: 41.

In some aspects, the polypeptide comprises an amino acid sequence at least 85% identical to the amino acid sequence of SEQ ID NO: 55. In some aspects, the polypeptide comprises an amino acid sequence at least 90% identical to the amino acid sequence of SEQ ID NO: 55. In some aspects, the polypeptide comprises an amino acid sequence at least 95% identical to the amino acid sequence of SEQ ID NO: 55. In some aspects, the polypeptide comprises an amino acid sequence at least 96% identical to the amino acid sequence of SEQ ID NO: 55. In some aspects, the polypeptide comprises an amino acid sequence at least 97% identical to the amino acid sequence of SEQ ID NO: 55. In some aspects, the polypeptide comprises an amino acid sequence at least 98% identical to the amino acid sequence of SEQ ID NO: 55. In some aspects, the polypeptide comprises an amino acid sequence at least 99% identical to the amino acid sequence of SEQ ID NO: 55.

In some aspects, the polypeptide comprises an amino acid sequence at least 85% identical to the amino acid sequence of SEQ ID NO: 14. In some aspects, the polypeptide comprises an amino acid sequence at least 90% identical to the amino acid sequence of SEQ ID NO: 14. In some sequence of SEQ ID NO: 14. In some aspects, the polypeptide comprises an amino acid sequence at least 96% identical to the amino acid sequence of SEQ ID NO: 14. In some aspects, the polypeptide comprises an amino acid sequence at least 97% identical to the amino acid sequence of SEQ ID NO: 14. In some aspects, the polypeptide comprises an amino acid sequence at least 98% identical to the amino acid sequence of SEQ ID NO: 14. In some aspects, the polypeptide comprises an amino acid sequence at least 99% identical to the amino acid sequence of SEQ ID NO: 14.

In some aspects, the polypeptide comprises an amino acid sequence at least 85% identical to the amino acid sequence of SEQ ID NO: 28. In some aspects, the polypeptide comprises an amino acid sequence at least 90% identical to the amino acid sequence of SEQ ID NO: 28. In some aspects, the polypeptide comprises an amino acid sequence at least 95% identical to the amino acid sequence of SEQ ID NO: 28. In some aspects, the polypeptide comprises an amino acid sequence at least 96% identical to the amino acid sequence of SEQ ID NO: 28. In some aspects, the polypeptide comprises an amino acid sequence at least 97% identical to the amino acid sequence of SEQ ID NO: 28. In some aspects, the polypeptide comprises an amino acid sequence at least 98% identical to the amino acid sequence of SEQ ID NO: 28. In some aspects, the polypeptide comprises an amino acid sequence at least 99% identical to the amino acid sequence of SEQ ID NO: 28.

In some aspects, the polypeptide comprises an amino acid sequence at least 85% identical to the amino acid sequence of SEQ ID NO: 42. In some aspects, the polypeptide comprises an amino acid sequence at least 90% identical to the amino acid sequence of SEQ ID NO: 42. In some aspects, the polypeptide comprises an amino acid sequence at least 95% identical to the amino acid sequence of SEQ ID NO: 42. In some aspects, the polypeptide comprises an amino acid sequence at least 96% identical to the amino acid sequence of SEQ ID NO: 42. In some aspects, the polypeptide comprises an amino acid sequence at least 97% identical to the amino acid sequence of SEQ ID NO: 42. In some aspects, the polypeptide comprises an amino acid sequence at least 98% identical to the amino acid sequence of SEQ ID NO: 42. In some aspects, the polypeptide comprises an amino acid sequence at least 99% identical to the amino acid sequence of SEQ ID NO: 42.

In some aspects, the polypeptide comprises an amino acid sequence at least 85% identical to the amino acid sequence of SEQ ID NO: 56. In some aspects, the polypeptide comprises an amino acid sequence at least 90% identical to the amino acid sequence of SEQ ID NO: 56. In some sequence of SEQ ID NO: 56. In some aspects, the polypeptide comprises an amino acid sequence at least 96% identical to the amino acid sequence of SEQ ID NO: 56. In some aspects, the polypeptide comprises an amino acid sequence at least 97% identical to the amino acid sequence of SEQ ID NO: 56. In some aspects, the polypeptide comprises an amino acid sequence at least 98% identical to the amino acid sequence of SEQ ID NO: 56. In some aspects, the polypeptide comprises an amino acid sequence at least 99% identical to the amino acid sequence of SEQ ID NO: 56.

In some aspects, the polypeptide comprises the amino acid sequence of SEQ ID NO: 13, SEQ ID NO: 27, SEQ ID NO: 41, SEQ ID NO: 55, SEQ ID NO: 14, SEQ ID NO: 28, SEQ ID NO: 42, or SEQ ID NO: 56. In some aspects, the polypeptide comprises the amino acid sequence of SEQ ID NO: 14, SEQ ID NO: 28, SEQ ID NO: 42, or SEQ ID NO: 56. In some aspects, the polypeptide comprises the amino acid sequence of SEQ ID NO: 13. In some aspects, the polypeptide comprises the amino acid sequence of SEQ ID NO: 27. In some aspects, the polypeptide comprises the amino acid sequence of SEQ ID NO: 41. In some aspects, the polypeptide comprises the amino acid sequence of SEQ ID NO: 55. In some aspects, the polypeptide comprises the amino acid sequence of SEQ ID NO: 14. In some aspects, the polypeptide comprises the amino acid sequence of SEQ ID NO: 28. In some aspects, the polypeptide comprises the amino acid sequence of SEQ ID NO: 42. In some aspects, the polypeptide comprises the amino acid sequence of SEQ ID NO: 56.

In some aspects, provided herein is a polypeptide that binds IL31 comprising a Fc region. In some aspects, the polypeptide comprises an IgG1, IgG2, IgG3, or IgG4 Fc region. In some aspects, the Fc region is a human Fc region. In some aspects, the polypeptide comprises a human IgG1, IgG2, IgG3, or IgG4 Fc region. In some aspects, the polypeptide comprises an Fc region with a modified effector function. In some aspects, the polypeptide comprises an effector null Fc region. In some aspects, the Fc region comprises a full or partial hinge region. In some aspects, the Fc region comprises a full or partial hinge, no CH1 region, a full or partial CH2 region, and a full or partial CH3 region. In some aspects, the Fc region comprises a full hinge region, no CH1 region, full CH2 region and full CH3 region. In some aspects, the full or partial hinge region comprises a cysteine (C) to serine(S) mutation at position 220 according to EU numbering (C220S). In some aspects, the Fc region includes one or more of the following CH2 region mutations: L234A, L235A, M252Y, S254T, and T256E as determined by EU numbering. In some aspects, the Fc region includes one or more of the following CH3 mutations: M428L and N434S as determined by EU numbering. In some aspects, the Fc region comprises one or more of the following mutations or substitutions (EU numbering): C220S, L234A, L235A, M252Y, S254T, T256E, M428L, N434S or any combination thereof. In some aspects, the Fc region comprises the amino acid sequence of SEQ ID NO:62 or the amino acid residues 1-231 of SEQ ID NO:62. In some aspects, the Fc region comprises the amino acid sequence of SEQ ID NO:90 or the amino acid residues 1-231 of SEQ ID NO:90.

In some aspects, the polypeptide provided herein comprises a linker as described herein and an Fc region. In some aspects, the linker is an amino acid linker. In some aspects, the amino acid linker connects two or more antibody variable domains together. In some aspects, the VHH1 is connected to the VHH2 by a linker. In some aspects, the Fc region is connected to the C-terminus of the VHH2. In some aspects, the polypeptide has the structure: [first IL31 binder]-linker-[second IL31 binder]-Fc region. In some aspects, the first and second IL31 binding moieties are the same. In some aspects, the first and second IL31 binding moieties are different. In some aspects, the polypeptide has the structure: [VHH1]-linker-[VHH2]-Fc region. In some aspects, VHH1 and VHH2 are the same. In some aspects, VHH1 and VHH2 are different.

In some aspects, a polypeptide of the present disclosure binds to an antigen comprising at least two binding moieties that comprise VHH1, VHH2, and a linker, wherein the polypeptide has the structure: [VHH1]-linker-[VHH2], wherein the linker comprises an amino acid sequence comprising (X)n-G, and the VHH2 comprises at the N-terminus Xa, Xb, and Xc, wherein X is an amino acid, G is glycine, n is any integer between 0 and 100, Xa is E (Glutamic acid), Q (Glutamine), or missing, Xb is V (Valine) or missing, and Xc is Q (Glutamine), K (Lysine), or missing is provided herein. In some aspects, VHH1 is any VHH disclosed herein, and VHH2 is any VHH disclosed herein.

In some aspects, a polypeptide of the present disclosure comprises at least two binding moieties that comprise VHH1, VHH2, and a linker, wherein the polypeptide has the structure: [VHH1]-linker-[VHH2], wherein VHH1 comprises (a) a CDR1 comprising the amino acid sequence of SEQ ID NO: 5, a CDR2 comprising the amino acid sequence of SEQ ID NO: 6, and a CDR3 comprising the amino acid sequence of SEQ ID NO: 7; (b) a CDR1 comprising the amino acid sequence of SEQ ID NO: 19, a CDR2 comprising the amino acid sequence of SEQ ID NO: 20, and a CDR3 comprising the amino acid sequence of SEQ ID NO: 21; (c) a CDR1 comprising the amino acid sequence of SEQ ID NO: 33, a CDR2 comprising the amino acid sequence of SEQ ID NO: 34, and a CDR3 comprising the amino acid sequence of SEQ ID NO: 35; (d) a CDR1 comprising the amino acid sequence of SEQ ID NO: 47, a CDR2 comprising the amino acid sequence of SEQ ID NO: 48, and a CDR3 comprising the amino acid sequence of SEQ ID NO: 49; (e) a CDR1 comprising the amino acid sequence of SEQ ID NO: 78, a CDR2 comprising the amino acid sequence of SEQ ID NO: 79, and a CDR3 comprising the amino acid sequence of SEQ ID NO: 80; or (f) a CDR1 comprising the amino acid sequence of SEQ ID NO: 81, a CDR2 comprising the amino acid sequence of SEQ ID NO: 82, and a CDR3 comprising the amino acid sequence of SEQ ID NO: 83.

In some aspects, a polypeptide of the present disclosure comprises at least two binding moieties that comprise VHH1, VHH2, and a linker, wherein the polypeptide has the structure: [VHH1]-linker-[VHH2], wherein VHH2 comprises (a) a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12; (b) a CDR1 comprising the amino acid sequence of SEQ ID NO: 24, a CDR2 comprising the amino acid sequence of SEQ ID NO:25, and a CDR3 comprising the amino acid sequence of SEQ ID NO: 26; (c) a CDR1 comprising the amino acid sequence of SEQ ID NO: 38, a CDR2 comprising the amino acid sequence of SEQ ID NO: 39, and a CDR3 comprising the amino acid sequence of SEQ ID NO: 40; (d) a CDR1 comprising the amino acid sequence of SEQ ID NO: 52, a CDR2 comprising the amino acid sequence of SEQ ID NO: 53, and a CDR3 comprising the amino acid sequence of SEQ ID NO: 54; (e) a CDR1 comprising the amino acid sequence of SEQ ID NO: 84, a CDR2 comprising the amino acid sequence of SEQ ID NO: 85, and a CDR3 comprising the amino acid sequence of SEQ ID NO: 86; or (f) a CDR1 comprising the amino acid sequence of SEQ ID NO: 87, a CDR2 comprising the amino acid sequence of SEQ ID NO: 88, and a CDR3 comprising the amino acid sequence of SEQ ID NO: 89.

In some aspects, the polypeptide of the present disclosure further comprises an Fc region. In some aspects, the linker (X) useful for the present disclosure comprises (GS)n, (G2S)n, (G3S)n, (G4S)n, (G5S)n, or any combination thereof, and n is an integer between 1 and 10. In some aspects, the linker (X) comprises (G4S)n, and n is 4, 5, or 6. In some aspects, the linker comprises the amino acid sequence of SEQ ID NO: 104 or SEQ ID NO: 188.

In some aspects, the polypeptide of the present disclosure comprises an IgG1, IgG2, IgG3, or IgG4 Fc region. In some aspects, the polypeptide of the present disclosure comprises a human Fc region. In some aspects, the Fc region comprises one or more substitutions, deletions, insertions, or any combination thereof. In some aspects, the one or more substitutions comprise C220S, M252Y, S254T, T256E, L234A, L235A, M428L, N434S, or any combination thereof, according to the EU numbering system. In some aspects, the C terminus of the Fc region is Lysine. In some aspects, the C terminus of the Fc region is not Lysine, e.g., the C-terminal lysine has been enzymatically removed.

In some aspects, the polypeptide that specifically binds to IL31 by a first binder and a second binder further comprises a binder that binds to a protein, but does not bind to IL31 ("third binder"). In some aspects, the third binder comprises a VHH (VHH3). In some aspects, the polypeptide that specifically binds to IL31 by a first binder and a second binder and that binds to a protein that is not IL31 by a third binder further comprises a binder that binds to the same protein as the third binder or a different protein from the third binder ("fourth binder"). In some aspects, the fourth binder comprises a VHH (VHH4). In some aspects, the VHH3 and the VHH4 are different. In some aspects, the VHH3 and the VHH4 are the same. In some aspects, VHH3 and VHH4 binders bind to the same target antigen. In some aspects, VHH3 and VHH4 binders bind to the same target antigen at the same epitope. In some aspects, VHH3 and VHH4 binders bind to the same target antigen at nonoverlapping epitopes allowing each of VHH3 and VHH4 to simultaneously bind the target antigen. In some aspects, VHH3 and VHH4 binders have the following structure: [VHH3]-linker-[VHH4]. In some aspects, the polypeptide has the following structure: [VHH1]-linker-[VHH2]-linker-[VHH3]-linker-[VHH4]. In some aspects, the polypeptide has the following structure: [VHH1]-linker-[VHH2]-linker-[VHH3]-linker-[VHH4]-Fc region or [VHH1]-linker-[VHH2]-linker-[VHH3]-linker-[VHH4]-linker-Fc region ("Tandem Format"). In other aspects, the polypeptide has the following structure: [VHH1]-linker-[VHH2]-Fc region-

[VHH3]-linker-[VHH4] or [VHH1]-linker-[VHH2]-Fc region-linker-[VHH3]-linker-[VHH4] ("Morrison Format").

In some aspects, the polypeptide is a multimeric polypeptide, such as a bispecific, trispecific or tetraspecific polypeptide. The multimeric polypeptide may further include an Fc region or portion thereof. A bispecific polypeptide, for example, can comprise two co-binders, wherein each co-binder comprises two biparatopic single binders, joined together by peptide linker, such as Tandem Format or Morrison Format. One co-binder (VHH1-linker-VHH2) is capable of specifically and simultaneously binding to IL-31, e.g., VHH1 and VHH2 specifically bind IL-31 at nonoverlapping epitopes, whereas the other co-binder (VHH3-linker-VHH4) is capable of specifically and simultaneously binding to a target antigen that is not IL-31. The non-IL31 antigen specifically targeted by the second or other co-binder may include, for example, IL31RA, IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-β7, α4-Intergrin, IL1, IL1α, IL1β, IL1RA, IL1R1, IL1RL1, IL1RL2, IL1RAcP, IL1R2, IL2, IL2R, IL2RB, IL2RY, IL3, IL3Rα, CSF2RB, IL5, IL5Rα, IL7, IL7R, IL7Rα, IL7α, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKCε, PKCδ, STAT3, Paxillin, IL33, IL34, CSF-IR, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, and CXCR2.

In one aspect, the bispecific polypeptide that binds IL31 and a target antigen comprises a first polypeptide that specifically binds IL31 comprising a first binder and a second binder, and a second polypeptide that specifically binds target antigen comprising a third binder and a fourth binder, wherein the first binder comprises a VHH1 comprising a CDR1 comprising an amino acid sequence of SEQ ID NO:5, a CDR2 comprising an amino acid sequence of SEQ ID NO:6, and a CDR3 comprising an amino acid sequence of SEQ ID NO:7; and the second binder comprises a VHH2 comprising a CDR1 comprising an amino acid sequence of SEQ ID NO:10, a CDR2 comprising an amino acid sequence of SEQ ID NO:11, and a CDR3 comprising an amino acid sequence of SEQ ID NO:12; wherein the first binder and second binder are joined by a peptide linker; wherein the third binder comprises a VHH3 and the fourth binder comprises a VHH4, wherein the first polypeptide and second polypeptide are joined by a peptide linker and/or Fc region, and wherein the target antigen is IL31RA, IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-β7, α4-Intergrin, IL1, IL1α, IL1β, IL1RA, IL1R1, IL1RL1, IL1RL2, IL1RAcP, IL1R2, IL2, IL2R, IL2Rβ, IL2Rγ, IL3, IL3Rα, CSF2RB, IL5, IL5Rα, IL7, IL7R, IL7Rα, IL7α, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKCε, PKCδ, STAT3, Paxillin, IL33, IL34, CSF-1R, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, or CXCR2.

In one aspect, the bispecific polypeptide that binds IL31 and a target antigen comprises a first polypeptide that specifically binds IL31 comprising a first binder and a second binder, and a second polypeptide that specifically binds target antigen comprising a third binder and a fourth binder, wherein the first binder comprises a VHH1 comprising a CDR1 comprising an amino acid sequence of SEQ ID NO:5 or SEQ ID NO:59, a CDR2 comprising an amino acid sequence of SEQ ID NO: 6, SEQ ID NO:60 or SEQ ID NO:63, and a CDR3 comprising an amino acid sequence of SEQ ID NO:7, SEQ ID NO:61 or SEQ ID NO:64; and the second binder comprises a VHH2 comprising a CDR1 comprising an amino acid sequence of SEQ ID NO: 10 or SEQ ID NO:251, a CDR2 comprising an amino acid sequence of SEQ ID NO:11 or SEQ ID NO:252, and a CDR3 comprising an amino acid sequence of SEQ ID NO: 12 or SEQ ID NO:253; wherein the first binder and second binder are joined by a peptide linker; wherein the third binder comprises a VHH3, and the fourth binder comprises a VHH4, wherein the first polypeptide and second polypeptide are joined by a peptide linker and/or Fc region, and wherein the target antigen is IL31RA, IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-β7, α4-Intergrin, IL1, IL1α, IL1β, IL1RA, IL1R1, IL1RL1, IL1RL2, IL1RAcP, IL1R2, IL2, IL2R, IL2Rβ, IL2Rγ, IL3, IL3Rα, CSF2RB, IL5, IL5Rα, IL7, IL7R, IL7Rα, IL7α, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKCε, PKCδ, STAT3, Paxillin, IL33, IL34, CSF-1R, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, or CXCR2.

In one aspect, the bispecific polypeptide that binds IL31 and a target antigen comprises a first polypeptide that specifically binds IL31 comprising a first binder and a second binder, and a second polypeptide that specifically binds target antigen comprising a third binder and a fourth binder, wherein the first binder comprises a VHH1 comprising a CDR1 comprising an amino acid sequence of SEQ ID NO:5, a CDR2 comprising an amino acid sequence of SEQ ID NO:6, and a CDR3 comprising an amino acid sequence of SEQ ID NO:7; and the second binder comprises a VHH2 comprising a CDR1 comprising an amino acid sequence of SEQ ID NO:10, a CDR2 comprising an amino acid sequence of SEQ ID NO:11, and a CDR3 comprising an amino acid sequence of SEQ ID NO:12; wherein the first binder and second binder are joined by a peptide linker; wherein the third binder comprises a VHH3 and the fourth binder comprises a VHH4, wherein the first polypeptide and second polypeptide are joined by a peptide linker and/or Fc region, and wherein the target antigen is IL-13.

In one aspect, the bispecific polypeptide that binds IL31 and a target antigen comprises a first polypeptide that specifically binds IL31 comprising a first binder and a second binder, and a second polypeptide that specifically binds target antigen comprising a third binder and a fourth binder, wherein the first binder comprises a VHH1 comprising a CDR1 comprising an amino acid sequence of SEQ ID NO:5 or SEQ ID NO:59, a CDR2 comprising an amino acid sequence of SEQ ID NO: 6, SEQ ID NO:60 or SEQ ID NO:63, and a CDR3 comprising an amino acid sequence of SEQ ID NO:7, SEQ ID NO:61 or SEQ ID NO:64; and the second binder comprises a VHH2 comprising a CDR1 comprising an amino acid sequence of SEQ ID NO:10 or SEQ ID NO:251, a CDR2 comprising an amino acid sequence of SEQ ID NO:11 or SEQ ID NO:252, and a CDR3 comprising an amino acid sequence of SEQ ID NO: 12 or SEQ ID NO:253; wherein the first binder and second binder are joined by a peptide linker; wherein the third binder comprises a VHH3 and the fourth binder comprises a VHH4, wherein the first polypeptide and second polypeptide are joined by a peptide linker and/or Fc region, and wherein the target antigen is IL-13.

In one aspect, the bispecific polypeptide that binds IL31 and a target antigen comprises a first polypeptide that specifically binds IL31 comprising a first binder and a second binder, and a second polypeptide that specifically binds target antigen comprising a third binder and a fourth binder, wherein the first binder comprises a VHH1 comprising a CDR1 comprising an amino acid sequence of SEQ ID NO:47, a CDR2 comprising an amino acid sequence of SEQ ID NO:48, and a CDR3 comprising an amino acid sequence of SEQ ID NO:49; and the second binder comprises a VHH2 comprising a CDR1 comprising an amino acid sequence of SEQ ID NO:52, a CDR2 comprising an amino acid sequence of SEQ ID NO:53, and a CDR3 comprising an amino acid sequence of SEQ ID NO:54; wherein the first binder and second binder are joined by a peptide linker; wherein the third binder comprises a VHH3 and the fourth binder comprises a VHH4, wherein the first polypeptide and second polypeptide are joined by a peptide linker and/or Fc region, and wherein the target antigen is IL31RA, IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-7, α4-Intergrin, IL1, IL1α, IL1β, IL1RA, IL1R1, IL1RL1, IL1RL2, IL1RAcP, IL1R2, IL2, IL2R, IL2Rβ, IL2Rγ, IL3, IL3Rα, CSF2RB, IL5, IL5Rα, IL7, IL7R, IL7Rα, IL7α, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKCε, PKCδ, STAT3, Paxillin, IL33, IL34, CSF-1R, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, or CXCR2.

In one aspect, the bispecific polypeptide that binds IL31 and a target antigen comprises a first polypeptide that specifically binds IL31 comprising a first binder and a second binder, and a second polypeptide that specifically binds target antigen comprising a third binder and a fourth binder, wherein the first binder comprises a VHH1 comprising a CDR1 comprising an amino acid sequence of SEQ ID NO:47 or SEQ ID NO:59, a CDR2 comprising an amino acid sequence of SEQ ID NO:48, SEQ ID NO:60 or SEQ ID NO:63, and a CDR3 comprising an amino acid sequence of SEQ ID NO:49, SEQ ID NO:61 or SEQ ID NO:64; and the second binder comprises a VHH2 comprising a CDR1 comprising an amino acid sequence of SEQ ID NO:52, a CDR2 comprising an amino acid sequence of SEQ ID NO:53, and a CDR3 comprising an amino acid sequence of SEQ ID NO:54; wherein the first binder and second binder are joined by a peptide linker; wherein the third binder comprises a VHH3 and the fourth binder comprises a VHH4, wherein the first polypeptide and second polypeptide are joined by a peptide linker and/or Fc region, and wherein the target antigen is IL31RA, IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-β7, α4-Intergrin, IL1, IL1α, IL1β, IL1RA, IL1R1, IL1RL1, IL1RL2, IL1RAcP, IL1R2, IL2, IL2R, IL2Rβ, IL2Rγ, IL3, IL3Rα, CSF2RB, IL5, IL5Rα, IL7, IL7R, IL7Rα, IL7α, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKCε, PKCδ, STAT3, Paxillin, IL33, IL34, CSF-1R, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, or CXCR2.

In one aspect, the bispecific polypeptide that binds IL31 and a target antigen comprises a first polypeptide that specifically binds IL31 comprising a first binder and a second binder, and a second polypeptide that specifically binds target antigen comprising a third binder and a fourth binder, wherein the first binder comprises a VHH1 comprising a CDR1 comprising an amino acid sequence of SEQ ID NO:47, a CDR2 comprising an amino acid sequence of SEQ ID NO:48, and a CDR3 comprising an amino acid sequence of SEQ ID NO:49; and the second binder comprises a VHH2 comprising a CDR1 comprising an amino acid sequence of SEQ ID NO:52, a CDR2 comprising an amino acid sequence of SEQ ID NO:53, and a CDR3 comprising an amino acid sequence of SEQ ID NO:54; wherein the first binder and second binder are joined by a peptide linker; wherein the third binder comprises a VHH3 and the fourth binder comprises a VHH4, wherein the first polypeptide and second polypeptide are joined by a peptide linker and/or Fc region, and wherein the target antigen is IL-13.

In one aspect, the bispecific polypeptide that binds IL31 and a target antigen comprises a first polypeptide that specifically binds IL31 comprising a first binder and a second binder, and a second polypeptide that specifically binds target antigen comprising a third binder and a fourth binder, wherein the first binder comprises a VHH1 comprising a CDR1 comprising an amino acid sequence of SEQ ID NO:47 or SEQ ID NO:59, a CDR2 comprising an amino acid sequence of SEQ ID NO:48, SEQ ID NO:60 or SEQ ID NO:63, and a CDR3 comprising an amino acid sequence of SEQ ID NO:49, SEQ ID NO:61 or SEQ ID NO:64; and the second binder comprises a VHH2 comprising a CDR1 comprising an amino acid sequence of SEQ ID NO:52, a CDR2 comprising an amino acid sequence of SEQ ID NO:53, and a CDR3 comprising an amino acid sequence of SEQ ID NO:54; wherein the first binder and second binder are joined by a peptide linker; wherein the third binder comprises a VHH3 and the fourth binder comprises a VHH4, wherein the first polypeptide and second polypeptide are joined by a peptide linker and/or Fc region, and wherein the target antigen is IL-13.

In one aspect, the multimeric polypeptide is a trispecific polypeptide. The trispecific polypeptide may further include an Fc region or portion thereof. A trispecific polypeptide, for example, can comprise three co-binders, wherein each co-binder comprises two biparatopic single binders joined together by peptide linker, such as Tandem Format, e.g., three co-binders joined by peptide linkers, which may include an Fc region N- or C-terminal to the three co-binders, or Morrison Format, e.g., 1stCoBinder-Linker-2ndCoBinder-Fc-3$^{rd}$Cobinder; 1stCoBinder-Linker-2ndCoBinder-Fc-Linker-3$^{rd}$Cobinder; 1$^{st}$CoBinder-Fc-Linker-2$^{nd}$Cobinder-Linker-3$^{rd}$Cobinder, 1$^{st}$CoBinder-Fc-2$^{nd}$Cobinder-Linker-3$^{rd}$Cobinder. Both binding moieties, e.g., VHHs, of one of the three co-binders will specifically target IL31, while the other two co-binders will target an antigen that is not IL31, and is selected from the group of IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-β7, α4-Intergrin, IL1, IL1α, IL1β, IL1RA, IL1R1, IL1RL1, IL1RL2, IL1RAcP, IL1R2, IL2, IL2R, IL2Rβ, IL2Rγ, IL3, IL3Rα, CSF2RB, IL5, IL5Rα, IL7, IL7R, IL7Rα, IL7a, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKCε, PKCδ, STAT3, Paxillin, IL33, IL34, CSF-1R, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, and CXCR2.

In one aspect, the trispecific polypeptide that binds IL31, a first target antigen, and a second target antigen comprises a first polypeptide that specifically binds IL31 comprising a first binder and a second binder, a second polypeptide that specifically binds the first target antigen comprising a third binder and a fourth binder, and a third polypeptide that specifically binds the second target antigen comprising a fifth binder and a sixth binder, wherein the first binder comprises a VHH1 comprising a CDR1 comprising an amino acid sequence of SEQ ID NO:5 or SEQ ID NO:59, a CDR2 comprising an amino acid sequence of SEQ ID NO:6, SEQ ID NO:60 or SEQ ID NO:63, and a CDR3 comprising an amino acid sequence of SEQ ID NO:7, SEQ ID NO:61 or SEQ ID NO:64, and the second binder comprises a VHH2 comprising a CDR1 comprising an amino acid sequence of SEQ ID NO:10 or SEQ ID NO:251, a CDR2 comprising an amino acid sequence of SEQ ID NO:11 or SEQ ID NO:252, and a CDR3 comprising an amino acid sequence of SEQ ID NO: 12 or SEQ ID NO:253; wherein the first binder and second binder are joined by a peptide linker; wherein the third binder comprises a VHH3, and the fourth binder comprises a VHH4, wherein the third binder and fourth binder are joined by a peptide linker; wherein the fifth binder comprises a VHH5, and the sixth binder comprises a VHH6, wherein the fifth binder and sixth binder are joined by a peptide linker; wherein the first polypeptide, second polypeptide and third polypeptide are joined by a peptide linker and/or Fc region, and wherein the first target antigen and/or second target antigen is IL31RA, IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-β7, α4-Intergrin, IL1, IL1α, IL1β, IL1RA, IL1R1, IL1RL1, IL1RL2, IL1RAcP, IL1R2, IL2, IL2R, IL2Rβ, IL2Rγ, IL3, IL3Rα, CSF2RB, IL5, IL5Rα, IL7, IL7R, IL7Rα, IL7α, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKCε, PKCδ, STAT3, Paxillin, IL33, IL34, CSF-1R, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, or CXCR2.

In one aspect, the trispecific polypeptide that binds IL31, a first target antigen, and a second target antigen comprises a first polypeptide that specifically binds IL31 comprising a first binder and a second binder, a second polypeptide that specifically binds the first target antigen comprising a third binder and a fourth binder, and a third polypeptide that specifically binds the second target antigen comprising a fifth binder and a sixth binder, wherein the first binder comprises a VHH1 comprising a CDR1 comprising an amino acid sequence of SEQ ID NO:5, a CDR2 comprising an amino acid sequence of SEQ ID NO:6, and a CDR3 comprising an amino acid sequence of SEQ ID NO:7, and the second binder comprises a VHH2 comprising a CDR1 comprising an amino acid sequence of SEQ ID NO: 10, a CDR2 comprising an amino acid sequence of SEQ ID NO:11, and a CDR3 comprising an amino acid sequence of SEQ ID NO: 12; wherein the first binder and second binder are joined by a peptide linker; wherein the third binder comprises a VHH3, and the fourth binder comprises a VHH4, wherein the third binder and fourth binder are joined by a peptide linker; wherein the fifth binder comprises a VHH5, and the sixth binder comprises a VHH6, wherein the fifth binder and sixth binder are joined by a peptide linker; wherein the first polypeptide, second polypeptide and third polypeptide are joined by a peptide linker and/or Fc region; wherein the first target antigen and/or second target antigen is IL31RA, IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-β7, α4-Intergrin, IL1, IL1α, IL1β, IL1RA, IL1R1, IL1RL1, IL1RL2, IL1RAcP, IL1R2, IL2, IL2R, IL2Rβ, IL2RY, IL3, IL3Rα, CSF2RB, IL5, IL5Rα, IL7, IL7R, IL7Rα, IL7α, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKCε, PKCδ, STAT3, Paxillin, IL33, IL34, CSF-1R, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, or CXCR2.

In one aspect, the trispecific polypeptide that binds IL31, a first target antigen, and a second target antigen comprises a first polypeptide that specifically binds IL31 comprising a first binder and a second binder, a second polypeptide that specifically binds the first target antigen comprising a third binder and a fourth binder, and a third polypeptide that specifically binds the second target antigen comprising a fifth binder and a sixth binder, wherein the first binder comprises a VHH1 comprising a CDR1 comprising an amino acid sequence of SEQ ID NO:5 or SEQ ID NO:59, a CDR2 comprising an amino acid sequence of SEQ ID NO:6, SEQ ID NO:60 or SEQ ID NO:63, and a CDR3 comprising an amino acid sequence of SEQ ID NO:7, SEQ ID NO:61 or SEQ ID NO:64, and the second binder comprises a VHH2 comprising a CDR1 comprising an amino acid sequence of SEQ ID NO:10 or SEQ ID NO:251, a CDR2 comprising an amino acid sequence of SEQ ID NO:11 or SEQ ID NO:252, and a CDR3 comprising an amino acid sequence of SEQ ID NO: 12 or SEQ ID NO:253; wherein the first binder and second binder are joined by a peptide linker; wherein the third binder comprises a VHH3, and the fourth binder comprises a VHH4, wherein the third binder and fourth binder are joined by a peptide linker; wherein the fifth binder comprises a VHH5, and the sixth binder comprises a VHH6, wherein the fifth binder and sixth binder are joined by a peptide linker; wherein the first polypeptide, second polypeptide and third polypeptide are joined by a peptide linker and/or Fc region; wherein the first target antigen is IL-13; and wherein second target antigen is IL31RA, IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-β7, α4-Intergrin, IL1, IL1α, IL1β, IL1RA, IL1R1, IL1RL1, IL1RL2, IL1RAcP, IL1R2, IL2, IL2R, IL2Rβ, IL2Rγ, IL3, IL3Rα, CSF2RB, IL5, IL5Rα, IL7, IL7R, IL7Rα, IL7a, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKCε, PKCδ, STAT3, Paxillin, IL33, IL34, CSF-1R, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, or CXCR2.

In one aspect, the trispecific polypeptide that binds IL31, a first target antigen, and a second target antigen comprises a first polypeptide that specifically binds IL31 comprising a first binder and a second binder, a second polypeptide that specifically binds the first target antigen comprising a third binder and a fourth binder, and a third polypeptide that specifically binds the second target antigen comprising a fifth binder and a sixth binder, wherein the first binder comprises a VHH1 comprising a CDR1 comprising an amino acid sequence of SEQ ID NO:5, a CDR2 comprising an amino acid sequence of SEQ ID NO:6, and a CDR3 comprising an amino acid sequence of SEQ ID NO:7, and the second binder comprises a VHH2 comprising a CDR1 comprising an amino acid sequence of SEQ ID NO: 10, a CDR2 comprising an amino acid sequence of SEQ ID NO:11, and a CDR3 comprising an amino acid sequence of SEQ ID NO: 12; wherein the first binder and second binder are joined by a peptide linker; wherein the third binder comprises a VHH3, and the fourth binder comprises a VHH4, wherein the third binder and fourth binder are joined by a peptide linker; wherein the fifth binder comprises a VHH5, and the sixth binder comprises a VHH6, wherein the fifth binder and sixth binder are joined by a peptide linker; wherein the first polypeptide, second polypeptide and third polypeptide are joined by a peptide linker and/or Fc region; wherein the first target antigen is IL13; and wherein the second target antigen is IL31RA, IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-β7, α4-Intergrin, IL1, IL1α, IL1β, IL1RA, IL1R1, IL1RL1, IL1RL2, IL1RAcP, IL1R2, IL2, IL2R, IL2Rβ, IL2Rγ, IL3, IL3Rα, CSF2RB, IL5, IL5Rα, IL7, IL7R, IL7Rα, IL7α, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKCε, PKCδ, STAT3, Paxillin, IL33, IL34, CSF-1R, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, or CXCR2.

In one aspect, the trispecific polypeptide that binds IL31, a first target antigen, and a second target antigen comprises a first polypeptide that specifically binds IL31 comprising a first binder and a second binder, a second polypeptide that specifically binds the first target antigen comprising a third binder and a fourth binder, and a third polypeptide that specifically binds the second target antigen comprising a fifth binder and a sixth binder, wherein the first binder comprises a VHH1 comprising a CDR1 comprising an amino acid sequence of SEQ ID NO:47 or SEQ ID NO:59, a CDR2 comprising an amino acid sequence of SEQ ID NO:48, SEQ ID NO:60 or SEQ ID NO:63, and a CDR3 comprising an amino acid sequence of SEQ ID NO:49, SEQ ID NO: 61 or SEQ ID NO:64, and the second binder comprises a VHH2 comprising a CDR1 comprising an amino acid sequence of SEQ ID NO:52, a CDR2 comprising an amino acid sequence of SEQ ID NO:53, and a CDR3 comprising an amino acid sequence of SEQ ID NO:54; wherein the first binder and second binder are joined by a peptide linker; wherein the third binder comprises a VHH3, and the fourth binder comprises a VHH4, wherein the third binder and fourth binder are joined by a peptide linker; wherein the fifth binder comprises a VHH5, and the sixth binder comprises a VHH6, wherein the fifth binder and sixth binder are joined by a peptide linker; wherein the first polypeptide, second polypeptide and third polypeptide are joined by a peptide linker and/or Fc region, and wherein the first target antigen and/or second target antigen is IL31RA, IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-β7, α4-Intergrin, IL1, IL1α, IL1β, IL1RA, IL1R1, IL1RL1, IL1RL2, IL1RAcP, IL1R2, IL2, IL2R, IL2Rβ, IL2Rγ, IL3, IL3Rα, CSF2RB, IL5, IL5Rα, IL7, IL7R, IL7Rα, IL7α, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKCε, PKCδ, STAT3, Paxillin, IL33, IL34, CSF-IR, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, or CXCR2.

In one aspect, the trispecific polypeptide that binds IL31, a first target antigen, and a second target antigen comprises a first polypeptide that specifically binds IL31 comprising a first binder and a second binder, a second polypeptide that specifically binds the first target antigen comprising a third binder and a fourth binder, and a third polypeptide that specifically binds the second target antigen comprising a fifth binder and a sixth binder, wherein the first binder comprises a VHH1 comprising a CDR1 comprising an amino acid sequence of SEQ ID NO:47, a CDR2 comprising an amino acid sequence of SEQ ID NO:48, and a CDR3 comprising an amino acid sequence of SEQ ID NO:49, and the second binder comprises a VHH2 comprising a CDR1 comprising an amino acid sequence of SEQ ID NO:52, a CDR2 comprising an amino acid sequence of SEQ ID NO:53, and a CDR3 comprising an amino acid sequence of SEQ ID NO:54; wherein the first binder and second binder are joined by a peptide linker; wherein the third binder comprises a VHH3, and the fourth binder comprises a VHH4, wherein the third binder and fourth binder are joined by a peptide linker; wherein the fifth binder comprises a VHH5, and the sixth binder comprises a VHH6, wherein the fifth binder and sixth binder are joined by a peptide linker; wherein the first polypeptide, second polypeptide and third polypeptide are joined by a peptide linker and/or Fc region, and wherein the first target antigen and/or second target antigen is IL31RA, IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-β7, α4-Intergrin, IL1, IL1α, IL1β, IL1RA, IL1R1, IL1RL1, IL1RL2, IL1RAcP, IL1R2, IL2, IL2R, IL2Rβ, IL2Rγ, IL3, IL3Rα, CSF2RB, IL5, IL5Rα, IL7, IL7R, IL7Rα, IL7α, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKCε, PKCδ, STAT3, Paxillin, IL33, IL34, CSF-1R, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, or CXCR2.

In one aspect, the trispecific polypeptide that binds IL31, a first target antigen, and a second target antigen comprises a first polypeptide that specifically binds IL31 comprising a first binder and a second binder, a second polypeptide that specifically binds the first target antigen comprising a third binder and a fourth binder, and a third polypeptide that specifically binds the second target antigen comprising a fifth binder and a sixth binder, wherein the first binder comprises a VHH1 comprising a CDR1 comprising an amino acid sequence of SEQ ID NO:47 or SEQ ID NO:59, a CDR2 comprising an amino acid sequence of SEQ ID NO:48, SEQ ID NO:60 or SEQ ID NO:63, and a CDR3 comprising an amino acid sequence of SEQ ID NO:49, SEQ ID NO: 61 or SEQ ID NO:64, and the second binder comprises a VHH2 comprising a CDR1 comprising an amino acid sequence of SEQ ID NO:52, a CDR2 comprising an amino acid sequence of SEQ ID NO:53, and a CDR3 comprising an amino acid sequence of SEQ ID NO:54; wherein the first binder and second binder are joined by a peptide linker; wherein the third binder comprises a VHH3, and the fourth binder comprises a VHH4, wherein the third binder and fourth binder are joined by a peptide linker; wherein the fifth binder comprises a VHH5, and the sixth binder comprises a VHH6, wherein the fifth binder and sixth binder are joined by a peptide linker; wherein the first polypeptide, second polypeptide and third polypeptide are joined by a peptide linker and/or Fc region, wherein the first target antigen is IL13, and wherein the second target antigen is IL31RA, IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-β7, α4-Intergrin, IL1, IL1α, IL1β, IL1RA, IL1R1, IL1RL1, IL1RL2, IL1RAcP, IL1R2, IL2, IL2R, IL2Rβ, IL2Rγ, IL3, IL3Rα, CSF2RB, IL5, IL5Rα, IL7, IL7R, IL7Rα, IL7α, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKCε, PKCδ, STAT3, Paxillin, IL33, IL34, CSF-IR, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, or CXCR2.

In one aspect, the trispecific polypeptide that binds IL31, a first target antigen, and a second target antigen comprises a first polypeptide that specifically binds IL31 comprising a first binder and a second binder, a second polypeptide that specifically binds the first target antigen comprising a third binder and a fourth binder, and a third polypeptide that specifically binds the second target antigen comprising a fifth binder and a sixth binder, wherein the first binder comprises a VHH1 comprising a CDR1 comprising an amino acid sequence of SEQ ID NO:47, a CDR2 comprising an amino acid sequence of SEQ ID NO:48, and a CDR3 comprising an amino acid sequence of SEQ ID NO:49, and the second binder comprises a VHH2 comprising a CDR1 comprising an amino acid sequence of SEQ ID NO:52, a CDR2 comprising an amino acid sequence of SEQ ID NO:53, and a CDR3 comprising an amino acid sequence of SEQ ID NO:54; wherein the first binder and second binder are joined by a peptide linker; wherein the third binder comprises a VHH3, and the fourth binder comprises a VHH4, wherein the third binder and fourth binder are joined by a peptide linker; wherein the fifth binder comprises a VHH5, and the sixth binder comprises a VHH6, wherein the fifth binder and sixth binder are joined by a peptide linker; wherein the first polypeptide, second polypeptide and third polypeptide are joined by a peptide linker and/or Fc region, wherein the first target antigen is IL13, and wherein the second target antigen is IL31RA, IL-13, IL13Rα1, IL13Rα2, TL1A, IL4, IL4RA, TXLNA, IL13RA, OSMR-beta, Ox40, Ox40L, PD1, PDL1, TSLP, IL-17, IL17A, IL17B, IL17RB, IL17C, IL17RA, IL17RB, IL17RE, IL17D, IL17E, IL17F, IL17RC, IL17A/A, IL-17A/F, IL-17F/F, TNFα, TNF-β, CD20, CD19, CD25, CD103, CD132, IL23, IL23R, IL-23p19, IgE, CD11α, IL6, IL6Rα, gp130, α4-β7, α4-Intergrin, IL1, IL1α, IL1β, IL1RA, IL1R1, IL1RL1, IL1RL2, IL1RAcP, IL1R2, IL2, IL2R, IL2Rβ, IL2Rγ, IL3, IL3Rα, CSF2RB, IL5, IL5Rα, IL7, IL7R, IL7Rα, IL7α, γ-chain, IL8, IL9, IL-9R, IL10, IL10Rα, IL10Rβ, IL11, IL11Rα, IL12, IL12A, IL12B, IL12Rβ1, IL12Rβ2, IL14, IL15, IL15Rα, IL16, IL18, IL18Rα, IL18RAcP, IL18BP, IL19, IL20, IL20Rα, IL20Rβ, IL21, IL21R, IL22, IL22Rα1, IL22Rα2, IL24, IL25, IL25/IL17E, IL26, IL27, IL27Rα, IL28A, IL28B, IL28RA, IL29, IL32, PR3, PKC&, PKCδ, STAT3, Paxillin, IL33, IL34, CSF-IR, IL35, IL36A, IL36B, IL36G, IL36RA, IL37, IL18R1, IL38, EPO, GM-CSF, G-CSF, M-CSF, Eotaxin, IL1β, BlyS, APRIL, BAFF-R, TACI, CKIT, MRGPRX2, Fc epsilon receptor (FcεRI), SIGLEC-6, CD28, CTLA-4, CD80, CD86, SIGLEC-8, TGF-β, CD40L, MCP-1, BASFF, MMPs, Elastase, MIF, Cathepsin G, Cathepsin K, IFN-γ, ROS, NO, RANTES, RANKL, PGE2, ADAMTSs, NGF, BDNF, NPY, MIG, BLC, IP-10, PDGF, CXCR1, or CXCR2.

In some aspects, the polypeptide comprises a Fc region, wherein the Fc region comprises an amino acid sequence at least 85%, at least 90%, at least 95%, at least 96%, at least 97%, at least 98%, or at least 99% identical to the amino acid sequence of SEQ ID NO: 62 or the amino acid residues 1-231 of SEQ ID NO: 62. In some aspects, the polypeptide comprises a Fc region, wherein the Fc region comprises an amino acid sequence at least 85% identical to the amino acid sequence of SEQ ID NO: 62 or the amino acid residues 1-231 of SEQ ID NO: 62. In some aspects, the polypeptide comprises a Fc region, wherein the Fc region comprises an amino acid sequence at least 90% identical to the amino acid sequence of SEQ ID NO: 62 or the amino acid residues 1-231 of SEQ ID NO: 62. In some aspects, the polypeptide comprises a Fc region, wherein the Fc region comprises an amino acid sequence at least 95% identical to the amino acid sequence of SEQ ID NO: 62 or the amino acid residues 1-231 of SEQ ID NO: 62. In some aspects, the polypeptide comprises a Fc region, wherein the Fc region comprises an amino acid sequence at least 96% identical to the amino acid sequence of SEQ ID NO: 62 or the amino acid residues 1-231 of SEQ ID NO: 62. In some aspects, the polypeptide comprises a Fc region, wherein the Fc region comprises an amino acid sequence at least 97% identical to the amino acid sequence of SEQ ID NO: 62 or the amino acid residues 1-231 of SEQ ID NO: 62. In some aspects, the polypeptide comprises a Fc region, wherein the Fc region comprises an amino acid sequence at least 98% identical to the amino acid sequence of SEQ ID NO: 62 or the amino acid residues 1-231 of SEQ ID NO: 62. In some aspects, the polypeptide comprises a Fc region, wherein the Fc region comprises an amino acid sequence at least 99% identical to the amino acid sequence of SEQ ID NO: 62 or the amino acid residues 1-231 of SEQ ID NO: 62.

In some aspects, the Fc region comprises an amino acid sequence at least 85%, at least 90%, at least 95%, at least 96%, at least 97%, at least 98%, or at least 99% identical to the amino acid sequence of SEQ ID NO: 62 or the amino acid residues 1-231 of SEQ ID NO: 62, and wherein residue 5 is serine, residue 37 is tyrosine, residue 39 is threonine, and/or residue 41 is glutamate according to SEQ ID NO: 62 or the amino acid residues 1-231 of SEQ ID NO: 62, or wherein residue 220 is serine, residue 252 is tyrosine, residue 254 is threonine, and/or residue 256 is glutamate according to EU numbering. In some aspects, the Fc region comprises an amino acid sequence at least 85% identical to the amino acid sequence of SEQ ID NO: 62 or the amino acid residues 1-231 of SEQ ID NO: 62, and wherein residue 5 is serine, residue 37 is tyrosine, residue 39 is threonine, and/or residue 41 is glutamate according to SEQ ID NO: 62 or the amino acid residues 1-231 of SEQ ID NO: 62, or wherein residue 220 is serine, residue 252 is tyrosine, residue 254 is threonine, and/or residue 256 is glutamate according to EU numbering. In some aspects, the Fc region comprises an amino acid sequence at least 90% identical to the amino acid sequence of SEQ ID NO: 62 or the amino acid residues 1-231 of SEQ ID NO: 62, and wherein residue 5 is serine, residue 37 is tyrosine, residue 39 is threonine, and/or residue 41 is glutamate according to SEQ ID NO: 62 or the amino acid residues 1-231 of SEQ ID NO: 62, or wherein residue 220 is serine, residue 252 is tyrosine, residue 254 is threonine, and/or residue 256 is glutamate according to EU numbering. In some aspects, the Fc region comprises an amino acid sequence at least 95% identical to the amino acid sequence of SEQ ID NO: 62 or the amino acid residues 1-231 of SEQ ID NO: 62, and wherein residue 5 is serine, residue 37 is tyrosine, residue 39 is threonine, and/or residue 41 is glutamate according to SEQ ID NO: 62 or the amino acid residues 1-231 of SEQ ID NO: 62, or wherein residue 220 is serine, residue 252 is tyrosine, residue 254 is threonine, and/or residue 256 is glutamate according to EU numbering. In some aspects, the Fc region comprises an amino acid sequence at least 96% identical to the amino acid sequence of SEQ ID NO: 62 or the amino acid residues 1-231 of SEQ ID NO: 62, and wherein residue 5 is serine, residue 37 is tyrosine, residue 39 is threonine, and/or residue 41 is glutamate according to SEQ ID NO: 62 or the amino acid residues 1-231 of SEQ ID NO: 62, or wherein residue 220 is serine, residue 252 is tyrosine, residue 254 is threonine, and/or residue 256 is glutamate according to EU numbering. In some aspects, the Fc region comprises an amino acid sequence at least 97% identical to the amino acid sequence of SEQ ID NO: 62 or the amino acid residues 1-231 of SEQ ID NO: 62, and wherein residue 5 is serine, residue 37 is tyrosine, residue 39 is threonine, and/or residue 41 is glutamate according to SEQ ID NO: 62 or the amino acid residues 1-231 of SEQ ID NO: 62, or wherein residue 220 is serine, residue 252 is tyrosine, residue 254 is threonine, and/or residue 256 is glutamate according to EU numbering. In some aspects, the Fc region comprises an amino acid sequence at least 98% identical to the amino acid sequence of SEQ ID NO: 62 or the amino acid residues 1-231 of SEQ ID NO: 62, and wherein residue 5 is serine, residue 37 is tyrosine, residue 39 is threonine, and/or residue 41 is glutamate according to SEQ ID NO: 62 or the amino acid residues 1-231 of SEQ ID NO: 62, or wherein residue 220 is serine, residue 252 is tyrosine, residue 254 is threonine, and/or residue 256 is glutamate according to EU numbering. In some aspects, the Fc region comprises an amino acid sequence at least 99% identical to the amino acid sequence of SEQ ID NO: 62 or the amino acid residues 1-231 of SEQ ID NO: 62, and wherein residue 5 is serine, residue 37 is tyrosine, residue 39 is threonine, and/or residue 41 is glutamate according to SEQ ID NO: 62 or the amino acid residues 1-231 of SEQ ID NO: 62, or wherein residue 220 is serine, residue 252 is tyrosine, residue 254 is threonine, and/or residue 256 is glutamate according to EU numbering. In some aspects, the Fc region comprises the amino acid sequence of SEQ ID NO: 62 or the amino acid residues 1-231 of SEQ ID NO: 62.

In some aspects, the polypeptide that binds IL31 comprises an Fc region comprising the amino acid sequence of SEQ ID NO: 62 or the amino acid residues 1-231 of SEQ ID NO: 62.

In some aspects, the polypeptide comprises a Fc region, wherein the Fc region comprises an amino acid sequence at least 85%, at least 90%, at least 95%, at least 96%, at least 97%, at least 98%, or at least 99% identical to the amino acid sequence of SEQ ID NO: 90 or the amino acid residues 1-231 of SEQ ID NO: 90. In some aspects, the polypeptide comprises a Fc region, wherein the Fc region comprises an amino acid sequence at least 85% identical to the amino acid sequence of SEQ ID NO: 90 or the amino acid residues 1-231 of SEQ ID NO: 90. In some aspects, the polypeptide comprises a Fc region, wherein the Fc region comprises an amino acid sequence at least 90% identical to the amino acid sequence of SEQ ID NO: 90 or the amino acid residues 1-231 of SEQ ID NO: 90. In some aspects, the polypeptide comprises a Fc region, wherein the Fc region comprises an amino acid sequence at least 95% identical to the amino acid sequence of SEQ ID NO: 90 or the amino acid residues 1-231 of SEQ ID NO: 90. In some aspects, the polypeptide comprises a Fc region, wherein the Fc region comprises an amino acid sequence at least 96% identical to the amino acid sequence of SEQ ID NO: 90 or the amino acid residues 1-231 of SEQ ID NO: 90. In some aspects, the polypeptide comprises a Fc region, wherein the Fc region comprises an amino acid sequence at least 97% identical to the amino acid sequence of SEQ ID NO: 90 or the amino acid residues 1-231 of SEQ ID NO: 90. In some aspects, the polypeptide comprises a Fc region, wherein the Fc region comprises an amino acid sequence at least 98% identical to the amino acid sequence of SEQ ID NO: 90 or the amino acid residues 1-231 of SEQ ID NO: 90. In some aspects, the polypeptide comprises a Fc region, wherein the Fc region comprises an amino acid sequence at least 99% identical to the amino acid sequence of SEQ ID NO: 90 or the amino acid residues 1-231 of SEQ ID NO: 90.

In some aspects, the Fc region comprises an amino acid sequence at least 85%, at least 90%, at least 95%, at least 96%, at least 97%, at least 98%, or at least 99% identical to the amino acid sequence of SEQ ID NO: 90 or the amino acid residues 1-231 of SEQ ID NO: 90, and wherein residue 5 is serine, residue 19 is alanine, residue 20 is alanine, residue 37 is tyrosine, residue 39 is threonine, and/or residue 41 is glutamate according to SEQ ID NO: 90 or the amino acid residues 1-231 of SEQ ID NO: 90, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 85% identical to the amino acid sequence of SEQ ID NO: 90 or the amino acid residues 1-231 of SEQ ID NO: 90, and wherein residue 5 is serine, residue 19 is alanine, residue 20 is alanine, residue 37 is tyrosine, residue 39 is threonine, and/or residue 41 is glutamate according to SEQ ID NO: 90 or the amino acid residues 1-231 of SEQ ID NO: 90, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 90% identical to the amino acid sequence of SEQ ID NO: 90 or the amino acid residues 1-231 of SEQ ID NO: 90, and wherein residue 5 is serine, residue 19 is alanine, residue 20 is alanine, residue 37 is tyrosine, residue 39 is threonine, and/or residue 41 is glutamate according to SEQ ID NO: 90 or the amino acid residues 1-231 of SEQ ID NO: 90, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 95% identical to the amino acid sequence of SEQ ID NO: 90 or the amino acid residues 1-231 of SEQ ID NO: 90, and wherein residue 5 is serine, residue 19 is alanine, residue 20 is alanine, residue 37 is tyrosine, residue 39 is threonine, and/or residue 41 is glutamate according to SEQ ID NO: 90 or the amino acid residues 1-231 of SEQ ID NO: 90, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 96% identical to the amino acid sequence of SEQ ID NO: 90 or the amino acid residues 1-231 of SEQ ID NO: 90, and wherein residue 5 is serine, residue 19 is alanine, residue 20 is alanine, residue 37 is tyrosine, residue 39 is threonine, and/or residue 41 is glutamate according to SEQ ID NO: 90 or the amino acid residues 1-231 of SEQ ID NO: 90, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 97% identical to the amino acid sequence of SEQ ID NO: 90 or the amino acid residues 1-231 of SEQ ID NO: 90, and wherein residue 5 is serine, residue 19 is alanine, residue 20 is alanine, residue 37 is tyrosine, residue 39 is threonine, and/or residue 41 is glutamate according to SEQ ID NO: 90 or the amino acid residues 1-231 of SEQ ID NO: 90, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 98% identical to the amino acid sequence of SEQ ID NO: 90 or the amino acid residues 1-231 of SEQ ID NO: 90, and wherein residue 5 is serine, residue 19 is alanine, residue 20 is alanine, residue 37 is tyrosine, residue 39 is threonine, and/or residue 41 is glutamate according to SEQ ID NO: 90 or the amino acid residues 1-231 of SEQ ID NO: 90, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 99% identical to the amino acid sequence of SEQ ID NO: 90 or the amino acid residues 1-231 of SEQ ID NO: 90, and wherein residue 5 is serine, residue 19 is alanine, residue 20 is alanine, residue 37 is tyrosine, residue 39 is threonine, and/or residue 41 is glutamate according to SEQ ID NO: 90 or the amino acid residues 1-231 of SEQ ID NO: 90, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises the amino acid sequence of SEQ ID NO: 90 or the amino acid residues 1-231 of SEQ ID NO: 90.

In some aspects, the polypeptide that binds IL31 comprises an Fc region comprising the amino acid sequence of SEQ ID NO: 90 or the amino acid residues 1-231 of SEQ ID NO: 90.

In some aspects, the polypeptide that binds IL31 comprises an amino acid sequence at least 85%, at least 90%, at least 95%, at least 96%, at least 97%, at least 98%, or at least 99% identical to the amino acid sequence of SEQ ID NO: 15 or the amino acid residues 1-506 of SEQ ID NO: 15, SEQ ID NO: 29 or the amino acid residues 1-496 of SEQ ID NO: 29, SEQ ID NO: 43 or the amino acid residues 1-487 of SEQ ID NO: 43, SEQ ID NO: 57 or the amino acid residues 1-507 of SEQ ID NO: 57, SEQ ID NO: 91 or the amino acid residues 1-506 of SEQ ID NO: 91, SEQ ID NO: 16 or the amino acid residues 1-506 of SEQ ID NO: 16, SEQ ID NO: 30 or the amino acid residues 1-496 of SEQ ID NO: 30, SEQ ID NO: 44 or the amino acid residues 1-487 of SEQ ID NO: 44, SEQ ID NO: 58 or the amino acid residues 1-507 of SEQ ID NO: 58, or SEQ ID NO: 92 or the amino acid residues 1-506 of SEQ ID NO: 92.

In some aspects, the polypeptide comprises an amino acid sequence at least 85% identical to the amino acid sequence of SEQ ID NO: 15 or the amino acid residues 1-506 of SEQ ID NO: 15. In some aspects, the polypeptide comprises an amino acid sequence at least 90% identical to the amino acid sequence of SEQ ID NO: 15 or the amino acid residues 1-506 of SEQ ID NO: 15. In some aspects, the polypeptide comprises an amino acid sequence at least 95% identical to the amino acid sequence of SEQ ID NO: 15 or the amino acid residues 1-506 of SEQ ID NO: 15. In some aspects, the polypeptide comprises an amino acid sequence at least 96% identical to the amino acid sequence of SEQ ID NO: 15 or the amino acid residues 1-506 of SEQ ID NO: 15. In some aspects, the polypeptide comprises an amino acid sequence at least 97% identical to the amino acid sequence of SEQ ID NO: 15 or the amino acid residues 1-506 of SEQ ID NO: 15. In some aspects, the polypeptide comprises an amino acid sequence at least 98% identical to the amino acid sequence of SEQ ID NO: 15 or the amino acid residues 1-506 of SEQ ID NO: 15. In some aspects, the polypeptide comprises an amino acid sequence at least 99% identical to the amino acid sequence of SEQ ID NO: 15 or the amino acid residues 1-506 of SEQ ID NO: 15.

In some aspects, the polypeptide comprises an amino acid sequence at least 85% identical to the amino acid sequence of SEQ ID NO: 29 or the amino acid residues 1-496 of SEQ ID NO: 29. In some aspects, the polypeptide comprises an amino acid sequence at least 90% identical to the amino acid sequence of SEQ ID NO: 29 or the amino acid residues 1-496 of SEQ ID NO: 29. In some aspects, the polypeptide comprises an amino acid sequence at least 95% identical to the amino acid sequence of SEQ ID NO: 29 or the amino acid residues 1-496 of SEQ ID NO: 29. In some aspects, the polypeptide comprises an amino acid sequence at least 96% identical to the amino acid sequence of SEQ ID NO: 29 or the amino acid residues 1-496 of SEQ ID NO: 29. In some aspects, the polypeptide comprises an amino acid sequence at least 97% identical to the amino acid sequence of SEQ ID NO: 29 or the amino acid residues 1-496 of SEQ ID NO: 29. In some aspects, the polypeptide comprises an amino acid sequence at least 98% identical to the amino acid sequence of SEQ ID NO: 29 or the amino acid residues 1-496 of SEQ ID NO: 29. In some aspects, the polypeptide comprises an amino acid sequence at least 99% identical to the amino acid sequence of SEQ ID NO: 29 or the amino acid residues 1-496 of SEQ ID NO: 29.

In some aspects, the polypeptide comprises an amino acid sequence at least 85% identical to the amino acid sequence of SEQ ID NO: 43 or the amino acid residues 1-487 of SEQ ID NO: 43. In some aspects, the polypeptide comprises an amino acid sequence at least 90% identical to the amino acid sequence of SEQ ID NO: 43 or the amino acid residues 1-487 of SEQ ID NO: 43. In some aspects, the polypeptide comprises an amino acid sequence at least 95% identical to the amino acid sequence of SEQ ID NO: 43 or the amino acid residues 1-487 of SEQ ID NO: 43. In some aspects, the polypeptide comprises an amino acid sequence at least 96% identical to the amino acid sequence of SEQ ID NO: 43 or the amino acid residues 1-487 of SEQ ID NO: 43. In some aspects, the polypeptide comprises an amino acid sequence at least 97% identical to the amino acid sequence of SEQ ID NO: 43 or the amino acid residues 1-487 of SEQ ID NO: 43. In some aspects, the polypeptide comprises an amino acid sequence at least 98% identical to the amino acid sequence of SEQ ID NO: 43 or the amino acid residues 1-487 of SEQ ID NO: 43. In some aspects, the polypeptide comprises an amino acid sequence at least 99% identical to the amino acid sequence of SEQ ID NO: 43 or the amino acid residues 1-487 of SEQ ID NO: 43.

In some aspects, the polypeptide comprises an amino acid sequence at least 85% identical to the amino acid sequence of SEQ ID NO: 57 or the amino acid residues 1-507 of SEQ ID NO: 57. In some aspects, the polypeptide comprises an amino acid sequence at least 90% identical to the amino acid sequence of SEQ ID NO: 57 or the amino acid residues 1-507 of SEQ ID NO: 57. In some aspects, the polypeptide comprises an amino acid sequence at least 95% identical to the amino acid sequence of SEQ ID NO: 57 or the amino acid residues 1-507 of SEQ ID NO: 57. In some aspects, the polypeptide comprises an amino acid sequence at least 96% identical to the amino acid sequence of SEQ ID NO: 57 or the amino acid residues 1-507 of SEQ ID NO: 57. In some aspects, the polypeptide comprises an amino acid sequence at least 97% identical to the amino acid sequence of SEQ ID NO: 57 or the amino acid residues 1-507 of SEQ ID NO: 57. In some aspects, the polypeptide comprises an amino acid sequence at least 98% identical to the amino acid sequence of SEQ ID NO: 57 or the amino acid residues 1-507 of SEQ ID NO: 57. In some aspects, the polypeptide comprises an amino acid sequence at least 99% identical to the amino acid sequence of SEQ ID NO: 57 or the amino acid residues 1-507 of SEQ ID NO: 57.

In some aspects, the polypeptide comprises an amino acid sequence at least 85% identical to the amino acid sequence of SEQ ID NO: 91 or the amino acid residues 1-506 of SEQ ID NO: 91. In some aspects, the polypeptide comprises an amino acid sequence at least 90% identical to the amino acid sequence of SEQ ID NO: 91 or the amino acid residues 1-506 of SEQ ID NO: 91. In some aspects, the polypeptide comprises an amino acid sequence at least 95% identical to the amino acid sequence of SEQ ID NO: 91 or the amino acid residues 1-506 of SEQ ID NO: 91. In some aspects, the polypeptide comprises an amino acid sequence at least 96% identical to the amino acid sequence of SEQ ID NO: 91 or the amino acid residues 1-506 of SEQ ID NO: 91. In some aspects, the polypeptide comprises an amino acid sequence at least 97% identical to the amino acid sequence of SEQ ID NO: 91 or the amino acid residues 1-506 of SEQ ID NO: 91. In some aspects, the polypeptide comprises an amino acid sequence at least 98% identical to the amino acid sequence of SEQ ID NO: 91 or the amino acid residues 1-506 of SEQ ID NO: 91. In some aspects, the polypeptide comprises an amino acid sequence at least 99% identical to the amino acid sequence of SEQ ID NO: 91 or the amino acid residues 1-506 of SEQ ID NO: 91.

In some aspects, the polypeptide comprises an amino acid sequence at least 85% identical to the amino acid sequence of SEQ ID NO: 16 or the amino acid residues 1-506 of SEQ ID NO: 16. In some aspects, the polypeptide comprises an amino acid sequence at least 90% identical to the amino acid sequence of SEQ ID NO: 16 or the amino acid residues 1-506 of SEQ ID NO: 16. In some aspects, the polypeptide comprises an amino acid sequence at least 95% identical to the amino acid sequence of SEQ ID NO: 16 or the amino acid residues 1-506 of SEQ ID NO: 16. In some aspects, the polypeptide comprises an amino acid sequence at least 96% identical to the amino acid sequence of SEQ ID NO: 16 or the amino acid residues 1-506 of SEQ ID NO: 16. In some aspects, the polypeptide comprises an amino acid sequence at least 97% identical to the amino acid sequence of SEQ ID NO: 16 or the amino acid residues 1-506 of SEQ ID NO: 16. In some aspects, the polypeptide comprises an amino acid sequence at least 98% identical to the amino acid sequence of SEQ ID NO: 16 or the amino acid residues 1-506 of SEQ ID NO: 16. In some aspects, the polypeptide comprises an amino acid sequence at least 99% identical to the amino acid sequence of SEQ ID NO: 16 or the amino acid residues 1-506 of SEQ ID NO: 16.

In some aspects, the polypeptide comprises an amino acid sequence at least 85% identical to the amino acid sequence of SEQ ID NO: 30 or the amino acid residues 1-496 of SEQ ID NO: 30. In some aspects, the polypeptide comprises an amino acid sequence at least 90% identical to the amino acid sequence of SEQ ID NO: 30 or the amino acid residues 1-496 of SEQ ID NO: 30. In some aspects, the polypeptide comprises an amino acid sequence at least 95% identical to the amino acid sequence of SEQ ID NO: 30 or the amino acid residues 1-496 of SEQ ID NO: 30. In some aspects, the polypeptide comprises an amino acid sequence at least 96% identical to the amino acid sequence of SEQ ID NO: 30 or the amino acid residues 1-496 of SEQ ID NO: 30. In some aspects, the polypeptide comprises an amino acid sequence at least 97% identical to the amino acid sequence of SEQ ID NO: 30 or the amino acid residues 1-496 of SEQ ID NO: 30. In some aspects, the polypeptide comprises an amino acid sequence at least 98% identical to the amino acid sequence of SEQ ID NO: 30 or the amino acid residues 1-496 of SEQ ID NO: 30. In some aspects, the polypeptide comprises an amino acid sequence at least 99% identical to the amino acid sequence of SEQ ID NO: 30 or the amino acid residues 1-496 of SEQ ID NO: 30.

In some aspects, the polypeptide comprises an amino acid sequence at least 85% identical to the amino acid sequence of SEQ ID NO: 44 or the amino acid residues 1-487 of SEQ ID NO: 44. In some aspects, the polypeptide comprises an amino acid sequence at least 90% identical to the amino acid sequence of SEQ ID NO: 44 or the amino acid residues 1-487 of SEQ ID NO: 44. In some aspects, the polypeptide comprises an amino acid sequence at least 95% identical to the amino acid sequence of SEQ ID NO: 44 or the amino acid residues 1-487 of SEQ ID NO: 44. In some aspects, the polypeptide comprises an amino acid sequence at least 96% identical to the amino acid sequence of SEQ ID NO: 44 or the amino acid residues 1-487 of SEQ ID NO: 44. In some aspects, the polypeptide comprises an amino acid sequence at least 97% identical to the amino acid sequence of SEQ ID NO: 44 or the amino acid residues 1-487 of SEQ ID NO: 44. In some aspects, the polypeptide comprises an amino acid sequence at least 98% identical to the amino acid sequence of SEQ ID NO: 44 or the amino acid residues 1-487 of SEQ ID NO: 44. In some aspects, the polypeptide comprises an amino acid sequence at least 99% identical to the amino acid sequence of SEQ ID NO: 44 or the amino acid residues 1-487 of SEQ ID NO: 44.

In some aspects, the polypeptide comprises an amino acid sequence at least 85% identical to the amino acid sequence of SEQ ID NO: 58 or the amino acid residues 1-507 of SEQ ID NO: 58. In some aspects, the polypeptide comprises an amino acid sequence at least 90% identical to the amino acid sequence of SEQ ID NO: 58 or the amino acid residues 1-507 of SEQ ID NO: 58. In some aspects, the polypeptide comprises an amino acid sequence at least 95% identical to the amino acid sequence of SEQ ID NO: 58 or the amino acid residues 1-507 of SEQ ID NO: 58. In some aspects, the polypeptide comprises an amino acid sequence at least 96% identical to the amino acid sequence of SEQ ID NO: 58 or the amino acid residues 1-507 of SEQ ID NO: 58. In some aspects, the polypeptide comprises an amino acid sequence at least 97% identical to the amino acid sequence of SEQ ID NO: 58 or the amino acid residues 1-507 of SEQ ID NO: 58. In some aspects, the polypeptide comprises an amino acid sequence at least 98% identical to the amino acid sequence of SEQ ID NO: 58 or the amino acid residues 1-507 of SEQ ID NO: 58. In some aspects, the polypeptide comprises an amino acid sequence at least 99% identical to the amino acid sequence of SEQ ID NO: 58 or the amino acid residues 1-507 of SEQ ID NO: 58.

In some aspects, the polypeptide comprises an amino acid sequence at least 85% identical to the amino acid sequence of SEQ ID NO: 92 or the amino acid residues 1-506 of SEQ ID NO: 92. In some aspects, the polypeptide comprises an amino acid sequence at least 90% identical to the amino acid sequence of SEQ ID NO: 92 or the amino acid residues 1-506 of SEQ ID NO: 92. In some aspects, the polypeptide comprises an amino acid sequence at least 95% identical to the amino acid sequence of SEQ ID NO: 92 or the amino acid residues 1-506 of SEQ ID NO: 92. In some aspects, the polypeptide comprises an amino acid sequence at least 96% identical to the amino acid sequence of SEQ ID NO: 92 or the amino acid residues 1-506 of SEQ ID NO: 92. In some aspects, the polypeptide comprises an amino acid sequence at least 97% identical to the amino acid sequence of SEQ ID NO: 92 or the amino acid residues 1-506 of SEQ ID NO: 92. In some aspects, the polypeptide comprises an amino acid sequence at least 98% identical to the amino acid sequence of SEQ ID NO: 92 or the amino acid residues 1-506 of SEQ ID NO: 92. In some aspects, the polypeptide comprises an amino acid sequence at least 99% identical to the amino acid sequence of SEQ ID NO: 92 or the amino acid residues 1-506 of SEQ ID NO: 92.

In some aspects, the polypeptide comprises the amino acid sequence of SEQ ID NO: 15 or the amino acid residues 1-506 of SEQ ID NO: 15, SEQ ID NO: 29 or the amino acid residues 1-496 of SEQ ID NO: 29, SEQ ID NO: 43 or the amino acid residues 1-487 of SEQ ID NO: 43, SEQ ID NO: 57 or the amino acid residues 1-507 of SEQ ID NO: 57, SEQ ID NO: 91 or the amino acid residues 1-506 of SEQ ID NO: 91, SEQ ID NO: 16 or the amino acid residues 1-506 of SEQ ID NO: 16, SEQ ID NO: 30 or the amino acid residues 1-496 of SEQ ID NO: 30, SEQ ID NO: 44 or the amino acid residues 1-487 of SEQ ID NO: 44, SEQ ID NO: 58 or the amino acid residues 1-507 of SEQ ID NO: 58, or SEQ ID NO: 92 or the amino acid residues 1-506 of SEQ ID NO: 92. In some aspects, the polypeptide comprises the amino acid sequence of SEQ ID NO: 16 or the amino acid residues 1-506 of SEQ ID NO: 16, SEQ ID NO: 30 or the amino acid residues 1-496 of SEQ ID NO: 30, SEQ ID NO: 44 or the amino acid residues 1-487 of SEQ ID NO: 44, SEQ ID NO: 58 or the amino acid residues 1-507 of SEQ ID NO: 58, or SEQ ID NO: 92 or the amino acid residues 1-506 of SEQ ID NO: 92. In some aspects, the polypeptide comprises the amino acid sequence of SEQ ID NO: 15 or the amino acid residues 1-506 of SEQ ID NO: 15. In some aspects, the polypeptide comprises the amino acid sequence of SEQ ID NO: 29 or the amino acid residues 1-496 of SEQ ID NO: 29. In some aspects, the polypeptide comprises the amino acid sequence of SEQ ID NO: 43 or the amino acid residues 1-487 of SEQ ID NO: 43. In some aspects, the polypeptide comprises the amino acid sequence of SEQ ID NO: 57 or the amino acid residues 1-507 of SEQ ID NO: 57. In some aspects, the polypeptide comprises the amino acid sequence of SEQ ID NO: 91 or the amino acid residues 1-506 of SEQ ID NO: 91. In some aspects, the polypeptide comprises the amino acid sequence of SEQ ID NO: 16 or the amino acid residues 1-506 of SEQ ID NO: 16. In some aspects, the polypeptide comprises the amino acid sequence of SEQ ID NO: 30 or the amino acid residues 1-496 of SEQ ID NO: 30. In some aspects, the polypeptide comprises the amino acid sequence of SEQ ID NO: 44 or the amino acid residues 1-487 of SEQ ID NO: 44. In some aspects, the polypeptide comprises the amino acid sequence of SEQ ID NO: 58 or the amino acid residues 1-507 of SEQ ID NO: 58. In some aspects, the polypeptide comprises the amino acid sequence of SEQ ID NO: 92 or the amino acid residues 1-506 of SEQ ID NO: 92.

In some aspects, the polypeptide that binds IL31 binds to human IL31. In some aspects, the human IL31 comprises a signal sequence. In some aspects, the human IL31 does not comprise a signal sequence. In some aspects, the human IL31 comprises an amino acid sequence at least 95%, at least 96%, at least 97%, at least 98%, or at least 99% identical to the amino acid sequence of the amino acid sequence of SEQ ID NO: 1 or SEQ ID NO: 2. In some aspects, the human IL31 comprises the amino acid sequence of SEQ ID NO: 1 or SEQ ID NO: 2.

The binding affinity of the polypeptide that binds IL31 can be determined by means of surface plasmon resonance. In some aspects, an equilibrium dissociation constant of an antigen-binding molecule and antigen interaction is determined, wherein the antigen is human IL31. In some aspects, the polypeptide binds to human IL31 at a kD of less than or equal to $1\times10^{-9}$ M, less than or equal to $5\times10^{-10}$ M, less than or equal to $1\times10^{-10}$ M, less than or equal to $5\times10^{-11}$ M, less than or equal to $1\times10^{-11}$ M, less than or equal to $5\times10^{-12}$ M, or less than or equal to $1\times10^{-12}$ M, as measured by surface plasmon resonance. In some aspects, the polypeptide binds to human IL31 at a kD of no more than or equal to $1\times10^{-9}$ M, no more than or equal to $5\times10^{-10}$ M, no more than or equal to $1\times10^{-10}$ M, no more than or equal to $5\times10^{-11}$ M, no more than or equal to $1\times10^{-11}$ M, no more than or equal to $5\times10^{-12}$ M, or no more than or equal to $1\times10^{-12}$ M, as measured by surface plasmon resonance. In some aspects, the polypeptide binds to human IL31 with a kD between about $1\times10^{-9}$ M and about $1\times10^{-12}$ M, about $5\times10^{-10}$ M and about $5\times10^{-11}$ M, or about $1\times10^{-10}$ M and about $1\times10^{-11}$ M, or about $5\times10^{-11}$ M, as measured by surface plasmon resonance. In some aspects, the polypeptide binds to human IL31 at a kD of about $1\times10^{-9}$ M, about $9\times10^{-10}$ M, about $8\times10^{-10}$ M, about $7\times10^{-10}$ M, about $6\times10^{-10}$ M, about $5\times10^{-10}$ M, about $4\times10^{-10}$ M, about $3\times10^{-10}$ M, about $2\times10^{-10}$ M, about $1\times10^{-10}$ M, about $9\times10^{-11}$ M, about $8\times10^{-11}$ M, about $7\times10^{-11}$ M, about $6\times10^{-11}$ M, about $5\times10^{-11}$ M, about $4\times10^{-11}$ M, about $3\times10^{-11}$ M, about $2\times10^{-11}$ M, about $1\times10^{-11}$ M, about $9\times10^{-12}$ M, about $8\times12^{-10}$ M, about $7\times10^{-12}$ M, about $6\times10^{-12}$ M, about $5\times10^{-12}$ M, about $4\times10^{-12}$ M, about $3\times10^{-12}$ M, about $2\times10^{-12}$ M, or about $1\times10^{-12}$ M, as measured by surface plasmon resonance.

In some aspects, the polypeptide binds to human IL31 at a kD of about $1\times10^{-9}$ M, about $5\times10^{-10}$ M, about $1\times10^{-10}$ M, about $5\times10^{-11}$ M, about $1\times10^{-11}$ M, about $5\times10^{-12}$ M, or about $1\times10^{-12}$ M, as measured by surface plasmon resonance. In some aspects, the polypeptide binds to human IL31 at a kD of about $1\times10^{-9}$ M. In some aspects, the polypeptide binds to human IL31 at a kD of about $5\times10^{-10}$ M. In some aspects, the polypeptide binds to human IL31 at a kD of about $1\times10^{-10}$ M. In some aspects, the polypeptide binds to human IL31 at a kD of about $5\times10^{-11}$ M. In some aspects, the polypeptide binds to human IL31 at a kD of about $1\times10^{-11}$ M. In some aspects, the polypeptide binds to human IL31 at a kD of about $5\times10^{-12}$ M. In some aspects, the polypeptide binds to human IL31 at a kD of about $1\times10^{-12}$ M.

In some aspects, the polypeptide binds to human IL31 at a kD of $1\times10^{-9}$ M, $5\times10^{-10}$ M, $1\times10^{-10}$ M, $5\times10^{-11}$ M, $1\times10^{-11}$ M, $5\times10^{-12}$ M, or $1\times10^{-12}$ M, as measured by surface plasmon resonance. In some aspects, the polypeptide binds to human IL31 at a kD of $1\times10^{-9}$ M. In some aspects, the polypeptide binds to human IL31 at a kD of $5\times10^{-10}$ M. In some aspects, the polypeptide binds to human IL31 at a kD of $1\times10^{-10}$ M. In some aspects, the polypeptide binds to human IL31 at a kD of $5\times10^{-11}$ M. In some aspects, the polypeptide binds to human IL31 at a kD of $1\times10^{-11}$ M. In some aspects, the polypeptide binds to human IL31 at a kD of $5\times10^{-12}$ M. In some aspects, the polypeptide binds to human IL31 at a kD of $1\times10^{-12}$ M.

In some aspects, the polypeptide that binds IL31 has a slow off-rate, wherein the off-rate ($K_{off}$) is the rate of dissociation between polypeptide and human IL31.

In some aspects, the polypeptide binds to human IL31 with a $k_{off}$ rate of less than or equal to $5\times10^{-4}$ M per second, less than or equal to $1\times1^{-4}$ M per second, less than or equal to $5\times10^{-5}$ M per second, less than or equal to $1\times10^{-5}$ M per second, less than or equal to $5\times10^{-6}$ M per second, or less than or equal to $1\times10^{-6}$ M per second, as measured by surface plasmon resonance. In some aspects, the polypeptide binds to human IL31 with a $k_{off}$ rate of no more than or equal to $5\times10^{-4}$ M per second, no more than or equal to $1\times1^{-4}$ M per second, no more than or equal to $5\times10^{-5}$ M per second, no more than or equal to $1\times10^{-5}$ M per second, no more than or equal to $5\times10^{-6}$ M per second, or no more than or equal to $1\times10^{-6}$ M per second, as measured by surface plasmon resonance. In some aspects, the polypeptide binds to human IL31 with a $k_{off}$ rate of between about $5\times10^{-4}$ M per second and $1\times10^{-6}$ M per second, between about $1\times1^{-4}$ M per second and $5\times10^{-6}$ M per second, or between about $5\times10^{-5}$ M per second and $1\times10^{-5}$ M per second, as measured by surface plasmon resonance. In some aspects, the polypeptide binds to human IL31 with a $k_{off}$ rate of about $9\times10^{-4}$ M per second, about $8\times10^{-4}$ M per second, about $7\times10^{-4}$ M per second, about $6\times10^{-4}$ M per second, about $5\times10^{-4}$ M per second, about $4\times10^{-4}$ M per second, about $3\times10^{-4}$ M per second, about $2\times10^{-4}$ M per second, about $1\times1^{-4}$ M per second, about $9\times10^{-5}$ M per second, about $8\times10^{-5}$ M per second, about $7\times10^{-5}$ M per second, about $6\times10^{-5}$ M per second, about $5\times10^{-5}$ M per second, about $4\times10^{-5}$ M per second, about $3\times10^{-5}$ M per second, about $2\times10^{-5}$ M per second, about $1\times10^{-5}$ M per second, about $9\times10^{-6}$ M per second, about $8\times10^{-6}$ M per second, about $7\times10^{-6}$ M per second, about $6\times10^{-6}$ M per second, about $5\times10^{-6}$ M per second, about $4\times10^{-6}$ M per second, about $3\times10^{-6}$ M per second, about $2\times10^{-6}$ M per second, or about $1\times10^{-6}$ M per second, as measured by surface plasmon resonance.

In some aspects, the polypeptide binds to human IL31 with a $k_{off}$ rate of about $5\times10^{-4}$ M per second, about $1\times1^{-4}$ M per second, about $5\times10^{-5}$ M per second, about $1\times10^{-5}$ M per second, about $5\times10^{-6}$ M per second, or about $1\times10^{-6}$ M per second, as measured by surface plasmon resonance. In some aspects, the polypeptide binds to human IL31 with a $k_{off}$ rate of about $5\times10^{-4}$ M per second, as measured by surface plasmon resonance. In some aspects, the polypeptide binds to human IL31 with a $k_{off}$ rate of about $1\times10^{-4}$ M per second, as measured by surface plasmon resonance. In some aspects, the polypeptide binds to human IL31 with a kor rate of about $5\times10^{-5}$ M per second, as measured by surface plasmon resonance. In some aspects, the polypeptide binds to human IL31 with a $k_{off}$ rate of about $1\times10^{-5}$ M per second, as measured by surface plasmon resonance. In some aspects, the polypeptide binds to human IL31 with a $k_{off}$ rate of about $5\times10^{-6}$ M per second, as measured by surface plasmon resonance. In some aspects, the polypeptide binds to human IL31 with a $k_{off}$ rate of about $1\times10^{-6}$ M per second, as measured by surface plasmon resonance.

In some aspects, the polypeptide binds to human IL31 with a $k_{off}$ rate of $5\times10^{-4}$ M per second, $1\times1^{-4}$ M per second, $5\times10^{-5}$ M per second, $1\times10^{-5}$ M per second, $5\times10^{-6}$ M per second, or $1\times10^{-6}$ M per second, as measured by surface plasmon resonance. In some aspects, the polypeptide binds to human IL31 with a $k_{off}$ rate of $5\times10^{-4}$ M per second, as measured by surface plasmon resonance. In some aspects, the polypeptide binds to human IL31 with a $k_{off}$ rate of $1\times10^{-4}$ M per second, as measured by surface plasmon resonance. In some aspects, the polypeptide binds to human IL31 with a $k_{off}$ rate of $5\times10^{-5}$ M per second, as measured by surface plasmon resonance. In some aspects, the polypeptide binds to human IL31 with a $k_{off}$ rate of $1\times10^{-5}$ M per second, as measured by surface plasmon resonance. In some aspects, the polypeptide binds to human IL31 with a $k_{off}$ rate of $5\times10^{-6}$ M per second, as measured by surface plasmon resonance. In some aspects, the polypeptide binds to human IL31 with a kor rate of $1\times10^{-6}$ M per second, as measured by surface plasmon resonance.

Also provided herein are multimeric polypeptides, each comprising two or more of the any one of the polypeptides provided herein. In some aspects, the present disclosure comprises a dimeric polypeptide comprising at least one polypeptide disclosed herein. In some aspects, the dimer polypeptide of the present disclosure comprises two polypeptides disclosed herein of SEQ ID NO: 90.

In some aspects, the polypeptide of the present disclosure is divalent, trivalent, tetravalent, pentavalent, hexavalent, heptavalent, octavalent, nonavalent, or decavalent. In some aspects, the polypeptide of the present disclosure is octavalent. In some aspects, the polypeptide of the present disclosure is tetravalent.

III. Exemplary Polypeptide Expression and Production

Nucleic acid molecules comprising polynucleotides that encode a polypeptide that binds IL31 described herein (e.g., Section II and the Examples) are provided. In some aspects, an isolated nucleic acid that encodes the polypeptide is provided. In some aspects, the nucleic acid molecule may also encode a leader sequence that directs secretion of the polypeptide that binds IL31, which leader sequence is typically cleaved such that it is not present in the secreted polypeptide. The leader sequence may be a native heavy chain (or VHH) leader sequence, or may be another heterologous leader sequence.

Nucleic acid molecules can be constructed using recombinant DNA techniques conventional in the art. In some aspects, a nucleic acid molecule is an expression vector that is suitable for expression in a selected host cell. In some aspects, a vector comprising the nucleic acid is provided.

Vectors comprising nucleic acids that encode the polypeptide that binds IL31 described herein are provided. Such vectors include, but are not limited to, DNA vectors, phage vectors, viral vectors, retroviral vectors, etc. In some aspects, a vector is selected that is optimized for expression of polypeptides in a desired cell type, such as CHO or CHO-derived cells, or in NSO cells. Exemplary such vectors are described, for example, in Running Deer et al., Biotechnol. Prog. 20:880-889 (2004).

In some aspects, an in vitro or ex vivo cell comprising the described nucleic acid is provided herein. In some aspects, an in vitro or ex vivo cell that expresses the polypeptide is provided herein. In some aspects, the in vitro or ex vivo cells express chimeric antigen receptor, T cell receptor, or any combination thereof.

In some aspects, a polypeptide that binds IL31 may be expressed in host cells, e.g., prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44, Lec13 CHO cells, and FUT8 CHO cells; PER.C6® cells (Crucell); and NSO cells. In some aspects, the polypeptide that binds IL31 may be expressed in yeast. See, e.g., U.S. Publication No. US 2006/0270045 A1. In some aspects, a particular eukaryotic host cell is selected based on its ability to make desired post-translational modifications to the polypeptide. For example, in some aspects, CHO cells produce polypeptides that have a higher level of sialylation than the same polypeptide produced in 293 cells.

Introduction of one or more nucleic acids (such as vectors) into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, 3rd ed. Cold Spring Harbor Laboratory Press (2001). Nucleic acids may be transiently or stably transfected in the desired host cells, according to any suitable method.

Host cells comprising any of the nucleic acids or vectors described herein are also provided. In some aspects, a host cell that expresses a polypeptide that binds IL31 described herein (e.g., Section II and the Examples) is provided. The IL31-binding polypeptides expressed in host cells can be purified by any suitable method. Such methods include, but are not limited to, the use of affinity matrices or hydrophobic interaction chromatography. Suitable affinity ligands include the ROR1 ECD and agents that bind Fc regions. For example, a Protein A, Protein G, Protein A/G, or an antibody affinity column may be used to bind the Fc region and to purify the polypeptide that binds IL31 that comprises an Fc region. Hydrophobic interactive chromatography, for example, a butyl or phenyl column, may also be suitable for purifying some polypeptides such as antibodies. Ion exchange chromatography (for example anion exchange chromatography and/or cation exchange chromatography) may also be suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also be suitable for purifying some polypeptides such as antibodies. Many methods of purifying polypeptides are known in the art.

Also provided is a host cell comprising a nucleic acid encoding any of the polypeptides described herein. Suitable host cells for cloning or expression of polypeptide-encoding vectors include prokaryotic or eukaryotic cells described herein. For example, the polypeptide may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B.K.C. Lo, ed., Humana Press, Totowa, NJ, 2003), pp. 245-254, describing expression of antibody fragments in *E. coli*.) After expression, the polypeptide may be isolated from the bacterial cell paste in a soluble fraction and can be further purified.

In some aspects, provided herein is a host cell comprising a vector comprising a nucleic acid(s) encoding a polypeptide of the present disclosure.

Suitable host cells for the expression of glycosylated polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CVI line transformed by SV40 (COS-7); human embryonic kidney line (293 or 293 cells as described, e.g., in Graham et al, J. Gen Virol. 36:59 (1977)); baby hamster kidney cells (BHK); mouse Sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3 A); human lung cells (W138); human liver cells (Hep G2); mouse mammary tumor (MMT 060562); TRI cells, as described, e.g., in Mather et al, Annals N Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al, Proc. Natl. Acad. Sci. USA 77:4216 (1980)); and myeloma cell lines such as Y0, NS0 and Sp2/0. For a review of certain mammalian host cell lines suitable for polypeptide production, see, e.g., Yazaki and Wu, Methods in Molecular Biology, Vol. 248 (B.K.C. Lo, ed., Humana Press, Totowa, NJ), pp. 255-268 (2003).

In some aspects, the polypeptide that binds IL31 is produced in a cell-free system. Nonlimiting exemplary cell-free systems are described, for example, in Sitaraman et al., Methods Mol. Biol. 498:229-44 (2009); Spirin, Trends Biotechnol. 22:538-45 (2004); Endo et al., Biotechnol. Adv. 21:695-713 (2003).

In some aspects, a method of producing the polypeptide described herein (e.g., Section II and the Examples) is provided. In some aspects, the method comprises culturing a host cell under conditions suitable for expression of the polypeptide. In some aspects, the method further comprises isolating the polypeptide.

In some aspects, a polypeptide that binds IL31 is prepared by the methods described above. In some aspects, the polypeptide that binds IL31 is prepared in a host cell. In some aspects, the polypeptide that binds IL31 is prepared in a cell-free system. In some aspects, the polypeptide that binds IL31 is purified.

IV. Exemplary Pharmaceutical Compositions

Pharmaceutical compositions comprising a polypeptide that binds IL31 are provided. In some aspects, the polypeptide that binds IL31 is any one of the polypeptides described herein (e.g., Section II and the Examples). The pharmaceutical compositions can additionally contain other therapeutic agents that are suitable for treating or preventing a given skin disease or disorder (e.g., see Section V). In some aspects, the pharmaceutical composition further comprises a pharmaceutically acceptable carrier.

Accordingly, described herein are pharmaceutical compositions comprising a polypeptide that binds IL31. In some aspects, the polypeptide that binds IL31 comprises one or more IL31 binder. In some aspects, the one or more IL31 binder comprises a VHH1. In some aspects, the one or more IL31 binder comprises a VHH1 and a VHH2. In some aspects, the VHH1 or the VHH2 comprises a CDR1 comprising the amino acid sequence of SEQ ID NO: 59; a CDR2 comprising the amino acid sequence of SEQ ID NO: 60 or SEQ ID NO: 63; and a CDR3 comprising the amino acid sequence of SEQ ID NO:61 or SEQ ID NO: 64. In some aspects, the antibody variable domain is a VHH domain. In some aspects, the two or more antibody variable domains are VHH domains. In some aspects, the polypeptide that binds IL31 comprises a first IL31 binder and a second IL31 binder. In some aspects, the first IL31 binder comprises a VHH1 comprising a CDR1 comprising the amino acid sequence of SEQ ID NO: 5, SEQ ID NO: 19, SEQ ID NO: 33, SEQ ID NO: 47, SEQ ID NO: 78, SEQ ID NO: 81, or SEQ ID NO: 59; a CDR2 comprising the amino acid sequence of SEQ ID NO: 6, SEQ ID NO: 20, SEQ ID NO: 34, SEQ ID NO: 48, SEQ ID NO: 79, SEQ ID NO: 82, SEQ ID NO: 60, or SEQ ID NO:63; and a CDR3 comprising the amino acid sequence of SEQ ID NO: 7, SEQ ID NO: 21, SEQ ID NO: 35, SEQ ID NO: 49, SEQ ID NO: 80, SEQ ID NO: 83, SEQ ID NO: 61, or SEQ ID NO:64. In some aspects, the second IL31 binder comprises a VHH2 comprising a CDR1 comprising the amino acid sequence of SEQ ID NO: 10, SEQ ID NO: 24, SEQ ID NO: 38, SEQ ID NO: 52, SEQ ID NO: 84, SEQ ID NO: 87, SEQ ID NO:59, or SEQ ID NO:251; a CDR2 comprising the amino acid sequence of SEQ ID NO: 11, SEQ ID NO: 25, SEQ ID NO: 39, SEQ ID NO: 53, SEQ ID NO: 85, SEQ ID NO: 88, SEQ ID NO: 60, SEQ ID NO:63, or SEQ ID NO:252; and a CDR3 comprising the amino acid sequence of SEQ ID NO: 12, SEQ ID NO: 26, SEQ ID NO: 40, SEQ ID NO: 54, SEQ ID NO: 86, SEQ ID NO: 89, SEQ ID NO:61, SEQ ID NO:64, or SEQ ID NO:253.

In some aspects, the pharmaceutical composition comprises a polypeptide that binds IL31, wherein (i) the VHH1 comprises a CDR1 comprising the amino acid sequence of SEQ ID NO: 59, a CDR2 comprising the amino acid sequence of SEQ ID NO: 60, or SEQ ID NO:63, and a CDR3 comprising the amino acid sequence of SEQ ID NO: 61, or SEQ ID NO:64; and (ii) the VHH2 comprises a CDR1 comprising the amino acid sequence of SEQ ID NO: 10, SEQ ID NO: 24, SEQ ID NO: 38, SEQ ID NO: 52, SEQ ID NO: 84, SEQ ID NO: 87, SEQ ID NO:59, or SEQ ID NO: 251, a CDR2 comprising the amino acid sequence of SEQ ID NO: 11, SEQ ID NO: 25, SEQ ID NO: 39, SEQ ID NO: 53, SEQ ID NO: 85, SEQ ID NO: 88, SEQ ID NO:60, SEQ ID NO: 63, or SEQ ID NO:252, and a CDR3 comprising the amino acid sequence of SEQ ID NO: 12, SEQ ID NO: 26, SEQ ID NO: 40, SEQ ID NO: 54, SEQ ID NO: 86, SEQ ID NO: 89, SEQ ID NO: 61, SEQ ID NO:64, or SEQ ID NO:253.

In some aspects, the pharmaceutical composition comprises a polypeptide that binds IL31, wherein (i) the VHH1 comprises an amino acid sequence at least 85%, at least 90%, at least 95%, at least 96%, at least 97%, at least 98%, at least 99%, or 100% identical to the amino acid sequence of SEQ ID NO: 3, SEQ ID NO: 17, SEQ ID NO: 31, or SEQ ID NO: 45; and/or (ii) the VHH2 comprises an amino acid sequence at least 85%, at least 90%, at least 95%, at least 96%, at least 97%, at least 98%, at least 99%, or 100% identical to the amino acid sequence of SEQ ID NO: 8, SEQ ID NO: 22, SEQ ID NO: 36, or SEQ ID NO: 50.

In some aspects, the pharmaceutical composition comprises a polypeptide that binds IL31, wherein (i) the VHH1 comprises an amino acid sequence at least 85%, at least 90%, at least 95%, at least 96%, at least 97%, at least 98%, at least 99%, or 100% identical to the amino acid sequence of SEQ ID NO: 4, SEQ ID NO: 18, SEQ ID NO: 32, or SEQ ID NO: 46; and/or (ii) the VHH2 comprises an amino acid sequence at least 85%, at least 90%, at least 95%, at least 96%, at least 97%, at least 98%, at least 99%, or 100% identical to the amino acid sequence of SEQ ID NO: 9, SEQ ID NO: 23, SEQ ID NO: 37, or SEQ ID NO: 51.

In some aspects, the pharmaceutical composition comprises a polypeptide that binds IL31, wherein the polypeptide comprises an amino acid sequence at least 85%, at least 90%, at least 95%, at least 96%, at least 97%, at least 98%, at least 99%, or 100% identical to the amino acid sequence of SEQ ID NO: 13, SEQ ID NO: 27, SEQ ID NO: 41, SEQ ID NO: 55, SEQ ID NO: 14, SEQ ID NO: 28, SEQ ID NO: 42, or SEQ ID NO: 56.

In some aspects, the pharmaceutical composition comprises a polypeptide that binds IL31, wherein the polypeptide comprises a Fc region, wherein the Fc region comprises an amino acid sequence at least 85%, at least 90%, at least 95%, at least 96%, at least 97%, at least 98%, at least 99%, or 100% identical to the amino acid sequence of SEQ ID NO: 62 or the amino acid residues 1-231 of SEQ ID NO: 62.

In some aspects, the pharmaceutical composition comprises a polypeptide that binds IL31, wherein the polypeptide comprises a Fc region, wherein the Fc region comprises an amino acid sequence at least 85%, at least 90%, at least 95%, at least 96%, at least 97%, at least 98%, at least 99%, or 100% identical to the amino acid sequence of SEQ ID NO: 90 or the amino acid residues 1-231 of SEQ ID NO: 90.

In some aspects, the pharmaceutical composition comprises a polypeptide that binds IL31, wherein the polypeptide comprises an amino acid sequence at least 85%, at least 90%, at least 95%, at least 96%, at least 97%, at least 98%, at least 99%, or 100% identical to the amino acid sequence of SEQ ID NO: 15 or the amino acid residues 1-506 of SEQ ID NO: 15, SEQ ID NO: 29 or the amino acid residues 1-496 of SEQ ID NO: 29, SEQ ID NO: 43 or the amino acid residues 1-487 of SEQ ID NO: 43, SEQ ID NO: 57 or the amino acid residues 1-507 of SEQ ID NO: 57, SEQ ID NO: 91 or the amino acid residues 1-506 of SEQ ID NO: 91, SEQ ID NO: 16 or the amino acid residues 1-506 of SEQ ID NO: 16, SEQ ID NO: 30 or the amino acid residues 1-496 of SEQ ID NO: 30, SEQ ID NO: 44 or the amino acid residues 1-487 of SEQ ID NO: 44, SEQ ID NO: 58 or the amino acid residues 1-507 of SEQ ID NO: 58, SEQ ID NO: 92 or the amino acid residues 1-506 of SEQ ID NO: 92.

A pharmaceutical composition of the present disclosure can be administered by a variety of methods known in the art. The route and/or mode of administration vary depending upon the desired results. In some aspects, the pharmaceutical composition is administered parenterally, intramuscularly, intraperitoneally, intravenously, or subcutaneously. In some aspects, the pharmaceutical composition is administered proximal to the site of the target. The pharmaceutically acceptable carrier should be suitable for parenterally, intramuscular, intraperitoneal, intravenous, subcutaneous, parenteral, spinal, or epidermal administration (e.g., by injection or infusion).

Pharmaceutical compositions can be manufactured under GMP conditions. Typically, a therapeutically effective dose or efficacious dose of the polypeptide that binds IL31 is employed in the pharmaceutical compositions of the disclosure. The polypeptide that bind to IL31 can be formulated into pharmaceutically acceptable dosage forms. Dosage regimens are adjusted to provide a desired response (e.g., a therapeutic response).

V. Exemplary Methods of Using IL31 Polypeptides

A. Exemplary Uses and Methods of Treatment

Provided herein are polypeptides that bind IL31 (e.g., VHH) that may have therapeutic effects against chronic inflammatory skin diseases such as atopic dermatitis (AD) and prurigo nodularis (PN), which lead to intensely pruritic skin lesions resulting in severe scratching and can be extremely disabling (e.g., major psychological problems, significant sleep loss, and impaired quality of life (QOL) that lead to a high socioeconomic cost). In some instances, the polypeptides that bind IL31 may be used to treat a subject having an IL31-associated condition, such as a disease or disorder (e.g., inflammatory skin disease). In some instances, the methods or uses provided herein are for treating a subject having an IL31-associated condition comprising administering to the subject a therapeutically effective amount of any one the polypeptides or multimeric polypeptides described herein (e.g., Section II and the Examples) or the pharmaceutical composition thereof (e.g., Section IV). Uses of the polypeptide that binds IL31, multimeric polypeptides, or pharmaceutical compositions thereof for the manufacture of a medicament, wherein the medicament is for treating a subject having an IL31-associated condition, such as an inflammatory skin disease (e.g., a pruritic condition) are provided herein. Also provided herein are polypeptides that bind IL31, multimeric polypeptides, or pharmaceutical compositions thereof for use in treating a subject having an IL31-associated condition, such as an inflammatory skin disease (e.g., a pruritic condition).

In some aspects, provided herein is a method for treating a subject having an IL31-associated condition, comprising administering to the subject a therapeutically effective amount of any of the polypeptides, multimeric polypeptides, or pharmaceutical compositions thereof disclosed herein.

In some aspects, provided herein is a use of any of the polypeptides, multimeric polypeptides, or pharmaceutical compositions thereof disclosed herein for treating a subject having an IL31-associated condition.

In some aspects, provided herein is a use of any of the polypeptides, multimeric polypeptides, or pharmaceutical compositions thereof disclosed herein for the manufacture of a medicament, wherein the medicament is for treating a subject having an IL31-associated condition.

In some aspects, the method comprises uses of a polypeptide that binds IL31. In some aspects, the polypeptide that binds IL31 comprises one or more IL31 binder. In some aspects, the one or more IL31 binder comprises a VHH1. In some aspects, the one or more IL31 binder comprises a VHH1 and a VHH2. In some aspects, the VHH1 or the VHH2 comprises a CDR1 comprising the amino acid sequence of SEQ ID NO: 59 or SEQ ID NO:251; a CDR2 comprising the amino acid sequence of SEQ ID NO:60, SEQ ID NO: 63, or SEQ ID NO:252; and a CDR3 comprising the amino acid sequence of SEQ ID NO:61, SEQ ID NO: 64, or SEQ ID NO:253.

In some aspects, the one or more IL31 binder comprises a VHH1 and optionally a VHH2, wherein the VHH1 comprises a CDR1 comprising the amino acid sequence of SEQ ID NO: 59; a CDR2 comprising the amino acid sequence of SEQ ID NO: 60 or SEQ ID NO: 63; and a CDR3 comprising the amino acid sequence of SEQ ID NO: 61 or SEQ ID NO: 64. In some aspects, the VHH1 comprises a CDR1 comprising the amino acid sequence of SEQ ID NO: 59; a CDR2 comprising the amino acid sequence of SEQ ID NO: 63; and a CDR3 comprising the amino acid sequence of SEQ ID NO: 61. In some aspects, the VHH1 comprises a CDR1 comprising the amino acid sequence of SEQ ID NO: 59; a CDR2 comprising the amino acid sequence of SEQ ID NO: 60; and a CDR3 comprising the amino acid sequence of SEQ ID NO: 61. In some aspects, the VHH1 comprises a CDR1 comprising the amino acid sequence of SEQ ID NO: 59; a CDR2 comprising the amino acid sequence of SEQ ID NO: 60; and a CDR3 comprising the amino acid sequence of SEQ ID NO: 64. In some aspects, the VHH1 comprises a CDR1 comprising the amino acid sequence of SEQ ID NO:59; a CDR2 comprising the amino acid sequence of SEQ ID NO:63; and a CDR3 comprising the amino acid sequence of SEQ ID NO:64.

In some aspects, the polypeptide that binds IL31 comprises a first IL31 binder and a second IL31 binder. In some aspects, the first IL31 binder comprises a VHH1 comprising a CDR1 comprising the amino acid sequence of SEQ ID NO: 5, SEQ ID NO: 19, SEQ ID NO: 33, SEQ ID NO: 47, SEQ ID NO: 78, SEQ ID NO: 81, SEQ ID NO: 59, SEQ ID NO:268, SEQ ID NO:276, SEQ ID NO:284, SEQ ID NO:292, SEQ ID NO:300, SEQ ID NO:308, SEQ ID NO:316, SEQ ID NO: 324, SEQ ID NO:332, or SEQ ID NO:340; a CDR2 comprising the amino acid sequence of SEQ ID NO: 6, SEQ ID NO: 20, SEQ ID NO: 34, SEQ ID NO: 48, SEQ ID NO: 79, SEQ ID NO: 82, SEQ ID NO: 60, SEQ ID NO:63, SEQ ID NO:269, SEQ ID NO:277, SEQ ID NO:285, SEQ ID NO: 293, SEQ ID NO:301, SEQ ID NO:309, SEQ ID NO:317, SEQ ID NO:325, SEQ ID NO: 333, or SEQ ID NO:341; and a CDR3 comprising the amino acid sequence of SEQ ID NO: 7, SEQ ID NO: 21, SEQ ID NO: 35, SEQ ID NO: 49, SEQ ID NO: 80, SEQ ID NO: 83, SEQ ID NO: 61, SEQ ID NO:64, SEQ ID NO:270, SEQ ID NO:278, SEQ ID NO:286, SEQ ID NO:294, SEQ ID NO: 302, SEQ ID NO:310, SEQ ID NO:318, SEQ ID NO:326, SEQ ID NO:334, or SEQ ID NO: 342. In some aspects, the second IL31 binder comprises a VHH2 comprising a CDR1 comprising the amino acid sequence of SEQ ID NO: 10, SEQ ID NO: 24, SEQ ID NO: 38, SEQ ID NO: 52, SEQ ID NO: 84, SEQ ID NO: 87, SEQ ID NO:59, SEQ ID NO:251, SEQ ID NO:272, SEQ ID NO:280, SEQ ID NO:288, SEQ ID NO:296, SEQ ID NO:304, SEQ ID NO:312, SEQ ID NO: 320, SEQ ID NO:328, SEQ ID NO:336, or SEQ ID NO:344; a CDR2 comprising the amino acid sequence of SEQ ID NO: 11, SEQ ID NO: 25, SEQ ID NO: 39, SEQ ID NO: 53, SEQ ID NO: 85, SEQ ID NO: 88, SEQ ID NO:60, SEQ ID NO:63, SEQ ID NO:252, SEQ ID NO: SEQ ID NO: 273, SEQ ID NO:281, SEQ ID NO:289, SEQ ID NO:297, SEQ ID NO: 305, SEQ ID NO:313, SEQ ID NO:321, SEQ ID NO:329, SEQ ID NO:337, or SEQ ID NO:345; and a CDR3 comprising the amino acid sequence of SEQ ID NO: 12, SEQ ID NO: 26, SEQ ID NO: 40, SEQ ID NO: 54, SEQ ID NO: 86, SEQ ID NO: 89, SEQ ID NO:61, SEQ ID NO:64, SEQ ID NO:253, or SEQ ID NO: 274, SEQ ID NO:282, SEQ ID NO:290, SEQ ID NO:298, SEQ ID NO:306, SEQ ID NO:314, SEQ ID NO:322, SEQ ID NO:330, SEQ ID NO:338, or SEQ ID NO:346.

In some aspects, the method comprises use of a polypeptide that binds IL31, wherein (i) the VHH1 comprises a CDR1 comprising the amino acid sequence of SEQ ID NO: 59, a CDR2 comprising the amino acid sequence of SEQ ID NO: 60 or SEQ ID NO:63, and a CDR3 comprising the amino acid sequence of SEQ ID NO: 61 or SEQ ID NO:64; and (ii) the VHH2 comprises a CDR1 comprising the amino acid sequence of SEQ ID NO: 10, SEQ ID NO: 24, SEQ ID NO: 38, SEQ ID NO: 52, SEQ ID NO: 84, SEQ ID NO: 87, SEQ ID NO:59, or SEQ ID NO:251, a CDR2 comprising the amino acid sequence of SEQ ID NO: 11, SEQ ID NO: 25, SEQ ID NO: 39, SEQ ID NO: 53, SEQ ID NO: 85, SEQ ID NO: 88, SEQ ID NO: 60, SEQ ID NO:63, or SEQ ID NO:252, and a CDR3 comprising the amino acid sequence of SEQ ID NO: 12, SEQ ID NO: 26, SEQ ID NO: 40, SEQ ID NO: 54, SEQ ID NO: 86, SEQ ID NO: 89, SEQ ID NO:61, SEQ ID NO:64, or SEQ ID NO:253.

In some aspects, the method comprises use of a polypeptide that binds IL31, wherein (i) the VHH1 comprises an amino acid sequence at least 85%, at least 90%, at least 95%, at least 96%, at least 97%, at least 98%, at least 99%, or 100% identical to the amino acid sequence of SEQ ID NO: 3, SEQ ID NO: 17, SEQ ID NO: 31, or SEQ ID NO: 45; and/or (ii) the VHH2 comprises an amino acid sequence at least 85%, at least 90%, at least 95%, at least 96%, at least 97%, at least 98%, at least 99%, or 100% identical to the amino acid sequence of SEQ ID NO: 8, SEQ ID NO: 22, SEQ ID NO: 36, or SEQ ID NO: 50.

In some aspects, the method comprises use of a polypeptide that binds IL31, wherein (i) the VHH1 comprises an amino acid sequence at least 85%, at least 90%, at least 95%, at least 96%, at least 97%, at least 98%, at least 99%, or 100% identical to the amino acid sequence of SEQ ID NO: 4, SEQ ID NO: 18, SEQ ID NO: 32, or SEQ ID NO: 46; and/or (ii) the VHH2 comprises an amino acid sequence at least 85%, at least 90%, at least 95%, at least 96%, at least 97%, at least 98%, at least 99%, or 100% identical to the amino acid sequence of SEQ ID NO: 9, SEQ ID NO: 23, SEQ ID NO: 37, or SEQ ID NO: 51.

In some aspects, the method comprises use of a polypeptide that binds IL31, wherein the polypeptide comprises an amino acid sequence at least 85%, at least 90%, at least 95%, at least 96%, at least 97%, at least 98%, at least 99%, or 100% identical to the amino acid sequence of SEQ ID NO: 13, SEQ ID NO: 27, SEQ ID NO: 41, SEQ ID NO: 55, SEQ ID NO: 14, SEQ ID NO: 28, SEQ ID NO: 42, or SEQ ID NO: 56.

In some aspects, the method comprises use of a polypeptide that binds IL31, wherein the polypeptide comprises a Fc region, wherein the Fc region comprises an amino acid sequence at least 85%, at least 90%, at least 95%, at least 96%, at least 97%, at least 98%, at least 99%, or 100% identical to the amino acid sequence of SEQ ID NO: 62 or the amino acid residues 1-231 of SEQ ID NO: 62.

In some aspects, the method comprises use of a polypeptide that binds IL31, wherein the polypeptide comprises a Fc region, wherein the Fc region comprises an amino acid sequence at least 85%, at least 90%, at least 95%, at least 96%, at least 97%, at least 98%, at least 99%, or 100% identical to the amino acid sequence of SEQ ID NO: 90 or the amino acid residues 1-231 of SEQ ID NO: 90.

In some aspects, the method comprises use of a polypeptide that binds IL31, wherein the polypeptide comprises an amino acid sequence at least 85%, at least 90%, at least 95%, at least 96%, at least 97%, at least 98%, at least 99%, or 100% identical to the amino acid sequence of SEQ ID NO: 15 or the amino acid residues 1-506 of SEQ ID NO: 15, SEQ ID NO: 29 or the amino acid residues 1-496 of SEQ ID NO: 29, SEQ ID NO: 43 or the amino acid residues 1-487 of SEQ ID NO: 43, SEQ ID NO: 57 or the amino acid residues 1-507 of SEQ ID NO: 57, SEQ ID NO: 91 or the amino acid residues 1-506 of SEQ ID NO: 91, SEQ ID NO: 16 or the amino acid residues 1-506 of SEQ ID NO: 16, SEQ ID NO: 30 or the amino acid residues 1-496 of SEQ ID NO: 30, SEQ ID NO: 44 or the amino acid residues 1-487 of SEQ ID NO: 44, SEQ ID NO: 58 or the amino acid residues 1-507 of SEQ ID NO: 58, SEQ ID NO: 92 or the amino acid residues 1-506 of SEQ ID NO: 92.

In some aspects, the method comprises using a multimeric polypeptide, which comprises two or more of any one of the polypeptides or co-binders provided herein.

Exemplary inflammatory skin diseases include, but are not limited to, IL31-associated skin diseases, such as atopic dermatitis, prurigo nodularis, chronic spontaneous urticaria, chronic pruritus of unknown origin, psoriasis, and eczema. Rare skin disorders having similar features include, for example, epidermolysis bullosa, toxic epidermal necrolysis, and folliculitis. In other instances, skin diseases involving inflammation and/or immune system dysregulation can result in mobility issues, partial disability, and even death if left untreated. For example, psoriatic arthritis, diabetic skin ulcers, and melanoma are skin diseases requiring medical attention. In some instances, the polypeptide that binds IL31, multimeric polypeptide, or pharmaceutical composition thereof as described herein is used for treatment of atopic dermatitis, prurigo nodularis, chronic spontaneous urticaria, chronic pruritus of unknown origin, psoriasis, and eczema. In some instances, the polypeptide that binds IL31, multimeric polypeptide, or pharmaceutical composition thereof is used for treating any of the inflammatory skin diseases described herein.

In some aspects, the IL31-associated condition is a pruritic condition. Uses of a polypeptide that binds IL31, multimeric polypeptide, or pharmaceutical composition thereof to inhibit, reduce, prevent, or minimize the effects of a pruritic condition are described herein. In some aspects, the IL31-associated condition is atopic dermatitis (AD). In some aspects, the IL31-associated condition is prurigo nodularis (PN). In some aspects, the IL31-associated condition is chronic spontaneous urticaria. In some aspects, the IL31-associated condition is chronic pruritus of unknown origin. In some aspects, the IL31-associated condition is eczema. In some aspects, the IL31-associated condition is psoriasis. In some aspects, the IL31-associated condition is uremic pruritus (chronic kidney disease-associated pruritus). In some aspects, the IL31-associated condition is bile acid induced urticaria.

The polypeptide that binds IL31, multimeric polypeptide, or pharmaceutical composition thereof can be administered as needed to subjects in need thereof. Determination of the frequency of administration can be made by persons skilled in the art, such as an attending physician based on considerations of the condition being treated, age of the subject being treated, severity of the condition being treated, general state of health of the subject being treated and the like. In some aspects, the method comprises administering to a subject having an IL31-associated condition a single dose of the polypeptide that binds IL31, multimeric polypeptide, or pharmaceutical composition thereof. In some aspects, the method comprises administering to a subject having an IL31-associated condition multiple doses of the polypeptide that binds IL31, multimeric polypeptide, or pharmaceutical composition thereof.

In some aspects, the polypeptide that binds IL31, multimeric polypeptide, or pharmaceutical composition thereof is administered in a therapeutically effective amount for treating an inflammatory skin disease (e.g., a pruritic condition). In some aspects, the polypeptide that binds IL31, multimeric polypeptide, or pharmaceutical composition thereof is administered in a therapeutically effective amount for prophylactic treatment of an inflammatory skin disease (e.g., a pruritic condition). In some aspects, use of the polypeptide that binds IL31, multimeric polypeptide, or pharmaceutical compositions thereof for treating an inflammatory skin disease (e.g., a pruritic condition), including prophylactic treatment is described, wherein the polypeptide that binds IL31, multimeric polypeptide, or pharmaceutical compositions thereof is administered in a therapeutically effective amount.

In some aspects, the method and uses provided herein comprises administering the polypeptide, multimeric polypeptide, or the pharmaceutical composition in combination with one or more therapeutic agent. In some aspects, the one or more therapeutic agent is a drug substance useful in treating an inflammatory skin disease (e.g., a pruritic condition).

Administration "in combination with" one or more further therapeutic agents includes simultaneous (concurrent) and consecutive or sequential administration in any order. The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes. The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes. As used herein, "in conjunction with" refers to administration of one treatment modality in addition to another treatment modality. As such, "in conjunction with" refers to administration of one treatment modality before, during or after administration of the other treatment modality to the animal.

In some aspects, the one or more therapeutic agent comprises, for example, an antibody, a small molecule inhibitor, and/or a systemic immunosuppressant agent.

In some aspects, the methods and uses comprise administering a polypeptide that binds IL31, multimeric polypeptide, or a pharmaceutical composition thereof in combination with, for example, a topical corticosteroid, a calcineurin inhibitor, an anti-IL4RA antibody, an anti-IL13RA antibody, an anti-OSMR antibody, an anti-Ox40 antibody, an anti-Ox40L antibody, an anti-TSLP antibody an anti-IL17 antibody, an anti-TNFα antibody, an anti-CD20 antibody, an anti-CD19 antibody, an anti-CD25 antibody, an anti-IL4 antibody, an anti-IL13 antibody, an anti-IL23 antibody, an anti-IL31 antibody, an anti-IgE antibody, an anti-CD11a antibody, anti-IL6R antibody, anti-α4-Intergrin antibody, an anti-IL12 antibody, an anti-IL1β antibody, an anti-BlyS antibody, an anti-CKIT antibody, an anti-MRGPRX2 antibody, an anti-Fc epsilon receptor (FcεRI) antibody, an anti-SIGLEC-6 antibody, or an anti-SIGLEC-8 antibody. In some aspects, the methods and uses comprise administering a polypeptide that binds IL31 or a pharmaceutical composition thereof in combination with, for example, a small molecule inhibitor of IL4RA, IL13RA, IL13, IL31, OSMR, Ox40, Ox40L, TSLP, IL17, TNFα, CD20, CD19, CD25, IL4, IL23, IgE, CD11α, IL6R, α4-Intergrin, IL12, IL1β, BlyS, CKIT, MRGPRX2, Fc epsilon receptor (FcεRI), SIGLEC-6, and/or SIGLEC-8. In some aspects, the methods and uses provided herein comprise administering a polypeptide that binds IL31 or a pharmaceutical composition thereof in combination with, for example, a STAT inhibitor, a JAK inhibitor, a PI3K inhibitor, an AKT inhibitor, a MAPK inhibitor, a MRGPRX2 inhibitor, a topical corticosteroid, a calcineurin inhibitor, and/or a fusion protein comprising a portion of CTLA-4 and an Fc region of an immunoglobulin, optionally wherein the fusion protein is abatacept or belatacept. In some aspects, the methods and uses comprise administering a polypeptide that binds IL31, multimeric polypeptide, or a pharmaceutical composition thereof in combination with, for example, a topical steroid or a calcineurin inhibitor. In some aspects, the methods and uses comprise administering a polypeptide that binds IL31, multimeric polypeptide, or a pharmaceutical composition thereof in combination with systemic immunosuppressant, for example, cyclosporine A, methotrexate, mycophenolate mofetil, azathioprine, an oral corticosteroid, and interferon-gamma.

A therapeutic agent of the disclosure may be mixed with the other drug substance in a fixed pharmaceutical composition, or it may be administered separately, before, simultaneously with or after the other drug substance. Accordingly, the disclosure includes a combination of an agent described herein with one or more therapeutic agent in the same or different pharmaceutical composition.

In some aspects, the methods, uses, or pharmaceutical compositions for use described herein are for treating an IL31-associated skin disease such as atopic dermatitis, prurigo nodularis, chronic spontaneous urticaria, chronic pruritus of unknown origin, psoriasis, eczema, epidermolysis bullosa, epidermolysis bullosa simplex, seborrheic dermatitis, rosacea, toxic epidermal necrolysis, Stevens Johnson syndrome, Lyell syndrome, erythema multiforme, necrobiosis lipoidica, peeling skin syndrome, ichthyosis, neurodermatitis, pemphigus, folliculitis, uremic pruritus (chronic kidney disease-associated pruritus), bile acid induced urticaria, psoriatic arthritis, diabetic skin ulcers, and/or melanoma.

In some aspects, the polypeptide that binds IL31, multimeric polypeptide, or pharmaceutical composition thereof can be administered in vivo by various routes, including, but not limited to, parenteral, intramuscular, intraperitoneal, intravenous, intra-arterial, or subcutaneous. The appropriate route of administration may be selected according to the intended application. In some aspects, the polypeptide, multimeric polypeptide, or the pharmaceutical composition is administered parenterally. In some aspects, the polypeptide, multimeric polypeptide, or the pharmaceutical composition is administered by a subcutaneous route. In some aspects, the polypeptide, multimeric polypeptide, or the pharmaceutical composition is administered by an intravenous route. In some aspects, the polypeptide, multimeric polypeptide, or the pharmaceutical composition is administered by an intramuscular route. In some aspects, the polypeptide, multimeric polypeptide, or the pharmaceutical composition is administered by an intraperitoneal route.

In some aspects, treatment according to the methods, uses, and pharmaceutical compositions for use provided herein results in improved skin health comprising reduced skin redness, smaller skin lesions, and reduced skin itching.

In some instances, the subject is a mammal. In some instances, the subject is a human. Subjects treated by methods described herein may be infants, adults, or children.

B. Exemplary Indications and Patient Populations

Disclosed methods, uses, or pharmaceutical compositions for use herein comprise treating an IL31-associated condition in a subject in need thereof. The subject may have one or more indication that may benefit from the application of any one of the polypeptides described herein or pharmaceutical compositions thereof.

In some aspects, the subject receiving treatment has one or more of an inflammatory skin disease, a pruritic condition, atopic dermatitis, prurigo nodularis, chronic spontaneous urticaria, chronic pruritus of unknown origin, psoriasis, eczema, epidermolysis bullosa, epidermolysis bullosa simplex, seborrheic dermatitis, rosacea, toxic epidermal necrolysis, Stevens Johnson syndrome, Lyell syndrome, erythema multiforme, necrobiosis lipoidica, peeling skin syndrome, ichthyosis, neurodermatitis, pemphigus, folliculitis, uremic pruritus (chronic kidney disease-associated pruritus), bile acid induced urticaria, psoriatic arthritis, diabetic skin ulcers, and/or melanoma.

In some aspects, the subject receiving treatment has an inflammatory skin disease. In some aspects, the subject receiving treatment has a pruritic condition. In some aspects, the subject receiving treatment has atopic dermatitis. In some aspects, the subject receiving treatment has prurigo nodularis. In some aspects, the subject receiving treatment has chronic spontaneous urticaria. In some aspects, the subject receiving treatment has chronic pruritus of unknown origin. In some aspects, the subject receiving treatment has psoriasis. In some aspects, the subject receiving treatment has eczema. In some aspects, the subject receiving treatment has epidermolysis bullosa. In some aspects, the subject receiving treatment has epidermolysis bullosa simplex. In some aspects, the subject receiving treatment has seborrheic dermatitis. In some aspects, the subject receiving treatment has rosacea. In some aspects, the subject receiving treatment has toxic epidermal necrolysis. In some aspects, the subject receiving treatment has Stevens Johnson syndrome. In some aspects, the subject receiving treatment has Lyell syndrome. In some aspects, the subject receiving treatment has erythema multiforme. In some aspects, the subject receiving treatment has Necrobiosis lipoidica. In some aspects, the subject receiving treatment has peeling skin syndrome. In some aspects, the subject receiving treatment has ichthyosis. In some aspects, the subject receiving treatment has neurodermatitis. In some aspects, the subject receiving treatment has pemphigus. In some aspects, the subject receiving treatment has folliculitis. In some aspects, the subject receiving treatment has uremic pruritus (chronic kidney disease-associated pruritus). In some aspects, the subject receiving treatment has bile acid induced urticaria. In some aspects, the subject receiving treatment has psoriatic arthritis. In some aspects, the subject receiving treatment has diabetic skin ulcers. In some aspects, the subject receiving treatment has melanoma. In some aspects, the subject receiving treatment has airway hyperresponsiveness. In some aspects, the subject receiving treatment has allergic asthma. In some aspects, the subject receiving treatment has allergic conjunctivitis. In some aspects, the subject receiving treatment has allergic contact dermatitis. In some aspects, the subject receiving treatment has allergic lung disease. In some aspects, the subject receiving treatment has allergic rhinitis. In some aspects, the subject receiving treatment has alopecia areata. In some aspects, the subject receiving treatment has Alzheimer's disease. In some aspects, the subject receiving treatment has aspirin-exacerbated respiratory disease. In some aspects, the subject receiving treatment has asthma. In some aspects, the subject receiving treatment has atopic keratoconjunctivitis. In some aspects, the subject receiving treatment has bronchial asthma. In some aspects, the subject receiving treatment has bullous pemphigoid. In some aspects, the subject receiving treatment has chronic hand eczema. In some aspects, the subject receiving treatment has chronic inducible urticaria. In some aspects, the subject receiving treatment has chronic obstructive pulmonary disease. In some aspects, the subject receiving treatment has chronic Rhinosinusitis with nasal polyposis. In some aspects, the subject receiving treatment has colitis. In some aspects, the subject receiving treatment has dermatitis. In some aspects, the subject receiving treatment has eosinophilic COPD. In some aspects, the subject receiving treatment has eosinophilic esophagitis. In some aspects, the subject receiving treatment has eosinophilic gastritis. In some aspects, the subject receiving treatment has eosinophilic duodenitis. In some aspects, the subject receiving treatment has a food allergy. In some aspects, the subject receiving treatment has goblet cell metaplasia. In some aspects, the subject receiving treatment has hepatic fibrosis. In some aspects, the subject receiving treatment has Hodgkin's disease. In some aspects, the subject receiving treatment has idiopathic pulmonary fibrosis. In some aspects, the subject receiving treatment has Netherton syndrome. In some aspects, the subject receiving treatment has progressive systemic sclerosis. In some aspects, the subject receiving treatment has rheumatoid arthritis. In some aspects, the subject receiving treatment has sinusitis. In some aspects, the subject receiving treatment has Sjogren's syndrome. In some aspects, the subject receiving treatment has systemic lupus erythematosus. In some aspects, the subject receiving treatment has systemic sclerosis. In some aspects, the subject receiving treatment has type 1 diabetes. In some aspects, the subject receiving treatment has ulcerative colitis. In some aspects, the subject receiving treatment has chronic cholestatic pruritus. In some aspects, the subject receiving treatment has chronic kidney disease-associated pruritus. In some aspects, the subject receiving treatment has psoriasis-related itch. In some aspects, the subject receiving treatment has cutaneous T-cell lymphoma. In some aspects, the subject receiving treatment has acne rosacea. In some aspects, the subject receiving treatment has acne vulgaris. In some aspects, the subject receiving treatment has pruritus. In some aspects, the subject receiving treatment has arthritis. In some aspects, the subject receiving treatment has check-point inhibitor induced pruritus. In some aspects, the subject receiving treatment has chronic urticaria. In some aspects, the subject receiving treatment has contact dermatitis. In some aspects, the subject receiving treatment has contact hypersensitivity. In some aspects, the subject receiving treatment has Crohn's disease. In some aspects, the subject receiving treatment has cutaneous (lichen) amyloidosis. In some aspects, the subject receiving treatment has dermatomyositis. In some aspects, the subject receiving treatment has a drug-induced allergic reactions. In some aspects, the subject receiving treatment has inflammatory bowel disease. In some aspects, the subject receiving treatment has intrahepatic cholestasis of pregnancy. In some aspects, the subject receiving treatment has itch associated with wound healing. In some aspects, the subject receiving treatment has an itch associated with a burn. In some aspects, the subject receiving treatment has an itch associated with a sunburn. In some aspects, the subject receiving treatment has lichen planus. In some aspects, the subject receiving treatment has metabolic dysfunction-associated (non-alcoholic) steatohepatitis. In some aspects, the subject receiving treatment has osteoarthritis. In some aspects, the subject receiving treatment has osteoporosis. In some aspects, the subject receiving treatment has pemphigus herpetiformis. In some aspects, the subject receiving treatment has porokeratosis. In some aspects, the subject receiving treatment has primary biliary cholangitis. In some aspects, the subject receiving treatment has primary sclerosing cholangitis. In some aspects, the subject receiving treatment has pruritus. In some aspects, the subject receiving treatment has pruritus associated with cutaneous T-cell lymphoma. In some aspects, the subject receiving treatment has scleroderma. In some aspects, the subject receiving treatment has skin-tropic viruses and viral associated pruritus. In some aspects, the subject receiving treatment has spondyloarthritis. In some aspects, the subject receiving treatment has stasis dermatitis. In some aspects, the subject receiving treatment has wound healing pruritus.

In some aspects, the subject receiving treatment is an adult. In some aspects, the subject receiving treatment is a child. In some aspects, the subject has an inflammatory skin condition but is otherwise healthy. In some aspects, the subject has one or more comorbidities.

C. Exemplary Methods of Detecting IL31

Also provided herein is a method of detecting human IL31 in a biological sample. Methods provided herein are useful for the detection, diagnosis, and monitoring of an IL31-associated condition. The methods may be useful in determining whether the polypeptides or multimeric polypeptides described herein (e.g., Section II and the Examples) are an appropriate treatment for the subject.

In some aspects, the method comprises contacting the biological sample with any one of the polypeptides or multimeric polypeptides described herein (e.g., Section II and the Examples). In some aspects, the biological sample is a serum sample. In some aspects, the biological ample is contacted with the polypeptide or multimeric polypeptide described herein under conditions permissive for binding of the polypeptide or multimeric polypeptide to a human IL31. In some aspects, the method comprises detecting whether a complex is formed between the polypeptide or multimeric polypeptide and the human IL31 in the biological sample. In some aspects, the polypeptide that binds to IL31 or multimeric polypeptide is labelled with a detectable label. In some aspects, the detectable label comprises a radioisotope or radionuclide. In some aspects, the detectable label comprises $^{3}H$, $^{14}C$, $^{32}P$, $^{35}S$, $^{90}Y$, $^{99}Tc$, $^{111}In$, $^{125}I$, $^{131}I$, $^{177}Lu$, $^{166}Ho$, or $^{153}Sm$. In some aspects, the detectable label comprises chromogen. In some aspects, the detectable label comprises a fluorescent label. In some aspects, the detectable label comprises FITC, rhodamine, lanthanide phosphors, phycoerythrin, GFP, or BFP. In some aspects, the detectable label comprises an enzymatic label. In some aspects, the detectable label comprises horseradish peroxidase, luciferase, alkaline phosphatase or p-galactosidase. In some aspects, the detectable label comprises a chemiluminescent marker. In some aspects, the detectable label comprises a biotinyl group. In some aspects, the detectable label comprises a predetermined polypeptide epitope recognized by a secondary reporter. In some aspects, the detectable label comprises a leucine zipper pair sequence, a binding site for a secondary antibody, a metal binding domain, or an epitope tag. In some aspects, the detectable label comprises a magnetic agent. In some aspects, the detectable label comprises a gadolinium chelate. Methods of conjugating labels to an antibody are known in the art. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety. In some aspects, the polypeptide that binds IL31 or multimeric polypeptide need not be labeled, and the presence thereof can be detected using a labeled antibody which binds to the polypeptide or multimeric polypeptide. In some aspects, the method of detecting human IL31 human comprises direct and/or indirect detection via a detectable label and one or more detectable moieties. In some aspects, the detectable label is detected with a method known in the art for detecting specific antigen-binding interactions.

Various methods known in the art for detecting specific antigen-binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the polypeptide or multimeric polypeptide and is selected so as to meet the needs of various uses of the method which are often dictated by the availability of assay equipment and compatible immunoassay procedures. General techniques to be used in performing the various immunoassays noted above are known to those of ordinary skill in the art.

VI. Exemplary Kits

Also provided are articles of manufacture and kits that include any of the polypeptides that bind to IL31 provided herein (e.g., Section II and the Examples) and suitable packaging. In some aspects, the disclosure includes a kit with (i) a polypeptide or multimeric polypeptide that binds IL31, and (ii) instructions for using the kit to administer the polypeptide or multimeric polypeptide to an individual. In some aspects, the disclosure includes a kit with (i) a pharmaceutical composition comprising a polypeptide or multimer polypeptide that binds IL31 (e.g., Section IV and the Examples), and (ii) instructions for using the kit to administer the pharmaceutical composition to an individual.

Suitable packaging for compositions described herein are known in the art, and include, for example, vials (e.g., sealed vials), vessels, ampules, bottles, jars, flexible packaging (e.g., sealed Mylar or plastic bags), and the like. These articles of manufacture may further be sterilized and/or sealed. Instructions supplied in the kits of the disclosure are typically written instructions on a label or package insert (e.g., a paper sheet included in the kit), but machine-readable instructions (e.g., instructions carried on a magnetic or optical storage disk) are also acceptable. The kit may further comprise a description of selecting an individual suitable or treatment.

The following examples illustrate particular aspects of the disclosure and are not intended in any way to limit the disclosure.

EXAMPLES

Example 1. Anti-IL31 Single Binder Library Construction

To identify IL31-specific single binders (VHHs), two immunization campaigns were carried out. In campaign 1, 4 llamas were immunized with His-tagged human IL31. In campaign 2, His-tagged human IL31 was crosslinked to itself or to keyhole limpet hemocyanin (KLH) or bovine serum albumin (BSA). Self-crosslinked IL31, non-cross-linked IL31, and KLH/BSA crosslinked IL31 were immunized to two animals each. Following repeated injections, plasma samples were collected from the llamas and analyzed for the presence of anti-IL31 single binders via ELISA. Specifically, MAXISORP™ 96-well plates were coated with human IL31 protein followed by incubation with plasma, anti-camelid VHH cocktail, and HRP-conjugated secondary antibody.

From the whole blood of animals demonstrating the presence of anti-IL31 single binders, red blood cells were lysed, whole RNA was extracted from the white blood cell using QIAGEN® RNeasy, and cDNA was synthesized by RevertAid H Minus First Strand cDNA Synthesis Kit (Thermo Fisher Scientific). The anti-IL31 single binder library was generated from cDNA by PCR using Q5® Hot Start DNA polymerase (New England Biolabs). Additionally, 5'-HR arm and 3'-HR arm, which are from upstream and downstream sequences of gene insertion site of yeast surface display vector respectively, were constructed by PCR using Q5R Hot Start DNA polymerase. The anti-IL31 single binder library was extended at 5' and 3' ends with 5'-HR arm and 3'-HR arm by overlap extension PCR using Q5® Hot Start DNA polymerase, and its product was further amplified in a PCR using ONETAQ® DNA polymerase (New England Biolabs) (WO2022147463A2, WO2022147463A3). The final PCR product was electroporated into EBY100 strain *Saccharomyces cerevisiae* together with the linearized yeast surface display plasmid for homologous recombination (Benatuil et al., Protein Eng Des Sel. 2010 April; 23(4):155-9; Wang, Protein Eng Des Sel. 2005 July; 18(7):337-43). The anti-IL31 single binder transformed cells were cultured in SDCAA (Synthetic Dextrose medium supplemented with Casamino Acids) medium.

Example 2. Campaign 1 Single Binder Library Selection

Figure 1:
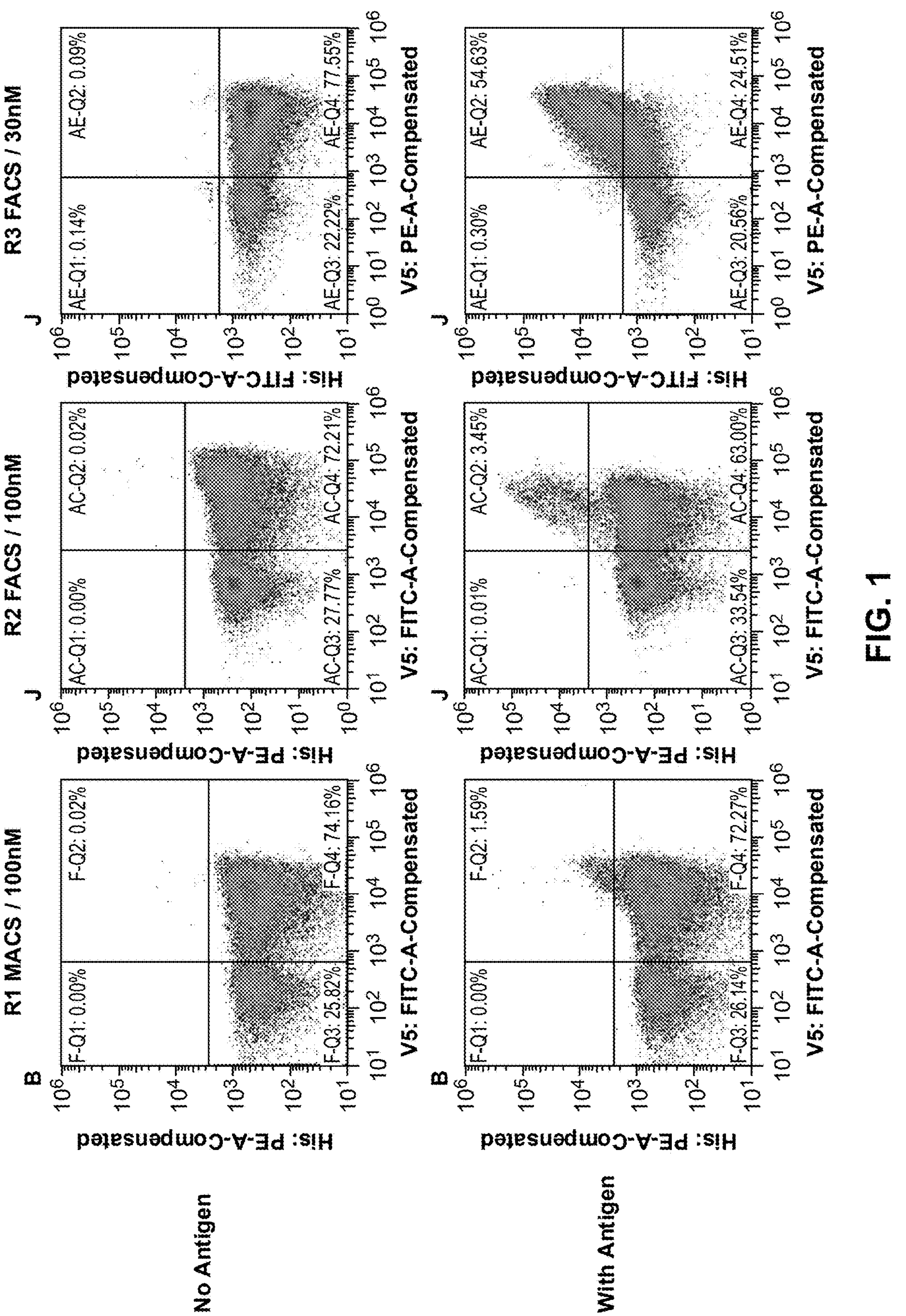
FIG. 1 shows flow cytometry plots for Campaign 1 anti-IL31 single binder selection. Round 1 (R1) MACS flow plot images were taken from flow cytometry analysis of R1

The anti-IL31 single binder yeast library was induced with 2% galactose (SGCAA, Synthetic Galactose medium supplemented with Casamino Acids) overnight. Library transformed cells were blocked in a blocking buffer (PBS containing 0.5% BSA). 100 nM His-tagged recombinant human IL31 was mixed with 2× mols (relative to His-tagged human IL31) of TrisNTA-Biotin and was used for binding the blocked cells. Cells were subsequently incubated with a mix of anti-biotin microbeads and streptavidin microbeads, and anti-IL31 displaying cells were enriched using magnetic activated cell sorting (MACS). Enrichment was confirmed via staining with phycoerythrin (PE) conjugated His antibody (Miltenyi Biotec, Inc. Auburn, CA) and fluorescein isothiocyanate (FITC) conjugated V5 antibody, followed by flow cytometric analysis (FIG. 1). Following MACS, anti-IL31 single binder displaying cells (second quadrant) were sorted via two consecutive rounds of FACS using 100 nM and 30 nM biotinylated human IL31, respectively. V5 tag is encoded downstream of single binder gene in the yeast surface display vector, and it is used to assess single binder expression. PE and FITC fluorophores were alternated between streptavidin and V5 antibody. Sorted cells were cultured in SDCAA medium for plasmid isolation.

For plasmid isolation, cultured cells were treated with Zymolyase, and plasmids were isolated using QIAGEN® Spin Miniprep Kits. Approximately 750 bases segment on the plasmid library covering anti-IL31 VHH and about 400 bases upstream segment of the anti-IL31 single binder was PCR amplified using Q5® Hot Start DNA polymerase with the first half of linker library sequences within reverse primer. Another 750 bases segment on the plasmid library covering anti-IL31 single binder and about 400 bases segment downstream of anti-IL31 single binder was PCR amplified using Q5® Hot Start DNA polymerase with the second half of linker library sequences within forward primer to generate VHH2. A linear co-binder library was constructed by GIBSON ASSEMBLY® between VHH1 and VHH2 (e.g., see WO2022147463A2, WO2022147463A3). The assembled co-binder library was purified on a 1% agarose E-gel. The purified library was further amplified via PCR using ONETAQ® DNA polymerase. The amplified library was electroporated into EBY100 *S. cerevisiae* cells together with linearized yeast surface display plasmid, which has about 400 bases overlap at 5' and 3' ends with co-binder library DNA, for homologous recombination. Anti-IL31 co-binder transformed cells were cultured in SDCAA medium.

Anti-IL31 co-binder library-transformed yeast cells were induced with 2% galactose overnight. Induced yeast cells were blocked with blocking buffer as described above. His-tagged human IL31 was mixed with 2× concentration (relative to His-tagged human IL31) of Tris-NTA Biotin trifluoroacetate salt (Sigma-Aldrich, St. Louis, MO) and was used for incubating the blocked cells at final His-tagged human IL31 concentration of 10 nM in blocking buffer. After further incubation with mix of anti-biotin microbeads and streptavidin microbeads, anti-IL31 co-binder-displaying cells were enriched using MACS in round 1. Enrichment was confirmed via staining with PE conjugated His antibody (Miltenyi Biotec, Inc. Auburn, CA) and FITC conjugated V5 antibody, followed by flow cytometric analysis (FIG. 2). MACS-enriched cells were further sorted (AH gate in round 2 and M gate in round 3) via three consecutive rounds of FACS using 10 nM, 3 nM, and 1 nM his-tagged human IL31. In the fourth round of FACS, AI, a higher affinity gate, and AJ, a lower affinity gate, were separately sorted into 96-well plates with single cell each well. PE, FITC, and allophycocyanin (APC) were rotated as fluorophore for His antibody and V5 antibody. Colony PCR was performed with sorted cells and PCR products were used for sequencing.

Example 3. Campaign 2 Single Binder Library Selection

Campaign 2 derived yeast surface display IL31 single binder library was enriched through a single round (R1) of MACS using 30 nM His-tagged human IL31 following the method described above (FIG. 3). MACS-enriched cells were subsequently sorted through two rounds of positive selection (M and I gates for round 2 (R2) and round 3 (R3), respectively) via FACS with human IL31 at 30 nM and 10 nM. Round 3 sorted cells were negatively selected (AL gate) in round 4 (R4) after staining with PE conjugated streptavidin and FITC conjugated V5 antibody without human IL31 via FACS to reduce potential off-target binders. Finally, cells were sorted (I gate) in round 5 (R5) via FACS for binding to 10 nM human IL31, and sorted cells were cultured in SDCAA medium for plasmid isolation.

Plasmids from campaign 1 and campaign 2 were mixed and the co-binder library was constructed following the method described above. Anti-IL31 co-binder-displaying yeast cells were MACS enriched with human IL31 at 0.3 nM in blocking buffer in round 1 (R1) (FIG. 4). Cells were subsequently enriched further using FACS with 3 nM human IL31 in round 2 (R2). To reduce potential off-target binders, cells were then incubated with biotinylated polyspecificity reagent prepared from CHO-K1 cell lysate (Xu et al., Protein Eng Des Sel. 2013 October; 26(10):663-70), PE conjugated streptavidin, APC conjugated His antibody, and FITC conjugated V5 antibody in blocking buffer. PE negative, APC negative, and FITC positive populations (K gate) were sorted in round 3 (R3), and anti-IL31 VHH-containing yeast cells were further enriched through two more rounds of FACS using 1 nM (round 4 (R4)) and 0.1 nM (round 5 (R5)) human IL31. Single cells with the higher affinity (K) and lower affinity (L) for IL31 were sorted into 96-well plates and colony PCR was performed with sorted cells and PCR products were used for sequencing.

Example 4. Preliminary Assessments for Selection of Co-Binder Candidates

A total of 2006 co-binders from the two co-binder campaign libraries were sequenced and subjected to initial binding affinity testing. Fc fusions were prepared and subjected to one or more further assessments to determine affinity, potency, and developability, including polyspecificity, melting temperature, hydrophobicity, and thermal stability. As shown in Table 3, four co-binder candidates, 1C10, 1D1, 1H5, and 21H7 showed strong binding affinity and potency and desirable developability characteristics.

TABLE 3

Co-Binder Selection Characteristics

| Clone | Activity (IC50, nM) | Affinity (KD, pM) | Tm (° C.) | BVP binding | HIC retention time (min) | Thermal Stability (% Aggregation, 2d) |
|---|---|---|---|---|---|---|
| 1C10 | 8.5 ± 1.3 | 58.7 ± 50.5 | 66.5 | No | 16.36 | −0.3 |
| 1D1 | 6.7 ± 0.9 | 24 ± 29 | 60.7 | No | 15.93 | 0.2 |
| 1H5 | 6.1 ± 0.7 | 3.2 ± 1.3 | 58.7 | No | 15.24 | 0.9 |
| 21H7 | 8.4 | 14.8 | 61 | No | 15.76 | 0 |

Tm: melting temperature;
BVP: Baculovirus particle;
HIC: hydrophobic interaction chromatography Binding affinity was measured using Biotin CAPture Kit (Cytiva Life Sciences) and the BIACORE™ T200 SPR system (Cytiva Life Sciences). Initially, Biotin CAPture Reagent (Cytiva Life Sciences) was flowed to immobilize 3 nM biotinylated IL31 (ligand). 3 nM, 9 nM, and 27 nM anti-IL31 co-binders were flowed as analyte with 180 seconds association and running buffer was flowed with 3000 seconds dissociation. The sensor chip was regenerated by guanidine hydrochloride and sodium hydroxide.

IC50 Assays (pSTAT Assay and IL31 Dimerization Assay)

(1) pSTAT3 Assay. Candidate co-binders were screened by a cell-based potency assay that measured direct response of IL31 co-binders in A549 cells expressing IL31Rα. After binding to IL31Rα, IL31 activates JAK1/2 signaling molecules, which, in turn, activate phosphorylation of STAT3. A decrease in IL31 signaling is evidenced by a reduction in STAT3 phosphorylation as the concentration of IL31 co-binders exposed to the cells is increased. A549 cells were cultured in Ham's F12K+2 mM Glutamine+10% FBS at 37° C. with 5% $CO_2$. 24 hours before the experiment, A549 cells were detached and plated into 96-well plates at $2\times10e^4$ cells/well in Ham's F12K+2 mM Glutamine+10% FBS and incubated overnight. The next day, the cell culture supernatant was removed from the plate and the cells were washed with 100 μl serum free medium followed by 1 hour serum starvation at 37° C. with 50 μl of serum free medium. Co-binders were diluted from 80 μg/ml with 2× dilution for 12 points and incubated with equal volume of 1 μg/ml IL-31 in serum free medium for 1 hour at room temperature. 50 μl of IL31 and co-binder complex were added to each well of the cell culture plate and incubated for 10 minutes at 37° C. The supernatant was then removed and the cells were lysed in 110 μl of lysis buffer. A pSTAT3 ELISA was performed using PATHSCAN® Phospho-Stat3 (Tyr705) Sandwich ELISA Kit #7300 (Cell signaling technologies, Danvers, MA).

(2) IL31 Dimerization Assay. IL-31 dimerization kits were purchased from Eurofins Scientific (Fremont, CA). The assay was performed according to the instructions. U2OS OSMRb/IL31R dimerization cells were seeded at 0.1 million/well in 80 μl assay complete cell plating 0 reagent medium into a 96-well Clear Flat Bottom White Plate and incubated at 37° C., 5% CO2 for overnight. Co-binders were diluted from 30 ug/ml with 3× dilution for 12 points and incubated with equal volume of 10 ng/ml IL-31 in assay complete cell plating 0 reagent for one hour at room temperature. 20 μl of IL31 and IL31 co-binders complex were added to each well of the cell culture plate and incubated for 16 hours. Plates and detection reagent were equilibrated to room temperature. 100 μl of detection reagent mix was added to each well of the plates and incubated at room temperature for 1 hour in the dark. RLU was read using VICTOR® Nivo™ Multimode Plate Reader.

Thermostability was also analyzed by differential scanning fluorimetry (DSF) according to the manufacturer's instructions using a CFX90 RT-PCR instrument (Bio-Rad). In triplicate, co-binder samples (2.5 μg to 10 μg) were added to 5× final dye (INVITROGEN™ SYPRO™ Orange; Thermo Fisher Scientific) solution in 30 μL final volume. The hydrophobic dye binds to proteins as they unfold due to an increase in temperature. Temperature was increased from 10° C. to 95° C. in increments of 0.5° C. per second to develop a melting curve. Data was analyzed using CFX Maestro Software (Bio-Rad) to find the first derivative, or Tm, of the melting curve. At Tm, 50% of co-binder is in native state and 50% is in denatured state. Tm≥55° C. was used as a minimal cutoff point to screen drug candidates.

To assess polyspecificity of co-binder candidates, baculovirus particle (BVP) binding was assessed by ELISA according to the manufacturer's protocol (MEDNA Scientific, Irving, TX). MAXISORP™ 96-well plates were coated with baculovirus particle in sodium carbonate buffer (pH9.6). Coated plates were blocked in blocking buffer (PBS with 0.5% BSA) and incubated with 1 μM samples. Horseradish peroxidase conjugated anti-human Fc was used for detection. Hits within ≤5x of the negative control (blank) were given a pass in the assay which is within the range of commercially viable mAb for polyspecificity.

Hydrophobicity was measured by hydrophobic interaction chromatography (HIC) using a published protocol (Jain et al., 2017 Proc Natl Acad Sci, 114(5):944-949.). This assay measures relative protein surface hydrophobicity which in turn can indicate protein tendency to self-associate under salt stress conditions. Co-binder samples (5 μg to 10 μg) were re-buffered to Buffer B (0.1 M sodium phosphate pH 6.5)+1M Ammonium Sulfate (AS) and then loaded on a 1.67 mL HPLC Proteomix HIC Butyl-NP5 column (4.6×100 mm) at 0.75 mL/min. The column was equilibrated with Buffer A (0.1 M Sodium Phosphate pH 6.5+2 M AS). A linear gradient to 100% Buffer B was developed over 20 minutes. Buffer B concentration was held for 5 minutes at 100% before the column was re-equilibrated with buffer A. Detection was performed with a UV detector set at 280 nm. HIC retention time was measured for one minute.

HPLC Size Exclusion Chromatography (SEC) was used to assess thermal stability of co-binders as measured by percent aggregation after storage for two days at 40° C. Co-binder samples (10 μg) were loaded onto a ZENIX®-C SEC-300 gel filtration column (7.8×150 mm) (SEPAX Technologies). An isocratic gradient was performed with 150 mM Sodium Phosphate pH 7.0 according to the manufacturer's instructions (SEPAX Technologies) at 1 mL/min. Additionally, percent aggregates and percent monomer were measured (data not shown).

Heparin Chromatography was performed as an in vitro predictor for antibody and co-binder clearance rate through pinocytosis and was based on previous methods (Kraft et al., 2020, MAbs; 12(1):1683432-949). Co-binder protein samples (5 to 10 μg) were diluted at least 10-fold in 15 mM MES pH 5.5 and then loaded on a 1.7 mL HPLC POROS™ Heparin column (4.6×100 mm) (Thermo Fisher Scientific) at 1 mL/min. Buffer A is 50 mM Tris buffer pH 7.4 and Buffer B is Buffer A+1 M NaCl. After 4-minute post injection, a 55% B linear gradient was developed over 23 min. Buffer B concentration was increased to 100% and held for 2 minutes before the column was re-equilibrated with buffer A. Detection of co-binder protein level was performed with a UV detector set at 280 nm.

Example 5. Sequencing and Alignment of Co-Binder Candidates

High-binder candidate co-binder clones were sequenced and decomposed into VHH1 and VHH2. VHH1 and VHH2 single binders exhibited low affinity in IL31 binding with Kds in the double digits to single digit nM range. In contrast, co-binder candidates were 100-1000-fold more potent. The bi-paratropic format of the co-binders led to significant synergy in binding.

Sequence alignments of candidate co-binder clones 1D1, 1H5, and 1C10 from the first campaign and 21H7 from the second campaign revealed similarities among the CDR sequences. In particular, the VHH1 CDRs of these candidates are very similar. In fact, the VHH1 CDRs of clone 1C10 from the first campaign and 21H7 from the second campaign are identical and the VHH1 CDRs of clone 1D1 and 1H5 from the first campaign are identical.

Table 1 provides amino acid sequences for clone 1C10 VHH1 single binder (SEQ ID NO: 3), 1C10 VHH2 single binder (SEQ ID NO: 8), and 1C10 co-binder (SEQ ID NO: 13); 1D1 VHH1 single binder (SEQ ID NO: 17), 1D1 VHH2 single binder (SEQ ID NO: 22), and IDI co-binder (SEQ ID NO: 27); clone 1H5 VHH1 single binder (SEQ ID NO: 31), 1H5 VHH2 single binder (SEQ ID NO: 36), and 1H5 co-binder (SEQ ID NO: 41); and clone 21H7 VHH1 single binder (SEQ ID NO: 45), 21H7 VHH2 single binder (SEQ ID NO: 50), and 21H7 co-binder (SEQ ID NO: 55). Also provided in Table 1 are clone 1C10 VHH1 CDR1, CDR2, and CDR3 (SEQ ID NOs: 5, 6, and 7, respectively), clone 1C10 VHH2 CDR1, CDR2, and CDR3 (SEQ ID NOs: 10, 11, and 12, respectively), clone 1D1 VHH1 CDR1, CDR2, and CDR3 (SEQ ID NOs: 19, 20, and 21, respectively), clone 1D1 VHH2 CDR1, CDR2, and CDR3 (SEQ ID NOs: 24, 25, and 26, respectively), clone 1H5 VHH1 CDR1, CDR2, and CDR3 (SEQ ID NOs: 33, 34, and 35, respectively), clone 1H5 VHH2 CDR1, CDR2, and CDR3 (SEQ ID NOs: 38, 39, and 40, respectively), clone 21H7 VHH1 CDR1, CDR2, and CDR3 (SEQ ID NOs: 47, 48, and 49, respectively), and clone 21H7 VHH2 CDR1, CDR2, and CDR3 (SEQ ID NOs: 52, 53, and 54).

Interestingly, several other candidate clones had VHH sequences (either VHH1 or VHH2) similar or identical to the VHH1 sequences of the candidates 1C10, 1D1, 1H5, and 21H7. See FIG. 5. However, as shown in Table 4, below, while many of the candidate clones having the same or similar VHH sequences to the candidates 1C10, 1D1, 1H5, and 21H7 exhibited good binding affinity and/or potency, they did not exhibit favorable developability properties like 1C10, 1D1, 1H5, and 21H7. Only the unique co-binders 1C10, 1D1, 1H5, and 21H7 displayed desirable binding affinity, potency, and developability characteristics and were carried forward for further characterization and development.

TABLE 4

Co-Binder Selection Characteristics

| Clone | Activity (IC50, nM) | Affinity (KD, pM) | Tm (° C.) | BVP binding | HIC retention time (min) | Thermal Stability (% Aggregation, 2d) |
|---|---|---|---|---|---|---|
| 1H5 | 6.1 ± 0.7 ($P^3$) | 3.2 ± 1.3 | 58.7 | No | 15.24 | 0.9 |
| 1D1 | 6.7 ± 0.9 ($P^3$) | 24 ± 29 | 60.7 | No | 15.93 | 0.2 |
| 1C10 | 8.5 ± 1.3 ($P^3$) | 58.7 ± 50.5 | 66.5 | No | 16.36 | −0.3 |
| 21H7 | 8.4 ($P^3$) | 14.8 | 61 | No | 15.76 | 0 |
| 20C7 | 9.8 ($P^3$) | 27.1 | 58.5 | No | 18 | 0 |
| 1H4 | 9.1 ± 1.6 ($P^3$) | 10.8 ± 9 | 53.5 | No | 16.15 | 49 |
| 1C2 | 10.5 ± 0.8 ($P^3$) | 109.9 ± 45.2[##] | 66.5 | No | 17.9^ | 0 |
| 1E3 | 12.1 ± 0.9 ($P^3$) | 8.6 ± 4 | 58 | No | 15.32 | 0 |
| 1D12 | 14.6 ± 0.2 ($P^3$) | 152.3 ± 42.6[##] | 60.5 | No | 18.09^ | 0 |

TABLE 4-continued

| Co-Binder Selection Characteristics | | | | | | |
|---|---|---|---|---|---|---|
| Clone | Activity (IC50, nM) | Affinity (KD, pM) | Tm (° C.) | BVP binding | HIC retention time (min) | Thermal Stability (% Aggregation, 2d) |
| 2H2 | 24.3 ± 0.2[#] (P[3]) | 97.7 ± 51.5 | 57.8 | No | 17.49 | 0 |
| 1H2 | 34.9 ± 1.7[#] (P[3]) | 3145 ± 3772.9[##] | 60.5 | No | No peak | 5.6 |
| 1C7 | 7.9 ± 1.0 (P[3]) | 202.3 ± 24.2[##] | 62 | Yes* | 15.91 | 0 |
| 1B10 | 12.6 ± 0.9 (P[3]) | 140.3 ± 12.9[##] | 63.5 | Yes* | 18.06^ | 1.8 |
| 1G6 | 13.4 ± 0.8 (P[3]) | 419.3 ± 9.3[##] | 46.8** | Yes* | 17 | 41.7 |
| 1E2 | 18.1 ± 0.8 (P[3]) | 94.3 ± 12.4 | 64.3 | Yes* | 15.86 | 0 |
| 1B12 | 19.8 ± 2.6 (P[3]) | 158.7 ± 8.3[##] | 59 | Yes* | 16.18 | 5 |
| 1C3 | 55.9 ± 1.6[#] (P[3]) | 466.5 ± 285[##] | 57.5 | Yes* | 18.42^ | 6.7 |
| 21A4 | 0.121 (D) | 300 ± 140 | 57 | | 15.3 | 6 |
| 21C11 | 0.007 (D) | 1600 ± 100 | 55.5 | | 15.3 | 45 |
| 21C8 | 0.013 (D) | 10000 ± 210 | 59 | | 14.9 | 1.4 |
| 21B11 | 0.002 (D) | 42 ± 14 | 57.5 | | 14.7 + 15.7 | 36 |
| 21G5 | 0.011 (D) | 890 ± 110 | 58.5 | | 14.1 + 15.7 | 5.5 |
| 21G7 | 0.082 (D) | 2100 ± 120 | 55.5 | | 14.3 + 15.5 | 60 |
| 21H2 | 0.032 (D) | 71 ± 19 | 56.5 | | 15 + 16 + 18.6 | 18.6 |
| 19B5 | 0.039 (D) | 260 ± 3 | 58.5 | | 15.7 | 27.5 |
| 22D1 | 0.062 (D) | 280 ± 2.5 | 57.5 | | 13.8 + 16 | 10.2 |
| 22D8 | 0.006 (D) | 560 ± 35 | 59.5 | | 14.6 | 1.8 |

Tm: melting temperature;
BVP: baculovirus protein;
HIC: hydrophobic interaction chromatography
[#]In vitro potency below the desired threshold;
[##]Binding affinity below the desired threshold;
*Polyspecificity score above the desired threshold;
**Melting temperature below the desired threshold;
^HIC retention time above the desired threshold
(P[3]) denotes pSTAT3 assay utilized for determining Activity (IC50)
(D) denotes IL31 Dimerization assay utilized for determining Activity (IC50)

Example 6. Further Characterization of Co-Binders

Large-scale expression of 1H5, 1D1, 1C10, and 21H7 showed co-binders exhibited strong affinity and cell potency (data not shown), similar to data described in Example 4. These four candidates were also assessed for several manufacturability criteria. 1H5, 1D1, 1C10, and 21H7 demonstrated good stability in a freeze-thaw assay in optimized buffer formulation (data not shown).

As shown in Table 5, below, 1H5, 1D1, 1C10, and 21H7 retained strong affinity after repeated freeze-thaw.

TABLE 5

| Co-binder Freeze-thaw Analysis | | | | |
|---|---|---|---|---|
| Co-binder clone | Sample | ka (1/s*M) | kd (1/s) | KD (M) |
| 1H5 | Baseline | 1.01E+06 | 1.38E−04 | 1.36E−10 |
| | 3x F/T | 8.90E+05 | 5.51E−04 | 6.19E−10 |
| 1D1 | Baseline | 2.09E+05 | 4.05E−04 | 1.94E−09 |
| | 3x F/T | 1.95E+05 | 6.28E−04 | 3.22E−09 |
| 1C10 | Baseline | 2.20E+05 | 3.30E−04 | 1.50E−09 |
| | 3x F/T | 1.96E+05 | 6.75E−04 | 3.45E−09 |
| 21H7 | Baseline | 2.28E+05 | 4.23E−03 | 1.86E−08 |
| | 3x F/T | 2.24E+05 | 4.35E−03 | 1.94E−08 |

When expressed at large-scale, 1H5, 1D1, 1C10, and 21H7 retained good thermostability (Tm≥55° C.) as measured by DSF assay and showed good hydrophobicity properties (data not shown). Among the four co-binders, 1H5 showed stronger non-specific binding to BVP, insulin, and DNA versus the other three co-binders (data not shown) and was deprioritized. Overall, however, 1H5, 1D1, 1C10, and 21H7 demonstrated good overall developability.

1D1, 1C10, and 21H7 were concentrated to concentrations of approximately 200 mg/ml and higher in Buffer 1 (20 mM Histidine, 5% sucrose, 50 mM NaCl, pH 6.0) without evidence of aggregation or degradation (see Table 6).

TABLE 6

| Co-binder Concentration and Recovery Percentage | | | |
|---|---|---|---|
| | 1D1Fc | 1C10Fc | 21H7Fc |
| mg/mL | 225 ± 21 | 185 ± 19 | 267 ± 9.5 |
| % Recovery | 105 | 92 | 92 |

Example 7. Designs of Fc Format and Humanization of Co-Binders

Fc formats having a general structure of Hinge-CH2-CH3 for 1C10, 1D1, 1H5, 21H7 were designed using huIgG1Fc_YTE_C→S (SEQ ID NO: 62), which includes (1) the CH2 YTE mutations (M252Y, S254T, T256E as determined by EU Numbering) to reduce binding to IgG Fc receptors and diminished capacity for ADCC, and (2) a hinge cysteine (C) to serine(S) mutation (C220S as determined by EU Numbering).

The amino acid sequences for 1C10, 1D1, 1H5, and 21H7 co-binders with huIgG1Fc_YTE_C→S are provided in Table 1 as SEQ ID NOs: 15, 29, 43, and 57, respectively.

VHH sequences of 1H5, 1D1, 1C10, and 21H7 were subjected to humanization. Framework regions 1, 2, 3, and 4 were converted to human VH framework regions by searching human VH germline sequences. The selected human frames were grafted into the VHH sequences. In certain cases, a part of VHH frame 2 from Llama were solvent exposed as opposed to being in the interface between VH/VL in IgG format. Thus, back mutations were introduced. The three CDRs were left intact from the original sequences.

For example, during the 1C10 humanization process, frames 1, 2 and 3 were grafted with human germline IGHV3-74*02 frames, except that frame 2 was maintained from the original sequence (with 3 back mutations). VHH2 frames 1, 2 and 3 were grafted from IGHV3-74*01 where frame 2 was maintained from the original 3 amino acids. Both VHH1 and VHH2 FR4 were grafted with human JH1. As shown in Table 7, below, a humanized version was derived of 1D1, 1C10, and 21H7 that retained the properties of the wildtype co-binder.

Biocytogen (Wakefield, MA) and were acclimated for one week before the start of the study. Prior to study initiation, all mice were administered recombinant hIL-31 (5 μg/mouse, Sino Biological, Beijing, China) via intravenous injection and observed for pruritic response for 1.5 hours. Mice that demonstrated a pruritic response to hIL31 injection were allocated randomly into 3 treatment groups. 21H7, 1C10, and 1D1 (SEQ ID NO: 58, 16, and 30, respectively) were administered on Study Day-1, Day 2, Day 6, Day 9, and Day 30 at 0.01, 0.1, 0.3, 1, and 3 mg/kg. Approximately 24 hours after test article administration, plasma was collected from all co-binder treated mice. Recombinant hIL31 was injected intravenously (5 μg/mouse) on Day 0, Day 3, Day 7, Day 10, and Day 31, and mouse scratching activity was recorded for 1.5 hours (FIG. 6A).

Scratching activity for all animals was normalized to scratching activity assessed prior to study initiation. Clear incidence of pruritic activity was observed in all treatment groups administered at 0.01 and 0.1 mg/kg. When test article was administered at 0.3 mg/kg a modest reduction in relative

TABLE 7

Properties of humanized co-binder candidates versus wild-type.

| Co-binder | Mutation | SEC_HPLC Purity (%) | Tm AVG | BVP Relative to blank | BVP Relative to WT | % Loss at 40° C., 2d | EC50 (pSTAT3) nM | KD (M) | HIC (min) | Humanization score |
|---|---|---|---|---|---|---|---|---|---|---|
| 1D1 | WT | 97.05 | 59.8 | 7.53 | 1.00 | Stable | 8.42 | 1.53E−11 | 16.4 | NA |
| 1D1 | M1M1M1M1 | 99.45 | 58.8 | 5.86 | 0.78 | Stable | 7.4 | 4.41E−11 | 16.7 | 0.965 |
| 1D1 | M1M2M1M1 | 99.26 | 59.0 | 7.23 | 0.96 | Stable | 9.57 | 5.97E−11 | 16.6 | 0.9675 |
| 1C10 | WT | 99.11 | 58.3 | 3.21 | 1.00 | Stable | 6.57 | 1.26E−11 | 16.9 | NA |
| 1C10 | M1M1M1M1 | 99.35 | 59.0 | 4.59 | 1.43 | Stable | 6.88 | 1.61E−11 | 17.3 | 0.9425 |
| 1C10 | M1MIM1M2 | 99.12 | 56.5 | 4.19 | 1.31 | Stable | 6.51 | 1.45E−11 | 17.1 | 0.9225 |
| 1C10 | M1M2M1M1 | 99.37 | 58.5 | 4.61 | 1.44 | Stable | 5.92 | 2.14E−11 | 17.1 | 0.9475 |
| 1C10 | M1M2M1M2 | 99.21 | 56.0 | 3.95 | 1.23 | Stable | 5.11 | 1.31E−11 | 17 | 0.9275 |
| 21H7 | WT | 93.22 | 59.8 | 4.41 | 1.00 | Stable | 6.65 | 1.04E−11 | 15.3 | NA |
| 21H7 | M1M1MIM1 | 98 | 57.8 | 3.13 | 0.71 | Stable | 13.7 | 7.95E−11 | 14.8 | 0.9375 |
| 21H7 | M1M1M1M2 | 96.52 | 60.0 | 3.17 | 0.72 | Stable | 6.39 | 1.28E−11 | 15 | 0.9525 |
| 21H7 | M1M2MIM1 | 95.43 | 59.3 | 3.53 | 0.80 | Stable | 7.79 | 1.13E−11 | 15 | 0.9425 |
| 21H7 | M1M2M1M2 | 95.01 | 59.5 | 4.06 | 0.92 | Stable | 6.7 | 1.14E−11 | 15 | 0.9575 |

Table 1 provides amino acid sequences for humanized 1C10 VHH1 single binder (SEQ ID NO: 4), humanized 1C10 VHH2 single binder (SEQ ID NO: 9), and humanized 1C10 co-binder (SEQ ID NO: 14); humanized 1D1 VHH1 single binder (SEQ ID NO: 18), humanized 1D1 VHH2 single binder (SEQ ID NO: 23), and humanized 1D1 co-binder (SEQ ID NO: 28); humanized 1H5 VHH1 single binder (SEQ ID NO: 32), humanized 1H5 VHH2 single binder (SEQ ID NO: 37), and humanized 1H5 co-binder (SEQ ID NO: 42); and humanized 21H7 VHH1 single binder (SEQ ID NO: 46), humanized 21H7 VHH2 single binder (SEQ ID NO: 51), and humanized 21H7 co-binder (SEQ ID NO: 56).

Fc formats of humanized 1C10, 1D1, 1H5, 21H7 were also designed using huIgG1Fc_YTE_C→S (SEQ ID NO: 62). The amino acid sequences for humanized 1C10, 1D1, 1H5, and 21H7 co-binders with huIgG1Fc_YTE_C→S are provided in Table 1 as SEQ ID NOs: 16, 30, 44, and 58, respectively.

Example 8. In Vivo Efficacy in Pruritic Mouse Model

Female transgenic mice (6 to 8 weeks old) that have been engineered to express the human IL31, IL31RA, and oncostatin M receptor (OSMR) genes in place of the murine IL31, IL31RA, and OSMR genes were purchased from pruritic activity was observed for 2 of 3 test articles. When administered at 1 and 3 mg/kg, all test articles resulted in a marked reduction in IL31-induced pruritic activity. Importantly, as assessed by plasma drug concentration analysis, the amount of co-binder did increase systemically with increased dose level. When administered at the efficacious doses of 1 and 3 mg/kg, plasma co-binder concentrations were approximately 3-6 μg/mL and 15-19 μg/mL, respectively at the time of IL31 administration (FIG. 6B).

Example 9. Anti-Pruritic Activity in Non-Human Primates

Male cynomolgus monkeys (3 to 5 years old) were selected from available stock animals at SNBL (Kagoshima, Japan). After two weeks of acclimation, all animals were administered recombinant cynomolgus IL-31 (1 μg/kg, Sino Biological, Beijing, China) via intravenous injection and observed for pruritic response for 3 hours. Animals that demonstrated a pruritic response to cyIL31 injection were allocated into 3 treatment groups of 3 monkeys each. 1C10 (SEQ ID NO: 16) was administered on Study Day 0 at 1 or 5 mg/kg. Approximately 24 hours after co-binder administration, serum was collected from all co-binder treated animals. Serum was also collected on Study Days 8, 15, 22, and 29. Recombinant cyIL31 was injected intravenously (1

μg/kg) on Study Days 1, 8, 15, and 29, and scratching activity was recorded to assess frequency and total duration over 3 hours.

Pruritic activity for all animals was normalized to activity assessed upon cyIL31 treatment prior to study initiation. Clear incidence of pruritic activity was observed in all treatment groups prior to study initiation. As shown in FIG. 7A, when 1C10 co-binder was administered at 1 or 5 mg/kg a clear reduction in relative duration of pruritic activity was observed. The reduction in relative duration of pruritic activity persisted to Day 8. After Day 8, animals in the 1 mg/kg treatment group began demonstrating increased pruritic activity over time, increasing to pre-study levels by Day 29. In contrast, animals treated with 5 mg/kg of test article failed to show a clear resumption of cyIL31-induced pruritic activity throughout the course of the study.

Serum collected from all animals was assessed for 1C10 co-binder concentration by ELISA. All animals possessed quantifiable levels of 1C10 co-binder at all time points tested with a clear reduction in serum drug concentration over time. These data suggest time and drug concentration effects of 1C10 co-binder on suppressing IL31-induced pruritus. This is further supported when comparing the relative duration of pruritic activity to calculated serum drug concentration (FIG. 7B). Specifically, animals with the highest serum drug concentration had the lowest relative pruritic activity upon cyIL31 treatment, in contrast with the notably higher pruritic activity in animals demonstrating the lowest serum drug concentrations.

EQUIVALENTS

The foregoing written specification is considered to be sufficient to enable one skilled in the art to practice the aspects. The foregoing description and Examples detail certain aspects and describe the best mode contemplated by the inventors. It will be appreciated, however, that no matter how detailed the foregoing may appear in text, the aspect may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all the values or ranges provided in the list. In some instances, the term about may include numerical values that are rounded to the nearest significant figure.

What is claimed is:

1. A polypeptide that binds IL31 comprising a first IL31 binder and a second IL31 binder wherein:

a) the first IL31 binder comprises a first variable heavy domain of heavy chain (VHH1) comprising a complimentary determining region (CDR) CDR1 of amino acid sequence SEQ ID NO: 5, a CDR2 of amino acid sequence SEQ ID NO: 6 and a CDR3 of amino acid sequence SEQ ID NO: 7; and the second IL31 binder comprises a second variable heavy domain of heavy chain (VHH2) comprising a CDR1 of amino acid sequence SEQ ID NO: 10, a CDR2 of amino acid sequence SEQ ID NO: 11 and a CDR3 of amino acid sequence SEQ ID NO: 12;

b) the first IL31 binder comprises a VHH1 comprising a CDR1 of amino acid sequence SEQ ID NO: 78, a CDR2 of amino acid sequence SEQ ID NO: 79 and a CDR3 of amino acid sequence SEQ ID NO: 80; and the second IL31 binder comprises a VHH2 comprising a CDR1 of amino acid sequence SEQ ID NO: 84, a CDR2 of amino acid sequence SEQ ID NO: 85 and a CDR3 of amino acid sequence SEQ ID NO: 86;

c) the first IL31 binder comprises a VHH1 comprising a CDR1 of amino acid sequence SEQ ID NO: 81, a CDR2 of amino acid sequence SEQ ID NO: 82 and a CDR3 of amino acid sequence SEQ ID NO: 83; and the second IL31 binder comprises a VHH2 comprising a CDR1 of amino acid sequence SEQ ID NO: 87, a CDR2 of amino acid sequence SEQ ID NO: 88 and a CDR3 of amino acid sequence SEQ ID NO: 89;

d) the first IL31 binder comprises a VHH1 comprising a CDR1 of amino acid sequence SEQ ID NO: 19, a CDR2 of amino acid sequence SEQ ID NO: 20 and a CDR3 of amino acid sequence SEQ ID NO: 21; and the second IL31 binder comprises a VHH2 comprising a CDR1 of amino acid sequence SEQ ID NO: 24, a CDR2 of amino acid sequence SEQ ID NO: 25 and a CDR3 of amino acid sequence SEQ ID NO: 26;

e) the first IL31 binder comprises a VHH1 comprising a CDR1 of amino acid sequence SEQ ID NO: 33, a CDR2 of amino acid sequence SEQ ID NO: 34 and a CDR3 of amino acid sequence SEQ ID NO: 35; and the second IL31 binder comprises a VHH2 comprising a CDR1 of amino acid sequence SEQ ID NO: 38, a CDR2 of amino acid sequence SEQ ID NO: 39 and a CDR3 of amino acid sequence SEQ ID NO: 40;

f) the first IL31 binder comprises a VHH1 comprising a CDR1 of amino acid sequence SEQ ID NO: 47, a CDR2 of amino acid sequence SEQ ID NO: 48 and a CDR3 of amino acid sequence SEQ ID NO: 49; and the second IL31 binder comprises a VHH2 comprising a CDR1 of amino acid sequence SEQ ID NO: 52, a CDR2 of amino acid sequence SEQ ID NO: 53 and a CDR3 of amino acid sequence SEQ ID NO: 54;

g) the first IL31 binder comprises a VHH1 comprising a CDR1 of amino acid sequence SEQ ID NO: 268, a CDR2 of amino acid sequence SEQ ID NO: 269 and a CDR3 of amino acid sequence SEQ ID NO: 270; and the second IL31 binder comprises a VHH2 comprising a CDR1 of amino acid sequence SEQ ID NO: 272, a CDR2 of amino acid sequence SEQ ID NO: 273 and a CDR3 of amino acid sequence SEQ ID NO: 274;

h) the first IL31 binder comprises a VHH1 comprising a CDR1 of amino acid sequence SEQ ID NO: 276, a CDR2 of amino acid sequence SEQ ID NO: 277 and a CDR3 of amino acid sequence SEQ ID NO: 278; and the second IL31 binder comprises a VHH2 comprising a CDR1 of amino acid sequence SEQ ID NO: 280, a CDR2 of amino acid sequence SEQ ID NO: 281 and a CDR3 of amino acid sequence SEQ ID NO: 282;

i) the first IL31 binder comprises a VHH1 comprising a CDR1 of amino acid sequence SEQ ID NO: 284, a CDR2 of amino acid sequence SEQ ID NO: 285 and a CDR3 of amino acid sequence SEQ ID NO: 286; and the second IL31 binder comprises a VHH2 comprising a CDR1 of amino acid sequence SEQ ID NO: 288, a CDR2 of amino acid sequence SEQ ID NO: 289 and a CDR3 of amino acid sequence SEQ ID NO: 290;

j) the first IL31 binder comprises a VHH1 comprising a CDR1 of amino acid sequence SEQ ID NO: 292, a CDR2 of amino acid sequence SEQ ID NO: 293 and a CDR3 of amino acid sequence SEQ ID NO: 294; and the second IL31 binder comprises a VHH2 comprising a CDR1 of amino acid sequence SEQ ID NO: 296, a CDR2 of amino acid sequence SEQ ID NO: 297 and a CDR3 of amino acid sequence SEQ ID NO: 298;

k) the first IL31 binder comprises a VHH1 comprising a CDR1 of amino acid sequence SEQ ID NO: 300, a CDR2 of amino acid sequence SEQ ID NO: 301 and a CDR3 of amino acid sequence SEQ ID NO: 302; and the second IL31 binder comprises a VHH2 comprising a CDR1 of amino acid sequence SEQ ID NO: 304, a CDR2 of amino acid sequence SEQ ID NO: 305 and a CDR3 of amino acid sequence SEQ ID NO: 306;

l) the first IL31 binder comprises a VHH1 comprising a CDR1 of amino acid sequence SEQ ID NO: 308, a CDR2 of amino acid sequence SEQ ID NO: 309 and a CDR3 of amino acid sequence SEQ ID NO: 310; and the second IL31 binder comprises a VHH2 comprising a CDR1 of amino acid sequence SEQ ID NO: 312, a CDR2 of amino acid sequence SEQ ID NO: 313 and a CDR3 of amino acid sequence SEQ ID NO: 314;

m) the first IL31 binder comprises a VHH1 comprising a CDR1 of amino acid sequence SEQ ID NO: 316, a CDR2 of amino acid sequence SEQ ID NO: 317 and a CDR3 of amino acid sequence SEQ ID NO: 318; and the second IL31 binder comprises a VHH2 comprising a CDR1 of amino acid sequence SEQ ID NO: 320, a CDR2 of amino acid sequence SEQ ID NO: 321 and a CDR3 of amino acid sequence SEQ ID NO: 322;

n) the first IL31 binder comprises a VHH1 comprising a CDR1 of amino acid sequence SEQ ID NO: 324, a CDR2 of amino acid sequence SEQ ID NO: 325 and a CDR3 of amino acid sequence SEQ ID NO: 326; and the second IL31 binder comprises a VHH2 comprising a CDR1 of amino acid sequence SEQ ID NO: 328, a CDR2 of amino acid sequence SEQ ID NO: 329 and a CDR3 of amino acid sequence SEQ ID NO: 330;

o) the first IL31 binder comprises a VHH1 comprising a CDR1 of amino acid sequence SEQ ID NO: 332, a CDR2 of amino acid sequence SEQ ID NO: 333 and a CDR3 of amino acid sequence SEQ ID NO: 334; and the second IL31 binder comprises a VHH2 comprising a CDR1 of amino acid sequence SEQ ID NO: 336, a CDR2 of amino acid sequence SEQ ID NO: 337 and a CDR3 of amino acid sequence SEQ ID NO: 338; or p) the first IL31 binder comprises a VHH1 comprising a CDR1 of amino acid sequence SEQ ID NO: 340, a CDR2 of amino acid sequence SEQ ID NO: 341 and a CDR3 of amino acid sequence SEQ ID NO: 342; and the second IL31 binder comprises a VHH2 comprising a CDR1 of amino acid sequence SEQ ID NO: 344, a CDR2 of amino acid sequence SEQ ID NO: 345 and a CDR3 of amino acid sequence SEQ ID NO: 346.

2. The polypeptide of claim 1, wherein:

a) the VHH1 comprises a CDR1 comprising the amino acid sequence of SEQ ID NO: 5, a CDR2 comprising the amino acid sequence of SEQ ID NO: 6, and a CDR3 comprising the amino acid sequence of SEQ ID NO: 7 and the VHH2 comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12;

b) the VHH1 comprises a CDR1 comprising the amino acid sequence of SEQ ID NO: 78, a CDR2 comprising the amino acid sequence of SEQ ID NO: 79, and a CDR3 comprising the amino acid sequence of SEQ ID NO: 80 and the VHH2 comprises a CDR1 comprising the amino acid sequence of SEQ ID NO: 84, a CDR2 comprising the amino acid sequence of SEQ ID NO: 85, and a CDR3 comprising the amino acid sequence of SEQ ID NO: 86; or c) the VHH1 comprises a CDR1 comprising the amino acid sequence of SEQ ID NO: 81, a CDR2 comprising the amino acid sequence of SEQ ID NO: 82, and a CDR3 comprising the amino acid sequence of SEQ ID NO: 83 and the VHH2 comprises a CDR1 comprising the amino acid sequence of SEQ ID NO: 87, a CDR2 comprising the amino acid sequence of SEQ ID NO: 88, and a CDR3 comprising the amino acid sequence of SEQ ID NO: 89.

3. The polypeptide of claim 1, wherein the VHH1 comprises the amino acid sequence of SEQ ID NO: 3 or SEQ ID NO: 4.

4. The polypeptide of claim 1, wherein the VHH2 comprises the amino acid sequence of SEQ ID NO: 8 or SEQ ID NO: 9.

5. A polypeptide that binds IL31 comprising a first IL31 binder and a second IL31 binder, wherein the first IL31 binder comprises a first variable heavy domain of heavy chain (VHH1) and the second IL31 binder comprises a second VHH (VHH2), wherein the VHH1 comprises the amino acid sequence of SEQ ID NO: 4 and the VHH2 comprises the amino acid sequence of SEQ ID NO: 9.

6. The polypeptide of claim 5, wherein the VHH1 is connected to the VHH2 by a linker, wherein the polypeptide has the structure: [VHH1]-linker-[VHH2].

7. The polypeptide of claim 1, wherein the polypeptide comprises the amino acid sequence of SEQ ID NO: 13 or SEQ ID NO: 14.

8. The polypeptide of claim 1, wherein the polypeptide comprises the amino acid sequence of SEQ ID NO: 14.

9. The polypeptide of claim 6, wherein the linker comprises an amino acid sequence comprising (X)n-G, and the VHH2 comprises at the N-terminus Xa, Xb, and Xc, wherein X is an amino acid, G is glycine, n is any integer between 0 and 100, Xa is E (Glutamic acid), Q (Glutamine), or missing, Xb is V (Valine) or missing, and Xc is Q (Glutamine), K (Lysine), or missing.

10. The polypeptide of claim 8, wherein the polypeptide further comprises a human IgG1, IgG2, IgG3, or IgG4 Fc region.

11. The polypeptide of claim 10, wherein the Fc region comprises the amino acid sequence of SEQ ID NO: 62 or the amino acid residues 1-231 of SEQ ID NO: 62; or wherein the Fc region comprises the amino acid sequence of SEQ ID NO: 90 or the amino acid residues 1-231 of SEQ ID NO: 90.

12. A polypeptide that binds IL31 comprising a first IL31 binder and a second IL31 binder, wherein the polypeptide comprises amino acid residues 1-506 of SEQ ID NO: 16.

13. The polypeptide of claim 1, wherein the polypeptide binds to human IL31 at a kD of less than or equal to $1\times10^{-9}$ M, as measured by surface plasmon resonance, or wherein the polypeptide binds to human IL31 with a koff rate of less than or equal to $5\times10^{-4}$ M per second, as measured by surface plasmon resonance.

14. A pharmaceutical composition comprising the polypeptide of claim 12 and a pharmaceutically acceptable carrier.

15. An isolated nucleic acid that encodes the polypeptide of claim 1.

16. A method of producing an IL31 co-binder polypeptide, comprising transfecting the isolated nucleic acid of claim 15 into a host cell under conditions suitable for expression of the polypeptide.

17. A method for treating a subject having an IL31-associated condition comprising administering to the subject a therapeutically effective amount of the polypeptide of claim 12.

18. The polypeptide of claim 12, wherein the polypeptide comprises the amino acid sequence of SEQ ID NO: 16.

19. The pharmaceutical composition of claim 14, further comprising the polypeptide comprising the amino acid sequence of SEQ ID NO: 16.

* * * * *